US006794491B1

(12) United States Patent
Hinuma et al.

(10) Patent No.: US 6,794,491 B1
(45) Date of Patent: Sep. 21, 2004

(54) POLYPEPTIDES, THEIR PRODUCTION AND USE

(75) Inventors: Shuji Hinuma, Tsukuba (JP); Yugo Habata, Tsukuba (JP); Yuji Kawamata, Tsukuba (JP); Masaki Hosoya, Tsuchiura (JP); Ryo Fujii, Tsukuba (JP); Shoji Fukusumi, Tsukuba (JP); Chieko Kitada, Sakai (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/576,290

(22) Filed: May 23, 2000

Related U.S. Application Data

(63) Continuation of application No. 08/776,971, filed as application No. PCT/JP96/03821 on Dec. 28, 1996, now Pat. No. 6,228,984.

(30) Foreign Application Priority Data

| Dec. 28, 1995 | (JP) | ............................................. | 7-343371 |
| Mar. 15, 1996 | (JP) | ............................................. | 8-059419 |
| Aug. 12, 1996 | (JP) | ............................................. | 8-211805 |
| Sep. 18, 1996 | (JP) | ............................................. | 8-246573 |

(51) Int. Cl.$^7$ ........................ C07K 14/475; C07K 7/08; C07K 14/00
(52) U.S. Cl. ...................... 530/324; 530/326; 530/345; 530/402; 530/408
(58) Field of Search ................................ 530/326, 324, 530/345, 402, 408, 399

(56) References Cited

U.S. PATENT DOCUMENTS

| 5,279,957 A | | 1/1994 | Gross ...................... 435/240.2 |
| 5,328,838 A | * | 7/1994 | Galli et al. .................. 435/472 |
| 5,474,766 A | * | 12/1995 | Schwartz et al. ......... 424/94.63 |
| 5,534,699 A | * | 7/1996 | Ferry .......................... 250/294 |
| 5,556,744 A | | 9/1996 | Weiner et al. .................. 435/5 |
| 6,228,984 B1 | * | 5/2001 | Hinuma et al. ........... 424/198.1 |

FOREIGN PATENT DOCUMENTS

| WO | WO 91/12273 | 8/1991 |
| WO | WO 96/05302 | 8/1995 |

OTHER PUBLICATIONS

Henriksen et al. Peptide amidation by chemical protein engineering. A combination of enzymic and photochemical synthesis. J. Am. Chem. Soc. (1992), 114(5), 1876–7.*
Whitcomb et al. Identification of tissue insulin receptors: use of a unique in vivo radioreceptor assay. Am J Physiol, (Dec. 1985) 249 (6 Pt 1) E561–7.*
European Search Report, mailed Jun. 17, 1997 for PCT/JP96/03821 (U.S.S.N. 08/776,971).
Bowie et al., *Science,* 247 (4948) 1306–1310 (1990).
Ngo et al., in the Protein Folding Problem and Tertiary Structure Prediction, Merz and Le Grand (Eds), Aug. 1994, Springer Verlag, pp. 433 and 492–495.
S. Welch et al., *Biochemical Biophysical Research Communications,* 209:606–613 (1995).
Marchese et al. Cloning and Chromosomal Mapping of Three Novel Genes, GPR9, GPR10, and GPR14, Encoding Receptors Related to Interleukin 8, Neropeptide Y, and Samatostatin Receptors, *GENOMICS,* 29:335–344 (1995).

* cited by examiner

*Primary Examiner*—David S. Romeo
(74) *Attorney, Agent, or Firm*—David C. Conlin; John B. Alexander; Edwards & Angell, LLP

(57) ABSTRACT

The present invention relates to the ligand polypeptide for the human pituitary- and mouse pancreas-derived G protein-coupled receptor proteins.

The ligand polypeptide or the DNA which codes for the ligand polypeptide can be used for (1) development of medicines such as pituitary function modulators, central nervous system function modulators, and pancreatic function modulators, and (2) development of receptor binding assay systems using the expression of recombinant receptor proteins and screening of pharmaceutical candidate compounds.

In particular, by the receptor binding assay systems utilizing the expression of recombinant G protein-coupled receptor proteins in accordance with the invention, agonists and antagonists of G protein-coupled receptors which are specific to human and other warm-blooded animals can be screened and the agonists or antagonists obtained can be used as therapeutic and prophylactic agents for various diseases.

7 Claims, 60 Drawing Sheets

```
                    9              18             27             36             45             54
5' GTG GGC ATG GTG GGC AAC GTC CTG CTG GTG CTG GTG ATC GCG CGG GTG CGC CGG
   --- --- --- --- --- --- --- --- --- --- --- --- --- --- --- --- --- ---
   Val Gly Met Val Gly Asn Val Leu Leu Val Leu Val Ile Ala Arg Val Arg Arg 63             72             81             90             99            108
   CTG CAC AAC GTG ACG AAC TTC CTC ATC GGC AAC CTG GCC TTG TCC GAC GTG CTC
   --- --- --- --- --- --- --- --- --- --- --- --- --- --- --- --- --- ---
   Leu His Asn Val Thr Asn Phe Leu Ile Gly Asn Leu Ala Leu Ser Asp Val Leu 117            126            135            144            153            162
   ATG TGC ACC GCC TGC GTG CCG CTC ACG CTG GCC TAT GCC TTC GAG CCA CGC GGC
   --- --- --- --- --- --- --- --- --- --- --- --- --- --- --- --- --- ---
   Met Cys Thr Ala Cys Val Pro Leu Thr Leu Ala Tyr Ala Phe Glu Pro Arg Gly 171            180            189            198            207            216
   TGG GTG TTC GGC GGC GGC CTG TGC CAC CTG GTC TTC TTC CTG CAG CCG GTC ACC
   --- --- --- --- --- --- --- --- --- --- --- --- --- --- --- --- --- ---
   Trp Val Phe Gly Gly Gly Leu Cys His Leu Val Phe Phe Leu Gln Pro Val Thr 225            234            243            252            261            270
   GTC TAT GTG TCG GTG TTC ACG CTC ACC ACC ATC GCA GTG GAC CGG TAC GTC GTG
   --- --- --- --- --- --- --- --- --- --- --- --- --- --- --- --- --- ---
   Val Tyr Val Ser Val Phe Thr Leu Thr Thr Ile Ala Val Asp Arg Tyr Val Val 279            288            297
   CTG GTG CAC CCG CTG AGG CGG CGC ATC 3'
   --- --- --- --- --- --- --- --- ---
   Leu Val His Pro Leu Arg Arg Arg Ile
```

FIG. 1

```
     9        18        27        36        45        54
5' GGC CTG CTG GTC ACC TAC CTG CCT CTG GTC CTG ATC CTC CTG TCT TAC
   --- --- --- --- --- --- --- --- --- --- --- --- --- --- --- ---
   Gly Leu Leu Val Thr Tyr Leu Pro Leu Val Ile Leu Leu Ser Tyr 63       72        81        90        99       108
   GTC CGG GTG TCA GTG AAG CTC CGC AAC CGC GTG GTG CCG GGC TGC GTG ACC CAG
   --- --- --- --- --- --- --- --- --- --- --- --- --- --- --- --- --- ---
   Val Arg Val Ser Val Lys Leu Arg Asn Arg Val Val Pro Gly Cys Val Thr Gln 117       126       135       144       153       162
   AGC CAG GCC GAC TGG GAC CGC GCT CGG CGG CGC ACC TTC TGC TTG CTG GTG
   --- --- --- --- --- --- --- --- --- --- --- --- --- --- --- --- ---
   Ser Gln Ala Asp Trp Asp Arg Ala Arg Arg Arg Thr Phe Cys Leu Leu Val 171       180       189       198
   GTG GTC GTG GTG GTG TTT GCC ATC TGC TGG TTG CCT TAC TAC 3'
   --- --- --- --- --- --- --- --- --- --- --- --- --- ---
   Val Val Val Val Val Phe Ala Ile Cys Trp Leu Pro Tyr Tyr
```

FIG. 2

```
p19P2      1 VGMVGNVLV LVIARVRRLH NVTNFLIGNL ALSDVLMCTA CVPLTLAYAF    50
S12863     1 LGVSGNLALI IILKQKEMR  NVTNILIVNL SFSDLLVAVM CLPFLFVYTL    50 p19P2     51 EPRGWVFGGG LCHLVFFLQP VIVYVSVFTL TTIAVDRYVV LVHPLRRRI-   100
S12863    51 MDH-WVFGET MCKLNPFVQC VSITVSIFSL VLIAVERHQL IINPRGWRPN   100 p19P2    101 --------- ---------- ---------- ---------- ----------   150
S12863   101 NRHAYIGITV IWLAVASSL  PFVIYQILTD EPFQNVSLAA FKDKYVCFDK   150 p19P2    151 -----GLLV TYLPLLWIL  LS-------- ---------- VRVSVKLRNR   200
S12863   151 FPSDSHRLSY TTLLVLQYF  GPLCFIFICY FKIYIRLKRR NNMMDKIRDS   200 p19P2    201 ADWDRARRR  TFCLLVVVV  VFEAICWLPY Y......... ..........   250
S12863   201 KYRSSETKRI NVMLLSIVA  -FAVCWLPLT .......... ..........   250
```

FIG. 5

| | FIG. 6A |
|---|---|
| | FIG. 6B |
| | FIG. 6C |

FIG. 6

```
                 9                  18                  27                  36                  45                  54
5' GTG GGC ATG GTG GGC AAC ATC CTG GTG CTC GTG ATC GCC CGG GTG CGC CGG
   --- --- --- --- --- --- --- --- --- --- --- --- --- --- --- --- ---
   Val Gly Met Val Gly Asn Ile Leu Val Leu Val Ile Ala Arg Val Arg Arg 63                 72                  81                  90                  99                 108
   CTG TAC AAC GTG ACG AAT TTC CTC ATC GGC AAC CTG GCC TTG TCC GAC GTG CTC
   --- --- --- --- --- --- --- --- --- --- --- --- --- --- --- --- --- ---
   Leu Tyr Asn Val Thr Asn Phe Leu Ile Gly Asn Leu Ala Leu Ser Asp Val Leu 117                126                 135                 144                 153                 162
   ATG TGC ACC GCC TGC GTG CCG CTC ACG CTG GCC TAT GCC TTC GAG CCA CGC GGC
   --- --- --- --- --- --- --- --- --- --- --- --- --- --- --- --- --- ---
   Met Cys Thr Ala Cys Val Pro Leu Thr Leu Ala Tyr Ala Phe Glu Pro Arg Gly
```

FIG. 6A

```
171       180       189       198       207       216
TGG GTG GGC GGC CTG TGC CAC CTG GTC TTC CTG CAG GCG GTC ACC
 |   |   |   |   |   |   |   |   |   |   |   |   |   |   |
Trp Val Gly Gly Leu Cys His Leu Val Phe Leu Gln Ala Val Thr 225       234       243       252       261       270
GTC TAT TCG GTG TTC ACC CTC ACC ATC GCA GTG GAC CGC TAC GTC GTG
 |   |   |   |   |   |   |   |   |   |   |   |   |   |   |
Val Tyr Ser Val Phe Thr Leu Thr Ile Ala Val Asp Arg Tyr Val Val 279       288       297       306       315       324
CTG CAC CCG AGG CGG CGC ATC TCG CTG CGC AGC CTC TAC GCT GTG
 |   |   |   |   |   |   |   |   |   |   |   |   |   |   |
Leu Val His Pro Leu Arg Arg Ile Ser Leu Arg Ser Ala Tyr Ala Val 333       342       351       360       369       378
CTG GCC ATC TGG GTG CTG TTC GCG GTG CTG GCG CCC GCC GTG CAC ACC
 |   |   |   |   |   |   |   |   |   |   |   |   |   |   |
Leu Ala Ile Trp Val Leu Phe Ala Val Leu Ala Leu Pro Ala Val His Thr 387       396       405       414       423       432
TAT CAC GTG GAG CTC AAG CCG CAC GAC GTC CTC TGC GAG TTC TGG GGC
 |   |   |   |   |   |   |   |   |   |   |   |   |   |   |
Tyr His Val Glu Leu Lys Pro His Asp Val Arg Leu Cys Glu Phe Trp Gly
```

FIG. 6B

```
      441                450                459                468                477                486
TCC CAG GAG CGC CAG CTC CGC CAG CTC TAC GCC TGG GGG CTG CTG CTG GTC ACC TAC
--- --- --- --- --- --- --- --- --- --- --- --- --- --- --- --- --- --- ---
Ser Gln Glu Arg Gln Leu Arg Gln Leu Tyr Ala Trp Gly Leu Leu Leu Val Thr Tyr 495                504                513                522                531                540
CTG CTC CCT CTG CTG GTG GTC ATC CTC GTG TCT TAC CGG GTG TCA GTG AAG CTC
--- --- --- --- --- --- --- --- --- --- --- --- --- --- --- --- --- --- ---
Leu Leu Pro Leu Leu Val Val Ile Leu Val Ser Tyr Ala Arg Val Ser Val Lys Leu 549                558                567                576                585                594
CGC AAC CGC GTG GTG CCG GGC CGC GTG ACC CAG AGC CAG GCC GAC TGG GAC CGC
--- --- --- --- --- --- --- --- --- --- --- --- --- --- --- --- --- --- ---
Arg Asn Arg Val Val Pro Gly Arg Val Thr Gln Ser Gln Ala Asp Trp Asp Arg 603                612                621                630                639                648
GCT CGG CGG CGG CCG ACC TTC TGC TTG CTG GTG GTC GTG GTG GTG GTG TTC ACC
--- --- --- --- --- --- --- --- --- --- --- --- --- --- --- --- --- --- ---
Ala Arg Arg Arg Pro Thr Phe Cys Leu Leu Val Val Val Val Val Val Phe Thr 657                666
CTC TGC TGG CTG CCC TTC TTC 3'
--- --- --- --- --- --- ---
Leu Cys Trp Leu Pro Phe Phe
```

FIG. 6C

| | | | | | | |
|---|---|---|---|---|---|---|
| p19P2 | 1 | VGMVGNV | LLV | LVTARVRRLH | NVTNFLIGNL | ALSDVLMCTA | CVPLTLAYAF | 50 |
| pG3-2/pG1-10 | 1 | VGMVGNI | LLV | LVTARVRRLx | NVTNFLIGNL | ALSDVLMCTA | CVPLTLAYAF | 50 |

| p19P2 | 51 | EPRGWFGGG | LCHLVFFLQP | VTVYVSVFTL | TTIAVDRYVV | LVHPLRRRI- | 100 |
| pG3-2/pG1-10 | 51 | EPRGWFGGG | LCHLVFFLQA | VTVYVSVFTL | TTIAVDRYVV | LVHPLRRRIs | 100 |

| p19P2 | 101 | ---------- | ---------- | ---------- | ---------- | ---------- | 150 |
| pG3-2/pG1-10 | 101 | LRLSAYAVLA | IWVLSAVLAL | PAAVHTYHVE | LKPHDVRLCE | EFWGSQERQR | 150 |

| p19P2 | 151 | ---------- | QLYAWGLLLV | TYLLPLLVIL | LSYVRVSVKL | RNRVVFGCVT | QSQADMDRAR | 200 |
| pG3-2/pG1-10 | 151 | GLLLV | TYLLPLLVIL | LSYARVSVKL | RNRVVFGRVT | QSQADMDRAR | 200 |

| p19P2 | 201 | RRRTFCLLVV | VVVFAICML | PYY........ | .......... | .......... | 250 |
| pG3-2/pG1-10 | 201 | RRRTFCLLVV | VVVFLCML | PFF........ | .......... | .......... | 250 |

FIG. 7

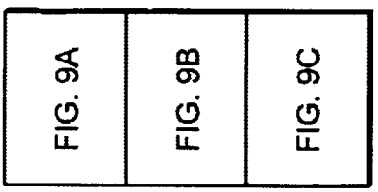

FIG. 9

```
  1   1 CATGGTCAAGCAGATGAGATCATCCAGGAGGATGGCTACTCCGAGGGCCAGGAGAAATT    60

61   1 CTGCCCCTTCTTCCCGGAGTGCTTCCCGCTTCCAAACCCCACTCCCAGGTGCCATG     120
                                                              Met
121   1 GCCTCATGACCACTCGGGGCCCCAGGGTTTCTGACTTATTTCTCGGGCTGCGCGGGCG    180
        AlaSerSerThrThrArgGlyProArgValSerAspLeuPheSerGlyLeuProProAla
181  21 GTCACAACTCCCGCCAACCAGAGCCCAGAGGCCCAACGGTCGGGGAACGGTCGGTGGCTGGC  240
        ValThrThrProAlaAsnGlnSerAlaSerAlaGluAlaSerAlaGlySerValAlaGly
241  41 GCGGAGGCTCCAGCGCCCTTCCAGAGCCTGAGCTGTCATCAGCTGAAGGGG          300
        AlaAspAlaProAlaValThrProPheGlnSerLeuGlnLeuValHisGlnLeuLysGly
```

FIG. 9A

```
301 CTGATCGTGCTGCTCTACAGGTGCTGGTGGTGGTGGGGCTGGTGGGGCAACTGCCTCTG       360
 61 LeuIleValLeuLeuTyrSerValValValValGlyLeuValGlyAsnCysLeuLeu         81

361 GTGCTGGTGATCGGCCGGGCGCGGCTGCACAAGTGACGAACTTCCATGGCAAC            420
 81 ValLeuValIleAlaArgValAlaArgLeuHisAsnValThrAsnPheLeuIleGlyAsn    101

421 CTGGCCCTGCTCTCCGACGTGCTCATGTGCACGGCCTGCGTGCCGCTGACGCTGGCCTATGCC  480
101 LeuAlaLeuSerAspValLeuMetCysThrAlaCysValProLeuThrLeuAlaTyrAla    121

481 TTCGAGCCACGGGGCCTGGGTGTTCGGGGGGTGTCTTCTTCCTGCAG                 540
121 PheGluProArgGlyTyrGlyValPheGlyGlyGlyLeuCysHisLeuValPhePheLeuGln 141

541 CCGGTGACCGTCTATGTGGTGTCACGCTCACCACCATCGCAGTGACCGTACGTC           600
141 ProValThrValTyrValValSerValPheThrThrIleAlaValAspArgTyrVal       161

601 GTGCTGGTGCACCCGCTGAGGCGGCATCGCGCCTAGCGCCTACGCTGGTG              660
161 ValLeuValHisProLeuArgArgHisIleSerLeuArgLeuSerAlaAlaTyrAlaValLeu 181

661 GCCATCTGGGCGCTGTCCGGCAGCAGTGCAGCCTGCCGGTGCACCACTATCAGTG           720
181 AlaIleTrpAlaLeuSerAlaAlaLeuAlaValLeuProAlaAlaValHisThrTyrHisVal 201

721 GAGCTCAAGCCCACGAGTGCCCTGTGGAGGAGTTCGGGCTTCGGGCTTCGGAGCGCCAG       780
201 GluLeuLysProHisAspValArgLeuCysGluPheTrpGlySerGlnGluArgGln        221

781 CGCCAGCTCTACGCCTGGGGCTGTGTCACTACTACCTCCTCCCTGCTGTCATC             840
221 ArgGlnLeuTyrAlaTrpAlaGlyLeuLeuLeuValThrTyrLeuLeuProLeuLeuValIle 241
```

FIG. 9B

```
841  CTCCTGTCTTAGTCCGGTGTCAGTGAAGCTCCGCAACCCGTGTGCCGTGGGCTGCGTG    900
241  LeuLeuSerTyrValArgValSerValLysLeuArgAsnArgValValProGlyCysVal  261

901  ACCCAGAGCCAGCCGACTGGGCCGGCGGTGGTGCGGCCACCTTCCTGCTTGCTGGTG    960
261  ThrGlnSerGlnAlaAspTrpAspArgAlaArgArgArgThrPheCysLeuLeuVal     281

961  GTGGTGGTGGTGGTGCCGTCCGCGCCTCCACGTCTCAACTCTGCGG                1020
281  ValValValValValPheAlaValCysTrpLeuProLeuHisValPheAsnLeuLeuArg  301

1021 GACCTCGACCCCACGCCATGAGTGCCCTTAGCCTTACAACCCCTGCAGTCTGCCAC      1080
301  AspLeuAspProHisAlaIleAspProTyrAlaPheGlyLeuValGlnLeuLeuCysHis  321

1081 TGGCTGCCATGAGTCCGGCAGCTGCTACAACCCTTTCATCTACGCCTGGCACGACAGC   1140
321  TrpLeuAlaMetSerSerAlaCysTyrAsnProPheIleTyrAlaTrpLeuHisAspSer  341

1141 TTCCGGAGGAGCTGGCAAACTGTTGGTGCTTGCCAAGATAGCCCCGCATGGC          1200
341  PheArgGluGluLeuArgLysLeuLeuValAlaAlaTrpProArgLysIleAlaProHisGly 361

1201 CAGAATATGACCGTCAGCGTGGTCATCGATGCCACTTAGCCAGGCCTTGGTCAAGGAGC  1260
361  GlnAsnMetThrValSerValValIle***                                371

1261 TCCACTTCAACTGCCCCTAGGCCACCACTCGAGTGTCAATCGTGTCTTATTCTCAGCA   1320
371                                                                371

1321 CCAGAGCTAGC                                                    1331
371                                                                371
```

FIG. 9C

```
         9              18              27              36              45              54
5' CTG TGT GTC ATC GCG GTG GAT AGG TAC GTG GTT CTG GTG CAC CCG CTA CGT CGG
   --- --- --- --- --- --- --- --- --- --- --- --- --- --- --- --- --- ---
   Leu Cys Val Ile Ala Val Asp Arg Tyr Val Val Leu Val His Pro Leu Arg Arg 63              72              81              90              99             108
   CGC ATT TCA CTG AGG CTC AGC GCC TAC GCG GTG CTG GGC ATC TGG GCT CTA TCT
   --- --- --- --- --- --- --- --- --- --- --- --- --- --- --- --- --- ---
   Arg Ile Ser Leu Arg Leu Ser Ala Tyr Ala Val Leu Gly Ile Trp Ala Leu Ser 117             126             135             144             153             162
   GCA GTG CTG GCG CTG CCG GCC GCG GTG CAC ACC TAC CAT GTG GAG CTC AAG CCC
   --- --- --- --- --- --- --- --- --- --- --- --- --- --- --- --- --- ---
   Ala Val Leu Ala Leu Pro Ala Ala Val His Thr Tyr His Val Glu Leu Lys Pro 171             180             189             198             207             216
   CAC GAC GTG AGC CTC TGC GAG GAG TTC TGG GGC TCG CAG GAG CGC CAA CGC CAG
   --- --- --- --- --- --- --- --- --- --- --- --- --- --- --- --- --- ---
   His Asp Val Ser Leu Cys Glu Glu Phe Trp Gly Ser Gln Glu Arg Gln Arg Gln 225             234             243             252             261             270
   ATC TAC GCC TGG GGG CTG CTT CTG GGC ACC TAT TTG CTC CCC CTG CTG GCC ATC
   --- --- --- --- --- --- --- --- --- --- --- --- --- --- --- --- --- ---
   Ile Tyr Ala Trp Gly Leu Leu Leu Gly Thr Tyr Leu Leu Pro Leu Leu Ala Ile 279             288             297             306             315             324
   CTC CTG TCT TAC GTA CGG GTG TCA GTG AAG CTG AGG AAC CGC GTG GTG CCT GGC
   --- --- --- --- --- --- --- --- --- --- --- --- --- --- --- --- --- ---
   Leu Leu Ser Tyr Val Arg Val Ser Val Lys Leu Arg Asn Arg Val Val Pro Gly 333             342             351             360             369             378
   AGC GTG ACC CAG AGT CAA GCT GAC TGG GAC CGA GCG CGT CGC CGC CGC ACT TTC
   --- --- --- --- --- --- --- --- --- --- --- --- --- --- --- --- --- ---
   Ser Val Thr Gln Ser Gln Ala Asp Trp Asp Arg Ala Arg Arg Arg Arg Thr Phe 387             396             405             414             423             432
   TGT CTG CTG GTG GTG GTG GTG GTA GTG TTC ACG CTC TGC TGG CTG CCC TTC TAC
   --- --- --- --- --- --- --- --- --- --- --- --- --- --- --- --- --- ---
   Cys Leu Leu Val Val Val Val Val Val Phe Thr Leu Cys Trp Leu Pro Phe Tyr

CT 3'
   --                        FIG. 12
   --
```

| | | | | | | |
|---|---|---|---|---|---|---|
| p19P2 | 1 | VGMVGN|LLV | LVIARVRR|LH | NVTNFLIGNL | ALSDVLMCTA | CVPLTLAYAF | 50 |
| pG3-2/pG1-10 | 1 | VGMVGN|LLV | LVIARVRR|LY | NVTNFLIGNL | ALSDVLMCTA | CVPLTLAYAF | 50 |
| p5S38 | -79 | .......... | .......... | .......... | .......... | .......... | -30 |

| p19P2 | 51 | EPRGWFGGG | LCHLVFF|LQP | VTVYVSVFTL | TTIAVDRYVV | LVHPLRRRI- | 100 |
| pG3-2/pG1-10 | 51 | EPRGWFGGG | LCHLVFF|LQA | VTVYVSVFTL | TTIAVDRYVV | LVHPLRRRIS | 100 |
| p5S38 | -29 | .......... | .......... | ......L | CV|IAVDRYVV | LVIIPLRRRIS | 21 |

| p19P2 | 101 | LRLSAYAVLA | IW|LSAVLAL | PAAVHTYHVE | LKPHDVR|LCE | EFWGSQERQR | 150 |
| pG3-2/pG1-10 | 101 | LRLSAYAVLG | IW|ALSAVLAL | PAAVHTYHVE | LKPHDVS|LCE | EFWGSQERQR | 150 |
| p5S38 | 22 | .......... | .......... | .......... | .......... | .......... | 71 |

| p19P2 | 151 | ------GILLV | TYLLPLLVIL | LSYVRVSVKL | RNRVVPG|CVT | QSQADWDRAR | 200 |
| pG3-2/pG1-10 | 151 | QI|YAWGLLLV | TYLLPLLVIL | LSYA|RVSVKL | RNRVVPG|RVT | QSQADWDRAR | 200 |
| p5S38 | 72 | QI|YAWGLLLG | TYLLPLIA|IL | LSYVRVSVKL | RNRVVPG|SVT | QSQADWDRAR | 121 |

| p19P2 | 201 | RRRTFCLLVV | VVVFA|ICWL | PY|Y....... | .......... | .......... | 250 |
| pG3-2/pG1-10 | 201 | RRRTFCLLVV | VVVFTLCWL | PF|F....... | .......... | .......... | 250 |
| p5S38 | 122 | RRRTFCLLVV | VVVFTLCWL | PF|Y....... | .......... | .......... | 171 |

FIG. 13 rat whole brain extract
$C_{18}$-column $CH_3CN$ elution (%)

bovine hypothalamus extract
$C_{18}$-column $CH_3CN$ elution (%)

```
     P5-1  →
5'         9            18           27           36           45           54
    GCC CAC CAG CAC TCC ATG GAG ATC CGC ACC CCC GAC ATC AAC CCT GCC TGG TAC
    ::: ::: ::: ::: ::: ::: ::: ::: ::: ::: ::: ::: ::: ::: ::: ::: ::: :::
    Ala His Gln His Ser Met Glu Ile Arg Thr Pro Asp Ile Asn Pro Ala Trp Tyr
                                                                          ↓
                63           72
    GCG GGC CGT GGG ATC CGG CCC G 3'
    ::: ::: ::: ::: ::: ::: :::
    Ala Gly Arg Gly Ile Arg Pro
    ─────────────────────────────
              P3-2
```

FIG. 22

```
  1  GTGGAATGAAGGCGGTGGGCCTCCTGCTCTGCCTGCTGCTGGGCCTGTGCTGGGCCCTG         59
  1                  MetLysAlaValGlyAlaTrpLeuLeuLeuCysLeuLeuLeuGlyLeuAlaLeu   18

60  CAGGGGCTGCCAGCAGAGCCCACCAGACCCCACCAGCACTCCATGGAGATCCGACACTCAAC       119
 19  GlnGlyAlaAlaSerArgArgAlaHisGlnHisSerMetGluIleArgThrProAspIleAsn       38
                                                    ──────────────────→
                                                              PDN
120  CCTGCCT                                                              126
 39  ProAla                                                                40
     ──────
```

FIG. 23

```
  1  GTGGAATGAAGGGGGTGGGGCTGGCTCCTCCTGCTGCTGTGCCTGCTGGGGCTGCTGGCCCTG                    59
  1                  MetLysAlaValGlyAlaTrpLeuLeuLeuCysLeuLeuLeuGlyLeuLeuAlaLeu         18

60  CAGGGGGCTGCCAGCAGAGACACTCCATGGAGATCCGCACCCCCGACATCAAC                              119
 19  GlnGlyAlaAlaSerArgAlaHisGlnHisSerMetGluIleArgThrProAspIleAsn                       38

120  CCTGCCTGGTACGCGGCCGTGGGATCCGGCGGGCCGTGGGCGCTTCGGGCGGAAGAGCT                        179
 39  ProAlaTrpTyrAlaAlaValGlySerArgGlyIleArgProValGlyArgPheGlyArgArgArgAla              58

180  GCCCCGGGGACGGACCCAGGCCTGTGCCGTGTTCCGCCTGGAA                                        239
 59  AlaProGlyAspGlyProArgProGlyProArgValProAlaCysPheArgLeuGlu                          78

240  GGCGGYGCTGAGCCCTCCCGAGCCCTGACGGCCAGCTGGTCCAGGAA                                    299
 79  GlyGlyAlaGluProSerArgAlaLeuThrAlaGlnLeuValGlnGlu                                   98

300  TAACAGCGGAGCCCTGGCCCTGCCCCCTCCCTCCACCAGCCACCTTCCCCTTCCAGTCCT                       359
 98

360  AATAAAAGCAGCTGGCTTGTT                                                              380
 98
```

FIG. 24A

```
  1  GTGGAATGAAGGCGGTGGGGCCTGGCTCCTCTGCCTGCTGCTGTGGGCCCTG                           59
  1                     MetLysAlaValGlyAlaTrpLeuLeuCysLeuLeuLeuGlyLeuAlaLeu        18

60  CAGGGGGCTGCCAGCAGAGCCCACCAGCCACTCCATGGAGATCCGACACCCCGACATCAAC                 119
 19     GlnGlyAlaAlaSerArgAlaHisGlnHisSerMetGluIleArgThrProAspIleAsn               38

120  CCTGCCTGGTACGCGCGGGCCGTGGGATCCGGCGGCTTCGGCCGGAAGAGCT                          179
 39     ProAlaTrpTyrAlaArgAlaValGlyIleArgGlyProValGlyArgPheGlyArgArgArgAla         58

180  GCCCTGGGGACGGACCCAGGCCTGCTGTGCCCCCGGGCTGTTCCGGCTGGAA                          239
 59     AlaLeuGlyThrAspProGlyLeuLeuCysProArgAlaCysPheArgLeuGlu                     78

240  GGGGGYGCTGAGCCCTCCCGAGCCCTCCCTGAGCGGCCAGCTGGTCAGGAA                           299
 79     GlyGlyAlaGluProSerArgAlaLeuProGlyArgLeuThrAlaGlnLeuValGlnGlu               98

300  TAACAGCGGGAGCCTGCCCCCCACCCCTCCTCCACCAGCACCTTCCCTCCAGTCCT                      359
 98                                                                                98

360  AATAAAAGCAGCTGGTT                                                             380
 98                                                                                98
```

FIG. 24B

```
         10         20         30         40         50         60
ATGAAGGCGG TGGGGGCCTG GCTCCTCTGC CTGCTGCTGC TGGGCCTGGC CCTGCAGGGG 70         80         90        100        110        120
GCTGCCAGCA GAGCCCACCA GCACTCCATG GAGATCCGCA GTGAGTGTCT AGCCCCGCCC 130        140        150        160        170        180
CTGCCCCCAG GGGTCACAGG GGGGGCCTGG CCACTTCCTG GGCTGGGACA TCCTTGCTAA 190        200        210        220        230        240
GCATCCTGGG GTTGGGGTTT GGCCTCCTGT TCCCCAGACC CTTCCCCCAG GTGGCCCGGA 250        260        270        280        290        300
CAGGTGCTCC CAAGGGTCCC GGCCCAGCAC ACGGGGGAGG GTCACTCCTC ACCACACGGG 310        320        330        340        350        360
TGGCCTGGGG CTGAGTGCAC GTCACCCATG AGAACGGGGC TGTGAGGACA GGAAAGGAAG 370        380        390        400        410        420
GGGAGTGTGT CCTGGTGTGA GTCTGAAATC CTACTTCCCA AAGCCACCCC AGCACCAGAA 430        440        450        460        470        480
ATGGGCGCTC CGGGTGAACC TCCTGTGCGG GTGGGTGGTC CTGGCATGGC CTGGGCGACA 490        500        510        520        530        540
GGCAGCCATG AGCTGAGCAC ACACCCGGCC CGGCCACCAG GGCTGTATGC TCCAGGGCAC 550        560        570        580        590        600
AGGCCTCCAT GCGCTCTTCT CTCTCTTTCC AGCCCCCGAC ATCAACCCTG CCTGGTACGC 610        620        630        640        650        660
AGGCCGTGGG ATCCGGCCCG TGGGCCGCTT CGGCCGGCGA AGAGCTGCCC TGGGGACGG 670        680        690        700        710        720
ACCCAGGCCT GGCCCCCGGC GTGTGCCGGC CTGCTTCCGC CTGGAAGGCG GTGCTGAGCC 730        740        750        760        770        780
CTCCCGAGCC CTCCCGGGGC GGCTGACGGC CCAGCTGGTC CAGGAATAA.. ..........
```

FIG. 29

| | FIG. 30A |
|---|---|
| | FIG. 30B |
| | FIG. 30C |

FIG. 30

```
                   10         20         30         40         50
genome    1 ATGAAGGGGG TGGGGCCTG GCTCCTCTGC CTGCTGCTGC TGGGCCTTGC  50
cDNA      1 ATGAAGGGGG TGGGGCCTG GCTCCTCTGC CTGCTGCTGC TGGGCCTTGC  50
                   60         70         80         90        100
genome   51 CCTGCAGGGG GCTGCCAGCA GAGCCCACCA GGACTCCATG GAGATCCGCA 100
cDNA     51 CCTGCAGGGG GCTGCCAGCA GAGCCCACCA GGACTCCATG GAGATCCGCA 100
                  110        120        130        140        150
genome  101 GTGAGTGTCT AGCCCCCGCC CTGCCCCCAG GGGTCACAGG GGGGGCCTGG 150
cDNA    101 ---------- ---------- ---------- ---------- ---------- 150
                  160        170        180        190        200
genome  151 CCACTTCCTG GGCTGGGACA TCCTTGCTAA GCATCCGGA GTTGGGGTTT 200
cDNA    151 ---------- ---------- ---------- ---------- ---------- 200
```

FIG. 30A

```
                  210        220        230        240        250
genome   201 GGCCTCCTGT TCCCCAGACC CTTCCCCCAG GTGGCCCGGA CAGGTGCTCC 250
cDNA     201 ---------- ---------- ---------- ---------- ---------- 250

260        270        280        290        300
genome   251 CAAGGGTCCC GGCCCAGCAC ACGGGGGAGG GTCACTCCTC ACCACACGGG 300
cDNA     251 ---------- ---------- ---------- ---------- ---------- 300

310        320        330        340        350
genome   301 TGGCCTGGGG CTGAGTGCAT GTCACCCATG AGAACGGGGC TGTGAGGACA 350
cDNA     301 ---------- ---------- ---------- ---------- ---------- 350

360        370        380        390        400
genome   351 GGAAAGGAAG GGGAGTGTGT CCTGGTGTGA GTCTGAAATC CTACTTCCCA 400
cDNA     351 ---------- ---------- ---------- ---------- ---------- 400

410        420        430        440        450
genome   401 AAGCCACCCC AGCACCAGAA ATGGGGCTC CGGGTGAACC TCCTGTGCGG 450
cDNA     401 ---------- ---------- ---------- ---------- ---------- 450

460        470        480        490        500
genome   451 GTGGTGGTC CTGGCATGGC CTGGGGGACA GGCAGCCATG AGCTGAGCAC 500
cDNA     451 ---------- ---------- ---------- ---------- ---------- 500
```

FIG. 30B

```
                510        520        530        540        550
genome  501 ACACCCGGCC CGGCCACCAG GGCTGTATGC TCCAGGGCAC AGGCCTCCAT  550
cDNA    501 ---------- ---------- ---------- ---------- ----------  550

560        570        580        590        600
genome  551 GGGCTCTTCT CTCTCTTTCC AGCCCCGGAC ATCAACCCTG CCTGGTACGC  600
cDNA    551 ---------- ---------- ---CCCCGAC ATCAACCCTG CCTGGTACGC  600

610        620        630        640        650
genome  601 AGGCCGGTGGG ATCCGGCCCG TGGGCGCGCTT CGGCCGGGGA AGAGCTGCCC  650
cDNA    601 GGGGCCGGTGGG ATCCGGCCCG TGGGCCGCTT CGGCCGGGCGA AGAGCTGCCC  650

660        670        680        690        700
genome  651 TGGGGGACGG ACCCAGGCCT GGCCCCGAGCC GTGTGCCGGC CTGCTTCCGC  700
cDNA    651 CGGGGGACGG ACCCAGGCCT GGCCCCCGGCC GTGTGCCGGC CTGCTTCCGC  700

710        720        730        740        750
genome  701 CTGGAAGGCG GTGCTGAGCC CTCCCGAGCC CTCCCGGGGC GGCTGACGGC  750
cDNA    701 CTGGAAGGCG GGGCTGAGCC CTCCCGAGCC CTCCCGGGGC GGCTGACGGC  750

760        770        780        790        800
genome  751 CCAGCTGGTC CAGGAATAA. .......... .......... ..........  800
cDNA    751 CCAGCTGGTC CAGGAATAA. .......... .......... ..........  800
```

5'
```
         9           18           27           36           45          54
ATG AAG GCG GTG GGG GCC TGG CTC CTC TGC CTG CTG CTG GGC GCC CTG
 M   K   A   V   G   A   W   L   L   C   L   L   L   G   A   L 63          72           81           90           99          108
CAG GGG GCT GCC AGC AGA CAC CAG TCC CAC GAG ATC ACC CCC GAC
 Q   G   A   A   S   R   H   Q   S   H   E   I   T   P   D 117         126          135          144          153         162
ATC AAC CCT GCC TAC GCA GGC CGT CAG CAC ATG GAG ATC CGC ACC TTC GGC
 I   N   P   A   Y   A   G   R   Q   H   M   E   I   R   T   F   G 171         180          189          198          207         216
CGG AGA GCT GCC CTG CTG GGA GAC CCT AGG GGC CCC GTG CGG CGT GTG CCG
 R   R   A   A   L   L   G   D   P   R   G   P   V   R   R   V   P 225         234          243          252          261         270
GCC TGC TTC CGC GAA GGC GGT GCT GAG CCC TCC AGG CCC CGA GCC CTC CCG GGG CGG
 A   C   F   R   E   G   G   A   E   P   S   R   P   R   A   L   P   G   R 279         288          297
CTG ACG GCC CAG GTC CTG CAG GAA TAA 3'
 L   T   A   Q   V   L   Q   E   *
```

```
  1 GGCATCATCCAGGAAGACGAGCATGGCCCTGAAGACGTGGCTTCTGTGCTTGCTGCTG          59
  1                            MetAlaLeuLysThrTrpLeuLeuCysLeuLeuLeu     12

60 CTAAGCTTGGTCCTCCCAGGGGCTTCCAGCCGAGCCACCAGCACTCCATGAGACACAAGA        119
 13 LeuSerLeuValLeuProGlyAlaSerArgAlaHisGlnHisSerMetGluThrArg           32

120 ACCCCTGATATCAATCCTGCCTGGTACACGGGCCGGGATCAGGCCTGTGGGCCGCTTC          179
 33 ThrProAspIleAsnProAlaTrpTyrThrGlyArgGlyIleArgProValGlyArgPhe         52

180 GGCAGGAGAAGGGCAACCCCGAGGATGTCACTGGACTTGGCCAACTCAGTGCCTCCA           239
 53 GlyArgArgArgAlaThrProArgAspValThrGlyLeuGlyLeuSerCysLeuPro            72

240 CTGGATGGACGCACCAAGTTCTCTCAGCGTGGATAACACCCCAGCTCGAGAAGACAGTGC        299
 73 LeuAspGlyArgThrLysPheSerGlnArgGly***                                 83

300 TGCTGAGCCCAGCCCACACTCCCGTCCCCTGCAGACCCTCCTCCTACCCTCCTCCTCCT         359
 83                                                                     83

360 CTGCT                                                               364
 83                                                                     83
```

FIG. 32

FIG. 33

| FIG. 33A |
|----------|
| FIG. 33B |

FIG. 33A

```
bovine.aa                                    M  K  A  V  G  A  W  L  L
                                                           40           50
bovine.seq  -18 .............GT GGAATGAAGG CGGTGGGGGC CTGGCTCTC          32
rat.seq       1 GGCATCATCC AGGAGAGACGG AGCATG---G CCCTGAAGAC GTGGCTTCTG   50
                      10          20          30          40          50 bovine.aa        C  L  L  L     L  G  L  A  L  Q     G  A  A  S     R  A  H
                                 60                  70                  80
bovine.seq   33 TGCCTGCTGC  TGCTGGGGCT GGCCCTGCAG GGGGTGCCA GGGGTGCCA         82
rat.seq      51 TGCTTGCTGC  TGCTAAGCTT GGTCCTCCCA GGGGCTTCCA GCCGAGCCCA       100
                      60          70          80          90         100
                          R1 bovine.aa        Q  H  S     M  E  I  R     T  P  D     I  N  P     A  W  Y  A
                                            120                 140          150
bovine.seq   83  CCAGCACTCC ATGGAGATCC GCACCCCCGA CATCAACCCT GCCTGGTACG        132
rat.seq     101  CCAGCACTCC ATGGAGACAA GAACCCCTGA TATCAATCCT GCCTGGTACA        150
                       110         120         130         140
                                                                    R3 bovine.aa        G  R  G     I  R  P     V  G  R  F     G  R  R     R  A  A
                                            170                 190          200
bovine.seq  133  CGGGCCGTGG GATCCGGCCC GTGGGCCGGT TCGGCCGGGG AAGAGCTGCC        182
rat.seq     151  CGGGCCGGGG GATCAGGCCT GTGGGCCGCT TCGGCAGGAG AAGGGCAACC        200
                       160         170         180         190
                                                            R4
```

```
bovine.aa              P   G   D   G       P   R   P       G   P   R       R   V   P   A       C   F   R
                                   210                 220                 230                 240                 250
bovine.seq  183  CCGGGGGACG  GACCCAGGCC  TGGCCCCCGG  GGTGTGCCGG  CCTGCTTCCG                          232
rat.seq     201  CCGAGGGATG  TCACTGGACT  TGGC------  ----CAACTCA  GCTGCCTCCC                         250 bovine.aa              L   E   G       G   A   E   P       S   R   A       L   P   G   R       L   T   A
                                   260                 270                 280                 290                 300
bovine.seq  233  CCTGGAAGGC  GGGGCTGAGC  CCTCCCGAGC  CCTCCCGGGG  CGGCTGACGG                          282
rat.seq     251  ACTGGATGGA  CGCACCAAGT  TCTCTCAGCG  CAAGCCCACA  CCCAGCTCGA                          300 bovine.aa              Q   L   V   Q   E   *
                                   310                 320                 330                 340                 350
bovine.seq  283  CCCAGCTGGT  CCAGGAATAA  CAGGGGGAGC  CTGCCCCCCA  CCCCTCTCC                           332
rat.seq     301  GAAGACAGTG  CTGCTGAGCC  CAAGCCCACA  CTCCCTGTCC  CCCTCAGACC                          350

360                 370                 380                 390                 400
bovine.seq  333  TCCACCAGCC  ACCTTCCCTC  CAGTCCTAAT  AAAAGCCAGCT  GGCTTGTT...                        382
rat.seq     351  CTCCCTCTACC  CTCCCTCTCC  TCTGCT....                                                 400
```

FIG. 33B

```
1    GGCCTCCTCGAGGAGCCAAGGGATGAAGGTGCTGAGGGCCTGGCTCCTGTGCCTGCTG      59
                              MetLysValLeuArgAlaTrpLeuLeuCysLeuLeu    12

60   ATGCTGGGCCTGCCCTGCCGGGAGCTGCAAGTCGTACCCATCGGCACTCCATGGAGATC    119
 13  MetLeuGlyLeuAlaLeuArgGlyAlaAlaSerArgThrHisArgHisSerMetGluIle    32

120  CGCACCCCTGACATCAATCCTGCCTGTACGCCAGTCGCGGGATCAGCCTGTGGGCCGC     179
 33  ArgThrProAspIleAsnProAlaTrpTyrAlaSerArgGlyIleArgProValGlyArg    52

180  TTCGGTCGGAGGAGGCAACCCTGGGACGTCCCAAGCCTGGACCCCCGGCTG           239
 53  PheGlyArgArgArgGlnProTrpLeuArgProLysProGlyLeuArgProArgLeu     72

240  ACCTGCTTCCCCCTGGAAGGCGGTGCTATGTCTTCCCAGGATGGCTGACAGCCAGCTTGT  299
 73  ThrCysPheProLeuGluGlyGlyAlaMetSerSerGlnAspGly***               87

300  CAAGAAACTCACTCTGGAGCCCTCCCCCAACCCCTCTCCTTCGGCTCCTTTC          359
                                                                    87

|  |  | 10 | 20 | 30 | 40 | 50 |
|---|---|---|---|---|---|---|
| bovine.aa | 1 | MKAVGAWLLC | LLLLGLALQG | AASRAHQHSM | EIRTPDINPA | WYAGRGIRPV | 50 |
| rat.aa | 1 | M-ALKTWLLC | LLLLSLVLPG | ASSRAHQHSM | EIRTPDINPA | WYTGRGIRPV | 50 |
| human.aa | 1 | MKVLRAWLLC | LLMLGLAIRG | AASRTHRHSM | EIRTPDINPA | WYASRGIRPV | 50 |

|  |  | 60 | 70 | 80 | 90 | 100 |
|---|---|---|---|---|---|---|
| bovine.aa | 51 | GRFGRRRAAP | GDGPRPGPRR | VPACFRLEGG | AEPSRALPGR | LTAQLVQE*. | 100 |
| rat.aa | 51 | GRFGRRRATP | RDVTGLG--- | QLSCLPLDGR | TKFSQRG*.. | .......... | 100 |
| human.aa | 51 | GRFGRRRAIL | GDVPKPGLRP | RLICFPLEGG | AMSSQDG*.. | .......... | 100 |

FIG. 35 direct blood pressure mean blood pressure

| FIG. 52A |
| FIG. 52B |
| FIG. 52C |
| FIG. 52D |
| FIG. 52E |

```
     9            18            27            36            45            54
5' ATG ACC TCA CTG CCC CCT GGA ACC ACT GGG GAC CCC GAT TTG TTT TCT GGG CCG
   --- --- --- --- --- --- --- --- --- --- --- --- --- --- --- --- --- ---
   Met Thr Ser Leu Pro Pro Gly Thr Thr Gly Asp Pro Asp Leu Phe Ser Gly Pro 63           72            81            90            89           108
   TCG CCA GCC GGC TCC ACT CCA GCC AAC CAG AGT GCA GAG GCT TCA GAG AGC AAT
   --- --- --- --- --- --- --- --- --- --- --- --- --- --- --- --- --- ---
   Ser Pro Ala Gly Ser Thr Pro Ala Asn Gln Ser Ala Glu Ala Ser Glu Ser Asn
```

```
         117         126         135         144         153         162
GTG TCT GCG ACG GTT CCC AGA GCT GCA GTC ACG CCG TTC CAG AGC CTG CAA
 |   |   |   |   |   |   |   |   |   |   |   |   |   |   |   |   |
Val Ser Ala Thr Val Pro Arg Ala Ala Val Thr Pro Phe Gln Ser Leu Gln 171         180         189         198         207         216
CTA GTG CAC CAG CTG AAG GCA CTG ATC GTG ATG TAC AGC GTG GTG GTG GTC
 |   |   |   |   |   |   |   |   |   |   |   |   |   |   |   |   |
Leu Val His Gln Leu Lys Ala Leu Ile Val Met Tyr Ser Val Val Val Val 225         234         243         252         261         270
GTG GGT CTG GTG AAC TGC CTT GTG CTG ATC GCG CGC GTG CGC CGC CGG
 |   |   |   |   |   |   |   |   |   |   |   |   |   |   |   |
Val Gly Leu Val Asn Cys Leu Val Leu Ile Ala Arg Val Arg Arg Arg 279         288         297         306         315         324
CTG CAC AAC GTG ACC AAC TTC CTC ATC GGC AAC CTG GCC TTG TCC GAT GTG CTC
 |   |   |   |   |   |   |   |   |   |   |   |   |   |   |   |   |   |
Leu His Asn Val Thr Asn Phe Leu Ile Gly Asn Leu Ala Leu Ser Asp Val Leu 333         342         351         360         369         378
ATG TGT GCC GCC TGT GTG CCT CTC ACG CTG GCC TAC GCC TTT GAA CCT CGT GGC
 |   |   |   |   |   |   |   |   |   |   |   |   |   |   |   |   |   |
Met Cys Ala Ala Cys Val Pro Leu Thr Leu Ala Tyr Ala Phe Glu Pro Arg Gly
```

FIG. 52B

```
      387  396  405  414  423  432
TGG GTG TTC GGT GGA CTG TGC CAC CTT GTT TTC CTG CAG CCG GTC ACC
--- --- --- --- --- --- --- --- --- --- --- --- --- --- --- ---
Trp Val Phe Gly Gly Leu Cys His Leu Val Phe Phe Leu Gln Pro Val Thr 441  450  459  468  477  486
GTC TAC GTA TCG GTG TTC ACA CTC ACC ACA ATC GCT GTG GAC CGC TAT GTG GTT
--- --- --- --- --- --- --- --- --- --- --- --- --- --- --- --- --- ---
Val Tyr Val Ser Val Phe Thr Leu Thr Thr Ile Ala Val Asp Arg Tyr Val Val 495  504  513  522  531  540
CTG GTG CAC CCG CTA CGT CGG CGC ATT TCA CTG AAG CTC AGC GCC TAC GCT GTG
--- --- --- --- --- --- --- --- --- --- --- --- --- --- --- --- --- ---
Leu Val His Pro Leu Arg Arg Arg Ile Ser Leu Lys Leu Ser Ala Tyr Ala Val 549  558  567  576  585  594
CTG ATC TGG GCT CTA TCT GCA GTG CTG GCG CTG CCG GCC GCG GTG CAC ACC
--- --- --- --- --- --- --- --- --- --- --- --- --- --- --- --- ---
Leu Ile Trp Ala Leu Ser Ala Val Leu Ala Leu Pro Ala Ala Val His Thr 603  612  621  630  639  648
TAC CAT GTA GAG CTC AAG CCC CAC GAC GTG CGC CTC TGC GAG TTC TGG GGT
--- --- --- --- --- --- --- --- --- --- --- --- --- --- --- --- ---
Tyr His Val Glu Leu Lys Pro His Asp Val Arg Leu Cys Glu Phe Trp Gly
```

FIG. 52C

```
        657         666         675         684         693         702
TCG CAG GAG CGC CAG CGA CAG ATC TAT GCC TGG GGG CTG CTG GGC ACC TAT
--- --- --- --- --- --- --- --- --- --- --- --- --- --- --- --- ---
Ser Gln Glu Arg Gln Arg Gln Ile Tyr Ala Trp Gly Leu Leu Gly Thr Tyr 711         720         729         738         747         756
TTG CTC CCC CTG CTG GCC ATT CTC CTG TCT TAC GTC CGG GTG TCG GTG AAG TTG
--- --- --- --- --- --- --- --- --- --- --- --- --- --- --- --- --- ---
Leu Leu Pro Leu Leu Ala Ile Leu Leu Ser Tyr Val Arg Val Ser Val Lys Leu 765         774         783         792         801         810
CGG AAC CGC GTG GTG CCT GGC AGC GTG ACC CAG AGC CAG GCT GAC TGG GAC CGA
--- --- --- --- --- --- --- --- --- --- --- --- --- --- --- --- --- ---
Arg Asn Arg Val Val Pro Gly Ser Val Thr Gln Ser Gln Ala Asp Trp Asp Arg 819         828         837         846         855         864
GCG CGT CGC CGT CGC ACT TTC TGC CTG GTG GTG GTG GTG GTC GTG TTC GCG
--- --- --- --- --- --- --- --- --- --- --- --- --- --- --- --- ---
Ala Arg Arg Arg Arg Thr Phe Cys Leu Val Val Val Val Val Val Phe Ala 873         882         891         900         909         918
GTC TGC TGG CTG CCT CTG CAC ATT TTC AAC CTG CTG CGG GAC CTG GAC CCG CGT
--- --- --- --- --- --- --- --- --- --- --- --- --- --- --- --- --- ---
Val Cys Trp Leu Pro Leu His Ile Phe Asn Leu Leu Arg Asp Leu Asp Pro Arg
```

FIG. 52D

```
      927            936            945            954            963            972
GCC ATC GAC CCC TAC GCC TTC GGG CTG GTG CAG CTC TGC CAC TGG CTT GCC
 --- --- --- --- --- --- --- --- --- --- --- --- --- --- --- --- ---
Ala Ile Asp Pro Tyr Ala Phe Gly Leu Val Gln Leu Cys His Trp Leu Ala 981            990            999           1008           1017           1026
ATG AGC TCC GCC TGC TAC AAC CCC TTC ATC TAT GCG TCG CTG CAC GAC AGC TTC
 --- --- --- --- --- --- --- --- --- --- --- --- --- --- --- --- --- ---
Met Ser Ser Ala Cys Tyr Asn Pro Phe Ile Tyr Ala Ser Leu His Asp Ser Phe 1035           1044           1053           1062           1071           1080
CGA GAG GAG CTA CGC AAG ATG CTT CTG TCT TGG CCC CGC AAG ATC GTG CCT CAT
 --- --- --- --- --- --- --- --- --- --- --- --- --- --- --- --- --- ---
Arg Glu Glu Leu Arg Lys Met Leu Leu Ser Trp Pro Arg Lys Ile Val Pro His 1089           1098           1107           1116
GGC CAG AAT ATG ACC GTC AGT GTG GTC ATC TGA TGA                    1'
 --- --- --- --- --- --- --- --- --- --- --- ---
Gly Gln Asn Met Thr Val Ser Val Val Ile
```

FIG. 52E

POLYPEPTIDES, THEIR PRODUCTION AND USE

This application is a continuation of U.S. application Ser. No. 08/776,971 filed Feb. 7, 1997 now issued as U.S. Pat. No. 6,228,984, which was the National Stage Application under §371 of PCT/JP96/03821 which was filed Dec. 28, 1996.

TECHNICAL FIELD

The present invention relates to a novel ligand polypeptide for the G protein-coupled receptor protein and a DNA comprising a DNA encoding the ligand polypeptide.

BACKGROUND

Many hormones and neurotransmitters mediate Of biological functions through specific receptors present on the cell membrane. Many of these receptors engage themselves in the intracellular transduction of signals through activation of the coupled guanine nucleotide-binding protein (hereinafter sometimes referred to briefly as G protein) and have the common structure comprising 7 transmembrane domains. Therefore, these receptors are collectively referred to as G protein-coupled receptor or 7-transmembrane receptor.

One of the pathways to modulate biological functions mediated by such hormones or neurotransmitters through G protein-coupled receptors is the hypothalamo-pituitary system. Thus, the secretion of pituitary hormone from the hypophysis is controlled by hypothalamic hormones (pituitatropic releasing factor) and the functions of the target cells or organs are regulated through the pituitary hormones released into the circulation. This pathway carries out functional modulations of importance to the living body, such as homeostasis and regulation of the reproduction, development, metabolism and growth of individuals. The secretion of pituitary hormones is controlled by a positive feedback or a negative feedback mechanism involving hypothalamic hormone and the peripheral hormone secreted from the target endocrine gland. The various receptor proteins present in the hypophysis are playing a central role in the regulation of the hypothalamus-pituitary system.

Meanwhile, it is known that these hormones and factors as well as their receptors are not localized in the hypothalamus-pituitary system but are broadly distributed in the brain. Therefore, it is suspected that, in the central nervous system, this substance called hypothalamus hormone is functioning as a neurotransmitter or a neuromodulator. Moreover, the substance is distributed in peripheral tissues as well and thought to be playing important roles in the respective tissue.

The pancreas is playing a crucial role in the carbohydrate metabolism by secreting glucagon and insulin as well as digestive juice. While insulin is secreted from the pancreatic β cells, its secretion is mainly stimulated by glucose. However, it is known that β cells have a variety of receptors and the secretion of insulin is controlled by a number of factors in addition to glucose as well as peptide hormones, e.g. galanine, somatostatin, gastric inhibitory polypeptide, glucagon, amyrin, etc.; sugars, e.g. mannose etc.; amino acids, and neurotransmitters, among others.

The means only heretofore available for identifying ligands for said G protein-coupled receptor proteins is estimation from the homology in primary structure of G protein-coupled receptor proteins.

Recently, investigation for novel opioid peptides by introducing a cDNA coding for a receptor protein which a ligand is unknown, i.e. an orphan G protein-coupled receptor protein, into animal cells have been reported (Reinsheid, R. K. et al., Science, 270, 792–35 794, 1995, Menular, J.-C., et al., Nature 377, 532–535, 1995). However, in view of similarities to known G protein-coupled receptor proteins and tissue distributions, it could be easily anticipated in these cases that the ligand would be belonging to the family of opioid peptides. The history of research and development in the realm of substances acting on the living body through the opioid receptor dates back to many years ago and various antagonists and agonists had been developed. Therefore, among the compounds artificially synthesized, an agonist of the receptor was picked out and, using it as a probe, expression of the receptor in the receptor cDNA-transfected cells was verified. Then, a search was made for an activator of the intracellular signal transduction which was similar to the agonist, the activator so found was purified, and the structure of the ligand was determined. However, when the homology of an orphan receptor to known G protein-coupled receptor proteins is low, it was very difficult to predict its ligand.

Ligands for orphan G protein-coupled receptors expressed in the hypophysis, central nervous system, and pancreatic β cells are considered to be useful for developing medicines, but their structures and functions have not been elucidated as yet.

DISCLOSURE OF INVENTION

Employing a cell in which a cDNA coding for orphan G protein-coupled receptor protein hare been expressed by a suitable means and using measurement of a specific cell stimulation activity exemplified by a signal transduction activity as an indicator, the inventors of the present invention succeeded in screening a polypeptide which said receptor protein recognizes as a ligand.

Furthermore, the inventors found that a compound can be screened which is capable of changing the binding activity of this ligand which is an activating factor to said receptor protein.

The present invention, therefore, relates to (1) A polypeptide which comprises an amino acid sequence represented by SEQ ID NO:73 or its substantial equivalent thereto, or its amide or ester, or a salt thereof.

(2) The polypeptide as described in (1) above, which comprises the amino acid sequence represented by SEQ ID NO:3, SEC ID NO:4, SEQ ID NO:5, SEQ ID NO:6, SEQ ID NO:7, SEQ ID NO:8, SEQ ID NO:9, SEQ ID NO:10, SEQ ID NO:47, SEQ ID NO:48, SEQ ID NO:49, SEQ ID NO:50, SEQ ID NO:51, SEQ ID NO:52, SEQ ID NO:61, SEQ ID NO:62, SEQ ID NO:63, SEQ ID NO:64, SEQ ID NO:65, or SEQ ID NO:66.

(3) The polypeptide as described in (1) above, which comprises the amino acid sequence represented by SEQ ID NO:1, SEQ ID NO:44, SEQ ID NO:45, or SEQ ID NO:59.

(4) A partial peptide of the polypeptide as described in (1) above its amide or ester, or a salt thereof.

(5) A DNA which comprises a DNA having a nucleotide sequence coding for the polypeptide as described in (1) above or the partial peptide as described in (4) above.

(6) The DNA as described in (5) above which comprises a nucleotide sequence represented by SEQ ID NO:2, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:18, SEQ ID NO:46, SEQ ID NO:53, SEQ ID NO:54, SEQ ID NO:55, SEQ ID NO:56, SEQ ID NO:57, SEQ ID NO:58, SEQ ID NO:60, SEQ ID NO:67, SEQ ID NO:68, SEQ ID NO:69, SEQ ID NO:70, SEQ ID NO:71, or SEQ ID NO:72.

(7) A recombinant vector comprising the DNA as described in (5) above.

(8) A transformant carrying the DNA as described in (5) above or the recombinant vector as described (7) above.

(9) A method for producing the polypeptide as described in (1) above or the partial peptide as described in (4) above, which comprises culturing the transformant as described in (8) above.

(10) A pharmaceutical composition containing the polypeptide, its amide or ester as described in (1) above, or a pharmaceutically acceptable salt thereof.

(11) A pharmaceutical composition containing the partial peptide peptide, its amide or ester as described in (4) above, or a pharmaceutically acceptable salt thereof.

(12) A pharmaceutical composition containing the DNA as described in (5) above.

(13) The pharmaceutical composition as described in (10), (11), or (12) above, which is a pituitary function modulator.

(14) The pharmaceutical composition as described in (10), (11), or (12) above, which is a central nervous system function modulator.

(15) The pharmaceutical composition as described in (10), (11), or (12) above, which is a pancreatic function modulator.

(16) An antibody against the polypeptide as described in (1) above or against the partial peptide as described in (4) above.

(17) A screening method for a compound capable of changing the binding activity of the polypeptide as described in (1) above or the partial peptide as described in (4) above, with a receptor protein comprising an amino acid sequence represented by SEQ ID NO:21 or its partial, peptide or its substantial equivalent thereto, or a salt thereof, which comprises making a comparison between: (i) at lease one case where said polypeptide as described in (1) above or the partial peptide as described in (4) above is contacted with a receptor protein comprising an amino acid sequence represented by SEQ ID:21 or its partial peptide or its substantial equivalent thereto, or a salt thereof, and (ii) at least one case where said polypeptide as described in (1) above or the partial peptide as described in (4) above together with a sample to be tested in contacted with protein comprising an amino acid sequence represented by SEQ ID NO:21 or its partial peptide or its substantial equivalent thereto, or a salt thereof.

(18) A kit for screening for a compound capable of changing the binding activity of the polypeptide as described in (1) above or the partial peptide as described in (4) above with a receptor protein comprising an amino acid sequence represented by SEQ ID NO:21 or its partial peptide or its substantial equivalent thereto, or a salt thereof.

(19) A compound capable of changing the binding activity of the polypeptide as described in (1) or the partial peptide as described in (4) with a receptor protein comprising an amino acid sequence represented by SEQ ID NO:21 or its partial peptide or its substantial equivalent thereto, or a salt thereof.

(20) A G protein-coupled receptor protein which recognizes the polypeptide as described in (1) above or the partial peptide as described in (4) above as a ligand, or a salt thereof.

The present invention further provides:

(21) the polypeptide as described in (1) above, or its amide or ester, or a salt thereof, which comprises an amino acid sequence selected from the group consisting of an amino acid sequence of SEQ ID NO:73, amino acid sequences wherein 1 to 15 amino acid residues, preferably 1 to 10 amino acid residues, more preferably 1 to 5 amino acid residues are deleted from the amino acid sequence of SEQ ID NO:73, amino acid sequences wherein 1 to 80 amino acid residues, preferably 1 to 50 amino acid residues, more preferably 1 to 10 amino acid residues are added to the amino acid sequence of SEQ ID NO:73, and amino acid sequences wherein 1 to 15 amino acid residues, preferably 1 to 10 amino acid residues, more preferably 1 to 5 amino acid resides in the amino acid sequence of SEQ ID NO:73 are substituted with one or more other amino acid residues;

(22) the polypeptide as described in (1) above, which comprises an amino acid sequence wherein the peptide of SEQ ID NO:74 is added to the N-terminus of the polypeptide comprising the amino acid sequence of SEQ ID NO:73;

(23) the polypeptide as described in (1) above, which in derived from bovine, rat or human; and

(24) the pharmaceutical composition described in (10), (11) or (12) above, which is a therapeutic and/or prophylactic agent for dementia, depression (melancholia), hyperkinetic (microencephalo-pathy) syndrome, disturbance of consciousness, anxiety syndrome, schizophrenia, horror, growth hormone secretory disease, hyperphagia, polyphagia, hypercholesterolemia, hyperglyceridemia, hyperlipemia, hyporprolactinemia, diabetes, cancer, pancreatitis, renal disease, Turner's syndrome, neurosis, rheumatoid arthritis, spinal injury, transient brain ischemia, amyotrophic lateral sclerosis, acute myocardial infarction, spinocerebellar degeneration, bone fracture, trauma, atopic dermatitis, osteoporosis, asthma, epilepsy, infertility and/or oligogalactia.

Referring to the G protein-coupled receptor protein for the ligand polypeptide in accordance with the present invention, the invention specifically provides:

(25) the G protein-coupled receptor protein described in (20) or a salt thereof, which comprises an amino acid sequence represented by SEQ ID NO:19 or its substantial equivalent thereto or/and an amino acid sequence represented by SEQ ID NO:20 or its substantial equivalene thereto;

(26) the G protein-coupled receptor protein described in (25) above or a salt thereof, which comprises an amino acid sequence represented by SEQ ID NO:21 or its substantial equivalent thereto;

(27) the G protein-coupled receptor protein described in (25) above or a salt thereof, which comprises an amino acid sequence represented by SEQ ID NO:22 or its substantial equivalent thereto;

(28) the G protein-coupled receptor protein described in (25) above or a salt thereof, which comprises an amino acid sequence represented by SEQ ID NO:23 or its substantial equivalent thereto;

(29) a partial peptide of any of the G protein-coupled receptor proteins described in (25)–(28) above or a salt thereof;

(30) a DNA which comprises a DNA having a nucleotide sequence coding for the G protein-coupled receptor protein described in (25) above;

(31) a DNA which comprises a DNA having a nucleotide sequence coding for the G protein-coupled receptor protein described in (26) above;

(32) a DNA which comprises a DNA having a nucleotide sequence coding for the G protein-coupled receptor protein described in (27) above;
(33) a DNA which comprises a DNA having a nucleotide sequence coding for the G protein-coupled receptor protein described in (28) above;
(34) the DNA described in (30) above, which comprises the nucleotide sequence of SEQ ID NO:24 or the nucleotide sequence of SEQ ID NO:25;
(35) the DNA described in (31) above, which comprises the nucleotide sequence of SEQ ID NO:26;
(36) the DNA described in (32) above, which comprises the nucleotide sequence of SEQ ID NO:27;
(37) the DNA described in (33) above, which comprises the nucleotide sequence of SEQ ID NO:28;
(38) a recombinant vector comprising any of the DNAs described in (30)–(33) above;
(39) a transformant carrying the recombinant vector described in (38) above;
(40) a method for producing the G protein-coupled receptor protein described in (28) above or a salt thereof, which comprises culturing the transformant of (39) to produce said G protein-coupled receptor protein on the cell membrane of the transformant;
(41) an antibody to any of the G protein-coupled receptor protein described in (25)–(28) above or a salt thereof, or the partial peptide described in (29) above or a salt thereof.

To be further specific, the G protein-coupled receptor protein relates to:
(42) the G protein-coupled receptor protein described in (25) above or a salt thereof, wherein the protein comprises (i) an amino acid sequence selected from the group consisting of an amino acid sequence of SEQ ID NO:19, amino acid sequences wherein 1 to 30 amino acid residues, preferably 1 to 10 amino acid residues are deleted from the amino acid sequence of SEQ ID NO:19, amino acid sequences wherein 1 to 30 amino acid residues, preferably 1 to 10 amino acid residues are added to the amino acid sequence of SEQ ID NO:19, and amino acid sequences wherein 1 to 30 amino acid residues, preferably 1 to 10 amino acid residues in the amino acid sequence of SEQ ID NO:19 are substituted with one or more than amino acid residues and/or (ii) an amino acid sequence selected from the group consisting of an amino acid sequence of SEQ ID NO:20, amino acid sequences wherein 1 to 30 amino acid residues, preferably 1 to 10 amino acid residues are deleted from the amino acid sequence of SEQ ID NO:20, amino acid sequences wherein 1 to 30 amino acid residues, preferably 1 to 10 amino acid residues are, added to the amino acid sequence of SEQ ID NO:20, and amino acid sequences wherein 1 to 30 amino acid residues, preferably 1 to 10 amino acid residues in the amino acid sequence of SEQ ID NO:20 are substituted with one or more other amino acid residues;
(43) the G protein-coupled receptor protein described in (26) above or a salt thereof, wherein the protein comprises an amino acid sequence selected from the group consisting of an amino acid sequence of SEQ ID NO:21, amino acid sequences wherein 1 to 30 amino acid residues, preferably 1 to 10 amino acid residues are deleted from the amino acid sequence of SEQ ID NO:21, amino acid sequences wherein 1 to 30 amino acid residues, preferably 1 to 10 amino acid residues are added to the amino acid sequence of SEQ ID NO:21, and amino acid sequences wherein 1 to 30 amino acid residues, preferably 1 to 10 amino acid residues in the amino acid sequence of SEQ ID NO:21 are substituted with one or more other amino acid residues;
(44) the G protein-coupled receptor protein described in (27) above or a salt thereof wherein the protein comprises an amino acid sequence selected from the group consisting of an amino acid sequence of SEQ ID NO:22, amino acid sequences wherein 1 to 30 amino acid residues, preferably 1 to 10 amino acid residues are deleted from the amino acid sequence of SEQ ID NO:22, amino acid sequences wherein 1 to 30 amino acid residues, preferably 1 to 10 amino acid residues are added to the amino acid sequence of SEQ ID NO:22, and amino acid sequences wherein 1 to 30 amino acid residues, preferably 1 to 10 amino acid residues in the amino acid sequence of SEQ ID NO:22 are substituted with one or more other amino acid residues;
(45) the G protein-coupled receptor protein described in (28) above or a salt thereof, wherein the protein comprises an amino acid sequence selected from the group consisting of an amino acid sequence of SEQ ID NO:23, amino acid sequences wherein 1 to 30 amino acid residues, preferably 1 to 10 amino acid residues are deleted from the amino acid sequence of SEQ ID NO:23, amino acid sequences wherein 1 to 30 amino acid residues, preferably 1 to 10 amino acid residues are added to the amino acid sequence of SEQ ID NO:23, and amino acid sequences wherein 1 to 30 amino acid residues, preferably 1 to 10 amino acid residues in the amino acid sequence of SEQ ID NO:23 are substituted with one or more other amino acid residues.

As used herein the term "substantial equivalent(s)" means that the activity of the protein, e.g., nature of the binding activity of the ligand and the receptor and physical characteristics are substantially the same. Substitutions, deletions or insertions of amino acids often do not produce radical changes in the physical and chemical characteristics of a polypeptide, in which case polypeptides containing the substitution, deletion, or insertion would be considered to be substantially equivalent to polypeptides lacking the substitution, deletion, or insertion. Substantially equivalent substitutes for an amino acid within the sequence may be selected from other members of the class to which the amino acid belongs. The non-polar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

BRIEF DESCRIPTION OF THE DRAWINGS

FIG. 1 (SEQ ID NOS:125–126) shows the nucleotide sequence of the human pituitary-derived G protein-coupled receptor protein cDNA fragment harbored in cDNA clone p19P2 isolated by PCR using human pituitary-derived cDNA and the amino acid encoded by the nucleotide sequence. The primer used for sequencing was −21M13. The underscored region correspond to the synthetic primer.

FIG. 2 (SEQ ID NOS:127–128) shows the nucleotide sequence of the human pituitary-derived G protein-coupled receptor protein cDNA fragment harbored in cDNA clone p19P2 isolated by PCR using human pituitary-derived cDNA and the amino acid sequence encoded thereby. The primer used for sequencing was M13RV-N (Takara). The underscored region correspond to the synthetic primer.

FIG. 5 (SEQ ID NOS:129–130) is a diagram comparing the partial amino acid sequence of the protein encoded by the human pituitary-derived G protein-coupled receptor protein cDNA fragment harbored in p19P2 as shown in FIGS. 1 and 2 with the known G protein-coupled receptor protein S12863. The shadowed region represents the region of agreement. The 1 to 9 amino acid sequence of p19P2 corresponds to the 1 to 99 amine acid sequence of FIG. 1 and the 156 to 230 amino acid sequence corresponds to the 1 to 68 amino acid sequence of FIG. 2.

FIG. 6 (SEQ ID NOS:99–100) shows the nucleotide sequence of the MIN6-derived G protein-coupled receptor protein cDNA fragment based on the nucleotide sequences of the MIN6-derived G protein-coupled receptor protein cDNA fragments harbored in the cDNA clones pG3-2 and pG1-10 isolated by PCR using MIN6-derived cDNA and the amino acid sequence encoded by the nucleotide sequence. The underscored region correspond to the synthetic primer.

FIG. 7 (SEQ ID NOS:101–102) is a diagram comparing the partial amino acid sequence encoded by pG3-2/pG1-10 of the MN6-derived G protein-coupled receptor protein shown in FIG. 6 with the partial amino acid sequence of the protein encoded by p19P2 shown in FIGS. 1 and 2. The shadowed region corresponds to the region of agreement. The 1 to 99 amino acid sequence of the protein encoded by p19P2 corresponds to the 1 to 99 amino acid sequence of FIG. 1 and the 156 to 223 amino acid sequence corresponds to the 1 to 68 amino acid sequence of FIG. 2. The 1 to 223 amino acid sequence of the protein encoded by pG3-2/pG1-10 corresponds to the 1 to 223 amino acid sequence of FIG. 6.

FIG. 9 (SEQ ID NOS: 103–104) shows the entire nucleotide sequence of the human pituitary-derived G protein-coupled receptor protein cDNA harbored in the cDNA clone phGR3 isolated from a human pituitary-derived cDNA library by the plaque hybridization method using the DNA fragment inserted in p19P2 as a probe and the amino acid sequence encoded by the nucleotide sequence.

FIG. 12 (SEQ ID NOS:105–106) shows the nucleotide sequence of the MIN6-derived G protein-coupled receptor protein cDNA fragment harbored in the cDNA clone p5S38 isolated by PCR using MIN6-derived cDNA Ad the amino acid sequence encoded by the nucleotide sequence. The underscored region correspond to the synthetic primer.

FIG. 13 (SEQ ID NOS: 107–108) shows a diagram comparing the partial amino acid sequence of MIN6-derived G protein-coupled receptor protein encoded by p5S38 shown in FIG. 12 with the partial amino acid sequence of G protein-coupled receptor protein encoded by the cDNA fragment harbored in p19P2 as shown in FIGS. 1 and 2 and the partial amino acid sequence of G protein-coupled receptor protein encoded by the nucleotide sequence generated from the nucleotide sequences of cDNA fragments contained in pG3-2 and pG1-10 shown in FIG. 6. The shadowed region represents the sequence region of agreement. The 1 to 144 amino acid sequence of the protein encoded by p5S38 corresponds to the 1 to 144 amino acid sequence of FIG. 12, the 1 to 99 amino acid sequence of the protein encoded by p19P2 corresponds to the 1 to 99 amino acid sequence of FIG. 1 and the 156 to 223 amino acid sequence corresponds to 1 to 68 amino acid sequence of FIG. 2. The 1 to 223 amino acid sequence of the protein encoded by pG3-21pG1-10 corresponds to the 1 to 223 amino acid sequence of FIG. 6.

FIG. 22 (SEQ ID NOS:110–111) shows the nucleotide sequence of bovine hypothalamus ligand polypeptide cDNA fragment as derived from the nucleotide sequence of the bovine hypothalamus-derived ligand polypeptide cDNA fragment which specifically promotes release of arachidonic acid metabolites from CHO-19P2 cells as harbored in a cDNA clone isolated by PCR using bovine hypothalamus-derived cDNA and the amino acid sequence encoded by said nucleotide sequence. The region indicated by the arrowmark corresponds to the synthetic primer.

FIG. 23 (SEQ ID NOS:112–113) shows the nucleotide sequence of the bovine hypothalamus-derived ligand polypeptide cDNA fragment generated according to the nucleotide sequence of the bovine hypothalamus-derived ligand polypeptide cDNA fragment which specifically promotes release of arachidonic acid metabolites from CHO-19P2 cells as harbored in a cDNA clone isolated by PCR using bovine hypothalamus-derived cDNA and the amino acid sequence encoded by said nucleotide sequence. The region indicated by the arrowmark corresponds to the synthetic primer.

FIG. 24 (SEQ ID NOS:114–117) shows the amino acid sequences (a) and (b) of the bovine hypothalamus-derived ligand polypeptides which specifically promote release of arachidonic acid metabolites from CHO19P2 cells and the cDNA sequence coding for the full coding region of the ligand poly-peptides defined by SEQ ID NO:1 and SEQ ID NO:44.

FIG. 29 (SEQ ID NO:118) shows the nucleotide sequence around the coding region as decoded from bovine genomic DNA. The 1st to 3rd bases (ATG) correspond to the translation start codon and the 767th to 769th bases (TAA) correspond to the translation end codon.

FIG. 30 (SEQ ID NO:119–120) shows a comparison between the nucleotide sequence (genome) around the coding region as deduced from bovine genomic DNA and the nucleotide sequence (cDNA) of bovine cDNA cloned by PCR. The sequence region of agreement is indicated by shading. As to the 101st to 572nd region, there is no corresponding region in the nucleotide sequence of cDNA, indicating that it is an intron.

FIG. 31 (SEQ ID NOS:121–122) shows the translation of the amino acid sequence encoded after elimination of the intron from the nucleotide sequence around the coding region as decoded from bovine genomic DNA.

FIG. 32 (SEQ ID NOS:123–124) shows the full-length amino acid sequence and the cDNA sequence coding for the full coding region of rat ligand polypeptide.

FIG. 33 (SEQ ID NOS:131–135) shows amino acid sequence of bovine ligand polypeptide and the nucleotide sequences of DNAs coding for bovine polypeptide and rat polypeptide. The arrowmark indicates the region corresponding to the synthetic primer.

FIG. 34 (SEQ ID NOS:134–135) shows the full-length amino acid sequence and the sequence of cDNA coding for the full coding region of human ligand polypeptide.

FIG. 35 (SEQ ID NO:136–138) shows a comparison of the amino acid sequences in the translation region of bovine ligand polypeptide, rat ligand polypeptide, and human ligand polypeptide.

In FIG. 45, the single star mark asterisk shows p<0.05 and the double star marks asterisks shows p<0.01.

The ligand polypeptide or PBS was administered into the third ventricle. At 10 min later, 5 µg/kg of GHRH was administered intravenously to the rat conscious. GH levels were measured just prior to intraventricular administration (time 0) and 10, 20, 30, 40, and 60 min after the intravenous injection of GHRH.

Figure 49:
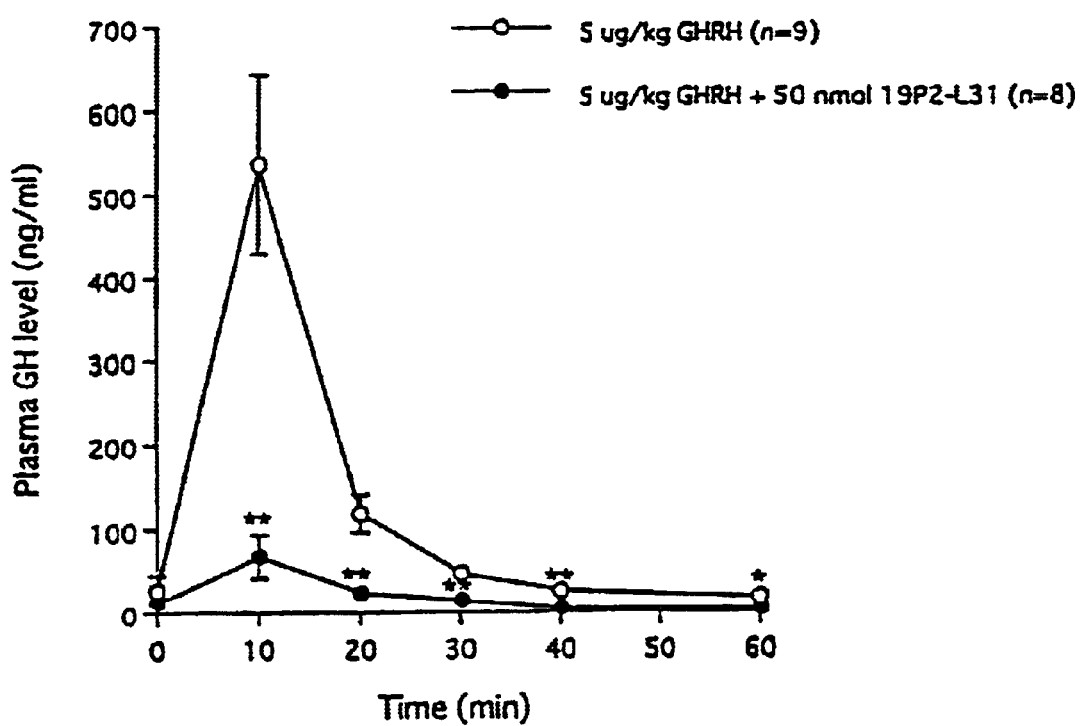
FIG. 49 shows the changes of secretion of GH in plasma by administration of 50 nmol of ligand polypeptide into the third ventricle in freely moving rats.

In FIG. 49, the single star mark asterisk shows p<0.05 and the double star marks asterisks show p<0.01.

Figure 50:
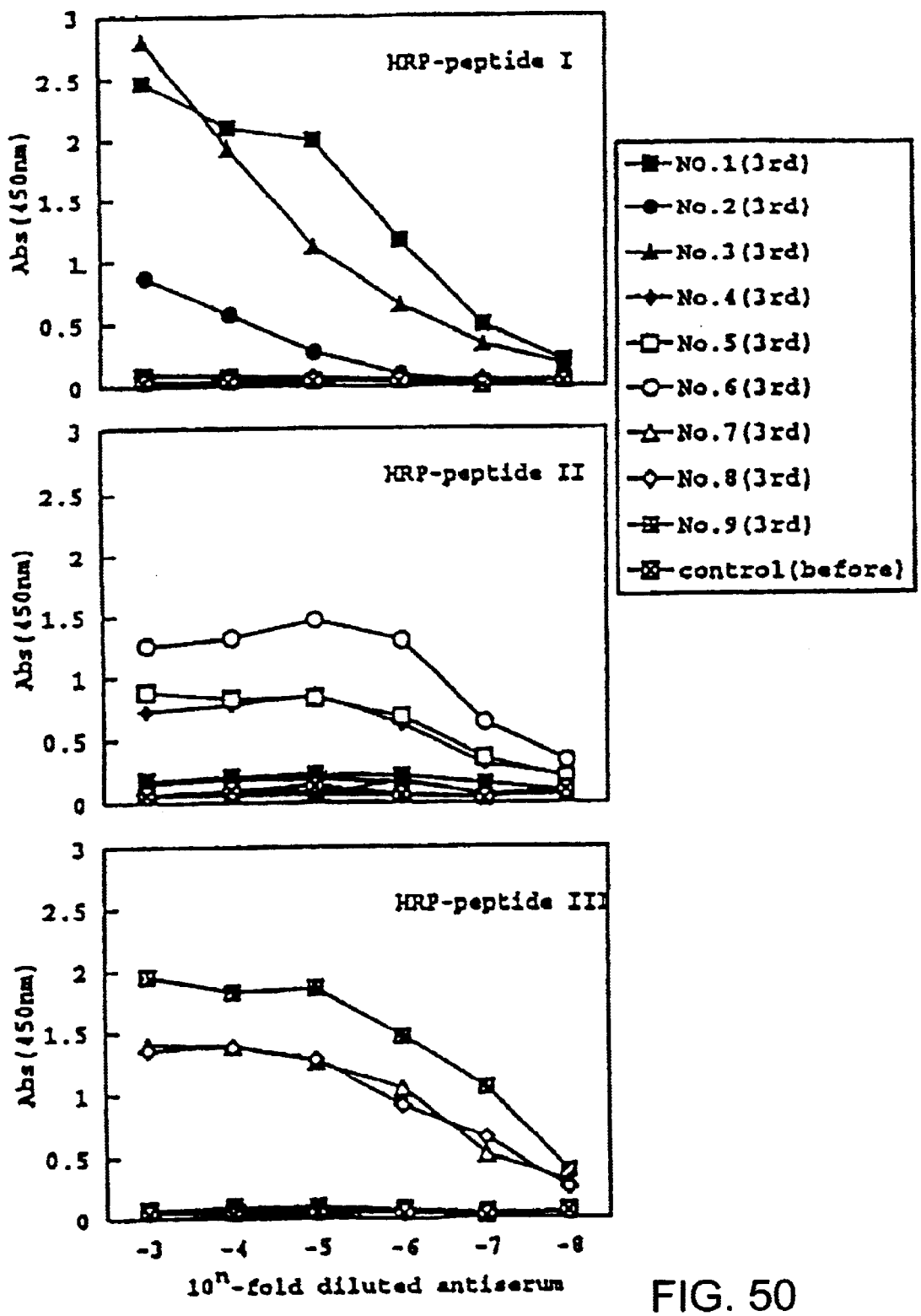

FIG. 50 shows the relationship between the ligand polypeptide serum and the absorbance.

Figure 51:
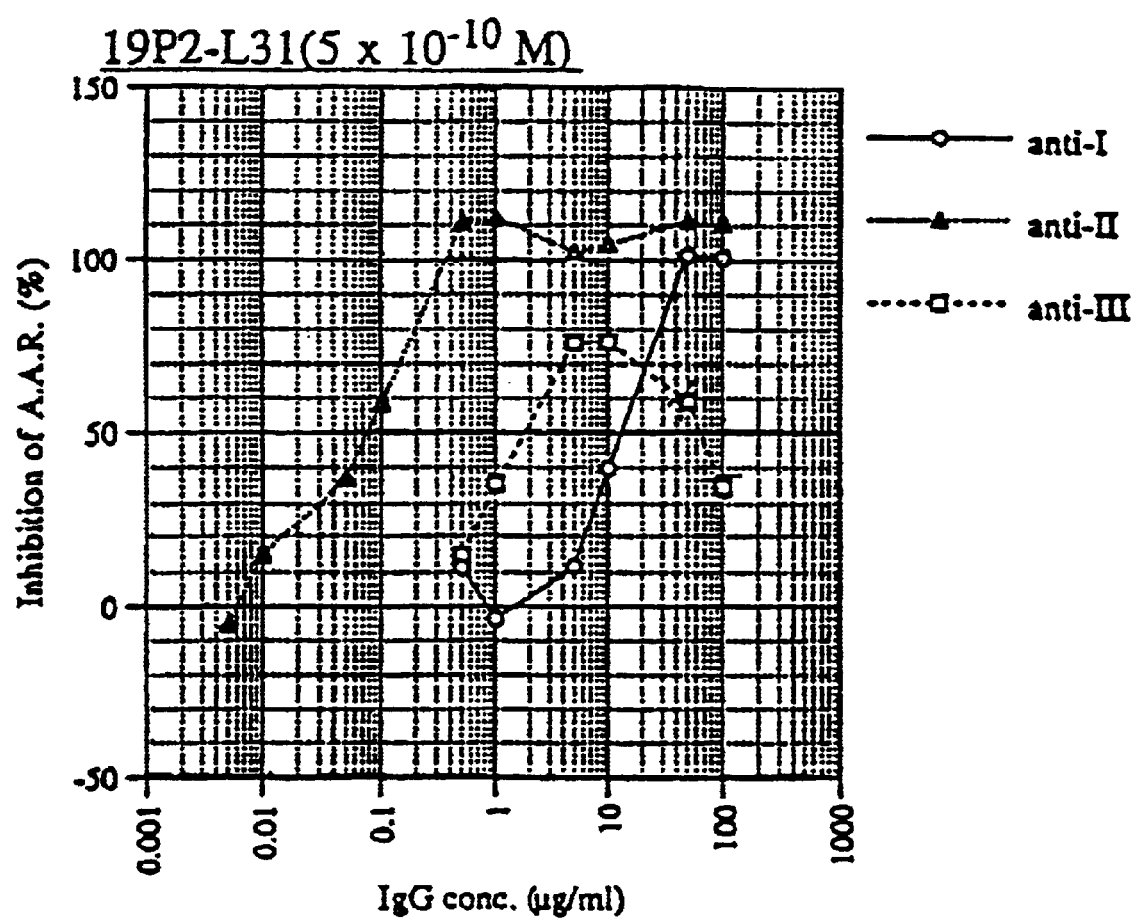

FIG. 51 shows the inhibition of the release of archidonic acid metabolites by anti-ligand polypeptide polyclonal antibody.

Figures 52, 52A:
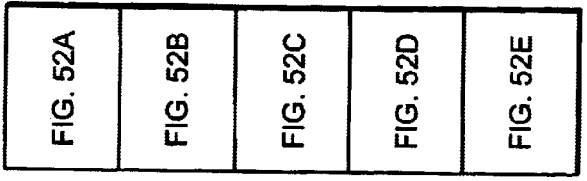

FIG. 52 (SEQ ID NOS:139–140) shows the sequence of cDNA coding for UHR-1, which is constructed on pAKKO-UHR1-7.

BEST MODE FOR CARRYING OUT THE INVENTION

The ligand polypeptide according to the present invention is a polypeptide which is capable of binding to G protein-coupled receptor protein and comprising an amino acid sequence represented by SEQ ID NO:73 or its substantial equivalent thereto or a partial peptide thereof, or its amide or ester, or a salt thereof. In SEQ ID NO:73, Xaa at 10th position is Ala or Thr; Xaa at 11th position is Gly or Ser; and Xaa at 21th position is H, Gly, or GlyArg.

The above ligand polypeptide, its amide or ester, or a salt thereof (hereinafter sometimes referred to briefly as the ligand polypeptide or the polypeptide), processes for their production, and uses for the polypeptide are now described in detail.

The above ligand polypeptide of the present invention includes any polypeptides derived from any tissues, e.g. pituitary gland, pancreas, brain, kidney, liver, gonad, thyroid gland, gall bladder, bone marrow, adrenal gland, skin, muscle, lung, digestive canal, blood vessel, heart, etc.; or cells of man and other warm-blooded animals, e.g. guinea pig, rat, mouse, swine, sheep, bovine, monkey, etc. and comprising an amino acid sequence represented by SEQ ID NO:73 or its substantial equivalent thereto. For example, in addition to the protein comprising the amino acid sequence of SEQ ID NO:73, the ligand polypeptide of the present invention includes the protein comprising an amino acid sequence having a homology of about 50–99.9%, preferably 70–99.9%, more preferably 80–99.9% and especially preferably 90–99.9% to the amino acid sequence of SEQ ID NO:73 and having qualitatively substantially equivalent activity to the protein comprising the amino acid sequence of SEQ ID NO:73. The term "substantially equivalent" means the nature of the receptor-binding activity, signal transduction activity and the like is equivalent. Thus, it is allowable that even differences among grades such as the strength of receptor binding activity and the molecular weight of the polypeptide are present.

To be more specific, the ligand polypeptide of the present invention includes the polypeptide derived from the rat wholebrain, bovine hypothalamus, or human whole brain and comprising the amino acid sequence of SEQ ID NO:73. In addition, the ligand polypeptide of the present invention includes the polypeptides which comprises substantial equivalent polypeptides such as polypeptides wherein 1 to 15, preferably 1 to 10, and more preferably 1 to 5 amino acid residues are deleted from the amino acid sequence of SEQ ID NO:73, polypeptides wherein 1 to 80, preferably 1 to 50, more preferably 1 to 10 amino acid residues are added to the amino acid sequence of SEQ ID NO:73, or polypeptides wherein 1 to 15, preferably 1 to 10, more preferably 1 to 5 amino acid residues are substituted with one or more other amino acid residues.

The amino acid sequence of SEQ ID NO:73 comprises SEQ ID NO:8, 9, 10, 50, 51, 52, 64, 65 or 66. The substantial equivalent polypeptides to the polypeptide comprising the amino acid sequence of SEQ ID NO: 73 are polypeptides comprising the amino acid sequences of SEQ ID NO:1, 3, 4, 5, 6, 7, 44, 45, 47, 48, 49, 59, 61, 62, or 63.

Among them, preferred is the polypeptide comprising the amino acid sequence of SEQ ID NO:73 and the polypeptide comprising the amino acid sequence which a peptide of SEQ ID NO:74 is added to the N-terminus of the polypeptide comprising the amino acid sequence of SEQ ID NO:73.

Furthermore, the polypeptide or partial peptide of the present invention includes those wherein the N-terminal side of Gln is cleaved in vivo to form pyroglutamyl peptide.

The peptides described in this specification, the left ends are the N-terminus (amino terminus) and the right end is the C-terminus (carboxyl terminus) according to the convention of the peptide indication. While the C-terminus of the polypeptide of SEQ ID NO:73 is usually carboxyl (—COOH) or carboxylate (—COO$^-$), it may be amide (—CONH$_2$) or ester (—COOR) form. The ester residue R includes a $C_{1-6}$ alkyl group such as methyl, ethyl, n-propyl, isopropyl, n-butyl, etc., a $C_{3-8}$ cycloalkyl group such as cyclopentyl, cyclohexyl, etc., a $C_{6-12}$ aryl group such as phenyl, α-naphthyl, etc., and a $C_{7-14}$ aralkyl group such as a phenyl-$C_{1-2}$ alkyl group, e.g. benzyl, phenethyl, benzhydryl, etc. or an α-naphthyl-$C_{1-2}$ alkyl, e.g. α-naphthylmethyl etc. In addition, the ester may be a pivaloyloxymethyl ester which is broadly used for oral administration. When the polypeptide of SEQ ID NO:73 has a carboxyl or carboxylate group in any position other than the C-terminus, the corresponding amide or ester are also included in the concept of the polypeptide of the present invention. The ester mentioned just above includes the esters mentioned for the C-terminus.

The preferred ligand polypeptide of the present invention is a peptide which the C-terminus is amidated. Especially preferred is a polypeptide comprising the amino acid sequence of SEQ ID NO:5, 8, 47, 50, 61 or 64 which the C-terminus is amidated.

The salt of polypeptide of the present invention includes salts with physiologically acceptable bases, e.g. alkali metals or acids such as organic or inorganic acids, and is preferably a physiologically acceptable acid addition salt. Examples of such salts are salts thereof with inorganic acids, e.g. hydrochloric acid, phosphoric acid, hydrobromic acid or sulfuric acid, etc. and salts thereof with organic acids, e.g. acetic acid, formic acid, propionic acid, fumaric acid, maleic acid, succinic acid, tartaric acid, citric acid, malic acid, oxalic acid, benzoic acid, methanesulfonic acid or benzenesulfonic acid, etc.

The ligand polypeptide or amide or ester, or a salt thereof of the present invention may be manufactured from the tissues or cells of warm-blooded animals inclusive of human by purifying techniques or manufactured by the peptide synthesis as described hereinafter. Moreover, it can be manufactured by culturing a transformant carrying a DNA coding for the polypeptide as described hereinafter.

In the production from the tissues or cells of human or other warmblooded animals, the ligand polypeptide can be purified and isolated by a process which comprises homogenizing the tissue or cells of human or other warm-blooded animal, extracting the homogenate with an acid, for instance, and subjecting the extract to a combination of chromatographic procedures such as reversed-phase chromatography, ion-exchange chromatography, affinity chromatography, etc.

As mentioned above, the ligand polypeptide in the present invention can be produced by the per se known procedures for peptide synthesis. The methods for peptide synthesis may be any of a solid-phase synthesis and a liquid-phase synthesis. Thus, the objective peptide can be produced by condensing a partial peptide or amino acid capable of constituting the protein with the residual part thereof and, when the product has a protective group, the protective group is detached whereupon a desired peptide can be manufactured. The known methods for condensation and deprotection includes the procedures described in the following literature (1)–(5).

(1) M. Bodanszky and M. A. Ondetti, Peptide all Synthesis, Interscience Publishers, New York, 1966

(2) Schroeder and Luebke, The Peptide, Academic Press, New York, 1965

(3) Nobuo Izumiya et al., Fundamentals and Experiments in Peptide Synthesis, Maruzen, 1975

(4) Haruaki Yajima and Shumpei Sakakibara, Biochemical Experiment Series 1, Protein Chemistry IV, 205, 1977

(5) Haruaki Yajima (ed.), Development of Drugs-Continued, 14, Peptide Synthesis, Hirokawa Shoten After the reaction, the protein can be purified and isolated by a combination of conventional purification techniques such as solvent extraction, column chromatography, liquid chromatography, and recrystallization. Where the protein isolated as above is a free compound, it can be converted to a suitable salt by the known method. Conversely where the isolated product is a salt, it can be converted to the free peptide by the known method.

The amide of polypeptide can be obtained by using a resin for peptide synthesis which is suited for amidation. The resin includes chloromethyl resin, hydroxymethyl resin, benzhydrylamine resin, aminomethyl resin, 4-benzyloxybenzyl alcohol resin, 4-methylbenzhydrylamine resin, PAM resin, 4-hydroxymethylmethylphenylacetamidomethyl resin, polyacrylamide resin, 4-(2',4'-dimethoxyphenylhydroxymethyl)phenoxy resin, 4-(2',4'-dimethoxyphenyl-Fmoc aminoethyl)phenoxy resin, and so on. Using such a resin, amino acids whose α-amino groups and functional groups of side-chain have been suitably protected are condensed on the resin according to the sequence of the objective peptide by various condensation techniques which are known per se. At the end of the series of reactions, the peptide or the protected peptide is removed from the resin and the protective groups are removed to obtain the objective polypeptide.

For the condensation of the above-mentioned protected amino acids, a variety of activating reagents for peptide synthesis can be used but a carbodiimide compound is particularly suitable. The carbodiimide includes DCC, N,N'-diisopropylcarbodiimide, and N-ethyl-N'-(3-dimethylaminoprolyl)carbodiimide. For activation with such a reagent, a racemization inhibitor additive, e.g. HOBt and the protected amino acid are directly added to the resin or the protected amino acid pre-activated as symmetric acid anhydride, HOBt ester, or HOOBt ester is added to the resin. The solvent for the activation of protected amino acids or condensation with the resin can be properly selected from among those solvents which are known to be useful for peptide condensation reactions. For example, N,N-dimethylformamide, N-methylpyrrolidone, chloroform, trifluoroethanol, dimethyl sulfoxide, DMF, pyridine, dioxane, methylene chloride, tetrahydrofuran, acetonitrile, ethyl acetate, or suitable mixtures of them can be mentioned. The reaction temperature can be selected from the range hitherto-known to be useful for peptide bond formation and is usually selected from the range of about −20° C.–50° C. The activated amino acid derivative is generally used in a proportion of 1.5–4 fold excess. If the condensation is found to be insufficient by a test utilizing the ninhydrin reaction, the condensation reaction can be repeated to achieve a sufficient condensation without removing the protective group. If repeated condensation still fails to provide a sufficient degree of condensation, the unreacted amino group can be acetylated with acetic anhydride or acetylimidazole.

The protecting group of amino group for the starting material amino acid includes Z, Boc, tertiary-amyloxycarbonyl, isobornyloxycarbonyl, 4-methoxybenzyloxycarbonyl, Cl-Z, Br-Z, adamantyloxycarbonyl, trifluoroacetyl, phthalyl, formyl, 2-nitrophenylsulfenyl, diphenylphosphinothioyl, or Fmoc. The carboxy-protecting group that can be used includes but is not limited to the above-mentioned $C_{1-6}$ alkyl, $C_{3-8}$ cycloalkyl and $C_{7-14}$ aralkyl as well as 2-adamantyl, 4-nitrobenzyl, 4-methoxybenzyl, 4-chlorobenzyl, phenacyl, benzyloxycarbonylhydrazido, tertiary-butoxycarbonylhydrazido, and tritylhydrazido.

The hydroxy group of serine and threonine can be protected by esterification or etherification. The group suited for said esterification includes carbon-derived groups such as lower alkanoyl groups, e.g. acetyl etc., aroyl groups, e.g. benzoyl etc., benzyloxycarbonyl, and ethoxycarbonyl. The group suited for said etherification includes benzyl, tetrahydropyranyl, and tertiary-butyl.

The protective group for the phenolic hydroxyl group of tyrosine includes Bzl, $Cl_2$-Bzl, 2-nitrobenzyl, Br-Z, and tertiary-butyl.

The protecting group of imidazole for histidine includes Tos, 4-methoxy-2,3,6-trimethylbenzenesulfonyl, DNP, benzyloxymethyl, Bum, Boc, Trt, and Fmoc.

The activated carboxyl group of the starting amino acid includes the corresponding acid anhydride, azide, and active esters, e.g. esters with alcohols such as pentachlorophenol, 2,4,5-trichlorophenol, 2,4-dinitrophenol, cyanomethyl alcohol, p-nitrophenol, HONB, N-hydroxysuccinimide, N-hydroxyphthalimide, HOBt, etc. The activated amino group of the starting amino acid includes the corresponding phosphoramide.

The method for elimination of protective groups includes catalytic reduction using hydrogen gas in the presence of a catalyst such as palladium black or palladium-on-carbon, acid treatment with anhydrous hydrogen fluoride, methanesulfonic acid, trifluoromethanesulfonic acid, trifluoroacetic acid, or a mixture of such acids, base treatment with diisopropylethylamine, triethylamine, piperidine, piperazine, reduction with sodium metal in liquid ammonia. The elimination reaction by the above-mentioned acid treatment is generally carried out at a temperature or −20° C.–40° C. and can be conducted advantageously with addition of a cation acceptor such as anisole, phenol, thioanisole, m-cresol, p-cresol, dimethyl sulfide, 1,4-butanedithiol, 1,2-ethanedithiol. The 2,4-dinitrophenyl group used for protecting the imidazole group of histidine can be eliminated by treatment with thiophenol, while the formyl group used for protecting the indole group of tryptophan can be eliminated by alkali treatment with dilute sodium hydroxide solution or dilute aqueous ammonia as well as the above-mentioned acid treatment in the presence of 1,2-ethanedithiol, 1,4-butanedithiol.

The method for protecting functional groups which should not take part in the reaction of the starting material, the protective groups that can be used, the method of removing the protective groups, and the method of activating the functional groups that are to take part in the reaction can all be selected judicially from among the known groups and methods.

An another method for obtaining the amide form of the polypeptide comprises amidating the α-carboxyl group of the C-terminal amino acid at first, then extending the peptide chain to the N-side until the desired chain length, and then selectively deprotecting the α-amino group of the C-terminal peptide and the 0-carboxy group of the amino acid or peptide that is to form the remainder of the objective polypeptide and condensing the two fragments whose α-amino group and side-chain functional groups have been protected with suitable protective groups mentioned above in a mixed solvent such as that mentioned hereinbefore. The parameters of this condensation reaction can be the same as described hereinbefore. From the protected peptide obtained by condensation, all the protective groups are removed by the above-described method to thereby provide the desired crude peptide. This crude peptide can be purified by known purification procedures and the main fraction be lyophilized to provide the objective amidated polypeptide.

To obtain an ester of the polypeptide, the α-carboxyl group of the C-terminal amino acid is condensed with a desired alcohol to give an amino acid ester and then, the procedure described above for production of the amide is followed.

The partial peptide of the ligand polypeptide of the present invention, its amide or ester, or a salt thereof can be any peptide that has the same activities, e.g. pituitary function modulating activity, central nervous system function modulating activity, or pancreatic function modulating activity as the polypeptide which has an amino acid sequence of SEQ ID NO:73 or its substantial equivalent thereto. As such peptides, there can be mentioned peptides wherein 1 to 15 amino acids residues are deleted from the above-mentioned amino acid sequence of SEQ ID NO:73. To be specific, the peptide having an amino acid sequence corresponding to the 2nd to 21st positions of the amino acid sequence of SEQ ID NO:73, the peptide corresponding to the 3rd to 21st positions of the amino acid sequence of SEQ ID NO:73, the peptide corresponding to the 4th to 21st positions of the amino acid sequence of SEQ ID NO:73, the peptide corresponding to the 5th to 21st positions of the amino acid sequence of SEQ ID NO:73, the peptide corresponding to the 6th to 21st positions of the amino acid sequence of SEQ ID NO:73, the peptide corresponding to the 7th to 21st positions of the amino acid sequence of SEQ ID NO:73, the peptide corresponding to the 8th to 21st positions of the amino acid sequence of SEQ ID NO:73, the peptide corresponding to the 9th to 21st positions of the amino acid sequence of SEQ ID NO:73, the peptide corresponding to the 10th to 21st positions of the amino acid sequence of SEQ ID NO:73, the peptide corresponding to the 11th to 21st positions of the amino acid sequence of SEQ ID NO:73, the peptide corresponding to the 12th to 21st positions of the amino acid sequence of SEQ ID NO:73, the peptide corresponding to the 13th to 21st positions of the amino acid sequence of SEQ ID NO:73, the peptide corresponding to the 14th to 21st positions of the amino acid sequence of SEQ ID NO:73, and the peptide corresponding to the 15th to 21st positions of the amino acid sequence of SEQ ID NO:73, can be mentioned as preferred examples. Moreover, the peptide having the amino acid sequence of SEQ ID NO:74 is also preferred.

The ligand polypeptide or partial peptide thereof can be used as antigen for preparation of anti-ligand polypeptide antibody. The polypeptide as antigen includes N-terminus peptides, C-terminus peptides or peptides of central portions other than above-mentioned ligand polypeptides or partial peptides thereof. To be more specifically includes the partial peptide of SEQ ID NO: 92, 93 or 94.

The partial peptide may be a peptide containing each of the domains or a peptide containing a plurality of the domains within the molecule.

The partial peptide mentioned in this specification may be one ending with an amide bond (—CONH$_2$) or an ester bond (—COOR) at the C-terminus. The ester here includes the same one of the above polypeptide. When the partial peptide has a carboxyl or carboxylate group in any position other than the C-terminus, the case in which such group or moiety has been amidated or esterified also falls within the scope of the partial peptide in the present invention. The ester here may be of the same one as the above-mentioned ester at the C-terminus.

The ligand polypeptide or its partial peptide of the present invention may be in the form of a fused protein which fused with a protein whose functions or properties are already known.

The salt of such partial peptide of the ligand polypeptide of present invention may be of the same one as the above-mentioned salt of the polypeptide.

The partial peptide of the ligand polypeptide of the invention, its amide or ester, or a salt thereof can be produced by the same synthetic processes as mentioned for the polypeptide or by cleaving the polypeptide of the present invention with a suitable peptidase.

The DNA coding for the ligand polypeptide or a partial peptide thereof of the present invention may be any DNA comprising the nucleotide sequence encoding a polypeptide having an amino acid sequence of SEQ ID NO:73 or its substantial equivalent thereto. Furthermore, the DNA may be any of genomic DNA, genomic DNA library, tissue- or cell-derived cDNA, tissue- or cell-derived cDNA library, and synthetic DNA. The vector for such as library may be any of bacteriophage, plasmide, cosmide, and phagimide. Moreover, it can be directly amplified by the RT-PCR method by using an RNA fraction may be prepared from a tissue or cells.

To be more specific, as the DNA coding for a polypeptide derived from rat whole brain or bovine hypothalmus and comprising the amino acid sequence of SEQ ID NO:1 or, SEQ ID NO:44, the DNA comprising the nucleotide sequence of SEQ ID NO:2 can be exemplified. In SEQ ID NO:2, R at 129th position represents G or A, and Y at 179th and 240th positions represents C or T. When Y at 179th position is C, the amino acid sequence of SEQ ID NO:1 is encoded, and when Y at 179th position is T, the amino acid sequence of SEQ ID NO:44 is encoded.

As the DNA coding for a bovine-derived polypeptide comprising the amino acid sequence of SEQ ID NO:3, 4, 5, 6, 7, 8, 9 or 10, a DNA comprising the nucleotide sequence of SEQ ID NO:11, 12, 13, 14, 15, 16, 17 or 18 can be exemplified. Here, R at 63th position of SEQ ID NO:11, 13, 14 or 15 and R at 29th position of SEQ ID NO:12, 16, 17, or 18 represent G or A.

As the DNA coding for a rat-derived polypeptide of SEQ ID NO:45, 47, 48; 49, 50, 51, or 52, a DNA comprising the nucleotide sequence of SEQ ID NO:46, 53, 54, 55, 56, 57, or 58 can be exemplified.

Furthermore, as the DNA coding for a human-derived peptide of SEQ ID NO:59, 61, 62, 63, 64, 65, or 66, a DNA comprising the nucleotide sequence of SEQ ID NO:60, 67, 68, 69, 70, 71, or 72 can be exemplified.

Among DNAs coding for the bovine-derived polypeptide comprising the amino acid sequence of SEQ ID NO:1 or SEQ ID NO:44, the rat-derived polypeptide comprising the amino acid sequence of SEQ ID NO:45, or the human-derived polypeptide comprising the amino acid sequence of SEQ ID NO:59, DNA fragments comprising partial nucleotide sequences of 6 to 90, preferably 6 to 60, more preferably 9 to 30, and especially preferably 12 to 30 can be advantageously used as DNA probes as well.

The DNA coding for the ligand polypeptide or a partial peptide thereof of the present invention can be produced by the following genetic engineering procedures.

The DNA fully encoding the polypeptide or partial peptide of the present invention can be cloned either by PCR amplification using synthetic DNA primers having a partial nucleotide sequence of the polypeptide or partial peptide or by hybridization using the DNA inserted in a suitable vector and labeled with a DNA fragment comprising a part or full region of a human-derived polypeptide or a synthetic DNA. The hybridization can be carried out typically by the procedure described in Molecular Cloning (2nd ed., J. Sambrook et al., Cold Spring Harbor Lab. Press, 1989). When a commercial library is used, the instructions given in the accompanying manual can be followed.

The cloned DNA coding for the polypeptide or partial peptide can be used directly or after digestion with a restriction enzyme or addition of a linker depending on purposes. This DNA has ATG as the translation initiation codon at the 5' end and may have TAA, TGA, or TAG as the termination codon at the 3' end. The translation initiation and termination codons can be added by means of suitable DNA adapters.

An expression vector for the polypeptide or partial peptide can be produced by, for example (a) cutting out a target DNA fragment from the DNA for the polypeptide or partial peptide of the present invention and (b) ligating the target DNA fragment with the downstream side of a promoter in a suitable expression vector.

The vector may include plasmids derived from *Escherichia coli*, e.g., pBR322, pBR325, pUC12, pUC13, etc.; plasmids derived from *Bacillus subtilis*, e.g., pUB110, pTP5, pC194, etc.; plasmids derived from yeasts e.g., pSH19, pSH15, etc.; bacteriophages such as λ-phage, and animal virus such as retrovirus, vaccinia virus and baculovirus.

According to the present invention, any promoter can be used as long as it is compatible with the host cell which is used for expressing a gene. When the host for the transformation is *E. coli*, the promoters are preferably trp promoters, lac promoters, recA promoters, $\lambda_{PL}$ promoters, lpp promoters, etc. When the host for the transformation is Bacillus, the promoters are preferably SPO1 promoters SPO2 promoters, penP promoters, etc. When the host is a yeast, the promoters are preferably PHO5 promoters, PGK promoters, GAP promoters, ADH promoters, etc. When the host is an animal cell, the promoters include SV40-derived promoters, retrovirus promoters, metallothionein promoters, heat shock promoters, cytomegalovirus (CMV) promoters, SRα promoters, etc. An enhancer can be effectively utilized for expression.

As required, furthermore, a host-compatible signal sequence is added to the N-terminal side of the polypeptide or partial peptide thereof. When the host is *E. coli*, the utilizable signal sequences may include alkaline phosphatase signal sequences, OmpA signal sequences, etc. When the host is Bacillus, they may include α-amylase signal sequences, subtilisin signal sequences, etc. When the host is a yeast, they may include mating factor a signal sequences, invertase signal sequences, etc. When the host is an animal cell, they may include insulin signal sequences, α-interferon signal sequences, antibody molecule signal sequences, etc.

A transformant or transfectant is produced by using the vector thus constructed, which carries the polypeptide or partial peptide-encoding DNA of the present invention. The host may be, for example, Escherichia microorganisms, Bacillus microorganisms, yeasts, insect cells, animal cells, etc. Examples of the Escherichia and Bacillus microorganisms include *Escherichia coli* K12. DH1 [Proc. Natl. Acad. Sci. USA, Vol. 60, 160 (1968)], JM103 [Nucleic Acids Research, Vol. 9, 309 (1981)], JA221 [Journal of Molecular Biology, Vol. 120, 517 (1978)], HB101 [journal of molecular Biology, Vol, 41, 459 (1969)], C600 [Genetics, Vol. 39, 440 (1954)], etc. Examples of the Bacillus microorganism are, for example *Bacillus subtilis* MI$^1$, [Gene, Vol. 24, 255 (1983)], 207–21 [Journal of Biochemistry, Vol. 95, 76 (1984)], etc.

The yeast may be, for example, *Saccharomyces cerevisiae* AH22, AH22R$^-$, NA87-11A, DKD-5D, 20B-12, etc. The insect may include a silkworm (*Bombvx mori* larva), [Maeda et al, Nature, Vol. 315, 592 (1985)] etc. The host animal cell may be, for example, monkey-derived cell line, COS-7, Vero, Chinese hamster ovary cell line (CHO cell), DHFR gene-deficient Chinese hamster cell line (dhfr$^-$ CHO cell), mouse L cell, mouse myeloma cell, human FL, etc.

Depending on the host cell used, transformation is done using standard techniques appropriate to such cells. Transformation of Escherichia microorganisms can be carried out in accordance with methods as disclosed in, for example, Proc. Natl. Acad. Sci. USA, Vol. 69, 2110 (1972), Gene, Vol. 17, 107 (1982), etc. Transformation of Bacillus microorganisms can be carried out in accordance with methods as disclosed in, for example, Molecular & General Genetics, Vol. 168, 111 (1979), etc. Transformation of the yeast can be carried out in accordance with methods as disclosed in, for example, Proc. Natl. Acad. Sci. USA, Vol. 75, 1929 (1978), etc. The insect cells can be transformed in accordance with methods as disclosed in, for example, Bio/Technology, 6, 47–55, 1988. The animal cells can be transformed by methods as disclosed in, for example, Virology, Vol. 52, 456, 1973, etc. The transformants or transfectants wherein the expression vector carrying a polypeptide or partial peptide thereof encoding DNA harbors are produced according to the aforementioned techniques.

Cultivation of the transformant (transfectant) in which the host is Escherichia or Bacillus microorganism can be carried out suitably in a liquid culture medium. The culture medium may contains carbon sources, nitrogen sources, minerals, etc. necessary for growing the transformant. The carbon source may include glucose, dextrin, soluble starch, sucrose, etc. The nitrogen source may include organic or inorganic substances such as ammonium salts, nitrates, corn steep liquor, peptone, casein, meat extracts, bean-cakes, potato extracts, etc. Examples of the minerals may include calcium chloride, sodium dihydrogen phosphate, magnesium chloride, etc. It is further allowable to add yeasts, vitamines, growth-promoting factors, etc. It is desired that the culture medium is pH from about 5 to about 8.

The Escherichia microorganism culture medium is preferably an M9 medium containing, for example, glucose and casamino acid (Miller, Journal of Experiments in Molecular Genetics), 431–433, Cold Spring Harbor Laboratory, New York, 1972. Depending on necessity, the medium may be supplemented with drugs such as 3β-indolyl acrylic acid in order to improve efficiency of the promoter. In the case of an Escherichia host, the cultivation is carried out usually at about 15 to 43° C. for about 3 to 24 hours. As required, aeration and stirring may be applied. In the case of Bacillus host, the cultivation is carried out usually at about 30 to 40° C. for about 6 to 24 hours. As required, aeration and stirring may be also applied. In the case of the transformant in which the host is a yeast, the culture medium used may include, for example, a Burkholder minimum medium [Bostian, K. L. et al., Proc. Natl. Acad. Sci. USA, Vol. 77, 4505 (1980)], an SD medium containing 0.5% casamino acid [Bitter, G. A. et al., Proc. Natl. Acad. Sci. USA, Vol. 81, 5330 (1984)], etc. It is preferable that the pH of the culture medium is adjusted to be from about 5 to about 8. The cultivation is carried out usually at about 20 to 35° C. for about 24 to 72 hours. As required, aeration and stirring may be applied. In the case of the transformant in which the host is an insect, the culture medium used may include those obtained by suitably adding additives such as passivated (or immobilized) 10% bovine serum and the like to the Grace's insect medium (Grace, T. C. C., Nature, 195, 788 (1962)). It is preferable that the pH of the culture medium is adjusted to be about 6.2 to 6.4. The cultivation is usually carried out at about 27° C. for about 3 to 5 days. As desired, aeration and stirring may be applied. In the case of the transformant in which the host is an animal cell, the culture medium used may include MEM medium [Science, Vol. 122, 501 (1952)], DMEM medium [Virology, Vol. 8, 396 (1959)], RPMI 1640 medium [Journal of the American Medical Association, Vol. 199, 519 (1967)], 199 medium [Proceedings of the Society of the Biological Medicine, Vol. 73, 1 (1950)], etc. which are containing, for example, about 5 to 20% of fetal calf serum. It is preferable that the pH is from about 6 to about 8. The cultivation is usually carried out at about 30 to 40° C. for about 15 to 60 hours. As required, medium exchange, aeration and stirring may be applied.

Separation and purification of the polypeptide or partial peptide from the above-mentioned cultures can be carried out according to methods described herein below.

To extract polypeptide or partial peptide from the cultured microorganisms or cells, the microorganisms or cells are collected by known methods after the cultivation, suspended in a suitable buffer solution, disrupted by ultrasonic waves, lysozyme and/or freezing and thawing, etc. and, then, a crude extract of the polypeptide or partial peptide is obtained by centrifugation or filtration. Other conventional extracting or isolating methods can be applied. The buffer solution may contain a protein-denaturing agent such as urea or guanidine hydrochloride or a surfactant such as Triton X-100 (registered trademark, hereinafter often referred to as "TM").

In the case where the polypeptide or partial peptide are secreted into culture media, supernatant liquids are separated from the microorganisms or cells after the cultivation is finished and the resulting supernatant liquid is collected by widely known methods. The culture supernatant liquid and extract containing the polypeptide or partial peptide can be purified by suitable combinations of widely known methods for separation, isolation and purification. The widely known methods of separation, isolation and purification may include methods which utilizes solubility, such as salting out or sedimentation with solvents methods which utilizes chiefly a difference in the molecular size or weight, such as dialysis, ultrafiltration, gel filtration and SDS-polyacrylamide gel electrophoresis, methods utilizing a difference in the electric charge, such as ion-exchange chromatography, methods utilizing specific affinity such as affinity chromatography, methods utilizing a difference in the hydrophobic property, such as reverse-phase high-performance liquid chromatography, and methods utilizing a difference in the isoelectric point such as isoelectric electrophoresis, or chromatofocusing, etc.

In cases where the polypeptide or partial peptide thus obtained is in a free form, the free protein can be converted into a salt thereof by known methods or method analogous thereto. In case where the polypeptide or partial peptide thus obtained is in a salt form vice versa, the protein salt can be converted into a free form or into any other salt thereof by known methods or method analogous thereto.

The polypeptide or partial peptide produced by the transformant can be arbitrarily modified or a polypeptide can be partly removed therefrom, by the action of a suitable protein-modifying enzyme before or after the purification. The protein-modifying enzyme may include trypsin, chymotrypsin, arginyl endopeptidase, protein kinase, glycosidase, etc. The activity of the polypeptide or partial peptide thus formed can be measured by experimenting the coupling (or binding) with receptor or by enzyme immunoassays (enzyme linked immunoassays) using specific antibodies.

The DNA coding for the ligand polypeptide of the present invention, the ligand polypeptide or a partial peptide thereof can be used for (1) synthesis of a part or the full length of the ligand for G protein-coupled receptor protein, (2) search for the physiological activities of the ligand polypeptide or partial peptide thereof of the present invention, (3) preparation of a synthetic oligonucleotide probe or a PCR primer, (4) acquisition of DNAs coding for ligands of G protein-coupled receptor proteins and precursor proteins, (5) development of receptor-binding assay systems using the expression of recombinant receptor proteins and screening of candidate medicinally active compounds, (6) acquisition of antibodies and antisera, (7) development of diagnostic agents utilizing said antibodies or antisera, (8) development of drugs such as pituitary function modulators, central nervous system function modulators, and pancreatic function modulators, and (9) gene therapies, among other uses.

Particularly by using the receptor binding assay system using the expression of a recombinant G protein-coupled receptor protein, which is described hereinafter, agonists or antagonists of G protein-coupled receptors which are specific to warm-blood animals including humans can be screened and such agonists and antagonists can be used as prophylactic and therapeutic agents for various diseases.

Further, referring to (8) above, the ligand poly-peptide, a partial peptide thereof, or the DNA encoding either of them of the present invention is useful as a safe pharmaceutical composition of low toxic potential because it is recognized as a ligand by the G protein-coupled receptor protein expressed in the hypophysis, central nervous system and pancreatic 5 cells. The ligand polypeptide, a partial peptide thereof, or the DNA encoding either of them of the present invention is associated with the modulation of pituitary function, central nervous system function, and pancreatic function and, therefore, can be used as a therapeutic and prophylactic pharmaceutical composition for dementia such as senile dementia, cerebrovascular dementia (dementia due to cerebrovascular disorder), dementia associated with phylodegenerative retroplastic diseases (e.g. Alzheimer's disease, Parkinson's disease, Pick's disease, Huntington's disease, etc.), dementia due to infectious diseases (e.g. delayed viral infections such as Creutzfelt-Jakob disease), dementia associated with endocrine, metabolic, and toxic diseases (e.g. hypothyroidism, vitamin B12 deficiency, alcoholism, and poisoning due to various drugs, metals, or organic compounds), dementia associated with oncogenous diseases (e.g. brain tumor), dementia due to traumatic diseases (e.g. chronic subdural hematoma):, depression (melancholia), hyperkinetic (microencephalo-pathy) syndrome, disturbance of consciousness, anxiety syndrome, schizophrenia, horror, growth hormone secretory disease (e.g. gigantism, acromegalic gigantism etc.), hyperphagia, polyphagia, hypercholesterolemia, hyperglyceridemia, hyperlipemia, hyperprolactinemia, diabetes (e.g. diabetic complications, diabetic nephropathy, diabetic neuropathy, diabetic retinopathy etc.), cancer (e.g. mammary cancer, lymphatic leukemia, cystic cancer, ovary cancer, prostatic cancer etc.), pancreatitis, renal disease (e.g. chromic renal failure, nephritis etc.), Turner's syndrome, neurosis, rheumatoid arthritis, spinal injury, transient brain ischemia, amyotrophic lateral sclerosis, acute myocardial infarction, spinocerebellar degeneration, bone fracture, trauma, atopic dermatitis, osteoporosis, asthma, epilepsy, infertility or oligogalactia. Furthermore, they can be also used as the agent for improvement in postoperative nutritional status and/or vasopressor.

When the polypeptide, a partial peptide thereof, or the DNA encoding either of them of the present invention is used as a pharmaceutical composition as described above, it can be used by conventional methods. For example, it can be used orally in the form of tablets which may be sugar coated as necessary, capsules, elixirs, microcapsules etc., or non-orally in the form of injectable preparations such as aseptic solutions and suspensions in water or other pharmaceutically acceptable liquids. These preparations can be produced by mixing the polypeptide, a partial peptide thereof, or the DNA encoding either of them with physiologically acceptable carriers, flavoring agents, excipients, vehicles, antiseptics, stabilizers, binders etc. in unit dosage forms required for generally accepted manners of pharmaceutical making. Active ingredient contents in these preparations are set so that an appropriate dose within the specified range is obtained.

Additives which can be mixed in tablets, capsules etc. include binders such as gelation, corn starch, tragacanth and gum arabic, excipients such as crystalline cellulose, swelling agents such as corn starch, gelatin and alginic acid, lubricants such as magnesium stearate, sweetening agents such as sucrose, lactose and saccharin, and flavoring agents such as peppermint, akamono oil and cherry. When the unit dosage form is the capsule, the above-mentioned materials may further incorporate liquid carriers such as oils and fats. Sterile compositions for injection can be formulated by ordinary methods of pharmaceutical making such as by dissolving or suspending active ingredients, naturally occurring vegetable oils such as sesame oil and coconut oil, etc. in vehicles such as water for injection.

Aqueous liquids for injection include physiological saline and isotonic solutions containing glucose and other auxiliary agents, e.g., D-sorbitol, D-mannitol and sodium chloride, and may be used in combination with appropriate dissolution aids such as alcohols, e.g., ethanol, polyalcohols, e.g., propylene glycol and polyethylene glycol, nonionic surfactants, e.g., polysorbate 80 (TM) and HCO-50 etc. Oily liquids include sesame oil and soybean oil, and may be used in combination with dissolution aids such as benzyl benzoate and benzyl alcohol. Furthermore the above-mentioned materials may also be formulated with buffers, e.g., phosphate buffer and sodium acetate buffer; soothing agents, e.g., benzalkonium chloride, procaine hydrochloride; stabilizers, e.g., human serum albumin, polyethylene glycol; preservatives, e.g., benzyl alcohol, phenol; antioxidants etc. The thus-prepared injectable liquid is normally filled in an appropriate ampule. Because the thus-obtained preparation is safe and of low toxicity, it can be administered to humans or warm-blooded mammals, e.g., mouse, rats, guinea pig, rabbits, chicken, sheep, pigs, bovines, cats, dogs, monkeys, baboons, chimpanzees, for instance.

The dose of said polypeptide, a partial peptide thereof, or the DNA encoding either of them is normally about 0.1–100 mg, preferably 1.0–50 mg, and more preferably 1.0–20 mg per day for an adult (weighing 60 kg) in oral administration, depending on symptoms etc. In non-oral administration, it is advantageous to administer the polypeptide, a partial peptide thereof, or the DNA encoding either of them in the form of injectable preparation at a daily dose of about 0.01–30 mg, preferably about 0.1–20 mg, and more preferably about 0.1–10 mg per administration by an intravenous injection for an adult (weighing 60 kg), depending on subject of administration, target organ, symptoms, method of administration etc. For other animal species, corresponding does as converted per 60 kg weight can be administered.

The G protein-coupled receptor protein for the above ligand polypeptide of the present invention may be any of G protein-coupled receptor proteins derived from various tissues, e.g. hypophysis, pancreas, brain, kidney, liver, gonad, thyroid gland, gall bladder, bone marrow, adrenal gland, skin, muscle, lung, alimentary canal, blood vessel, heart, etc. of human and other warm-blooded animals, e.g. guinea pig, rat, mouse, swine, sheep, bovine, monkey, etc.; and comprising an amino acid sequence of SEQ ID NO:19, 20, 21, 22 or 23, or substantial equivalent thereto. Thus, the G protein-coupled receptor protein of the present invention includes, in addition to proteins comprising the SEQ ID NO:19, 20, 21, 22 or 23, those proteins comprising amino acid sequences of about 90–99.9% homology to the amino acid sequence of SEQ ID NO:19, 20, 21, 22 or 23 and having qualitatively substantially equivalent activity to proteins comprising the amino acid sequence of SEQ ID NO:19, 20, 21, 22, or 23. The activities which these proteins are possessed may include ligand binding activity and signal transduction activity. The term "substantially equivalent" means that the nature of the ligand binding activity and the like is equivalent. Therefore, it is allowable that even differences among grades such as the strength of ligand binding activity and the molecular weight of receptor protein are present.

To be further specific, the G protein-coupled receptor proteins include human pituitary-derived G protein-coupled receptor proteins which comprises the amino acid sequence of SEQ ID NO:19 or/and SEQ ID NO:20, mouse pancreas-derived G protein-coupled receptor proteins which comprises the amino acid sequence of SEQ ID NO:22, and mouse pancreas-derived G protein-coupled receptor proteins which comprises the amino acid sequence of SEQ ID NO:23. As the human pituitary-derived G protein-coupled receptor proteins which comprises the amino acid sequence of SEQ ID NO:19 and/or SEQ ID NO:20 include the human pituitary-derived G protein-coupled receptor protein which comprises the amino acid sequence of SEQ ID NO:21. The G protein-coupled receptor proteins further include proteins wherein 1 to 30 amino acid residues, preferably 1 to 10 amino acid residues are deleted from the amino acid sequence of SEQ ID NO:19, 20, 21, 22 or 23, proteins wherein 1 to 30 amino acid residues, preferably 1 to 10 amino acid residues are added to the amino acid sequence of SEQ ID NO:19, 20, 21, 22, or 23, the proteins wherein 1 to 30 amino acid residues, preferably 1 to 10 amino acid residues in the amino acid sequence of SEQ ID NO:19, 20, 21, 22, or 23 are substituted with one or more other amino acid residues.

Here, the protein which comprises an amino acid sequence of SEQ ID NO:21 or substantial equivalent thereto contain, the full-length of the amino acid sequence for human pituitary-derived G protein-coupled receptor protein. The protein which comprises an amino acid sequence of SEQ ID NO:19 or/and SEQ ID NO:20 or substantial equivalent thereto may be a partial peptide of the protein which comprises an amino acid sequence of SEQ ID NO:21 or substantial equivalent thereto. The protein which comprises an amino acid sequence of SEQ ID NO:22 or SEQ ID NO:23 or substantial equivalent thereto is a G protein-coupled receptor protein which is derived from mouse pancreas but since its amino acid sequence is quite similar to the amino acid sequence of SEQ ID NO:19 or/and SEQ ID NO:20 (cf. Example 8, FIG. 13 in particular), the protein which comprises an amino acid sequence of SEQ ID NO:22 or 23 or substantial equivalent thereto is also subsumed in the category of said partial peptide of the protein which comprises an amino acid sequence of SEQ ID NO:21 or substantial equivalent thereto.

Thus, the above-mentioned protein comprising an amino acid sequence of SEQ ID NO:21 or substantial equivalent thereto or a partial peptide of the protein or a salt thereof, which will be described below, includes the protein comprising an amino acid sequence of SEQ ID NO:19, 20, 22, or 23 or substantial equivalent thereto, or a salt thereof.

Furthermore, the G protein-coupled receptor protein includes the protein in which the N-terminal Met has been protected with a protective group, e.g. $C_{1-6}$ acyl such as formyl or acetyl, the protein in which the N-terminal side of Glu has been cleaved in vivo to form pyroglutamine, the protein in which the side chain a of any relevant constituent amino acid has been protected with a suitable protective group, e.g. $C_{1-6}$ acyl such as formyl or acetyl, and the complex protein such as glycoproteins available upon attachment of sugar chains.

The salt of G protein-coupled receptor protein includes the same kinds of salts as mentioned for the ligand polypeptide.

The G protein-coupled receptor protein or a salt thereof or a partial peptide thereof can be produced from the tissues or cells of human of other warm-blooded animals by the per se known purification technology or, as described above, by culturing a transformant carrying a DNA coding for the G protein-coupled receptor protein. It can also be produced in accordance with the procedures for peptide synthesis which are described above.

A partial peptide of G protein-coupled receptor protein may include, for example, a fragment containing an extracellular portion of the G protein-coupled receptor protein, i.e. the site which is exposed outside the cell membranes. Examples of the partial peptide are fragments containing a region which is an extracellular area (hydrophilic region) as analyzed in a hydrophobic plotting analysis of the G protein-coupled receptor protein, such as shown in FIG. 3, FIG. 4, FIG. 8, FIG. 11, or FIG. 14. Furthermore, a fragment which partly contains a hydrophobic region may also be used. While peptides which separately contains each domain may be used too, peptides which contains multiple domains at the same time will be used as well.

The salt of a partial peptide of G protein-coupled receptor protein may be the same one of salt mentioned for the salt of ligand polypeptide.

The DNA coding for the G protein-coupled receptor protein may be any DNA comprising a nucleotide sequence encoding the G protein-coupled receptor protein which comprises an amino acid sequence of SEQ ID NO:19, 20, 21, 22, or 23 or substantial equivalent thereto. It may also be any one of genomic DNA, genomic DNA library, tissue- or cell-derived cDNA, tissue- or cell-derived cDNA library, and synthetic DNA. The vector for such a library may include bacteriophage, plasmid, cosmid, and phargimide. Furthermore, using an RNA fraction prepared from a tissue or cells, a direct amplification can be carried out by the RT-PCR method.

To be specific, the DNA encoding the human pituitary-derived G protein-coupled receptor protein which comprises the amino acid sequence of SEQ ID NO:19 include a DNA which comprises the nucleotide sequence of SEQ ID NO:24. The DNA encoding the human pituitary-derived G protein-coupled receptor protein which comprises the amino acid sequence of SEQ ID NO:20 include a DNA which comprises the nucleotide sequence of SEQ ID NO:25. The DNA encoding the human pituitary-derived G protein-coupled receptor protein which comprises the amino acid sequence of SEQ ID NO:21 include a DNA which comprises the nucleotide sequence of SEQ ID NO:26. The DNA encoding the mouse pancreas-derived G protein-coupled receptor protein which comprises the amino acid sequence of SEQ ID NO:22 include a DNA which comprises the nucleotide sequence of SEQ ID NO:27. The DNA encoding the mouse pancreas-derived G protein-coupled receptor protein which comprises the amino acid sequence of SEQ ID NO:23 include a DNA comprising the nucleotide sequence of SEQ ID NO:28.

A method for cloning the DNA completely coding for the G protein-coupled receptor protein, vector, promoter, host cell, a method for transformation, a method for culturing the transformant or a method for separation and purification of the G protein-coupled receptor protein may include the same one as mentioned for the ligand polypeptide.

To be specific, the plasmid phGR3 obtained in Example 5, described hereinafter, is digested with the restriction enzyme SalI and the translation frame for the full-length cDNA encoding hGR3 is isolated. This frame is subjected to ligation to, for example, the expression vector pAKKO-111 for animal cell use which has been treated with BAP (bacterial alkaline phosphatase) after SalI digestion for inhibition of autocyclization. After completion of the ligation reaction, a portion of the reaction mixture is used for transfection of, for example, $Escherichia\ coli$ DH5. Among the transformants obtained, a transformant in which the cDNA coding for hGR3 has been inserted in the forward direction with respect to a promoter, such as SRα, which has been inserted into the expression vector beforehand is selected by mapping after cleavage with restriction enzymes or by nucleotide sequencing and the plasmid DNA is prepared on a production scale.

The thus-constructed DNA of the expression vector is introduced into CHO dhfr⁻ cells using a kit for introducing a gene into animal cells by the calcium phosphate method, the liposome method or the like to provide a high G protein-coupled receptor protein (hGR3) expression CHO cell line.

The resulting CHO cells are cultured in a nucleic acid-free screening medium in a $CO_2$ incubator at 37° C. using 5% $CO_2$ for 1–4 days so as to give the G protein-coupled receptor protein (hGR3).

The G protein-coupled receptor protein is purified from the above CHO cells using an affinity column prepared by conjugating an antibody to the G protein-coupled receptor protein or a partial peptide thereof to a support or an affinity column prepared by conjugating a ligand for the G protein-coupled receptor protein.

The activity of the G protein-coupled receptor protein thus formed can be measured by experimenting the binding with a ligand or by enzyme immunoassays using specific antibodies.

The G protein-coupled receptor protein, the partial peptide thereof and the G protein-coupled receptor protein-encoding DNA can be used for:

1) determining a ligand to the G protein-coupled receptor protein,
2) obtaining an antibody and an antiserum,
3) constructing a system for expressing a recombinant receptor protein,
4) developing a receptor-binding assay system using the above developing system and screening pharmaceutical candidate compounds,
5) designing drugs based upon comparison with ligands and receptors which have a similar or analogous structure,
6) preparing a probe for the analysis of genes and preparing a PCR primer,
7) gene manipulation therapy.

In particular, it is possible to screen a G protein-coupled receptor agonist or antagonist specific to a warm-blooded animal such as human being by a receptor-binding assay system which uses a system for expressing a recombinant G protein-coupled receptor protein. The agonist or antagonist thus screened or characterized permits various applications including prevention and/or therapy of a variety of diseases.

Described below are uses of ligand polypeptide of the present invention, G protein-coupled receptor proteins to the ligand polypeptide, ligand polypeptide-encoding DNAs, G protein-coupled receptor protein-encoding DNAs and their antibodies.

(1) Method for Determining a Ligand to the G Protein-coupled Receptor Protein

The G protein-coupled receptor protein, the partial peptide thereof or a salt thereof is useful as a reagent for investigating or determining a ligand to said G protein-coupled receptor protein.

According to the present invention, methods for determining a ligand to the G protein-coupled receptor protein which comprises contacting the G protein-coupled receptor protein or the partial peptide thereof with the compound to be tested, and measuring the binding amount, the cell stimulating activity, etc. of the test compound to the G protein-coupled receptor protein or the partial peptide thereof are provided.

The compound to be tested may include not only known ligands such as angiotensins, bombesins, canavinoids, cholecystokinins, glutamine, serotonin, melatonins, neuropeptides Y, opioids, purine, vasopressins, oxytocins, VIP (vasoactive intestinal and related peptides), somatostatins, dopamine, motilins, amylins, bradykinins, CGRP (calcitonin gene related peptides), leukotrienes, pancreastatins, prostaglandins, thromboxanes, adenosine, adrenaline, α- and β-chemokines such as IL-8, GROα, GROβ, GROγ, NAP-2, ENA-78, PF4, IP10, GCP-2, MCP-1, HC14, MCP-3, I-309, MIP1α, MIP-1β, RANTES, etc.; endothelins, enterogastrins, histamine, neurotensins, TRH, pancreatic polypeptides, galanin, modified derivatives thereof, analogues thereof, family members thereof and the like but also tissue extracts, cell culture supernatants, etc. of human or warm-blooded animals such as mice, rats, swines, cattle, sheep and monkeys, etc. For example, said tissue extract, said cell culture supernatant, etc. is added to the G protein-coupled receptor protein for measurement of the cell stimulating activity, etc. and fractionated by relying on the measurements whereupon a single ligand can be finally determined and obtained.

In one specific embodiment of the present invention, said method for determining the ligand includes a method for determining whether a sample (including a compound or a salt thereof) is capable of stimulating a target cell which comprises binding said compound with the G protein-coupled receptor protein either in the presence of the G protein-coupled receptor protein, the partial peptide thereof or a salt thereof, or in a receptor binding assay system in which the expression system for the recombinant receptor protein is constructed and used; and measuring the receptor-mediated cell stimulating activity, etc. Examples of said cell stimulating activities that can be measured include promoting or inhibiting biological responses, e.g. liberation of arachidonic acid, liberation of acetylcholine, liberation of endocellular $Ca^{2+}$, production of endocellular cAMP, production of endocellular cGMP, production of inositol phosphate, changes in the cell membrane potential, phosphorylation of endocellular protein, activation of c-fos, decrease in pH, etc, and preferably liberation of arachidonic acid. Examples of said compound or a salt thereof capable of stimulating the cell via binding with the G protein-coupled receptor protein include peptides, proteins, nonpeptidic compounds, synthetic compounds, fermented products, etc.

In more specific embodiments of the present invention, said methods for screening and identifying a ligand includes:
1) a method of screening for a ligand to a G protein-coupled receptor protein, which comprises contacting a labeled test compound with a G protein-coupled receptor protein or a salt thereof or its partial peptide or a salt thereof, and measuring the amount of the labeled test compound binding with said protein or salt thereof or with said partial peptide or salt thereof;
2) a method of screening for a ligand to a G protein-coupled receptor protein, which comprises contacting a labeled test compound with cells containing the G protein-coupled receptor protein or the membrane fraction of said cell, and measuring the amount of the labeled test compound binding with said cells or said membrane fraction;
3) a method of screening for a ligand to a G protein-coupled receptor protein, which comprises contacting a labeled test compound with the G protein-coupled receptor protein expressed on cell membranes by culturing transformants carrying the G protein-coupled receptor protein-encoding DNA and measuring the amount of the labeled test compound binding with said G protein-coupled receptor protein;
4) a method of screening for a ligand to a G protein-coupled receptor protein, which comprises contacting a test compound with cells containing the G protein-coupled receptor protein, and measuring the cell stimulating activity, e.g. promoting or inhibiting activity on biological responses such as liberation of arachidonic acid, liberation of acetylcholine, liberation of endocellular $Ca^{2+}$, production of endocullular cAMP, production of endocellular cGMP, production of inositol phosphate, changes in the cell membrane potential, phosphorylation of endocellular protein, activation of c-fos, lowering in pH, etc. via the G protein-coupled receptor protein; and
5) a method of screening for a ligand to the G protein-coupled receptor protein, which comprises contacting a test compound with the G protein-coupled receptor protein expressed on the cell membrane by culturing transformants carrying the G protein-coupled receptor protein-encoding DNA, and measuring at least one cell stimulating activity, e.g., an activity for promoting or inhibiting physiological responses such as liberation of arachidonic acid, liberation of acetylcholine, liberation of endocellular $Ca^{2+}$, production of endocellular cAMP, production of endocellular cGMP, production of inositol phosphate, changes in the cell membrane potential, phosphorylation of endocellular protein, activation of c-fos, lowering in pH etc. via the G protein-coupled receptor protein.

Described below are specific illustrations of the method for screening and identifying ligands.

First, the G protein-coupled receptor protein used for the method for determining the ligand may include any material so far as it contains a G protein-coupled receptor protein, a partial peptide thereof or a salt thereof although it is preferable to express large amounts of the G protein-coupled receptor proteins in animal cells.

In the manufacture of the G protein-coupled receptor protein, the above-mentioned method can be used and carried out by expressing said protein encoding DNA in mammalian cells or in insect cells. With respect to the DNA fragment coding for a particular region such as an extracellular epitope, the extracellular domains, etc., complementary DNA may be used although the method of expression is not limited thereto. For example, gene fragments or synthetic DNA may be used as well.

In order to introduce the G protein-coupled receptor protein-encoding DNA fragment into host animal cells and to express it efficiently, it is preferred that said DNA fragment is incorporated into the downstream side of polyhedron promoters derived from nuclear polyhedrosis virus belonging to baculovirus, promoters derived from SV40, promoters derived from retrovirus, metallothionein promoters, human heat shock promoters, cytomegalovirus promoters, SRα promoters, etc. Examinations of the quantity and the quality of the expressed receptor can be carried out by methods per se known to those of skill in the art or methods similar thereto based upon the present disclosure. For example, they may be conducted by methods described in publications such as Nambi, P. et al: The Journal of Biochemical Society, vol.267, pages 19555–19559 (1992).

Accordingly, with respect to the determination of the ligand, the material containing a G protein-coupled receptor protein or partial peptide thereof may include products containing G protein-coupled receptor proteins which are purified by methods per se known to those of skill in the art or methods similar thereto, peptide fragments of said G protein-coupled receptor protein, cells containing said G protein-coupled receptor protein, membrane fractions of the cell containing said protein, etc.

When the G protein-coupled receptor protein-containing cell is used in the determining method of the ligand, said cell may be immobilized with binding agents including glutaraldehyde, formalin, etc. The immobilization may be carried out by methods per se known to those of skill in the art or methods similar thereto.

The G protein-coupled receptor protein-containing cells are host cells which express the G protein-coupled receptor protein. Examples of said host cells are microorganisms such as *Escherichia coli, Bacillus subtilis*, yeasts, insect cells, animal cells, etc.

The cell membrane fraction is a cell membrane-rich fraction which is prepared by methods per se known to those of skill in the art or methods similar thereto after disruption of cells. Examples of cell disruption may include a method for squeezing cells using a Potter-Elvehjem homogenizer, a disruption by a Waring blender or a Polytron manufactured by Kinematica, a disruption by ultrasonic waves, a disruption via blowing out cells from small nozzles together with applying a pressure using a French press or the like, etc. In the fractionation of the cell membrane, a fractionation method by means of centrifugal force such as a fractional centrifugal separation and a density gradient centrifugal separation is mainly used. For example, disrupted cellular liquid is centrifuged at a low speed (500 rpm to 3,000 rom) for a short period (usually, from about one to ten minutes), the supernatant liquid is further centrifuged at a high speed (15,000 rpm to 30,000 rom) usually for 30 minutes to two hours and the resulting precipitate is used as a membrane fraction. Said membrane fraction contains a lot of the expressed G protein-coupled receptor protein and a lot of membrane components such as phospholipids and membrane proteins derived from the cells.

The amount of the G protein-coupled receptor protein in the membrane fraction cell containing said G protein-coupled receptor protein is preferably $10^3$ to $10^8$ molecules per cell or, more preferably, $10^5$ to $10^7$ molecules per cell. Incidentally, the greater the expressed amount, the higher the ligand binding activity (specific activity) per membrane fraction whereby the construction of a highly sensitive screening system becomes possible and, moreover, it permits measurement of a large amount of samples within the same lot.

In conducting the above-mentioned methods 1) to 3) wherein ligands capable of binding with the G protein-coupled receptor protein are determined, a suitable G protein-coupled receptor fraction and a labeled test compound are necessary. The G protein-coupled receptor fraction is preferably a naturally occurring (natural type) G protein-coupled receptor, a recombinant G protein-coupled receptor having the activity equivalent to that of the natural type. Here, the term "activity equivalent to" means the equivalent ligand binding activity, etc. as discussed above.

Suitable examples of the labeled test compound include above-mentioned compound to be tested which are labeled with $[^3H]$, $[^{125}I]$, $[^{14}C]$, $[^{35}S]$, etc.

Specifically, the determination of ligands capable of binding with G protein-coupled receptor proteins is carried out as follows:

First cells or cell membrane fractions containing the G protein-coupled receptor proteins are suspended in a buffer suitable for the assay to prepare the receptor sample for conducting the method of determining the ligand binding with the G protein-coupled receptor protein. The buffer may include any buffer such as Tris-HCL buffer or phosphate buffer with pH 4–10, preferably, pH 6–8, etc., as long as it does not inhibit the binding of the ligand with the receptor. In addition, surface-active agents such as CHAPS, Tween 80™ (Kao-Atlas, Japan), digitonin, deoxycholate, etc. and various proteins such as bovine serum albumin (BSA), gelatin, milk derivatives, etc. may be added to the buffer with an object of descreasing the non-specific binding. Further, a protease inhibitor such as PMSF, leupeptin, E-64 (manufactured by Peptide Laboratory), pepstatin, etc. may be added with an object of inhibiting the decomposition of the receptor and the ligand by protease. A test compound labeled with a predetermined (or certain) amount (5,000 cpm to 500,000 cpm) of $[^3H]$, $[^{125}I]$, $[^{14}C]$, $[^{35}S]$, etc. coexists in 0.01 ml to 10 ml of said receptor solution. In order to know the non-specific binding amount (NSB), a reaction tube to which a great excessive amount of the unlabeled test compound is added is prepared as well. The reaction is carried out at 0–50° C., preferably at 4–37° C. for 20 minutes to 24 hours, preferably 30 minutes to three hours. After the reaction, it is filtered through a glass fiber filter or the like, washed with a suitable amount of the same buffer and the radioactivity remaining in the glass fiber filter is measured by means of a liquid scintillation counter or a gamma-counter. The test compound in which the compound (B–NSB) obtained by subtracting the non-specific binding amount (NSB) from the total binding amount (B) is more than 0 cpm is identified as a ligand to the G protein-coupled receptor protein.

In conducting the above-mentioned methods 4) to 5) wherein ligands capable of binding with the G protein-coupled receptor protein are determined, the cell stimulating activity, e.g. the liberation of arachidonic acid, the liberation of acetylcholine, endocellular $Ca^{2+}$ liberation, endocellular cAMP production, the production of inositol phosphate, changes in the cell membrane potential, the phosphorylation of endocellular protein, the activation of c-fos, lowering of pH, the activation of G protein, cell promulgation, etc.; mediated by the G protein-coupled receptor protein may be measured by known methods or by the use of commercially available measuring kits. To be more specific, G protein-coupled receptor protein-containing cells are at first cultured in a multi-well plate or the like.

In conducting the determination of ligand, it is substituted with a fresh medium or a suitable buffer which does not show toxicity to the cells in advance of the experiment, and incubated under appropriate conditions and for sufficient time after adding a test compound, etc. thereto. Then, the cells are extracted or the supernatant liquid is recovered and the resulting product is determined by each of the methods. When it is difficult to identify the production of the substance, e.g. arachidonic acid, etc. which is to be an index for the cell stimulating activity due to the decomposing enzyme contained in the cell, an assay may be carried out by adding an inhibitor against said decomposing enzyme. With respect to an activity such as an inhibitory action against cAMP production, it may be detected as an inhibitory action against the production of the cells whose fundamental production is increased by forskolin or the like.

The kit used for the method of determining the ligand binding with the G protein-coupled receptor protein includes a G protein-coupled receptor protein or a partial peptide thereof, cells containing the G protein-coupled receptor protein, a membrane fraction from the cells containing the G protein-coupled receptor protein, etc.

Examples of the kit for determining the ligand are as follows:

1. Reagent for Determining the Ligand.
   1) Buffer for Measurement and Buffer for Washing.
   The buffering product wherein 0.05% of bovine serum albumin (manufactured by Sigma) is added to Hanks' Balanced Salt Solution (manufactured by Gibco).
   This product may be sterilized by filtration through a membrane filter with a 0.45 μm pore size, and stored at 4° C. or may be formulated upon use.
   2) G Protein-coupled Receptor Protein Sample.
   CHO cells in which G protein-coupled receptor proteins are expressed are subcultured at the rate of 5×10⁵ cells/well in a 12-well plate and cultured at 37° C. in a humidified 5% $CO_2$/95% air atmosphere for two days to prepare the sample.
   3) Labeled Test Compound.
   The compound which is labeled with commercially available [$^3$H], [$^{125}$I], [$^{14}$C], [$^{35}$S], etc. or labeled with a suitable method.
   The product in a state of an aqueous solution is stored at 4° C. or at −20° C. and, upon use, diluted to 1 μM with a buffer for the measurement. In the case of a test compound which is barely soluble in water, it may be dissolved in an organic solvent such as dimethylformamide DMSO, methanol and the like.
   4) Unlabeled Test Compound.
   The same compound as the labeled one is prepared in a concentration of 100 to 1,000-fold concentrated state.
2. Method of Measurement
   1) G protein-coupled receptor protein-expressing CHO cells cultured in a 12-well tissue culture plate are washed twice with 1 ml of buffer for the measurement and then 490 μl of buffer for the measurement is added to each well.
   2) Five μl of the labeled test compound is added and the mixture is made to react at room temperature for one hour. For measuring the nonspecific binding amount, 5 μl of the unlabeled test compound is added.
   3) The reaction solution is removed from each well, which is washed with 1 ml of a buffer for the measurement three times. The labeled test compound which is binding with the cells is dissolved in 0.2N NaOH-1% SDS and mixed with 4 ml of a liquid scintillator A manufactured by WAKO Pure Chemical, Japan.
   4) Radioactivity is measured using a liquid scintillation counter such as one manufactured by Beckmann.

(2) Prophylactic and Therapeutic Agent for G Protein-coupled Receptor Protein or Ligand Polypeptide Deficiency Diseases If a ligand to the G protein-coupled receptor protein is revealed via the aforementioned method (1), the ligand or the G protein-coupled receptor protein-encoding DNA can be used as a prophylactic and/or therapeutic agent for treating said G protein-coupled receptor protein or ligand polypeptide deficiency diseases depending upon the action that said ligand exerts.

For example, when there is a patient for whom the physiological action of the ligand, e.g. pituitary function modulating action, central nervous system function modulating action or pancreatic function modulating action; cannot be expected because of a descrease in the G protein-coupled receptor protein or ligand polypeptide in vivo, the amount of the G protein-coupled receptor protein or ligand polypeptide in the brain cells of said patient can be increased whereby the action of the ligand can be fully achieved by:

(a) administering the G protein-coupled receptor protein-encoding DNA to the patient to express it; or
(b) inserting the G protein-coupled receptor protein or ligand polypeptide-encoding DNA into brain cells or the like to said patient. Accordingly, the G protein-coupled receptor protein- or ligand polypeptide-encoding DNA can be used as a safe and less toxic preventive and therapeutic agent for the G protein-coupled receptor protein or ligand polypeptide deficiency diseases.

When the above-mentioned DNA is used as the above-mentioned agent, said DNA may be used alone or after inserting it into a suitable vector such as retrovirus vector, adenovirus vector, adenovirus-associated virus vector, etc. followed by subjecting the product vector to a conventional means which is the same means as using the DNA coding for the ligand polypeptide or partial peptide thereof as the pharmaceutical composition.

(3) Quantitative Determination of the G Protein-coupled Receptor Protein to the Ligand Polypeptide The ligand polypeptide that has a binding property for a G protein-coupled receptor protein or a partial peptide thereof, or a salt thereof are capable of determining quantitatively an amount of a G protein-coupled receptor protein or a partial peptide thereof, or a salt thereof in vivo with good sensitivity.

This quantitative determination may be carried out by, for example, combining with a competitive analysis. Thus, a sample to be determined is contacted with the ligand polypeptide so that the concentration of a G protein-coupled receptor protein or partial peptide thereof in said sample can be determined. In one embodiment of the quantitative determination, the protocols described in the following 1) and 2) or methods similar thereto may be used:
1) Hiroshi Irie (ed): "Radioimmunoassay" (Kodansha, Japan, 1974); and
2) Hiroshi Irie (ed): "Radioimmunoassay, Second Series" (Kodansha, Japan, 1979).

(4) Screening of Compound Changing the Binding Activity of Ligand Polypeptide, Partial Peptide Thereof or Salt Thereof (Hereinafter Sometimes Referred to Briefly as Ligand or Ligand Polypeptide) With the G Protein-coupled Receptor Protein G protein-coupled receptor proteins or partial peptide or salt thereof can be used. Alternatively, expression systems for recombinant G protein-coupled receptor proteins are constructed and receptor binding assay systems using said expression system are used. In these assay systems, it is possible to screen compounds, e.g. peptides, proteins, non-peptidic compounds, synthetic compounds, formented products, cell extracts, animal tissue extracts, etc.; or salts thereof which changes the binding activity of a ligand polypeptide with the G protein-coupled receptor protein. Such a compound includes a compound exhibiting a G protein-coupled receptor-mediated cell stimulating activity, e.g. activity of promoting or activity of inhibiting physiological reactions including liberation of arachidonic acid, liberation of acetylchloline, endocellular $Ca^{2+}$ liberation, endocellular cAMP production, endocellular cGMP production, production of inositol phosphate, changes in cell membrane potential, phosphorylation of endocellular protein,s activation of c-fos, lowering of pH, activation of G protein, cell promulgation, etc.; so-called "G protein-coupled receptor-agonist", a compound free from such a cell stimulating activity, so-called "G protein coupled receptor-antagonist", etc. The term of "change the binding activity of a ligand polypeptide" includes the both concept of the case in which the binding of ligand is inhibited and the case in which the binding of ligand is promoted.

Thus, the present invention provides a method of screening for a compound which changes the binding activity of a ligand with a G protein-coupled receptor protein or a salt thereof, characterized by comparing the following two cases:
(i) the case wherein the ligand is contacted with the G protein-coupled receptor protein or salt thereof, or a partial peptide thereof or a salt thereof; and
(ii) the case wherein the ligand is contacted with a mixture of the G protein-coupled receptor protein or salt thereof or the partial peptide or salt thereof and said test compound.

In said screening method, one characteristic feature of the present invention resides in that the amount of the ligand bonded with said G protein-coupled receptor protein or the partial peptide thereof, the cell stimulating activity of the ligand, etc. are measured in both the case where (i) the ligand polypeptide is contacted with G protein-coupled receptor proteins or partial peptide thereof and in the case where (ii) the ligand polypeptide and the test compound are contacted with the G protein-coupled receptor protein or the partial peptide thereof, respectively and then compared therebetween.

In one more specific embodiment of the present invention, the following is provided:
1) a method of screening for a compound or a salt thereof which changes the binding activity of a ligand polypeptide with a G protein-coupled receptor protein, characterized in that, when a labeled ligand polypeptide is contacted with a G protein-coupled receptor protein or a partial peptide thereof and when a labeled ligand polypeptide and a test compound are contacted with a G protein-coupled receptor protein or a partial peptide thereof, the amounts of the labeled ligand polypeptide bonded with said protein or a partial peptide thereof or a salt thereof are measured and compared;
2) a method of screening for a compound or a salt thereof which changes the binding activity of a ligand polypeptide with a G protein-coupled receptor protein, characterized in that, when a labeled ligand polypeptide is contacted with cells containing G protein-coupled receptor proteins or a membrane fraction of said cells and when a labeled ligand polypeptide and a test compound are contacted with cells containing G protein-coupled receptor proteins or a membrane fraction of said cells, the amounts of the labeled ligand polypeptide binding with said protein or a partial peptide thereof or a salt thereof are measured and compared;
3) a method of screening for a compound or a salt thereof which chances the binding activity of a ligand polypeptide with a G protein-coupled receptor protein, characterized in that, when a labeled ligand polypeptide is contacted with G protein-coupled receptor proteins expressed on the cell memberane by culturing a transformant carrying a G protein-coupled receptor protein-encoding DNA and when labeled ligand polypeptide and a test compound are contacted with G protein-coupled receptor proteins expressed on the cell membrane by culturing a transformant carrying a G protein-coupled receptor protein-encoding DNA, the amounts of the labeled ligand polypeptide binding with said G protein-coupled receptor protein are measured and compared;
4) a method of screening for a compound or a salt thereof which changes the binding of a ligand polypeptide with a G protein-coupled receptor protein, characterized in that, when a G protein-coupled receptor protein-activating compound, e.g. a ligand polypeptide of the present invention, etc. is contacted with cells containing G protein-coupled receptor proteins and when the G protein-coupled receptor protein-activating compound and a test compound are contacted with cells containing G protein-coupled receptor proteins, the resulting G protein-coupled receptor protein-mediated cell stimulting activities, e.g. activities of promoting or activities of inhibiting physiological responses including liberation of arachidonic acid, liberation of acetylcholine, endocellular $Ca^{2+}$ liberation, endocellular cAMP production, endocellular cGMP production, production of inositol phosphate, changes in cell membrane potential, phosphorylation of endocellular proteins, activation of c-fos, lowering of pH, activation of G protein, cell promulgation, etc.; are measured and compared; and
5) a method of screening for a compound or a salt thereof which changes the binding activity of a ligand polypeptide with a G protein-coupled receptor protein, characterized in that, when a G protein-coupled receptor protein-activating compound, e.g. a ligand polypeptide of the present invention, etc. is contacted with G protein-coupled receptor proteins expressed on cell membranes by culturing transformants carrying G protein-coupled receptor protein-encoding DNA and when a G protein-coupled receptor protein-activating compound and a test compound are contacted with the G protein-coupled receptor protein expressed on the cell membrane by culturing the transformant carrying the G protein-coupled receptor protein-encoding DNA, the resulting G protein-coupled receptor protein-mediated cell stimulating activities, e.g. activities of promoting or activities of inhibiting physiological responses such as liberation of arachidonic acid, liberation of acetylcholine, endocellular $Ca^{2+}$ liberation, endocellular cAMP production, endocellular cGMP production, production of inositol phosphate, changes in cell membrane potential, phosphorylation of endocellular proteins, activation of c-fos, lowering of pH, activation of G protein, and cell promulgation, etc.; are measured and compared.

The G protein-coupled receptor agonist or antagonist have to be screened by, first, obtaining a candidate compound by using G protein-coupled receptor protein-containing cells, tissues or cell membrane fractions derived from rat or the like (primary screening), then, making sure whether the candidate compound really inhibits the binding between human G protein-coupled receptor proteins and ligands (secondary screening). Other receptor proteins inevitably exist and when the cells, the tissues or the cell membrane fractions were used, they intrinsically make it difficult to screen agonists or antagonists to the desired receptor proteins. By using the human-derived G protein-coupled receptor protein, however, there is no need of effecting the primary screening, whereby it is possible to efficiently screen a compound that changes the binding activity between a ligand and a G protein-coupled receptor. Additionally, it is possible to evaluate whether the compound that is screened is a G protein-coupled receptor agonist or a G protein-coupled receptor antagonist.

Specific explanations of the screening method will be given as hereunder.

First, with respect to the G protein-coupled receptor protein used for the screening method of the present invention, any product may be used so far as it contains G protein-coupled receptor proteins or partial peptides thereof although the use of a membrane fraction of mammalian organs is preferable. However, human organs can be extremely scarce and, accordingly, G protein-coupled receptor proteins which are expressed in a large amount using a recombinant technique are suitable for the screening.

In the manufacture of the G protein-coupled receptor protein, the above-mentioned method can be used.

When the G protein-coupled receptor protein-containing cells or cell membrane fractions are used in the screening method, the above-mentioned method can be used.

In conducting the above-mentioned methods 1) to 3) for screening the compound capable of changing the binding activity of the ligand with the G protein-coupled receptor protein, a suitable G protein-coupled receptor fraction and a labeled ligand polypeptide are necessary. With respect to the G protein-coupled receptor fraction, it is preferred to use naturally occurring G protein-coupled receptors (natural type G protein-coupled receptors) or recombinant type G protein-coupled receptor fractions with the activity equivalent to that of the natural type G protein coupled. Here the term "activity equivalent to" means the same ligand binding activity, or the substantially equivalent ligand binding activity.

With respect to the labeled ligand, it is possible to use labeled ligands, labeled ligand amalogized compounds, etc. For example, ligands labeled with [$^3$H], [$^{125}$I], [$^{14}$C], [$^{35}$S], etc. and other labeled substances may be utilized.

Specifically, G protein-coupled receptor protein-containing cells or cell membrane fractions are first suspended in a buffer which is suitable for the determining method to prepare the receptor sample in conducting the screening for a compound which changes the binding activity of the ligand with the G protein-coupled receptor protein. With respect to the buffer, any buffer such as Tris-HCl buffer or phosphate buffer of pH 4–10, preferably, pH 6–8 which does not inhibit the binding of the ligand with the receptor may be used.

In addition, a surface-active agent such as CHAPS, Tween 80™ (Kao-Atlas, Japan), digitonin, deoxycholate, etc. and/or various proteins such as bovine serum albumin (BSA), gelatine, etc. may be added to the buffer with an object of decreasing the nonspecific binding. Further, a protease inhibitor such as PMSF, leupeptin, E-64 manufactured by Peptide Laboratory, Japan, pepstatin, etc. may be added with an object of inhibiting the decomposition of the receptor and the ligand by protease. A labeled ligand in a certain amount (5,000 cpm to 500,000 cpm) is added to 0.01 ml to 10 ml of said receptor solution and, at the same time, $10^{-4}$M to $10^{-10}$M of a test compound coexists. In order to determine the nonspecific binding amount (NSB), a reaction tube to which a great excessive if amount of unlabeled test compounds is added is prepared as well.

The reaction is carried out at 0–50° C., preferably at 4–37° C. for 20 minutes to 24 hours, preferably 30 minutes to three hours. After the reaction, it is filtered thorough a glass fiber filter, a filter paper, or the like, washed with a suitable amount of the same buffer and the radioactivity retained in the glass fiber filter, etc. is measured by means of a liquid scintillation counter of a gamma-counter. Supposing that the count ($B_0$–NSB) obtained by subtracting the non-specific binding amount (NSB) from the total binding amount ($B_0$) wherein an antagonizing substance is not present is set at 100%, a test compound in which the specific binding amount (B–NSB) obtained by subtracting the non-specific binding amount (NSB) from the total binding amount (B) is, for example, less than 50% may be selected as a candidate ligand to the G protein-coupled receptor protein of the present invention.

In conducting the above-mentioned methods 4) to 5) for screening the compound which changes the binding activity of the ligand with the G protein-coupled receptor protein, the G protein-coupled receptor protein-mediated cell stimulating activity, e.g. activities of promoting or activities of inhibiting physiological responses such as release of arachidonic acid, release of acetylcholine, intracellular $Ca^{2+}$ increase, intracellular cAMP production, production of inositol phosphate, changes in the cell membrane potential, phosphorylation of intracullular proteins, activation of c-fos, lowering of pH, activation of G protein and cell proliferation, etc.; may be measured by known methods or by the use of commercially available measuring kits. To be more specific, G protein-coupled receptor protein-containing cells are at first cultured in a multiwell plate or the like.

In conducting the screening, it is substituted with a suitable buffer which does not show toxicity to fresh media or cells in advance, incubated under appropriate conditions and for a specified time after adding a test compound, etc. thereto. The resultant cells are extracted or the supernatant liquid is recovered and the resulting product is determined, preferably quantitatively, by each of the methods. When it is difficult to identify the production of the indicative substance, e.g. arachidonic acid, etc. which is to be an indication for the cell stimulating activity due to the presence of decomposing enzymes contained in the cell, an assay may be carried out by adding an inhibitor against said decomposing enzyme. With respect to the activities such as an inhibitory action against cAMP production, it may be detected as an inhibitory action against the cAMP production in the cells whose fundamental production has been increased by forskolin or the like.

In conducting a screening by measuring the cell stimulating activity, cells in which a suitable G protein-coupled receptor protein is expressed are necessary. Preferred G protein-coupled receptor protein-expressing cells are naturally occurring G protein-coupled receptor protein (natural type G protein-coupled receptor protein)-containing cell lines or strains, e.g. mouse pancreatic β cell line, MIN6, etc., the above-mentioned recombinant type G protein-coupled receptor protein-expressing cell lines or strains, etc.

Examples of the test compound includes peptide, proteins, non-peptidic compounds, synthesized compounds, fermented products, cell extracts, plant extracts, animal tissue extracts, serum, blood, body fluid, etc. Those compounds may be novel or known.

A kit for screening the compound which changes the binding activity of the ligand with the G protein-coupled receptor protein or a salt thereof comprises a G protein-coupled receptor protein or a partial peptide thereof, or G protein-coupled receptor protein-containing cells or cell membrane fraction thereof.

Examples of the screening kit include as follows:

1. Reagent for Determining Ligand.

1) Buffer for Measurement and Buffer for Washing.

The product wherein 0.05% of bovine serum albumin (manufactured by Sigma) is added to Hanks' Balanced Salt Solution (manufactured by Gibco).

This may be sterilized by filtration through a membrane filter with a 0.45 μm pore size, and stored at 4° C. or may be prepared upon use.

2) Sample of G Protein-coupled Receptor Protein.

CHO cells in which a G protein-coupled receptor protein is expressed are subcultured at the rate of $5\times10^5$ cells/well in a 12-well plate and cultured at 37° C. with a 5% $CO_2$ and 95% air atmosphere for two days to prepare the sample.

3) Labeled Ligand.

The ligand which is labeled with commercially available [$^3$H], [$^{125}$I], [$^{14}$C], [$^{35}$S], etc.

The product in a state of an aqueous solution is stored at 4° C. or at −20° C. and, upon use, diluted to 1 $\mu$M with a buffer for the measurement.

4) Standard Ligand Solution.

Ligand is dissolved in PBS containing 0.1 of bovine serum albumin (manufactured by Sigma) to make 1 mM and stored at −20° C.

2. Method of the Measurement.

1) CHO cells are cultured in a 12-well tissue culture plate to express G protein-coupled receptor proteins. The G protein-coupled receptor protein-expressing CHO cells are washed with 1 ml of buffer for the measurement twice. Then 490 $\mu$l of buffer for the measurement is added to each well.

2) Five $\mu$l of a test compound solution of $10^{-3}$ to $10^{-10}$ M is added, then 5 $\mu$l of a labeled ligand is added and is made to react at room temperature for one hour. For knowing the non-specific binding amount 5 $\mu$l of the ligand of $10^{-3}$ M is added instead of the test compound.

3) The reaction solution is removed from the well, which is washed with 1 ml of buffer for the measurement three times. The labeled ligand binding with the cells is dissolved in 0.2N NaOH-1% SDS and mixed with 4 ml of a liquid scintillator A (such as manufactured by Wako Pure Chemical, Japan).

4) Radioactivity is measured using a liquid scintillation counter (e.g., one manufactured by Beckmann) and PMB (percent maximum binding) is calculated by the following equation:

$$PMB=[(B-NSB)/(B_0-NSB)]\times 100$$

PMB: Percent maximum binding
B: Value when a sample is added
NSB: Nonspecific binding
$B_0$: Maximum binding The compound or a salt thereof obtained by the screening method or by the screening kit is a compound which changes the binding activity of a ligand polypeptide with a G protein-coupled receptor protein, wherein the compound inhibits or promotes the bonding, and, more particularly, it is a compound having a cell stimulating activity mediated via a G protein-coupled receptor or a salt thereof, so-called "G protein-coupled receptor agonist" or a compound having no said stimulating activity, so-called "G protein-coupled receptor antagonist". Examples of said compound are peptides, proteins, non-peptidic compounds, synthesized compounds, fermented products, etc. and the compound may be novel or known.

Said G protein coupled receptor agonist has the same physiological action as the ligand to the G protein-coupled receptor protein has and, therefore, it is useful as a safe and less toxin pharmaceutical composition depending upon said ligand activity.

On the other hand, said G protein-coupled receptor antagonist is capable of inhibiting the physiological activity of the ligand to the G protein-coupled receptor protein and, therefore, it is useful as a safe and less toxic pharmaceutical composition for inhibiting said ligand activity.

The ligand polypeptide of the present invention relates to the pituitary function modulating action, central nervous system function modulating action or pancreatic function modulating action. Therefore, the above-mentioned agonist or antagonist can be used as a therapeutic and/or prophylactic agent for dementia such as senile dementia, cerebrovascular dementia (dementia due to cerebrovascular disorder), dementia associated with phylodegenerative retroplastic diseases (e.g. Alzheimer's disease, Parkinson's disease, Pick's disease, Huntington's disease, etc.), dementia due to infectious diseases (e.g. delayed viral infections such as Creutzfelt-Jakob disease), dementia associated with endocrine, metabolic, and toxic diseases (e.g. hypothyroidism, vitamin B12 deficiency, alcoholism, and poisoning due to various drugs, metals, or organic compounds), dementia associated with oncogenous diseases (e.g. brain tumor), dementia due to traumatic diseases (e.g. chronic subdural hematoma):, depression (melancholia), hyperkinetic (microencephalo-pathy) syndrome, disturbance of consciousness, anxiety syndrome, schizophrenia, horror, growth hormone secretory disease (e.g. gigantism, acromegalic gigantism etc.), hyperphagia, polyphagia, hypercholesterolemia, hyperglyceridemia, hyperlipemia, hyperprolactinemia, hypoglycemia, pituitarism, pituitary drawfism, diabetes (e.g. diabetic complications, diabetic nephropathy, diabetic neurophathy, diabetic retinopathy etc.), cancer (e.g. mammary cancer, lymphatic leukemia, cystic cancer, ovary cancer, prostatic cancer etc.), pancreatitis, renal disease (e.g. chromic renal failure, nephritis etc.), Turner's syndrome, neurosis, rheumatoid arthritis, spinal injury, transient brain ischemia, amyotrophic lateral sclerosis, acute myocardial infarction, spinocerebellar degeneration, bone fracture, trauma, atopic dermatitis, osteoporosis, asthma, epilepsy, infertility or oligogalactia. Furthermore, the agonist or antagonist can be also used as hypnotic-sedative, agent for improvement in postoperative nutritional status, vasopressor or depressor.

When the compound or the salt thereof obtained by the screening method or by the screening kit is used as the pharmaceutical composition, a conventional means which is the same means as using above-mentioned ligand polypeptide as the pharmaceutical composition may be applied therefor.

(5) Manufacture of Antibody or Antiserum Against the Ligand Polypeptide or the G Protein-coupled receptor Protein Antibodies, e.g. polyclonal antibody, monoclonal antibody, and antisera against the ligand polypeptide or the G protein-coupled receptor protein may be manufactured by antibody- or antiserum-manufacturing methods per se known to those of skill in the art or methods similar thereto, using the ligand polypeptide or the G protein-coupled receptor protein as antigen. For example, polyclonal antibodies can be manufactured by the method as given below.

[Preparation of a Polyclonal Antibody]

The above-mentioned polypeptide or protein as the antigen is coupled to a carrier protein. The carrier protein may for example be bovine thyroglobulin, bovine serum albumin, bovine gamma-globulin, hemocyanine, or Freund's complete adjuvant (Difco).

The coupling reaction between the antigen protein and the carrier protein can be carried out by the known procedure. The reagent for use in the coupling reaction includes but is not limited to glutaraldehyde and water-soluble carbodiimide. The suitable ratio of the antigen protein to the carrier protein is about 1:1 through about 1:10 and as to the reaction pH, satisfactory results are obtained in many cases when the reaction is carried out around neutral, particularly in the range of pH about 6–8. The reaction time is preferably about 1 to 12 hours in many cases and more preferably about 2 to 6 hours. The conjugate thus obtained is dialyzed against water at about 0 to 18° C. in the routine manner and stored frozen or optionally lyophilized and stored.

For the production of a polyclonal antibody, a warm-blooded animal is inoculated with the immunogen produced in the manner described hereinbefore. The warm-blooded animal that can be used for this purpose includes mammalian warm-blooded animals, e.g. rabbit, sheep, goat, rat, mouse, guinea pig, bovine, equine, swine, etc.; and avian species, e.g. chicken, dove, duck, goose, quail, etc. Regarding the methodology for inoculating a warm-blooded animal with the immunogen, the inoculum size of the immunogen may be just sufficient for antibody production. For example, the desired antibody can be produced in many instances by emulsifying 1 mg of the immunogen in 1 ml of saline with Freund's complete adjuvant and injecting the emulsion subcutaneously at the back and hind-limb footpad of rabbits 5 times at 4-week intervals. For harvesting the antibody produced in the warm-blooded animal, for example a rabbit, the blood is withdrawn from the auricelar vein usually during day 7 through day 12 after the last inoculation dose and centrifuged to recover an antiserum. For purification, the antiserum is generally subjected to affinity chromatography using a carrier to which each antigen peptide has been conjugated and the adsorbed fraction is recovered to provide a polyclonal antibody.

The monoclonal antibody can be produced by the following method.

[Preparation of Monoclonal Antibody]

(a) Preparation of Monoclonal Antibody-producing Cells.

The ligand polypeptide or G protein-coupled receptor protein is administered to warm-blooded animals either solely or together with carriers or diluents to the site where the production of antibody is possible by the administration. In order to potentiate the antibody productivity upon the administration, complete Freund's adjuvants or incomplete Freund's adjuvants may be administered. The administration is usually carried out once every two to six weeks and two to ten times in total. Examples of the applicable warm-blooded animals are monkeys, rabbits, dogs, guinea pigs, mice, rats, sheep, goats and chickens and the use of mice and rats is preferred.

In the preparation of the cells which produce monoclonal antibodies, an animal wherein the antibody titer is noted is selected from warm-blooded animals (e.g. mice) immunized with antigens, then spleen or lymph node is collected after two to five days from the final immunization and antibody-producing cells contained therein are fused with myeloma cells to give monoclonal antibody-producing hybridomas. Measurement of the antibody titer in antisera may, for example, be carried out by reacting a labeled ligand polypeptide or a labeled G protein-coupled receptor protein (which will be mentioned later) with the antiserum followed by measuring the binding activity of the labeling agent with the antibody. The operation for fusing may be carried out, for example, by a method of Koehler and Milstein (Nature, 256, 495, 1975), Examples of the fusion accelerator are polyethylene glycol (PEG), Sendai virus, etc. and the use of PEG is preferred.

Examples of the myeloma cells are NS-1, P3U1, SP2/0, AP-1, etc. and the use of P3U1 is preferred. The preferred fusion ratio of the numbers of antibody-producing cells used (spleen cells) to the numbers of myeloma cells is within a range of about 1:1 to 20:1. When PEG (preferably, PEG 1000 to PEG 6000) is added in a concentration of about 10–80% followed by incubating at 20–40° C. (preferably, at 30–37° C.) for one to ten minutes, an efficient cell fusion can be carried out.

Various methods may be applied for screening a hybridoma which produces anti-ligand polypeptide antibody or anti-G protein-coupled receptor antibody. For example, a supernatant liquid of hybridoma culture is added to a solid phase (e.g. microplate) to which the ligand polypeptide antigen or the G protein-coupled receptor protein antigen is adsorbed either directly or with a carrier, then anti-immunoglobulin antibody (anti-mouse immunoglobulin antibody is used when the cells used for the cell fusion are those of mouse) which is labeled with a radioactive substance, an enzyme or the like, or protein A is added thereto and then anti-ligand polypeptide monoclonal antibodies or anti-G protein-coupled receptor monoclonal antibodies bound on the solid phase are detected; or a supernatant liquid of the hybridoma culture is added to the solid phase to which anti-immunoglobulin or protein A is adsorbed, then the ligand polypeptide or the G protein-coupled receptor labeled with a radioactive substance or an enzyme is added and anti-ligand polypeptide or anti-G protein-coupled receptor monoclonal antibodies bonded with the solid phase is detected.

Selection and cloning of the anti-ligand polypeptide monoclonal antibody- or the anti-G protein-coupled receptor monoclonal antibody-producing hybridoma may be carried out by methods per se known to those of skill in the art or methods similar thereto. Usually, it is carried out in a medium for animal cells, containing HAT (hypoxanthine, aminopterin and thymidine). With respect to a medium for the selection, for the cloning and for the growth, any medium may be used so far as hybridoma is able to grow therein. Examples of the medium are an RPMI 1640 medium (Dainippon Pharmaceutical Co., Ltd., Japan) containing 1–20% (preferably 10–20%) of fetal calf serum (FCS), a GIT medium (Wako Pure Chemical, Japan) containing 1–20% of fetal calf serum and a serum-free medium for hybridoma culturing (SFM-101; Nissui Seiyaku, Japan). The culturing temperature is usually 20–40° C. and, preferably, about 37° C. The culturing time is usually from five days to three weeks and, preferably, one to two weeks. The culturing is usually carried out in 5% carbon dioxide gas. The antibody titer of the supernatant liquid of the hybridoma culture may be measured by the same manner as in the above-mentioned measurement of the antibody titer of the anti-ligand polypeptide or the anti-G protein-coupled receptor in the antiserum.

(b) Purification of the Monoclonal Antibody.

Like in the separation/purification of conventional polyclonal antibodies, the separation/purification of the anti-ligand polypeptide monoclonal antibody or the anti-G protein-coupled receptor monoclonal antibody may be carried out by methods for separating/purifying immunoglobulin such as salting-out, precipitation with an alcohol, isoelectric precipitation, electrophoresis, adsorption/deadsorption using ion exchangers such as DEAE, ultracentrifugation, gel filtration, specific purifying methods in which only an antibody is collected by treatment with an active adsorbent such as an antigen-binding solid phase, protein A or protein G and the bond is dissociated whereupon the antibody is obtained.

The ligand polypeptide antibody or the G protein-coupled receptor antibody which is manufactured by the aforementioned method (a) or (b) is capable of specifically recognizing ligand polypeptide or G protein-coupled receptors and, accordingly, it can be used for a quantitative determination of the ligand polypeptide or the G protein-coupled receptor in test liquid samples and particularly for a quantitative determination by sandwich immunoassays.

Thus, the present invention provides, for example, the following methods:

(i) a quantitative determination of a ligand polypeptide or a G protein-coupled receptor in a test liquid sample, which comprises
 (a) competitively reacting the test liquid sample and a labeled ligand polypeptide or a labeled G protein-coupled receptor with an antibody which reacts with the ligand polypeptide or the G protein-coupled receptor, and
 (b) measuring the ratio of the labeled ligand polypeptide or the labeled G protein-coupled receptor binding with said antibody; and (ii) a quantitative determination of a ligand polypeptide or a G protein-coupled receptor in a test liquid sample, which comprises
 (a) reacting the test liquid sample with an antibody immobilized on an insoluble carrier and a labeled antibody simultaneously or continuously, and
 (b) measuring the activity of the labelling agent on the insoluble carrier wherein one antibody is capable of recognizing the N-terminal region of the ligand polypeptide or the G protein-coupled receptor while another antibody is capable of recognizing the C-terminal region of the ligand polypeptide or the G protein-coupled receptor.

When the monoclonal antibody of the present invention recognizing a ligand polypeptide or G protein-coupled receptor (hereinafter, may be referred to as "anti-ligand polypeptide or anti-G protein-coupled receptor antibody") is used, ligand polypeptide or G protein-coupled receptors can be measured and, moreover, can be detected by means of a tissue staining, etc. as well. For such an object, antibody molecules per se may be used or $F(ab')_2$, Fab' or Fab fractions of the antibody molecule may be used too. There is no particular limitation for the measuring method using the antibody of the present invention and any measuring method may be used so far as it relates to a method in which the amount of antibody, antigen or antibody-antigen complex, depending on or corresponding to the amount of antigen, e.g. the amount of ligand polypeptide or G protein-coupled receptor, etc. in the liquid sample to be measured, is detected by a chemical or a physical means and then calculated using a standard curve prepared by a standard solution containing the known amount of antigen. For example, nephrometry, competitive method, immunometric method and sanwich method are suitably used and, in terms of sensitivity and specificity, the sandwich method which will be described herein later is particularly preferred.

Examples of the labeling agent used in the measuring method using the labeling substance are radioisotopes, enzymes, fluorescent substances, luminescent substances, colloids, magnetic substances, etc. Examples of the radioisotope are $[^{125}I]$, $[^{131}I]$, $[^{3}H]$, $[^{14}C]$; preferred examples of the enzyme are those which are stable and with big specific activity, such as β-galactosidase, β-glucosidase, alkali phosphatase, peroxidase and malate dehydrogenase; examples of the fluorescent substance are fluorescamine, fluorescein isothiocyanate, etc.; and examples of the luminescent substance are luminol, luminol derivatives, luciferin, lucigenin, etc. Further, a biotin-avidin system may also be used for binding an antibody or antigen with a labeling agent.

In an insolubilization (immobilization) of antigens or antibodies, a physical adsorption may be used or a chemical binding which is usually used for insolubilization or immobilization of proteins or enzymes may be used as well. Examples of the carrier are insoluble polysaccharides such as agarose, dextran and cellulose; synthetic resins such as polystyrene, polyacrylamide and silicone; glass; etc.

In a sandwich (or two-site) method, the test liquid is made to react with an insolubilized anti-ligand polypeptide or anti-G protein-coupled receptor antibody (the first reaction), then it is made to react with a labeled anti-ligand polypeptide or a labeled anti-G protein-coupled receptor antibody (the second reaction) and the activity of the labeling agent on the insoluble carrier is measured whereupon the amount of the ligand polypeptide or the G protein-coupled receptor in the test liquid can be determined. The first reaction and the second reaction may be conducted reversely or simultaneously or they may be conducted with an interval. The type of the labeling agent and the method of insolubilization (immobilization) may be the same as those mentioned already herein. In the immunoassay by means of a sandwich method, it is not always necessary that the antibody used for the labeled antibody and the antibody for the solid phase is one type or one species but, with an object of improving the measuring sensitivity, etc., a mixture of two or more antibodies may be used too.

In the method of measuring ligand polypeptide or G protein-coupled receptors by the sandwich method of the present invention, the preferred anti-ligand polypeptide antibodies or anti-G protein-coupled receptor antibodies used for the first and the second reactions are antibodies wherein their sites binding to the ligand polypeptide or the G protein-coupled receptors are different each other. Thus, the antibodies used in the first and the second reactions are those wherein, when the antibody used in the second reaction recognizes the C-terminal region of the ligand polypeptide or the G protein-coupled receptor, then the antibody recognizing the site other than C-terminal regions, e.g. recognizing the N-terminal region, is preferably used in the first reaction.

The anti-ligand polypeptide antibody or the anti-G protein-coupled receptor antibody of the present invention may be used in a measuring system other than the sandwich method such as a competitive method, an immunometric method and a naphrometry. In a competitive method, an antigen in the test solution and a labeled antigen are made to react with an antibody in a competitive manner, then an unreacted labeled antigen (F) and a labeled antigen binding with an antibody (B) are separated (i.e. B/F separation) and the labeled amount of any of B and F is measured whereupon the amount of the antigen in the test solution is determined. With respect to a method for such a reaction, there are a liquid phase method in which a soluble antibody is used as the antibody and the B/F separation is conducted by polyethylene glycol, a second antibody to the above-mentioned antibody, etc.; and a solid phase method in which an immobilized antibody is used as the first antibody or a soluble antibody is used as the first antibody while an immobilized antibody is used as the second antibody.

In an immunometric method, an antigen in the test solution and an immobilized antigen are subjected to a competitive reaction with a certain amount of a labeled antibody followed by separating into solid and liquid phases; or the antigen in the test solution and an excess amount of labeled antibody are made to react, then a immobilized antigen is added to bind an unreacted labeled antibody with the solid phase and separated into solid and liquid phases. After that, the labeled amount of any of the phases is measured to determine the antigen amount in the test solution.

In a nephrometry, the amount of insoluble sediment which is produced as a result of the antigen-antibody reaction in a gel or in a solution is measured. Even when the antigen amount in the test solution is small and only a small amount of the sediment is obtained, a laser nephrometry wherein scattering of laser is utilized can be suitably used.

In applying each of those immunological measuring methods (immunoassays) to the measuring method of the present invention, it is not necessary to set up any special condition, operation, etc. therefor. A measuring system (assay system) for ligand polypeptide or G protein-coupled receptor may be constructed taking the technical consideration of the persons skilled in the art into consideration in the conventional conditions and operations for each of the methods. With details of those conventional technical means, a variety of reviews, reference books, etc. may be referred to. They are, for example, Hiroshi Irie (ed): "Radioimmunoassay" (Kodansha, Japan, 1974); Hiroshi Irie (ed): "Radioimmunoassay; Second Series" (Kodansha, Japan, 1979); Eiji Ishikawa et al. (ed): "Enzyme Immunoassay" (Igaku Shoin, Japan, 1978); Eiji Ishikawa et al. (ed): "Enzyme Immunoassay" (Second Edition) (Igaku Shoin, Japan, 1982); Eiji Ishikawa et al. (ed): "Enzyme Immunoassay" (Third Edition) (Igaku Shoin, Japan, 1987); "Methods in Enzymology" Vol. 70 (Immunochemical Techniques (Part A)); ibid. Vo. 73 (Immunochemical Techniques (Part B)); ibid. Vo. 74 (Immunochemical Techniques (Part C)); ibid. Vo. 84 (Immunochemical Techniques (Part D: Selected Immunoassays)); ibid. Vol. 92 (Immunochemical Techniques (Part E: Monoclonal Antibodies and General Immunoassay Methods)); ibid. Vol. 121 (Immunochemical Techniques (Part I: Hybridoma Technology and Monoclonal Antibodies)) (Academic Press); etc.

As such, the amount of ligand polypeptide or G protein-coupled receptor proteins can now be determined with a high precision using the anti-ligand polypeptide or the anti-G protein-coupled receptor antibody of the present invention.

In the specification and drawings of the present application, the abbreviations used for bases (nucleotides), amino acids and so forth are those recommended by the IUPAC-IUB Commission on Biochemical Nomenclature or those conventionally used in the art. Examples thereof are given below. Amino acids for which optical isomerism is possible are, unless otherwise specified, in the L form.
DNA: Deoxyribonucleic acid
cDNA: Complementary deoxyribonucleic acid
A: Adenine
T: Thymine
G: Guanine
C: Cytosine
RNA: Ribonucleic acid
mRNA: Messenger ribonucleic acid
dATP: Deoxyadenosine triphosphate
dTTP: Deoxythymidine triphosphate
dGTP: Deoxyguanosine triphosphate
dCTP: Deoxycytidine triphosphate
ATP: Adenosine triphosphate
EDTA: Ethylenediamine tetraacetic acid
SDS: Sodium dodecyl sulfate
EIA: Enzyme Immunoassay
  G, Gly: Glycine (or Glycyl)
  A, Ala: Alanine (or Alanyl)
  V, Val: Valine (or Valyl)
  L, Leu: Leucine (or Leucyl)
  I, Ile: Isoleucine (or Isoleucyl)
  S, Ser: Serine (or Seryl)
  T, Thr: Threonine (or Threonyl)
  C, Cys: Cysteine (or Cysteinyl)
  M, Met: Methionine (or Methionyl)
  E, Glu: Glutamic acid (or Glutamyl)
  D, Asp: Aspartic acid (or Aspartyl)
  K, Lys: Lysine (or Lysyl)
  R, Arg: Arginine (or Arginyl)
  H, His: Histidine (or Histidyl)
  F, Phe: Phenylalamine (or Phenylalanyl)
  Y, Tyr: Tyrossine (or Tyrosyl)
  W, Trp: Tryptophan (or Tryptophanyl)
  P, Pro: Proline (or Prolyl)
  N, Asn: Asparagine (or Asparaginyl)
  Q, Gln: Glutamine (or Glutaminyl)
  pGlu: Pyroglutamic acid (or Pyroglutamyl)
  Me: Methyl
  Et: Ethyl
  Bu: Butyl
  Ph: Phenyl
  TC: Thiazolidinyl-4(R)-carboxamide In this specification, substitutions, protective groups and reagents commonly used are indicated by the following abbreviations:
  BHA: benzhydrylamine
  pMBHA: p-methylbenzhydrylamine
  Tos: p-toluenesulfonyl
  CHO: formyl
  HONB: N-hydroxy-5-norbornene-2,8-dicarboxyimide
  OcHex: cyclohexyl ester
  Bzl: benzyl
  Bom: benzyloxymethyl
  Br-Z: 2-bromobenzyloxycarbonyl
  Boc: t-butoxycarbonyl
  DCM: dichloromethane
  HOBt: 1-hydroxybenztriazole
  DCC: N,N'-dicyclohexylcarbodiimide
  TFA: trifluoro acetate
  DIEA: diisopropylethylamine
  Fmoc: N-9-fluorenylmethoxycarbonyl
  DNP: dinitrophenyl
  Bum: t-butoxymethyl
  Trt: trityl Each SEQ ID NO set forth in the SEQUENCE LISTING of the specification refers to the following sequence:

[SEQ ID NO:1] is an entire amino acid sequence of the bovine pituitary-derived ligand polypeptide encoded by the cDNA included in pBOV3.

[SEQ ID NO:2] is an entire nucleotide sequence of the bovine pituitary-derived ligand polypeptide cDNA.

[SEQ ID NO:3] is an amino acid sequence of the bovine pituitary-derived ligand polypeptide which was obtained by purification and analysis of N-terminal sequence for P-3 fraction. The amino acid sequence corresponds to 23rd to 51st positions of the amino acid sequence of SEQ ID NO:1.

[SEQ ID NO:4] is an amino acid sequence of the bovine pituitary-derived ligand polypeptide which was obtained by purification and analysis of N-terminal sequence for P-2 fraction. The amino acid sequence corresponds to 34th to 52nd positions of the amino acid sequencce of SEQ ID NO:1.

[SEQ ID NO:5] is an amino acid sequence of the bovine pituitary-derived ligand polypeptide. The amino acid sequence corresponds to 23rd to 53rd positions of the amino acid sequence of SEQ ID NO:1.

[SEQ ID NO:6] is an amino acid sequence of the bovine pituitary-derived ligand polypeptide. The amino acid sequence corresponds to 23rd to 54th positions of the amino acid sequence of SEQ ID NO:1.

[SEQ ID NO:7] is an amino acid sequence of the bovine pituitary-derived ligand polypeptide. The amino acid sequence corresponds to 23rd to 55th positions of the amino acid sequence of SEQ ID NO:1.

[SEQ ID NO:8] is an amino acid sequence of the bovine pituitary-derived ligand polypeptide. The amino acid sequence corresponds to 34th to 53rd positions of the amino acid sequence of SEQ ID NO:1.

[SEQ ID NO:9] is an amino acid sequence of the bovine pituitary-derived ligand polypeptide. The amino acid sequence corresponds to 34th to 54th positions of the amino acid sequence of SEQ ID NO:1.

[SEQ ID NO:10] is an amino acid sequence of the bovine pituitary-derived ligand polypeptide. The amino acid sequence corresponds to 34th to 55th positions of the amino acid sequence of SEQ ID NO:1.

[SEQ ID NO:11] is a nucleotide sequence of DNA coding for the bovine pituitary-derived ligand polypeptide (SEQ ID NO:3).

[SEQ ID NO:12] is a nucleotide sequence of DNA coding for the bovine pituitary-derived ligand polypeptide (SEQ ID NO:4).

[SEQ ID NO:13] is a nucleotide sequence of DNA coding for the bovine pituitary-derived ligand polypeptide (SEQ ID NO:5).

[SEQ ID NO:14] is a nucleotide sequence of DNA coding for the bovine pituitary-derived ligand polypeptide (SEQ ID NO:6).

[SEQ ID NO:15] is a nucleotide sequence of DNA coding for the bovine pituitary-derived ligand polypeptide (SEQ ID NO:7).

[SEQ ID NO:16] is a nucleotide sequence of DNA coding for the bovine pituitary-derived ligand polypeptide (SEQ ID NO:8).

[SEQ ID NO:17] is a nucleotide sequence of DNA coding for the bovine pituitary derived ligand polypeptide (SEQ ID NO:9).

[SEQ ID NO:18] is a nucleotide sequence of DNA coding for the bovine pituitary-derived ligand polypeptide (SEQ ID NO:10).

[SEQ ID NO:19] is a partial amino acid sequence of the human pituitary-derived G protein-coupled receptor protein encoded by the human pituitary-derived G protein-coupled receptor protein cDNA fragment included in p19P2.

[SEQ ID NO:20] is a partial amino acid sequence of the human pituitary-derived G protein-coupled receptor protein encoded by the human pituitary-derived G protein-coupled receptor protein cDNA fragment include in p19P2.

[SEQ ID NO:21] is an entire amino acid sequence of the human pituitary-derived G protein-coupled receptor protein encoded by the human pituitary-derived G protein-coupled receptor protein cDNA include in phGR3.

[SEQ ID NO:22] is a partial amino acid sequence of the mouse pancreatic β-cell line, MIN6-derived G protein-coupled receptor protein encoded by the mouse pancreatic β-cell line, MIN6-derived G protein-coupled receptor protein cDNA fragment having a nucleotide sequence (SEQ ID NO:27), derived based upon the nucleotide sequences of the mouse pancreatic β-cell line, MIN6-derived G protein-coupled receptor protein cDNA fragments each included in pG3-2 and pG1-10.

[SEQ ID NO:23] is a partial amino acid sequence of the mouse pancreatic β-cell line, MIN6-derived G protein-coupled receptor protein encoded by p5S38.

[SEQ ID NO:24] is a nucleotide sequence of the human pituitary-derived G protein-coupled receptor protein cDNA fragment include in p19P2.

[SEQ ID NO:25] is a nucleotide sequence of the human pituitary-derived G protein-coupled receptor protein cDNA fragment include in p19P2.

[SEQ ID NO:26] is an entire nucleotide sequence of the human pituitary-derived G protein-coupled receptor protein cDNA include in phGR3.

[SEQ ID NO:27] is a nucleotide sequence of the mouse pancreatic β-cell line, MIN6-derived G protein-coupled receptor protein cDNA, derived based upon the nucleotide sequences of the mouse pancreatic β-cell line, MIN6-derived G protein-coupled receptor protein cDNA fragments each included in pG3-2 and pG1-10.

[SEQ ID NO: 28] is a nucleotide sequence of the mouse pancreatic β-cell line, MIN6-derived G protein-coupled receptor protein cDNA include in p5S38.

[SEQ ID NO:29] is a synthetic DNA primer for screening of cDNA coding for the G protein-coupled receptor protein.

[SEQ ID NO:30] is a synthetic DNA primer for screening of cDNA coding for the G protein-coupled receptor protein.

[SEQ ID NO:31] is a synthetic DNA primer for screening of cDNA coding for the G protein-coupled receptor protein.

[SEQ ID NO:32] is a synthetic DNA primer for screening of cDNA coding for the G protein-coupled receptor 20 protein.

[SEQ ID NO:33] is a synthetic DNA primer for screening of cDNA coding for the 6 protein-coupled receptor protein.

[SEQ ID NO:34] is a synthetic DNA primer for screening of cDNA coding for the G protein-coupled receptor protein.

[SEQ ID NO:35] is a synthetic DNA primer for screening of cDNA coding for the bovine pituitary-derived ligand polypeptide, wherein the primer is represented by P5-1.

[SEQ ID NO:36] is a synthetic DNA primer for screening of cDNA coding for the bovine pituitary-derived ligand polypeptide, wherein the primer is represented by P3-1.

[SEQ ID NO:37] is a synthetic DNA primer for screening of cDNA coding for the bovine pituitary-derived ligand polypeptide, wherein the primer is represented by P3-2.

[SEQ ID NO:38] is a synthetic DNA primer for screening of cDNA coding for the bovine pituitary-derived ligand polypeptide, wherein the primer is represented by PE.

[SEQ ID NO:39] is a synthetic DNA primer for screening of cDNA coding for the bovine pituitary-derived ligand polypeptide, wherein the primer is represented by PDN.

[SEQ ID NO:40] is a synthetic DNA primer for screening of cDNA coding for the bovine pituitary-derived ligand polypeptide, wherein the primer is represented by FB.

[SEQ ID NO:41] is a synthetic DNA primer for screening of cDNA coding for the bovine pituitary-derived ligand polypeptide, wherein the primer is represented by FC.

[SEQ ID NO:42] is a synthetic DNA primer for screening of cDNA coding for the bovine pituitary-derived ligand polypeptide, wherein the primer is represented by BOVF.

[SEQ ID NO:43] is a synthetic DNA primer for screening of cDNA coding for the bovine pituitary-derived ligand polypeptide, wherein the primer is represented by BOVR.

[SEQ ID NO:44] is an entire amino acid sequence of the bovine genome-derived ligand polypeptide.

[SEQ ID NO: 45] is an entire amino acid sequence of the rat type ligand polypeptide encoded by the cDNA included in pRAV3.

[SEQ ID NO:46] is an entire nucleotide sequence of the rat type ligand polypeptide cDNA.

[SEQ ID NO:47] is an amino acid sequence of the rat type ligand polypeptide. The amino acid sequence corresponds to 22nd to 52nd positions of the amino acid sequence of SEQ ID NO:45.

[SEQ ID NO:48] is an amino acid sequence of the rat type ligand polypeptide. The amino acid sequence corresponds to 22nd to 53rd positions of the amino acid sequence of SEQ ID NO:45.

[SEQ ID NO:49] is an amino acid sequence of the rat type ligand polypeptide. The amino acid sequence corresponds to 22nd to 54th positions of the amino acid sequence of SEQ ID NO:45.

[SEQ ID NO:50] is an amino acid sequence of the rat type ligand polypeptide. The amino acid sequence corresponds to 33rd to 52nd positions of the amino acid sequence of SEQ ID NO:45.

[SEQ ID NO:51] is an amino acid sequence of the rat type ligand polypeptide. The amino acid sequence corresponds to 33rd to 53rd positions of the amino acid sequence of SEQ ID NO:45.

[SEQ ID NO:52] is an amino acid sequence of the rat type ligand polypeptide. The amino acid sequence corresponds to 33rd to 54th positions of the amino acid sequence of SEQ ID NO.45.

[SEQ ID NO:53] is a nucleotide sequence encoding for the rat type ligand polypeptide of SEQ ID NO:47.

[SEQ ID NO:54] is a nucleotide sequence encoding for the rat type ligand polypeptide of SEQ ID NO:48.

[SEQ ID NO:55] is a nucleotide sequence encoding for the rat type ligand polypeptide of SEQ ID NO:49.

[SEQ ID NO:56] is a nucleotide sequence encoding for the rat type ligand polypeptide of SEQ ID NO:50.

[SEQ ID NO:57] is a nucleotide sequence encoding for the rat type ligand polypeptide of SEQ ID NO:51.

[SEQ ID NO:58] is a nucleotide sequence encoding for the rat type ligand polypeptide of SEQ ID NO:52.

[SEQ ID NO:59] is an entire amino acid sequence of the human type ligand polypeptide encoded by the cDNA included in pHOB7.

[SEQ ID NO:60] is an entire nucleotide sequence of the human type ligand polypeptide cDNA.

[SEQ ID NO:61] is an amino acid sequence of the human type ligand polypeptide. The amino acid sequence corresponds to 23rd to 53rd positions of the amino acid sequence of SEQ ID NO.59.

[SEQ ID NO:62] is an amino acid sequence of the human type ligand polypeptide. The amino acid sequence corresponds to 23rd to 54th positions of the amino acid sequence of SEQ ID NO.59.

[SEQ ID NO:63] is an amino acid sequence of the human type ligand polypeptide. The amino acid sequence corresponds to 23rd to 55th positions of the amino acid sequence of SEQ ID NO.59.

[SEQ ID NO:64] is an amino acid sequence of the human type ligand polypeptide. The amino acid sequence corresponds to 34th to 53rd positions of the amino acid sequence of SEQ ID NO.59.

[SEQ ID NO:65] is an amino acid sequence of the human type ligand polypeptide. The amino acid sequence corresponds to 34th to 54th positions of the amino acid sequence of SEQ ID NO.59.

[SEQ ID NO:66] is an amino acid sequence of the human type ligand polypeptide. The amino acid sequence corresponds to 34th to 55th positions of the amino acid sequence of SEQ ID NO.59.

[SEQ ID NO:67] is a nucleotide sequence encoding for the human type ligand polypeptide of SEQ ID NO:61.

[SEQ ID NO:68] is a nucleotide sequence encoding for the human type ligand polypeptide of SEQ ID NO:62.

[SEQ ID NO:69] is a nucleotide sequence encoding for the human type ligand polypeptide of SEQ ID NO:63.

[SEQ ID NO:70] is a nucleotide sequence encoding for the human type ligand polypeptide of SEQ ID NO:64.

[SEQ ID NO:71] is a nucleotide sequence encoding for the human type ligand polypeptide of SEQ ID NO:65.

[SEQ ID NO:72] is a nucleotide sequence encoding for the human type ligand polypeptide of SEQ ID NO:66.

[SEQ ID NO:73] is a partial amino acid sequence of the ligand polypeptide, wherein Xaa of the 10th position is Ala or Thr, Xaa of the 11th position is Gly or Ser and Xaa of the 21st position is H, Gly or GlyArg.

[SEQ ID NO:74] is a partial amino acid sequence of the ligand polypeptide, wherein Xaa of the 3rd position is Ala or Thr, Xaa of the 5th position is Gln or Arg and Xaa of the 10th position is Ile or Thr.

[SEQ ID NO:75] is a synthetic DNA primer for screening of cDNA coding for the rat type ligand polypeptide, wherein the primer is represented by RA.

[SEQ ID NO:76] is a synthetic DNA primer for screening of cDNA coding for the rat type ligand polypeptide, wherein the primer is represented by RC.

[SEQ ID NO:77] is a synthetic DNA primer for screening of cDNA coding for the rat type ligand polypeptide, wherein the primer is represented by rF.

[SEQ ID NO:78] is a synthetic DNA primer for screening of cDNA coding for the rat type ligand polypeptide, wherein the primer is represented by rR.

[SEQ ID NO:79] is a synthetic DNA primer for screening of cDNA coding for the human type ligand polypeptide, wherein the primer is represented by R1.

[SEQ ID NO:80] is a synthetic DNA primer for screening of cDNA coding for the human type ligand polypeptide, wherein the primer is represented by R3.

[SEQ ID NO:81] is a synthetic DNA primer for screening of cDNA coding for the human type ligand polypeptide, wherein the primer is represented by R4.

[SEQ ID NO:82] is a synthetic DNA primer for screening of cDNA coding for the human type ligand polypeptide, wherein the primer is represented by HA.

[SEQ ID NO:83] is a synthetic DNA primer for screening of cDNA coding for the human type ligand polypeptide, wherein the primer is represented by HB.

[SEQ ID NO:84] is a synthetic DNA primer for screening of cDNA coding for the human type ligand polypeptide, wherein the primer is represented by HE.

[SEQ ID NO:85] is a synthetic DNA primer for screening of cDNA coding for the human type ligand polypeptide, wherein the primer is represented by HF.

[SEQ ID NO:86] is a synthetic DNA primer for screening of cDNA coding for the human type ligand polypeptide, wherein the primer is represented by SH.

[SEQ ID NO:87] is a synthetic DNA primer for screening of cDNA coding for the human type ligand polypeptide, wherein the primer is represented by 3HN.

[SEQ ID NO:88] is a synthetic DNA primer for screening of cDNA coding for the rat type G protein-coupled receptor protein (UHR-1), wherein the primer is represented by rRECF.

[SEQ ID NO:89] is a synthetic DNA primer for screening of cDNA coding for the rat type G protein-coupled receptor protein (UHR-1), wherein the primer is represented by rRECR.
[SEQ ID NO:90] is a synthetic DNA which is used for amplification of G3PDH, UHR-1 and ligand, wherein the primer represented by r19F.
[SEQ ID NO:91] is a synthetic DNA which is used for amplification of G3PDH, UHR-1 and ligand, wherein the primer represented by r19R.
[SEQ ID NO:92] is a N-terminal peptide of the ligand polypeptide, which is used for antigen. (Peptide-I)
[SEQ ID NO:93] is a C-terminal peptide of the ligand polypeptide, which is used for antigen. (Peptide-II)
[SEQ ID NO:94] is a peptide of the central portion in ligand polypeptide, which is used for antigen. (Peptide-III)
[SEQ ID NO:95] is a synthetic DNA primer for screening of cDNA coding for rat type G protein-coupled receptor protein (UHR-1).
[SEQ ID NO:96] is a synthetic DNA primer for screening of cDNA coding for rat type G protein-coupled receptor protein (UHR-1).

The transformant *Escherichia coli*, designated INVαF'/p19P2, which is obtained in the Example 2 mentioned herein below, is on deposit under the terms of the Budapest Treaty from Aug. 9, 1994, with the National Institute of Bioscience and Human-Technology (NIBH), Agency of Industrial Science and Technology, Ministry of International Trade and Industry, Japan and has been assigned the Accession Number FERM BP-4776. It is also on deposit from Aug. 22, 1994 with the Institute for Fermentation, Osaka, Japan (IFO) and has been assigned the Accession Number IFO 15739.

The transformant *Escherichia coli*, designated INVαF'/pG3-2, which is obtained in the Example 4 mentioned herein below, is on deposit under the terms of the Budapest Treaty from Aug. 9, 1994, with NIBH and has been assigned the Accession Number FERM BP-4775. It is also on deposit from Aug. 22, 1994 with IFO and has been assigned the Accession Number IFO 15740.

The transformant *Escherichia coli*, designated JM109/phGR3, which is obtained in the Example 5 mentioned herein below, is on deposit under the terms of the Budapest Treaty from Sep. 27, 1994, with NIBH and has been assigned the Accession Number FERM BP-4807. It is also on deposit from Sep. 22, 1994 with IFO and has been assigned the Accession Number IFO 15748.

The transformant *Escherichia coli*, designated JM109/p5S38, which is obtained in the Example 8 mentioned herein below, is on deposit under the terms of the Budapest Treaty from Oct. 27, 1994, with NIBH and has been assigned the Accession Number FERM BP-4856. It is also on deposit from Oct. 25, 1994 with IFO and has been assigned the Accession Number IFO 15754.

The transformant *Escherichia coli*, designated JM109/pBOV3, which is obtained in the Example 20 mentioned herein below, is on deposit under the terms of the Budapest Treaty from Feb. 13, 1996, with NIBH and has been assigned the Accession Number FERM BP-5391. It is also on deposit from Jan. 25, 1996 with IFO and has been assigned the Accession Number IFO 15910.

The transformant *Escherichia coli*, designated JM109/pRAV3, which is obtained in the Example 29 mentioned herein below, is on deposit under the terms of the Budapest Treaty from Sep. 12, 1996, with NIBH and has been assigned the Accession Number FERM BP-5665. It is also on deposit from Sep. 3, 1996 with IFO and has been assigned the Accession Number IFO 16012.

The transformant *Escherichia coli*, designated JM109/pHOV7, which is obtained in the Example 32 mentioned herein below, is on deposit under the terms of the Budapest Treaty from Sep. 12, 1996, with NIBH and has been assigned the Accession Number FERM BP-5666. It is also on deposit from Sep. 5, 1996 with IFO and has been assigned the Accession Number IFO 16013.

[Industrial Application]

The bioactive substance the of the present invention, namely the ligand polypeptide or its amide or ester thereof, or a salt thereof, a partial peptide thereof, or the DNA coding for said ligand polypeptide, has function modulating activity for various tissues or internal organs, e.g. heart, lung, liver, spleen, thymus, kidney, adrenal glands, skeletal muscle, testis etc., besides pituitary, central nervous system or pancreas, and are useful as medicines. Furthermore, the substance is useful for the screening of agonists or antagonists of G protein-coupled receptor proteins. The compounds which can be obtained by such screening also have function modulating activity for above-described tissues or internal organs, and are useful as medicines.

EXAMPLES

Described below are working examples of the present invention which are provided only for illustrative purposes, and not to limit the scope of the present invention.

Reference Example 1

Preparation of Synthetic DNA Primer for Amplifying DNA Coding for G Protein-coupled Receptor Protein A compariton of deoxyribonucleotide sequences coding for the known amino acid sequences corresponding to or near the first membrane-spanning domain each of human-derived TRH receptor protein (HTRHR), human-derived RANTES receptor protein (L10918, HUMRANTES), human Burkitt's lymphoma-derived unknown ligand receptor protein (X68149, HSBLR1A), human-derived somatostatin receptor protein (L14856, HUMSOMAT), rat-derived µ-opioid receptor protein (U02083, RNU02083), rat-derived κ-opioid receptor protein (U00442, U00442), human-derived neuromedin B receptor protein (M73482, HUMNMBR), human-derived muscarinic acetylcholine receptor protein (U015266, HSHM4), rat-derived adrenaline α$_1$B receptor protein (L08609, RATAADRE01), human-derived somatostatin 3 receptor protein (M96738, HUMSSTR3X), human-derived C$_5$a receptor protein (HUMC5AAR), human-derived unknown ligand receptor protein (HUMRDC1A), human-derived unknown ligand receptor protein (M84605, HUMOPIODRE) and rat-derived adrenaline α$_2$B receptor protein (M91466, RATA2BAR) was made. As a result, highly homologous regions or parts were found.

Further, a comparison of deoxynucleotide sequences coding for the known amino acid sequences corresponding to or near the sixth membrane-spanning domain each of mouse-derived unknown ligand receptor protein (M80481, MUSGIR), human-derived bombesin receptor protein (L08893, HUMBOMB3S), human-derived adenosine A2 receptor protein (546950, S46950), mouse-derived unknown ligand receptor protein (D21061, MUSGPCR), mouse-derived TRH receptor protein (S43387, S43387), rat-derived neuromedin K receptor protein (J05189, RATNEURA), rat-derived adenosine A1 receptor proteirl (M69045, RATA1ARA), human-derived neurokinin A receptor protein (M57414, HUMNEKAR), rat-derived adenosine A3 receptor protein (M94152, DATADENREC), human-derived somatostatin 1 receptor protein (M81829, HUMSRI1A), human-derived neurokinin 3 receptor protein (S86390, S86371S4), rat-derived unknown ligand receptor protein. (X61496, RNCGPCR), human-derived somatostatin 4 receptor protein (L07061, HUMSSTR4Z) and rat-derived GnRH receptor protein (M31670, RATGNRHA) was made. As a result, highly homologous regions or parts were found.

The aforementioned abbreviations in the parentheses are identifiers (reference numbers) which are indicated when GenBank/EMBL Data Bank is retrieved by using DNASIS Gene/Protein Sequencing Data Base (CD019, Hitachi Software Engineering, Japan) and are usually called "Accession Numbers" or "Entry Names". HTRHR is, however, the sequence as disclosed in Japanese Patent Publication No. 304797/1993 (EPA 638645).

Specifically, it was planned to incorporate mixed bases relying upon the base regions that were in agreement with cDNAs coding for a large number of receptor proteins in order to enhance base agreement of sequences with as many receptor cDNAs as possible even in other regions. Based upon these sequences, the degenerate synthetic DNA having a nucleotide sequence represented by SEQ ID NO:29 or SEQ ID NO:30 which is complementary to the homologous nucleotide sequence were produced.

[Synthetic DNAs]

5'-CGTGG (G or C) C (A or C) T (G or C) (G or C) TGGGCAAC (A, G, C or T) (C or T) CCTG-3' (SEQ ID NO:29)

5'-GT (A, G, C or T) G (A or T) (A or G) (A or G) GGCA (A, G, C or T) CCAGCAGA (G or T) GGCAAA-3' (SEQ ID NO:30)

The parentheses indicate the incorporation of a plurality of bases, leading to multiple oligonucleotides in the primer preparation. In other words, nucleotide resides in parentheses of the aforementioned DNAs were incorporated in the presence of a mixture of plural bases at the time of synthesis.

Example 1

Amplification of Receptor cDNA by PCR Using Human Pituitary Gland-derived cDNA

By using human pituitary gland-derived cDNA (QuickClone, CLONTECH Laboratories, Inc.) as a template, PCR amplification using the DNA primers synthesized in Reference Example 1 was carried out. The composition of the reaction solution consisted of the synthetic DNA primers (SEQ: 5' primer sequence and 3' primer sequence) each in an amount of 1 µM, 1 ng of the template cDNA, 0.25 mM dNTPs, 1 µl of Taq DNA polymerase and a buffer attached to the enzyme kit, and the total amount of the reaction solution was made to be 100 µl. The cycle for amplification including 95° C. for 1 min., 55° C. for 1 min. and 72° C. for 1 min. was repeated 30 times by using a Thermal Cycler (Perkin-Elmer Co.). Prior to adding Taq DNA polymerase, the remaining reaction solution was mixed and was heated at 95° C. for 5 minutes and at 65° C. for 5 minutes. The amplified products were confirmed relying upon 1.2% agarose gel electrophoresis and ethidium bromide staining.

Example 2

Subcloning of PCR Product Into Plasmid Vector and Selection of Novel Receptor Candidate Clone via Decoding Nucleotide Sequence of Inserted cDNA Region The PCR products were separated by using a 0.8% low-melting temperature agarose gel, the band parts were excised from the gel with a razor blade, and were heat-melted, extracted with phenol and precipitated in ethanol to recover DNAs. According to the protocol attached to a TA Cloning Kit (Invitrogen Co.), the recovered DNAs were subcloned into the plasmid vector, pCR™II (™ represents registered trademark). The recombinant vectors were introduced into E. coli INVαF' competent cells (Invitrogen Co.) to produce transformants. Then, transformant clones having a cDNA-inserted fragment were selected in an LB agar culture medium containing ampicillin and X-gal. Only transformant clones exhibiting white color were picked with a sterilized toothstick to obtain transformant *Escherichia coli* INVαF'/p19P2.

The individual clones were cultured overnight in an LB culture medium containing ampicillin and treated with an automatic plasmid extracting machine (Kurabo Co., Japan) to prepare plasmid DNAs. An aliquot of the DNA thus prepared was cut by EcoRI to confirm the size of the cDNA fragment that was inserted. An aliquot of the remaining DNA was further processed with RNase, extracted with phenol/chloroform, and precipitated in ethanol so as to be condensed. Sequencing was carried out by using a DyeDeoxy terminator cycle sequencing kit (ABI Co.), the DNAs were decoded by using a fluorescent automatic sequencer, and the data of the nucleotide sequences obtained were read by using DNASIS (Hitachi System Engineering Co., Japan). The underlined portions represent regions corresponding to the synthetic primers.

Homology retrieval was carried out based upon the determined nucleotide sequences [SEQ ID NO:24 and 25 (Here, the determined nucleotide sequence is the nucleotide sequence which the underlined portion is deleted from the sequence of FIG. 1 or FIG. 2 respectively)].

As a result, it was learned that a novel G protein-coupled receptor protein was encoded by the cDNA fragment insert in the plasmid, p19P2, possessed by the transformant *Escherichia coli* INVαF'/p19P2. To further confirm this fact, by using DNASIS (Hitachi System Engineering Co., Japan) the nucleotide sequences were converted into amino acid sequences [SEQ ID NO:19 and 20], and homology retrieval was carried out in view of hydrophobicity plotting [FIGS. 3 and 4] and at the amino acid sequence level to find homology relative to neuropeptide Y receptor proteins [FIG. 5].

Example 3

Preparation of Poly(A)+ RNA Fraction From Mouse Pancreatic β-Cell Strain, MIN6 and Synthesis of cDNA A total RNA was prepared from the mouse pancreatic β-cell strain, MIN6 (Jun-ichi Miyazaki et al., Endocrinology, Vol. 127, No. 1, p.126–132) according to the guanidine thiocyanate method (Kaplan B. B. et al., Biochem. J., 183, 181–184 (1979) and, then, poly(A)+ RNA fractions were prepared with a mRNA purifying kit (Pharmacia Co.). Next, to 5 µg of the poly(A)+ RNA fraction was added a random DNA hexamer (BRL Co.) as a primer, and the resulting mixture was subjected to reaction with mouse Moloney Leukemia virus (MMLV) reverse transcriptase (BRL Co.) in the buffer attached to the MMLV reverse transcriptase kit to synthesize complementary DNAs. The reaction product was extracted with phenol/chloroform (1:1), precipitated in ethanol, and was then dissolved in 30 µl of TE buffer (10 mM Tris-HCL at pH8.0, 1 mM EDTA at pH8.0).

Example 4

Amplification of Receptor cDNA by PCR Using MIN6-Derived cDNA and Sequencing

By suing, as a template, 5 µl of cDNA prepared from the mouse pancreatic β-cell strain, MIN6 in the above Example 3, PCR amplification using the DNA primers synthesized in Reference Example 1 was carried out under the same condition as in Example 1. The resulting PCR product was subcloned into the plasmid vector, pCR™II, in the same manner as in Example 2 to obtain a plasmid, pG3-2. The plasmid pG3-2 was transfected into E. coli INVαF' to obtain transformed Escherichia coli INVαF'/pG3-2.

By using, as a template, 5 μl of the cDNA prepared from the mouse pancreatic β-cell strain, MIN6, PCR amplification using DNA primers as disclosed in Libert F. et al., "Science, 244:569–572, 1989", i.e., a degenerate synthetic primer represented by the following sequence:

5'-CTGTG (C or T) G (C or T) (G or C) AT (C or T) GCIIT (G or T) GA (C or T) (A or C) G (G or C) CAC-3' (SEQ ID NO:31)
wherein I is inosine; and
a degenerate synthetic primer represented by the following sequence:

5'-A (G or T) G (A or T) AG (A or T) AGGGCAGC-CAGCAGAI (G or C) (A or G) (C or T) GAA-3' (SEQ ID NO:32)
wherein I is inosine,
was carried out under the same conditions as in Working Example 1. The resulting PCR product was subcloned into the plasmid vector, pCR™II, in the same manner as described in Example 2 to obtain a plasmid, pG1-10.

The reaction for determining the nucleotide sequence (sequencing) was carried out with a DyeDeoxy terminator cycle sequencing kit (ABI Co.), the DNA was decoded with the fluorescent automatic sequencer (ABI Co.), and the data of the nucleotide sequence obtained were analyzed with DNASIS (Hitachi System Engineering Co., Japan).

FIG. 6 shows a mouse pancreatic β-cell strain MIN6-derived G protein-coupled receptor protein-encoding DNA (SEQ ID NO:27) and an amino acid sequence (SEQ ID NO:22) encoded by the isolated DNA based upon the nucleotide sequences of plasmids pG3-2 and pG1-10 which are held by the transformant Escherichia coli INVαF'/pG3-2. The underlined portions represent regions corresponding to the synthetic primers.

Homology retrieval was carried out based upon the determined necleotide sequence [FIG. 6]. As a result, it was learned that a novel G protein-coupled receptor protein was encoded by the cDNA fragment obtained. To further confirm this fact, by using DNASIS (Hitachi System Engineering Co., Japan) the nucleotide sequence was converted into an amino acid sequence [FIG. 6], hydrophobicity plotting was carried out to confirm the presence of six hydrophobic regions [FIG. 8]. Upon comparing the amino acid sequence with that of p19P2 obtained in Example 2, furthermore, a high degree of homology was found as shown in [FIG. 7]. As a result, it is strongly suggested that the C protein-coupled receptor proteins encoded by pG3-2 and pG1-10 recognize the same ligand as the G protein-coupled receptor protein encoded by p19P2 does while the animal species from which the receptor proteins encoded by pG3-2 and pG1-10 are derived is different from that from which the receptor protein encoded by p19P2 is.

Example 5

Cloning of cDNA Comprising Whole Coding Regions for Receptor Protein From Human Pituitary Gland-derived cDNA Library The DNA library constructed by Clontech Co. wherein λ gt11 phage vector is used (CLONTECH Laboratories, Inc.; CLH L1139b) was employed as a human pituitary gland-derived cDNA library. The human pituitary gland cDNA library (2×10⁶ pfu (plaque forming units)) was mixed with E. coli Y1090⁻ treated with magnesium sulfate, and incubated at 37° C. for 15 minutes followed by addition of 0.5% agarose (Pharmacia Co.) LB. The E. coli was plated onto a 1.5% agar (Wako-Junyaku Co.) LB plate (containing 50 μg/ml of ampicillin). A nitrocellulose filter was placed on the plate on which plaques were formed and the plaque was transferred onto the filter. The filter was denatured with an alkali and then heated at 80° C. for 3 hours to fix DNAs.

The filter was incubated overnight at 42° C. together with the probe mentioned herein below in a buffer containing 50% formamide, 5×SSPE (20×SSPE (pH 7.4) is 3 M NaCl, 0.2 M $NaH_2PO_4 \cdot H_2O$, 25 mM EDTA), 5×Denhardt's solution (Nippon Gene, Japan), 0.1% SDS and 100 μg/ml of salmon sperm DNA for hybridization.

The probe used was obtained by cutting the DNA fragment inserted in the plasmid, p19P2, obtained in Working Example 2, with EcoRI, followed by recovery and labelling by incorporation of [³²P]dCTP (Dupont Co.) with a random prime DNA labelling kit (Aasham Co.).

It was washed with 2×SSC (20×SSC is 3 M NaCl, 0.3 M sodium citrate), 0.1% SDS at 55° C. for 1 hour and, then, subjected to an autoradiography at −80° C. to detect hybridized plaques.

In this screening, hybridization signals were recognized in three independent plaques. Each DNA was prepared from the three clones. The DNAs digested with EcoRI were subjected to an agarose electrophoresis and were analyzed by the southern blotting using the same probe as the one used in the screening. Hybridizing bands were identified at about 0.7 kb, 0.8 kb and 2.0 kb, respectively. Among them, the DNA fragment corresponding to the band at about 2.0 kb (λ hGR3) was selected. The λ hGR3-derived EcoRI fragment with a hybridizable size was subcloned to the EcoRI site of the plasmid, pUC₁8, and E. coli JM109 was transformed with the plasmid to obtain transformant E. coli JM109/phGR3. A restriction enzyme map of the plasmid, phGR3, was prepared relying upon a restriction enzyme map deduced from the nucleotide sequence as shown in Example 2. As a result, it was learned that it carried a full-length receptor protein-encoding DNA which was predicted from the receptor protein-encoding DNA as shown in Example 2.

Example 6

Sequencing of Human Pituitary Gland-derived Receptor Protein cDNA

Among the EcoRI fragments inserted in the plasmid, phGR3, obtained in the above Example 5, the from EcoRI to NheI nucleotide sequence with about 1330 bp that is considered to be a receptor protein-coding region was sequenced. Concretely speaking, by utilizing restriction enzyme sites that exist in the EcoRI fragments, unnecessary parts were removed or necessary fragments were subcloned in order to prepare template plasmids for analyzing the nucleotide sequence.

The reaction for determining the nucleotide sequence (sequencing) was carried out with a DyeDeoxy terminator cycle sequencing kit (ABI Co.), the DNA was decoded with the fluorescent automatic sequencer (ABI Co.), and the data of the nucleotide sequence obtained were analyzed with DNASIS (Hitachi System Engineering Co., Japan).

FIG. 9 shows a nucleotide sequence of from immediate after the EcoRI site up to the NheI site encoded by phGR3.

The nucleotide sequence of the human pituitary gland-derived receptor protein-encoding DNA corresponds to the nucleotide sequence (SEQ ID NO:26) of from 118th to 1227th nucleotides [FIG. 9]. An amino acid sequence of the receptor protein that is encoded by the nucleotide sequence is shown in SEQ ID NO:21.

Example 7

Northern Hybridization With Human Pituitary Gland-derived Receptor Protein-encoding phGR3

Northern blotting was carried out in order to detect the expression of phGR3-encoded human pituitary gland-derived receptor proteins obtained in Example 5 in the pituitary gland at a mRNA level. Human pituitary gland mRNA (2.5 µg, Clontech Co.) was used as a template mRNA and the same as the probe used in Working Example 5 was used as a probe. Nylon membrane (Pall Biodyne, U.S.A.) was used as a filter for northern blotting and migration of the mRNA and adsorption (sucking) thereof with the blotting filter was carried out according to the method as disclosed in Molecular Cloning, Cold Spring Harbor Laboratory Press, 1989.

Figure 3:
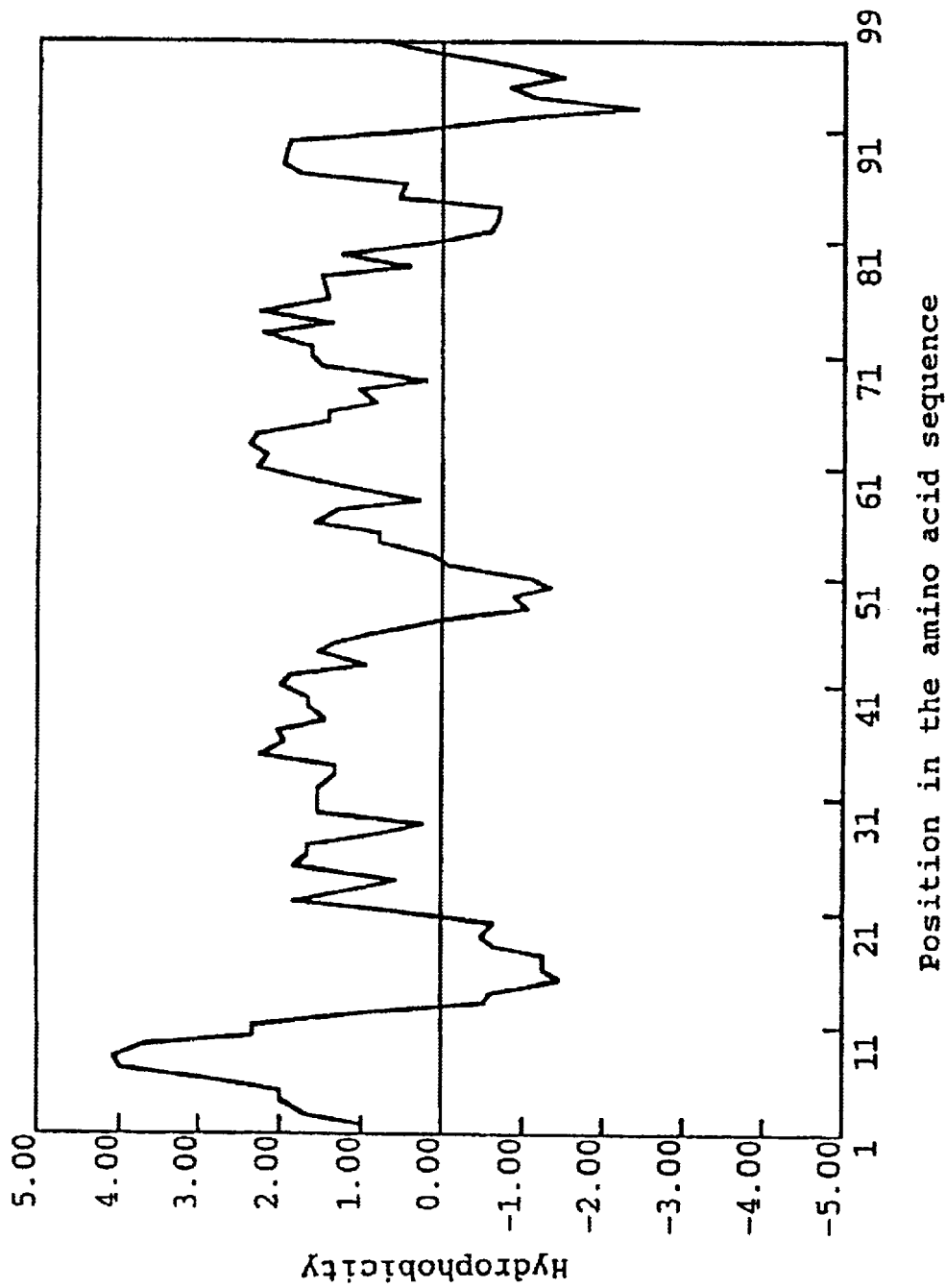
FIG. 3 shows a partial hydrophobic plot of the protein encoded by the human pituitary-derived G protein-coupled receptor protein cDNA fragment harbored in p19P2 constructed according to the amino acid sequence shown in FIG. 1.
Figure 4:
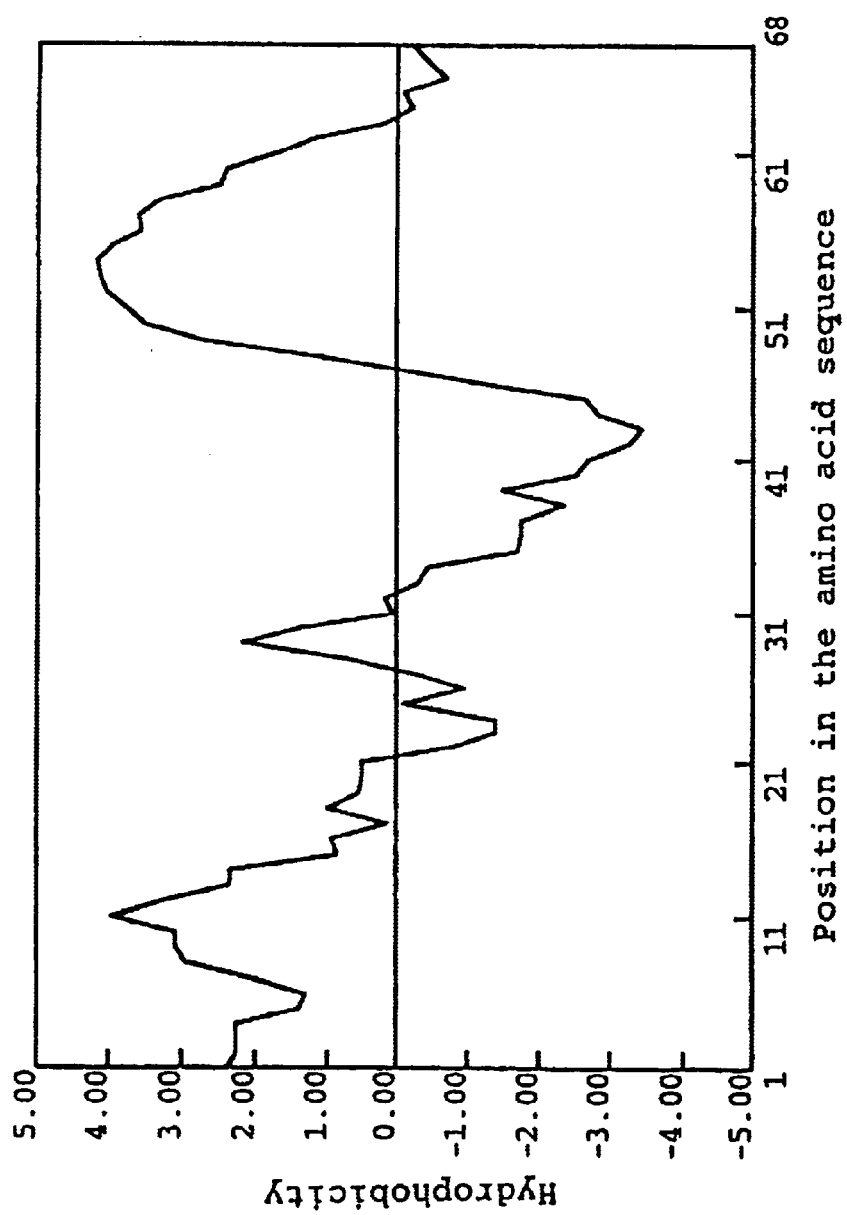
FIG. 4 shows a partial hydrophobic plot of the protein encoded by the human pituitary-derived G protein-coupled receptor protein cDNA fragment harbored in p19P2 constructed according to the amino acid sequence shown in FIG. 2.
Figure 8:
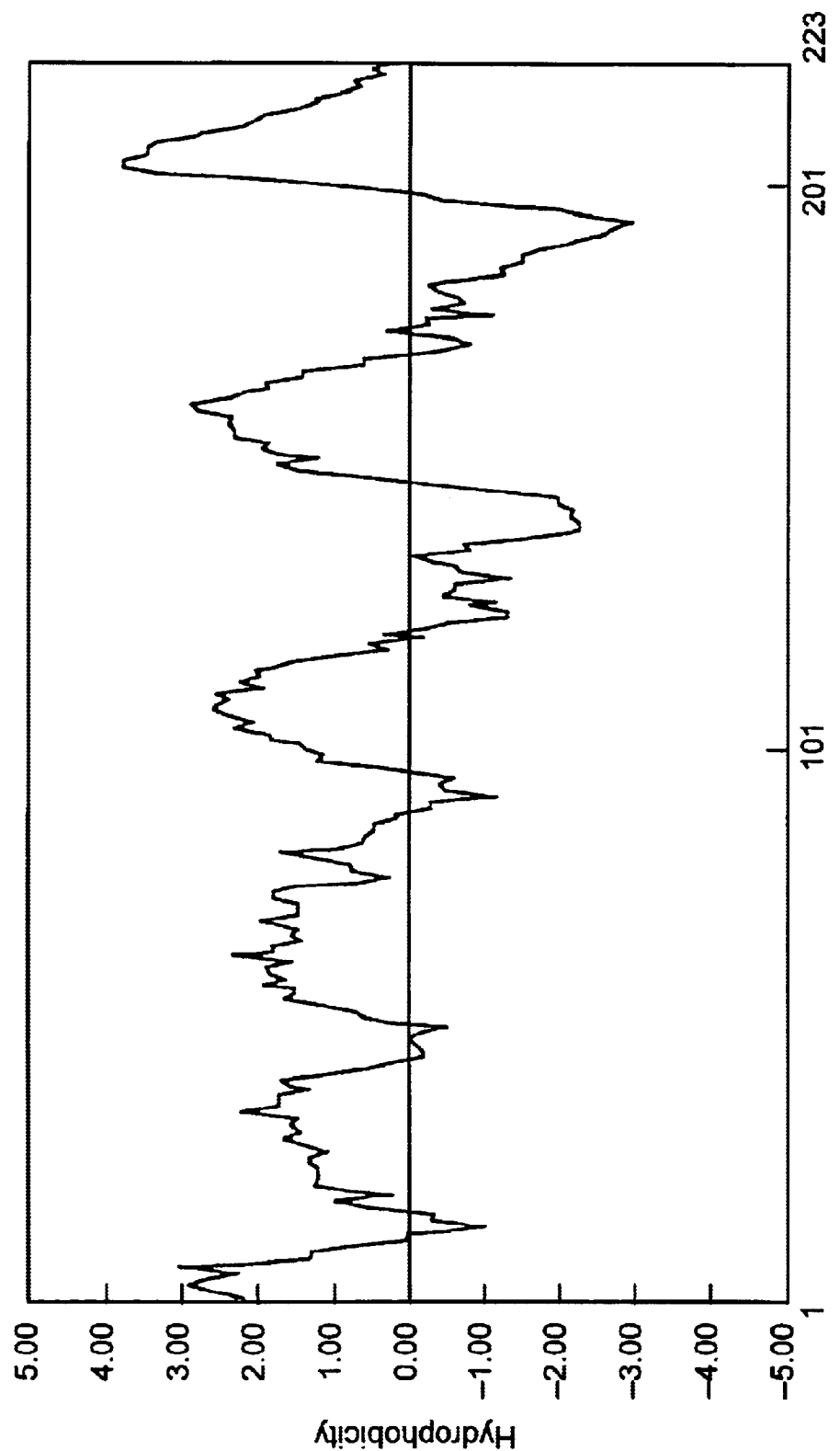
FIG. 8 is a partial hydrophobic plot of the MIN6-derived G protein-coupled receptor protein constructed according to the partial amino acid sequence shown in FIG. 6.
Figure 10:
FIG. 10 shows the result of Northern blotting of human pituitary mRNA hybridized with radioisotope-labeled human pituitary cDNA clone phGR3.
Figure 11:
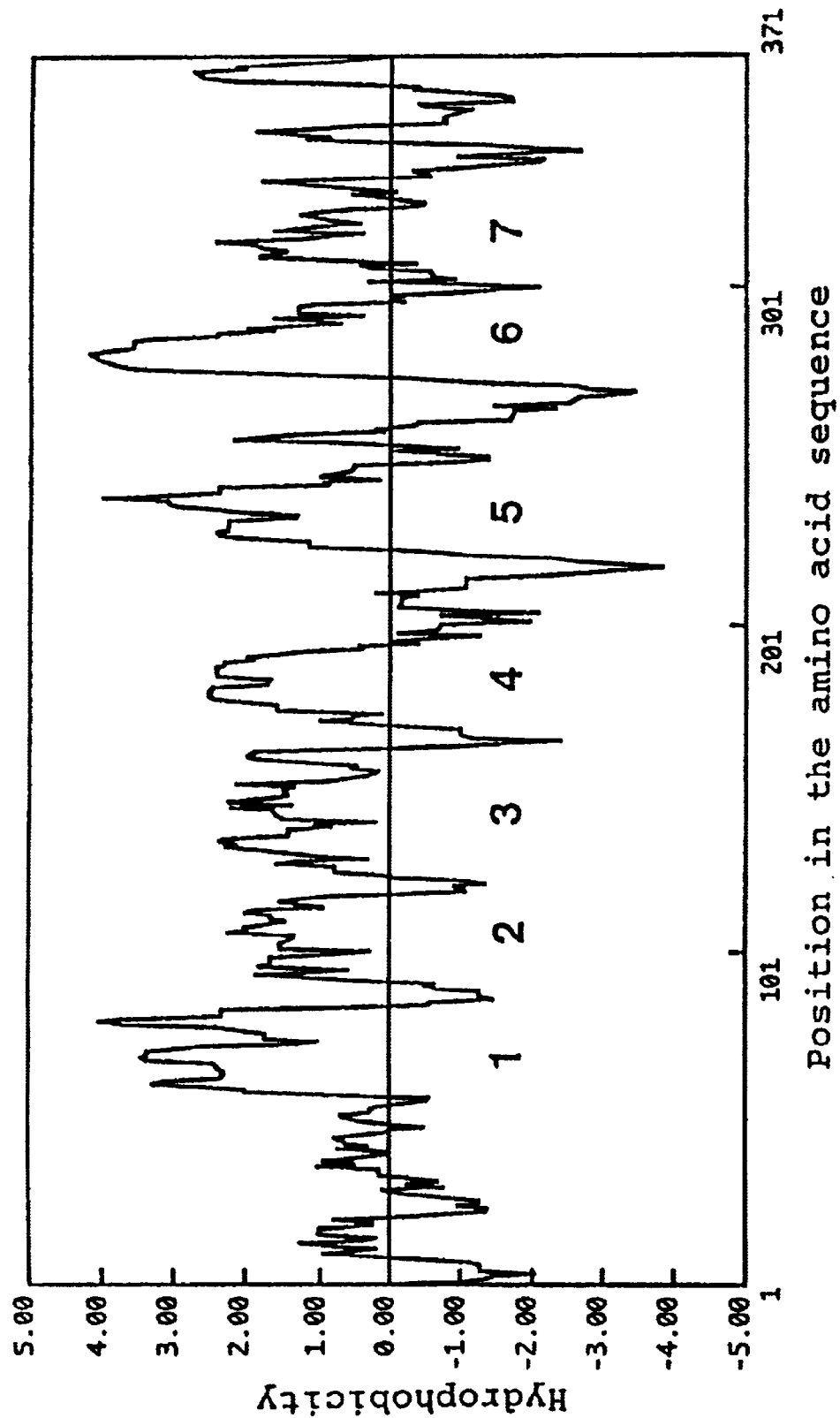
FIG. 11 shows a hydrophobic plot of the protein encoded by the human pituitary-derived G protein-coupled receptor protein cDNA harbored in the phGR3 as constructed according to the amino acid sequence shown in FIG. 9.
Figure 14:
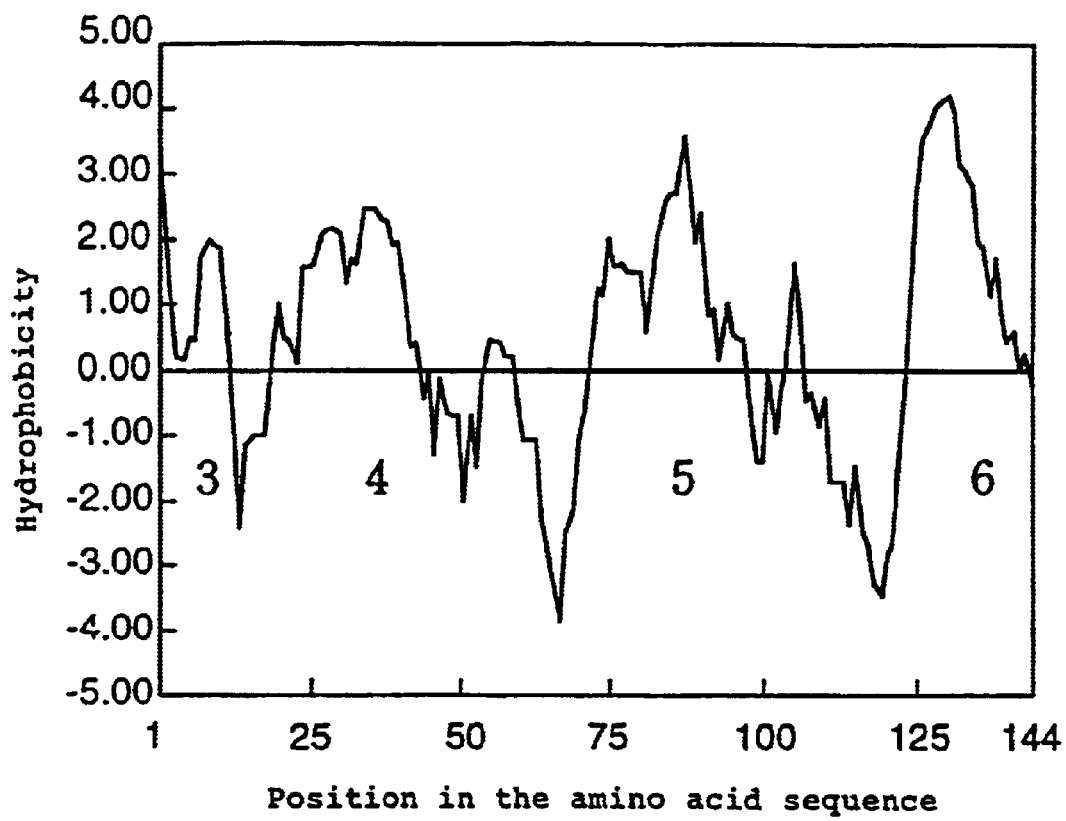
FIG. 14 shows a partial hydrophobic plot of the protein encoded by the MIN6-derived G protein-coupled receptor protein cDNA harbored in p5S38 as constructed according to the partial amino acid sequence shown in FIG. 12.

The hybridization was effected by incubating the above-mentioned filter and probe in a buffer containing 50% formamide, 5×SSPE, 5×Denhardt's solution, 0.1% SDS and 100 µg/ml of salmon sperm DNA overnight at 42° C. The filter was washed with 0.1×SSC, 0.1% SDS at 50° C. and, after drying with an air, was exposed to an X-ray film (XAR5, Kodak) for three days at −80° C. The results were as shown in FIG. 10 from which it is considered that the receptor gene encoded by phGR3 is expressed in the human pituitary gland.

Example 8

Amplification of Receptor cDNA by PCR Using MIN6-Derived cDNA and Sequencing

By using, as a template, 5 µl of cDNA prepared from the mouse pancreatic β-cell strain, MIN6 in Working Example 3, PCR amplification using the DNA primers synthesized in Example 4 as disclosed in Libert F. et al., "Science, 244:569–572, 1999", i.e., a synthetic primer represented by the following sequence:

5'-CTGTG (C or T) G (C or T) (G or C) AT (C or T) GCIIT (G or T) GA (C or T) (A or C) G (G or C) TAC-3' (SEQ ID NO:31)
wherein I is inosine; and
a synthetic primer represented by the following sequence:

5'-A (G or T) G (A or T) AG (A or T) AGGGCAGC-CAGCAGAI (G or C) (A or G) (C or T) GAA-3' (SEQ ID NO:32)
wherein I is inosine, was carried out under the same conditions as in Example 1. The resulting PCR product was subcloned to the plasmid vector, pCR™II, in the same manner as in Example 2 to obtain a plasmid, p5S38. The plasmid p5S38 was transfected into E. coli JM109 to obtain transformant Escherichia coli JM109/p5S38.

The reaction for determining the nucleotide sequence (sequencing) was carried out with a DyeDeoxy terminator cycle sequencing kit (ABI Co.), the DNA was decoded with the fluorescent automatic sequencer (ABI Co.), and the data of the nucleotide sequence obtained were read with DNASIS (Hitachi System Engineering Co., Japan).

FIG. 12 shows a mouse pancreatic β-cell strain MIN6-derived G protein-coupled receptor protein-encoding DNA (SEQ ID NO:28) and an amino acid sequence (SEQ ID NO:23) encoded by the isolated DNA based upon the nucleotide sequence of plasmid, p5S38. The underlined portions represent regions corresponding to the synthetic primers.

Homology retrieval was carried out based upon the determined nucleotide sequence [FIG. 12]. As a result, it was learned that a novel G protein-coupled receptor protein was encoded by the cDNA fragment obtained. To further confirm this fact, by using DNASIS (Hitachi System Engineering Co., Japan), the nucleotide sequence was converted into an amino acid sequence [FIG. 12], and hydrophobicity plotting was carried out to confirm the presence of four hydrophobic regions [FIG. 14]. Upon comparing the amino acid sequence with those encoded by p19P2 obtained in Example 2 and encoded by pG3-2 obtained in Example 4, furthermore, a high degree of homology was found as shown in FIG. 13. As a result, it is strongly suggested that the mouse pancreatic β-cell strain, MIN6-derived G protein-coupled receptor protein encoded by p5S38 recognizes the same ligand as the human pituitary gland-derived G protein-coupled receptor protein encoded by p19P2 does while the animal species from which the receptor protein encoded by p5S38 is derived is different from that from which the receptor protein encoded by p19P2 is. It is also strongly suggested that the mouse pancreatic β-cell strain, MIN6-derived G protein-coupled receptor protein encoded by p5S38 recognized the same ligand as the mouse pancreatic β-cell strain, MIN6-derived G protein-coupled receptor proteins encoded by pG3-2 and pG1-10 do and they are analogous receptor proteins one another (so-called "subtype").

Example 9

Preparation of CHO Cells Which Express phGR3

The plasmid phGR3 (Example 5) containing a cDNA encoding the full-length amino acid sequence of human pituitary receptor protein was digested with the restriction enzyme NcoI and electrophoresed on agarose gel and a fragment of about 1 kb was recovered. Both ends of the recovered fragment were blunted with a DNA blunting kit (Takara Shuzo Co., Japan) and, with the SalI linker added, treated with SalI and inserted into the SalI site of pUC119 to provide plasmid S10. Then, S10 was treated with SalI and SacII to prepare a fragment of about 700 bp (containing the N-terminal coding region). Then, a fragment of about 700 bp (containing the C-terminal coding region including initiation and termination codons) was cut out from phGR3 with SacII and NheI. These two fragments were added to the animal cell expression vector plasmid pAKKO-111H (the vector plasmid identical to the pAKKO1.11H described in Biochim. Biophys. Acta, Hinuma, S., et al., 1219 251–259, 1994) and a ligation reaction was carried out to construct a full-length receptor protein expression plasmid pAKKO-19P2.

E. coli transfected with pAKKO-19P2 was cultured and the pAKKO-19P2 plasmid DNA was mass-produced using QUIAGEN Maxi. A 20 µg portion of the plasmid DNA was dissolved in 1 ml of sterile PBS, and in a gene transfer vial (Wako Pure Chemical Ind.), the solution was vortexed well for riposome formation. This riposome, 125 µl, was added to CHOdhfr⁻ cells subcultured at 1×10⁶ per 10 cm-dia. dish 24 hr before and placed in fresh medium immediately before addition and overnight culture was carried out. After a further one-day culture in fresh medium, the medium was changed to a screening medium and the incubation was further carried out for a day. For efficient screening of transformants, subculture was carried out at a low cell density and only the cells growing in the screening medium were selected to establish a full-length receptor protein expression CHO cell line CHO-19P2.

Example 10

Confirmation of the Amount of Expression of the Full-length Receptor Protein in the CHO-19P2 Cell Line at the Transcription Level Using FastTrack Kit (Invitrogen), CHO cells transfected with pAKKO-19P2 according to the kit manual and mock CHO cells were used to prepare poly(A)$^+$ RNA. Using 0.02 µg of this poly(A)$^+$ RNA, a cDNA was synthesized by means of RNA PCR Kit (Takara Shuzo, Co., Japan). The kind of primer used was a random 9mer and the total volume of the reaction mixture was 40 µl. As a negative control of cDNA synthesis, a reverse transcriptase-free reaction mixture was also provided. First, the reaction mixture was incubated at 30° C. for 10 minutes to conduct an amplification reaction to some extent. Then, it was incubated at 42° C. for 30 minutes to let the reverse transcription reaction proceed. The enzyme was inactivated by heating at 99° C. for 5 minutes and the reaction system was cooled at 5° C. for 5 minutes.

After completion of the reverse transcription reaction, a portion of the reaction mixture was recovered and after dilution with distilled water, extraction was carried out with phenol/chloroform and further with diethyl ether. The extract was subjected to precipitation from ethanol and the recipitate was dissolved in a predetermined amount of distilled water for use as a cDNA sample. This cDNA solution and the plasmid DNA (pAKKO-19P2) were serially diluted and using primers specific to full-length receptor protein, PCR was carried out. The sequences of the primers prepared according to the base sequence of the coding region of the full-length receptor protein were CTGACT-TATTTTCTGGGCTGCCGC (SEQ ID NO:33) for 5' end and AACACCGACACATAGACGGTGACC (SEQ ID NO:34) for 31 end.

Figure 15:
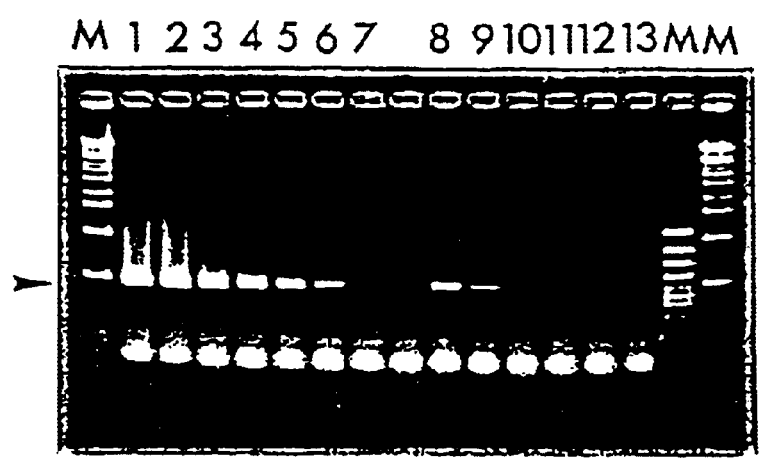
FIG. 15 shows the results of the following analysis. Thus, RT-PCR was carried out to confirm the expression of mRNA in CHO cells transfected by PAKKO-19P2. Lanes 1–7 represent the results obtained by performing PCRs using serial dilutions of pAKKO-19P2 for comparison, i.e. the 10 $\mu$l stock solution (lane 1), 1/2 dilution (lane 2), 1/4 dilution (lane 3), 1/64 dilution (Lane 4), 1/256 dilution (lane 5), 1/1024 dilution (lane 6), and 1/4096 dilution (lane 7) of the plasmid as templates, and analyzing the reaction mixtures by 1.2% agarose gel electrophoresis. Lanes 8 through 11 are the results obtained by performing PCRs using a 1/10 dilution (lane 8), a 1/100 dilution (lane 9), and a 1/1000 dilution (lane 10) of the cDNA prepared from the CHO 19P2 cell line as templates and subjecting the respective reaction mixtures to electrophoresis. Lane 11 was obtained by performing PCR using a template obtained by carrying out cDNA synthesis without reverse transcriptase and subjecting the PCR reaction product to electrophoresis. Lanes 12 and 13 were obtained by performing PCR using cDNAs prepared from mock CHO cells with and without addition of reverse transcriptase, respectively, as templates and subjecting the respective reaction products to electrophoresis. M represents the DNA size marker. The lanes at both ends were obtained by electrophoresing 1 $\mu$l of .lambda/StyI digest (Nippon Gene) and the second lane from right was obtained with 1 $\mu$l of .o slashed./.chi.174/HincII digest (Nippon Gene). The arrowmark indicates the position of the band amplified by PCR of about 400 bp.

The PCR reaction was carried out in a total volume of 100 µl using 1 µM each of the primers, 0.5 µl of Taq DNA polymerase (Takara Shuzo Co., Japan), the reaction buffer and dNTPs accompanying the enzyme, and 10 µl of template DNA (cDNA or plasmid solution). First the reaction mixture was heat-treated at 94° C. for 2 minutes for sufficient denaturation of the template DNA and subjected to 25 cycles of 95° C.×30 seconds, 65° C.×30 seconds, and 72° C.×60 seconds. After completion of the reaction, 10 µl of the reaction mixture was subjected to agarosegel electrophoresis and the detection and quantitative comparison of amplification products were carried out. As a result, a PCR product of the size (400 bp) predictable from the sequence of the cDNA coding for the full-length receptor protein was detected [FIG. 15]. In the lane of the PCR reaction mixture using the product of the reverse transcriptase-free transcription system as the template, no specific band was detected, thus extruding the possibility of its being a PCR product derived from the genomic DNA of CHO cells. Moreover, no specific band appeared in the lane of mock cells, either. Therefore, it was clear that the product was not derived from the mRNA initially expressed in CHO cells [FIG. 15].

Example 11

Detection of the Activity to Specifically Promote Release of Arachidonic Acid Metabolites From CHO-19P2 Cells in a Rat Whole Brain Extract A crude peptide fraction was prepared from rat whole brain by the following procedure. The rat whole brain enucleated immediately after sacrifice was frozen in liquefied nitrogen and stored at −80° C. The frozen rat whole brain, 20 g (the equivalent of 10 rats) was finely divided and boiled in 80 ml of distilled water for 10 minutes. After the boiled tissue was quenched on ice, 4.7 ml of acetic acid was added at a final concentration of 1.0 M and the mixture was homogenized using a Polytron (20,000 rpm, 6 min.). The homogenate was stirred overnight and then centrifuged (10,000 rpm, min.) to separate the supernatant. The sediment was homogenized in 40 ml of 1.0 M acetic acid and centrifuged again to recover the supernatant. The supernatants were pooled, diluted in 3 volumes of acetone, allowed to stand on ice for 30 minutes, and centrifuged (10,000 rpm, 20 min.) to recover the supernatant. The recovered supernatant was evaporated to remove acetone. To the resulting acetone-free concentrate was added 2 volumes of 0.05% trifluoroacetic acid(TFA)/H$_2$O and the mixture was applied to a reversed-phase C18 column (Prep C18 125 Å, Millipore). After application of the supernatant, the column was washed with 0.05% TFA/H$_2$O, and gradient elution was carried out with 10%, 20%, 30%, 40%, 50%, and 60% CH$_3$CN/0.05%TFA/H$_2$O. The fractions were respectively divided into 10 equal parts and lyophilized. The dried sample derived from one animal equivalent of rat whole brain was dissolved in 20 µl of dimethyl sulfoxide (DMSO) and suspended in 1 ml of Hank's balanced saline solution (HBSS) supplemented with 0.05% bovine serum albumin (BSA) to provide a crude peptide fraction.

Figure 16:
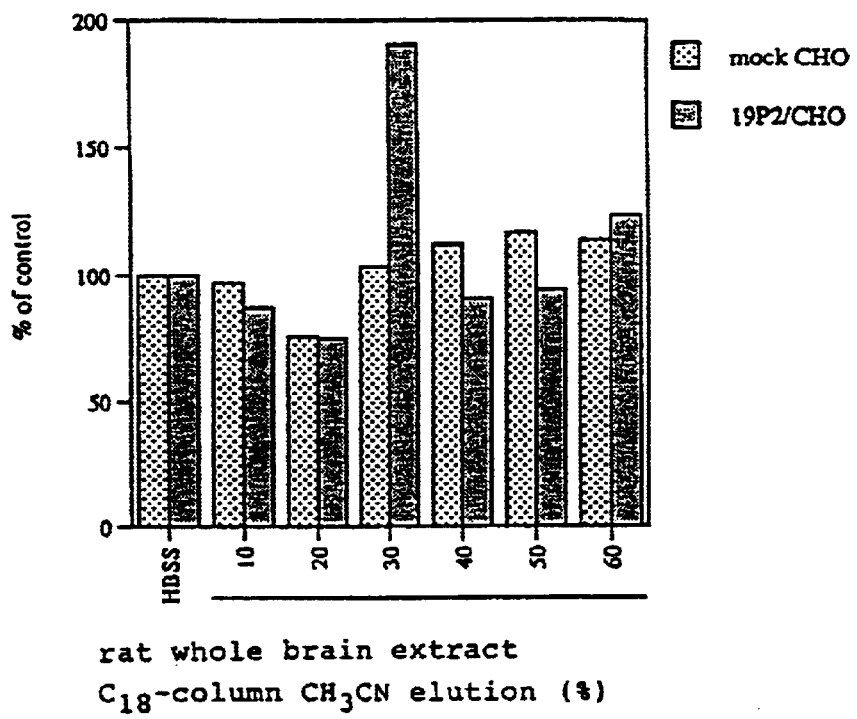
FIG. 16 shows the activity of the crude ligand peptide fraction extracted from rat whole brain to promote release of arachidonic acid metabolites from CHO-19P2 cells. The arachidonic acid metabolite releasing activity was expressed as % of the amount of [$^3$H] arachidonic acid metabolites released in the presence of the crude ligand polypeptide fraction with the amount of [$^3$H] arachidonic acid metabolites released in the presence of 0.05% BAS-HABB being taken as 100%. The activity to promote release of arachidonic acid metabolites from the CHO19P2 cell line was detected in a 30% $CH_3CN$ fraction.

The full-length receptor protein-expressed CHO cells and mock CHO cells were seeded in a 24-well plate, 0.5×10$^5$ cells/well, and cultured for 24 hours. Then, [$^3$H] arachidonic acid was added at a final concentration of 0.25 µCi/well. Sixteen (16) hours after addition of [$^3$H] arachidonic acid, the cells were rinsed with 0.05% BSA-HBSS and the above-mentioned crude peptide fraction was added, 400 µl/well. The mixture was incubated at 37° C. for 30 minutes and a 300 µl portion of the reaction mixture (400 µl) was added to 4 ml of a scintillator and the amount of [$^3$H] arachidonic acid metabolite released into the reaction mixture was determined with a scintillation counter. As a result, an arachidonic acid metabolite-releasing activity specific to the full-length receptor protein expressed CHO cells (CHO-19P2) was detected in the 30% CH$_3$CN fraction of the eluate [FIG. 16].

Example 12

Figure 17:
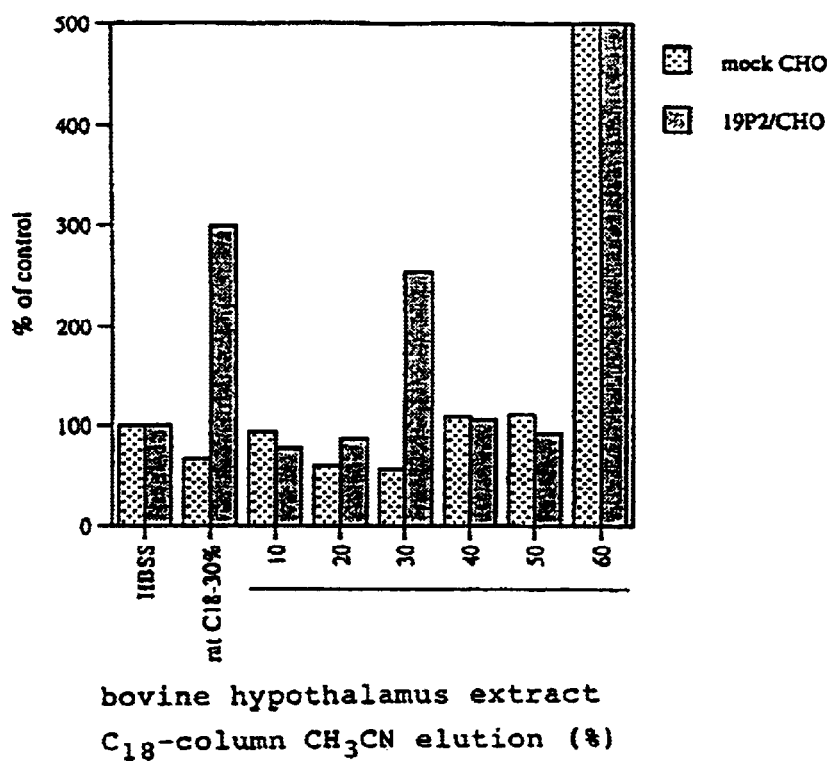
FIG. 17 shows the activity of the crude ligand polypeptide fraction extracted from bovine hypothalamus to promote release of arachidonic acid metabolites from CHO-19P2 cells. The arachidonic acid metabolite release-promoting activity was expressed as % of the amount of [$^3$H] arachidonic acid metabolites released in the presence of the crude ligand polypeptide fraction with the amount of [$^3$H] arachidonic acid metabolites released in the presence of 0.05% BAS-HABB being taken as 100%. The activity to promote release of arachidonic acid metabolites from the CHO-19P2 cell line was detected in a 30% $CH_3CN$ fraction just as in the crude ligand polypeptide fraction from rat whole brain.

Detection of the Activity to Specifically Promote Release of Arachidonic Acid Metabolites From CHO-19P2 Cells in a Bovine Hypothalamus Extract A crude peptide fraction was prepared from 360 g (the equivalent of 1 animals) of bovine brain tissue including hypothalamus in the same manner as in Example 11. A dried peptide sample per 0.05 animal was dissolved in 40 µl of DMSO and suspended in 2 ml of 0.05% BSA-HBSS and the detection of arachidonic acid metabolite-releasing activity was attempted in the same manner as in Example 11. As a result, the activity to specifically promote release of arachidonic acid metabolites from the CHO-19P2 cell line was detected in the fraction eluted with 30% CH$_3$CN from a C18 column to which the crude bovine hypothalamus peptide fraction had been applied [FIG. 17].

Example 13

Figure 18:
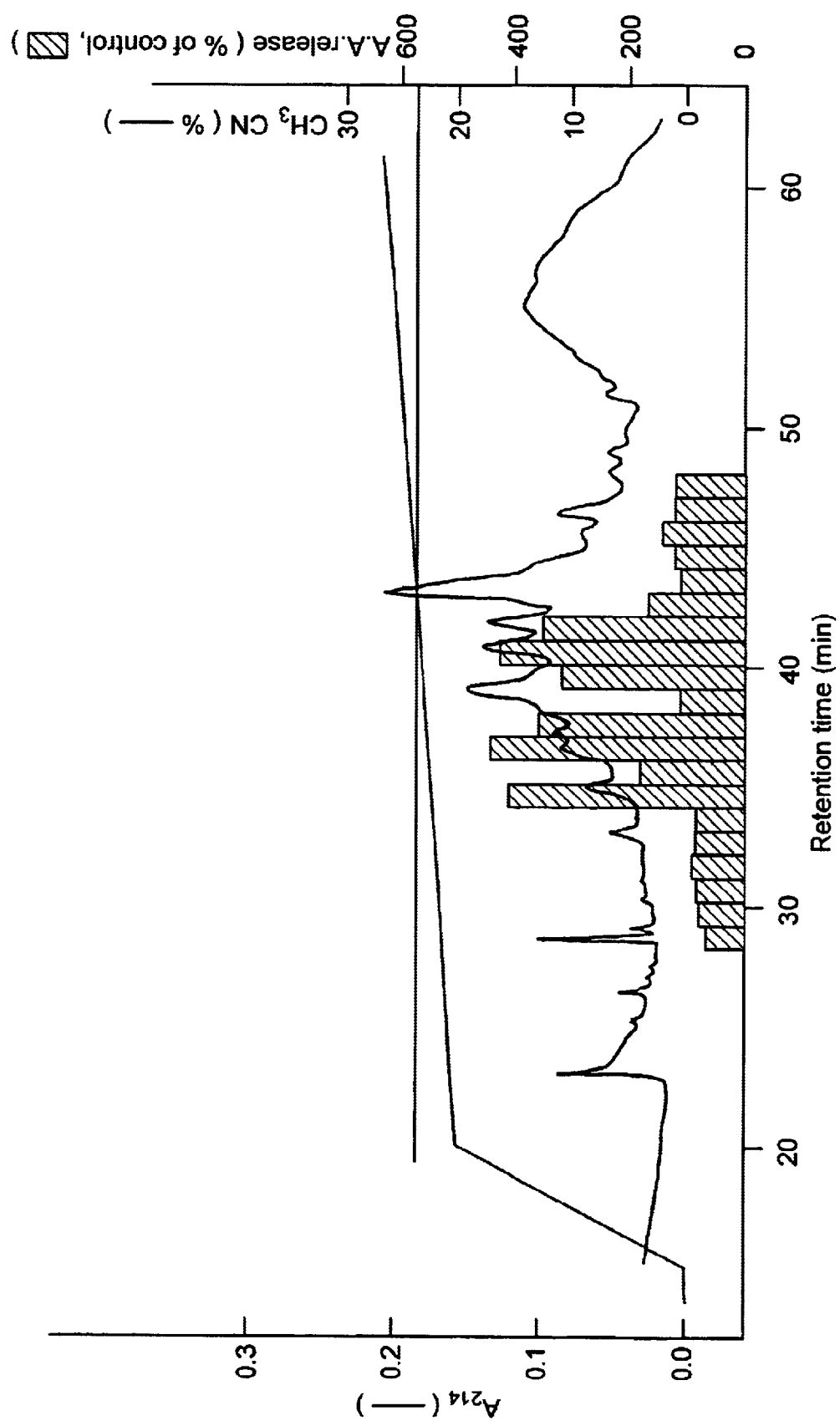
FIG. 18 shows the activity of the fraction purified with the reversed-phase column C18 218TP5415 to specifically promote release of arachidonic acid metabolites from CHO-19P2 cells. The active fraction from RESOURCE S was fractionated on C18 218TP5415. Thus, chromatography was carried out at a flow rate of 1 ml/min. on a concentration gradient of 20%–30% $CH_3CN/0.1\%$ $TFA/H_2O$, the eluate was collected in 1 ml fractions, and each fraction was lyophilized. Then, the activity of each fraction to specifically promote release of arachidonic acid metabolites from the CHO-19P2 cell line was determined. As a result, the activity was fractionated into 3 fractions (designated, in the order of elution, as P-1, P-2, and P-3).
Figure 19:
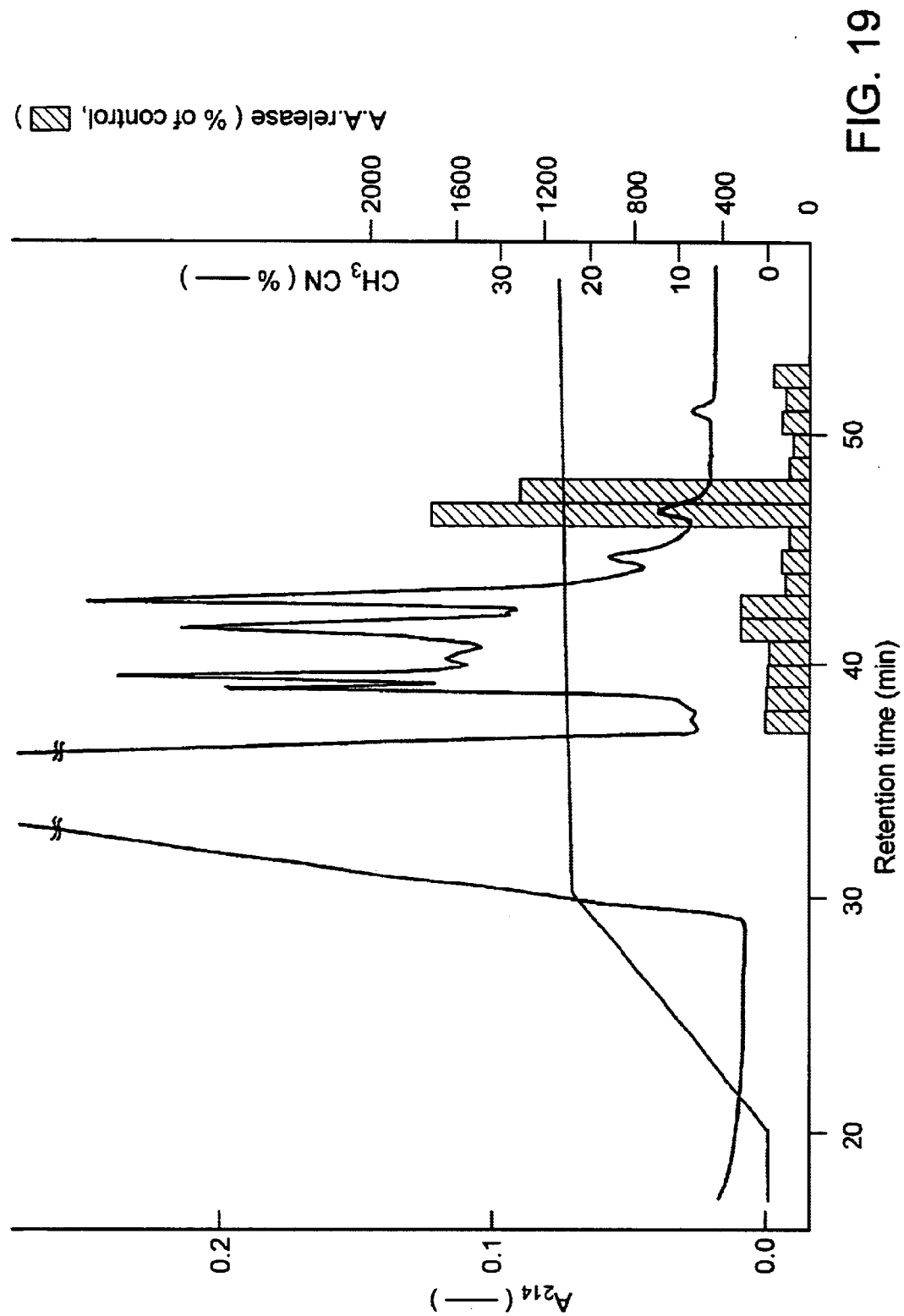
FIG. 19 shows the activity of the fraction purified with the reversed-phase column diphenyl 219TP5415 to specifically promote arachidonic acid metabolite release from CHO-19P2 cells. The P-3 active fraction from C18 218TP5415 was fractionated on diphenyl 219TP5415. The chromatography was carried out at a flow rate of 1 ml/min. on a concentration gradient of 22%–25% $CH_3CN/0.1\%$ $TFA/H_2O$, the eluate was collected in 1 ml fractions, and each fraction was lyophilized. Then, the activity to specifically promote release of arachidonic acid metabolites from CHO-19P2 cells in each fraction was determined. As a result, the activity converged in a single peak.
Figure 20:
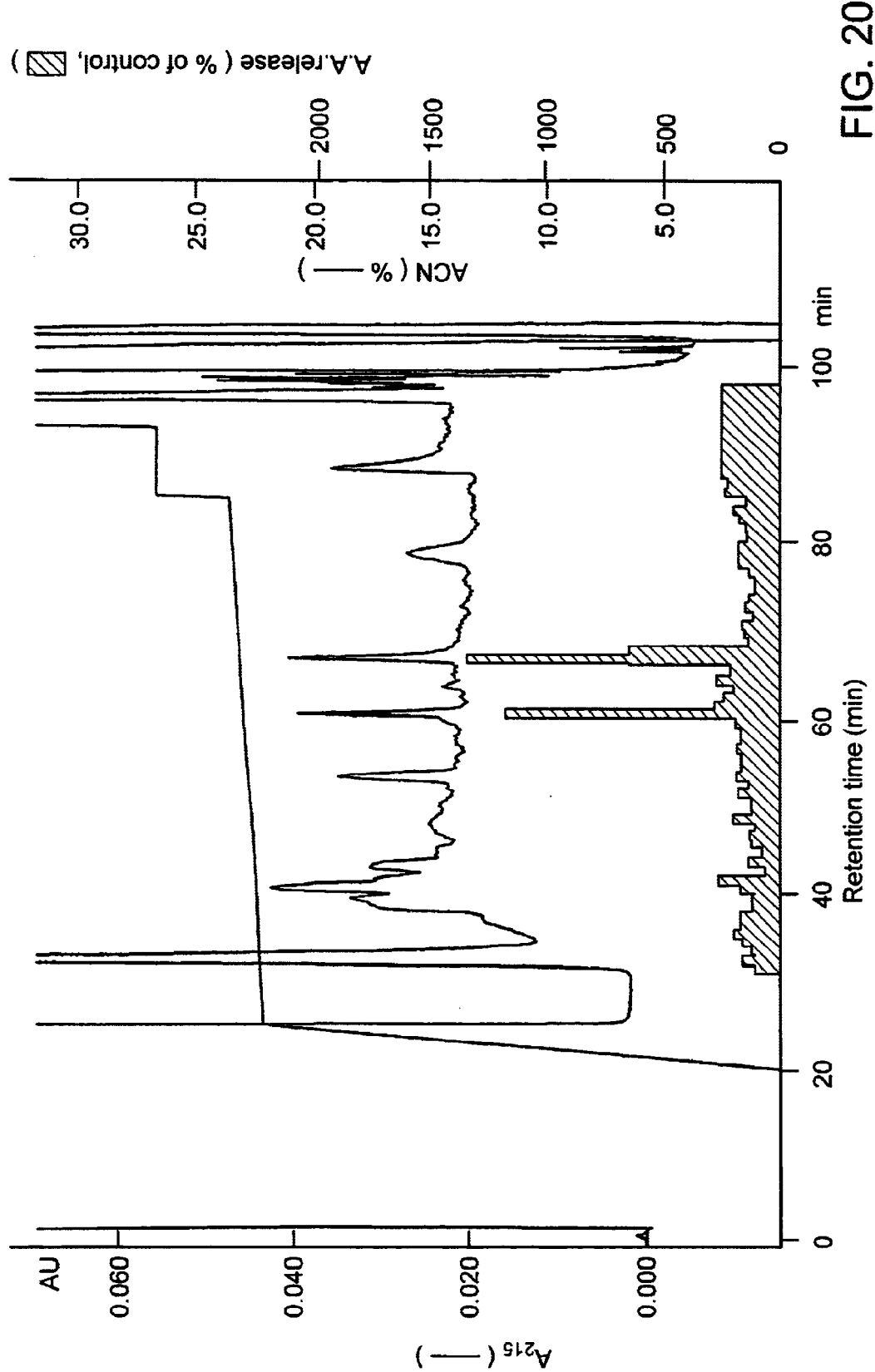
FIG. 20 shows the activity of the fraction purified by reversed-phase column $\mu$RPC C2/C18 SC 2.1/10 to specifically promote release of arachidonic acid metabolites from CHO-19P2 cells. The peak active fraction from diphenyl 219TP5415 was fractionated on $\mu$RPC C2/C18 SC 2.1/10. The chromatography was carried out at a flow rate of 100 $\mu$l/min. on a concentration gradient of 22%–23.5% $CH_3CN/0.1\%$ $TFA/H_2O$, the eluate was collected in 100 $\mu$l fractions, and each fraction was lyophilized. Then, the activity to specifically promote release of arachidonic acid metabolites from CHO-19P2 cells in each fraction was determined. As a result, the activity was found as two peaks of apparently a single substance (peptide).

Preparation of the Activity (Peptide) to Specifically Promote Release of Arachidonic Acid Metabolites From CHO-19P2 Cells by Purification From Bovine Hypothalamus A typical process for harvesting the activity to specifically promote release of arachidonic acid metabolites from the CHO19P2 cell line by purification from bovine hypothalamus is now described. A frozen bovine brain tissue specimen including hypothalamus, 4.0 kg (the equivalent of 80 animals) was ground and boiled in 8.0 L of distilled water for 20 minutes. After quenching on ice, 540 ml of acetic acid was added at a final concentration of 1.0 M and the mixture was homogenized using a Polytron (10,000 rpm, 12 min.). The homogenate was stirred overnight and then centrifuged (9,500 rpm, 20 min) to recover a supernatant. The sediment was suspended in 4.0 L of 1.0 M acetic acid and homogenized with the Polytron and centrifuged again to recover a further supernatant. The supernatants were pooled and TFA was added at a final concentration of 0.05%. The mixture was applied to reversed-phase C18 (Prep C18 125 Å, 160 ml; Millipore) packed in a glass column. After addition, the column was washed with 320 ml of 0.05% TFA/$H_2O$ and 3-gradient elution was carried out with 10%, 30%, and 50% $CH_3CN$/0.05% TPA/$H_2O$. To the 30% $CH_3CN$/0.05% TFA/$H_2O$ fraction was added 2 volumes of 20 mM $CH_3COONH_4$/$H_2O$ and the mixture was applied to the cation exchange column HiPrep CM Sepharose FF (Pharmacia). After the column was washed with 20 mM $CH_3COONH_4$/10% $CH_3CN$/$H_2O$, 4-gradient elution was carried out with 100 mM, 200 mM, 500 mM, and 1000 mM $CH_3COONH_4$/10% $CH_3CN$/$H_2O$. In the 200 mM $CH_3COONH_4$ fraction, activity to specifically promote release of arachidonic acid metabolites from CHO-19P2 was detected. Therefore, this fraction was diluted with 3 volumes of acetone, centrifuged for deproteination, and concentrated in an evaporator. To the concentrated fraction was added TFA (final concentration 0.1%) and the mixture was adjusted to pH 4 with acetic acid and applied to 3 ml of the reversed-phase column RESOURCE RPC (Pharmacia). Elution was carried out on a concentration gradient of 15%–30% $CH_3CN$. As a result, activity to specifically promote the release of arachidonic acid metabolites from the CHO-19P2 cell line was detected in the 19%–21% $CH_3CN$ fraction. The active fraction eluted from RESOURCE RPC was lyophilized, dissolved with DMSO, suspended in 50 mM MES pH 5.0/10% $CH_3CN$, and added to 1 ml of the cation exchange column RESOURCE S. Elution was carried out on a concentration gradient of 0 M–0.7 M NaCl. As a result, the activity to specifically promote release of arachidonic acid metabolites from CHO-19P2 cells was detected in the 0.32 M–0.46 M NaCl fraction. The active eluate from RESOURCE S was lyophilized, dissolved with DMSO, suspended in 0.1% TFA/$H_2O$, and added to reversed-phase column C18 218TP5415 (Vydac), and elution was carried out on a concentration gradient of 20%–30% $CH_3CN$. As a result, the activity to specifically promote release of arachidonic acid metabolites from CHO-19P2 cells was detected in the three fractions 22.5%, 23%, and 23.5% $CH_3CN$ (these active fractions are designated as P-1, P-2, and P-3) [FIG. 18]. Of the three active fractions, the 23.5% $CH_3CN$ fraction (P-3) was lyophilized, dissolved with DMSO, suspended in 0.1% TFA/$H_2O$, and added to the reversed-phase column diphenyl 219TP5415 (Vydac), and elution was carried out on a gradient of 22%–25% $CH_3CN$. As a result, the activity to specifically promote release of arachidonic acid metabolites from CHO-19P2 cells was converged by recovered in one elution peak obtained with 23% $CH_3CN$ [FIG. 19]. The peak activity fraction from the reverse-phased column diphenyl 219TP5415 was lyophilized, dissolved with DMSO, suspended in 0.1% TFA/$H_2O$, and added to the reversed-C3 phase column µRPC C2/C18 SC 2.1/10 (Pharmacia), and elution was carried out on a gradient of 22%–23.5% $CH_3CN$. As a result, the activity to specifically promote release of arachidonic acid metabolites from CHO-19P2 cells was detected in the two peaks eluted with 23.0% and 23.2% $CH_3CN$ [FIG. 20].

Example 14

Determination of the Amino Acid Sequence of the Peptide Having the Activity to Specifically Promote Release of Arachidonic Acid Metabolites From CHO-19P2 Cells as Purified From Bovine Hypothalamus The amino acid sequence of the peptide (P-3) having activity to specifically promote release of arachidonic acid metabolites from CHO-19P2 cells as purified in Example 13 was determined. The fraction of peak activity from the reversed-phase µRPC C2/C18 SC 2.1/10 was lyophilized and dissolved in 20 µl of 70% $CH_3CN$ and analyzed for amino acid sequence with the peptide sequencer (ABI.491). As a result, the sequence defined by SEQ ID NO:3 was obtained. However, the 7th and 19th amino acids were not determined by only the analysis of amino acid sequence.

Example 15

Figure 21:
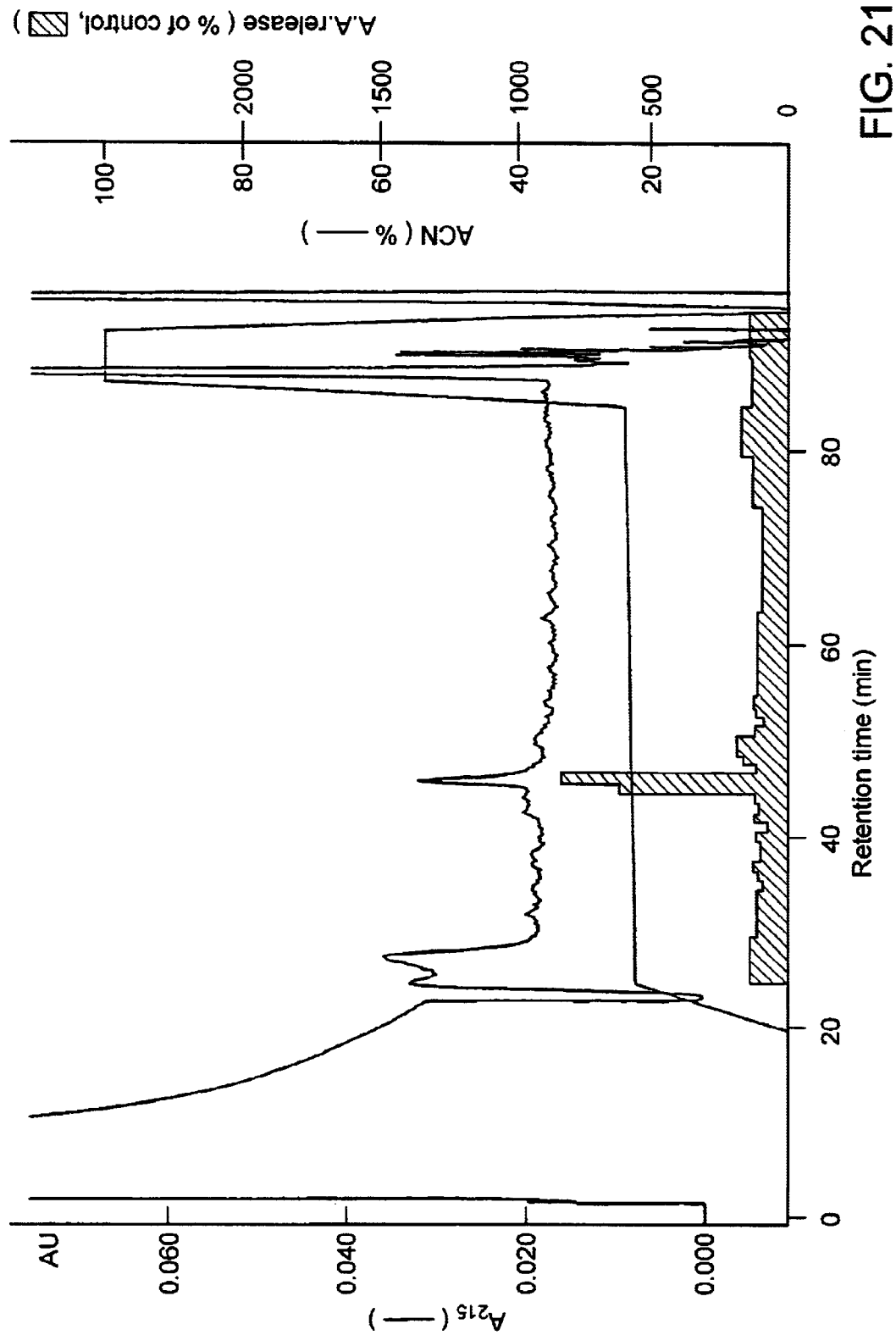
FIG. 21 shows the activity of the P-2 fraction purified by reversed-phase column $\mu$RPC C2/C18 SC 2.1/10 to specifically promote release of arachidonic acid metabolites from CHO-19P2 cells. The chromatography was carried out at a flow rate of 100 $\mu$l/min. on a concentration gradient of 21.3%–23.0% $CH_3CN/0.1\%$ $TFA/dH_2O$, the eluate was collected in 100 $\mu$l fractions, and each fraction was lyophilized. Then, the activity to specifically promote release of arachidonic acid metabolites from CHO-19P2 cells in each fraction was determined. As a result, the activity was found as a peak of apparently a single substance.

Preparation of the Active Substance (Peptide) Which Specifically Promotes Release of Arachidonic Acid Metabolites From CHO-19P2 Cells as Purified From Bovine Hypothalamus Of the three active fractions obtained with Vydac C18 218TP5415 in Example 13, the active fraction (P-2) eluted with 23.0% $CH_3CN$ was further purified. This active fraction was lyophilized, dissolved with DMSO, suspended in 0.1% TFA/dH20, and added to reversed-phase column diphenyl 219TP5415 (Vydac), and elution was carried out on a gradient of 21.0%–24.0% $CH_3CN$. As a result, activity to specifically promote release of arachidonic acid metabolites from CHO-19P2 cells was detected in a peak eluted with 21.9% $CH_3CN$. This fraction was lyophilized, dissolved with DMSO, suspended in 0.1% TFA/dH$_2$O, and added to reversed-phase µRPC C2/C18 SC 2.1/10 (Pharmacia), and elution was carried out on a $CH_3CN$ gradient of 21.5%–23.0%. As a result, the activity to specifically promote release of arachidonic acid metabolites from CHO-19P2 cells converged in one peak eluted with 22.0% $CH_3CN$ [FIG. 21].

Example 16

Determination of the Amino Acid Sequence of the Peptide (P-2) Purified From Bovine Hypothalamus Which Specifically Promotes Release of Arachidonic Acid Metabolites From CHO-19P2 Cells The amino acid sequence of the peptide (P-2) having the activity to specifically promote release of arachidonic acid metabolites from CHO-19P2 cells as purified in Example 15 was determined. The peak activity fraction from the reversed-phase column µRPC C2/C18 SC 2.1/10 was lyophilized, dissolved in 20 µl of 70% $CH_3CN$, and analyzed for amino acid sequence with the peptide sequencer (ABI, 492): (SEQ ID NO:4).

Example 17

Preparation of a Poly(A)+ RNA Fraction From Bovine Hypothalamus and Synthesis of a cDNA Using Isogen (Nippon Gene), total RNA was prepared from one animal equivalent of bovine hypothalamus. Then, using Fast Track (Invitrogen), a poly(A)+ RNA fraction was prepared. From 1 µg of this poly(A)+ RNA fraction, cDNA was synthesized using 3' RACE system (GIBCO BRL) and Marathon cDNA amplification kit (Clontech) according to the manuals and disolved in 20 and 10 µl, respectively.

Example 18

Acquisition of cDNA Coding for the Amino Acid Sequence Established in Example 14

To obtain a cDNA coding for a polypeptide comprising the amino acid sequence established in Example 14, the acquisition of a base sequence coding for SEQ ID NO:1 was attempted in the first place. Thus, primers P5-1 (SEQ ID NO:35), P3-1 (SEQ ID NO:36), and P3-2 (SEQ ID NO:37) were synthesized. (In the Sequence Table, I represents inosine). Using 0.5 µl of the cDNA prepared by 3' RACE in Example 17 as a template and EXTaq (Takara Shuzo Co., Japan) as DNA polymerase, 2.5 µl of accompanying buffer, 200 µM of accompanying DNTP, and primers P5-1 and P3-1 were added each at a final concentration of 200 nM, with water added to make 25 µl, and after one minute at 94° C., the cycle of 98° C.×10 seconds, 50° C.×30 seconds, 68° C.×10 seconds was repeated 30 times. This reaction mixture was diluted 50-fold with tricine-EDTA buffer and using 2.5 µl of the dilution as a template and the primer combination of P5-1 and P3-2, the reaction was carried out in otherwise the same manner as described above. As the thermal cycler, Gene Amp 9600 (Perkin Elmer) was used. The amplification product was subjected to 4% agarose electrophoresis and ethidium bromide staining and a band of about 70 bp was cut out and subjected to thermal fusion, phenol extraction, and ethanol precipitation. The recovered DNA was subcloned into plasmid vector PCR™II according to the manual of TA Cloning kit (Invitrogen). The vector was,then introduced into *E. coli* JM109 and the resultant transformant was cultured in ampicillin-containing LB medium. The plasmid obtained with an automatic plasmid extractor (Kurabo) was reacted according to the manual of Dye Terminator Cycle Sequencing Kit (ABI) and decoded with a fluorescent automatic DNA sequencer (ABI). As a result, the sequence shown in FIG. 22 was obtained and confirmed to be part of the base sequence coding for SEQ ID NO:1.

Example 19

Acquisition of a Bioactive Polypeptide cDNA by RACE Using the Sequence Established in Example 18

First, for amplification (5' RACE) of the sequence at 5' end, the two primers PE (SEQ ID NO:38) and PDN (SEQ ID NO:39) were synthesized by utilizing the sequence shown in FIG. 22. The cDNA prepared using Marathon cDNA amplification kit in Example 17 was diluted 100-fold with tricine-EDTA buffer. Then, in the same manner as Example 2, a reaction mixture was prepared using 2.5 µl of the dilution and a combination of the adapter primer AP1 accompanying the kit and the primer PE and after one minute at 94° C., the cycle of 98° C.×10 seconds and 68° C.×5 minutes was repeated 30 times. This reaction system was further diluted 50-fold with tricine-EDTA buffer and using 2.5 µl of the dilution as a template and the changed primer combination of AP1 and PDN, the reaction was conducted at 94° C. for one minute, followed by 4 cycles of 94° C.×1 minute, 98° C.×10 seconds, 72° C.×5 minutes, 4 cycles of 98° C.×10 seconds, 70° C.×5 minutes, and 26 cycles of 98° C.×10 seconds, 68° C.×5 minutes. The amplification product was electrophoresed on 1.2% agarose gel and stained with ethidium bromide and a band of about 150 bp was cut out and centrifugally filtered through a centrifugal filter tube (Millipore), extracted with phenol, and precipitated from ethanol. The recovered DNA was subcloned into plasmid vector PCR™II according to the manual of TA Cloning Kit (Invitrogen). The vector was then introduced into *E. coli* JM109 and the resulting transformant was cultured and the sequence of the inserted cDNA fragment was analyzed as in Example 18. As a result, the sequence shown in FIG. 23 was obtained. Based on this sequence, primers FB (SEQ ID NO:40) and FG (SEQ ID NO:41) were synthesized and the 3' sequence was cloned (3' RACE). Using the same template as that for 5' RACE in the same quantity and the combination of the accompanying adapter primer AP1 with the primer FC, PCR was carried out at 94° C. for 1 minute, followed by 5 cycles of 98° C.×10 seconds, 72° C.×5 minutes, 5 cycles of 98° C.×10 seconds, 70° C.×5 minutes, and 25 cycles of 98° C.×10 seconds, 68° C.×5 minutes. Then, using 2.5 µl of a 50-fold dilution of this reaction mixture in tricine-EDTA buffer as the template and the combination of the accompanying primer AP2 with the primer FB, the reaction was further conducted at 94° C. for one minute, followed by 4 cycles of 98C×10 seconds, 72° C.×5 minutes, 4 cycles of 98° C.×10 seconds, 70° C.×5 minutes, and 27 cycles of 98° C.×10 seconds, 68° C.×5 minutes. The amplification product was electrophoresed on 1.2% agarose gel and stained with ethidium bromide and a band of about 400 bp was cut out and the DNA was recovered as in 5'-RACE. This DNA fragment was subcloned into plasmid vector pCR™II and introduced into *E. coli* JM109 and the sequence of the inserted cDNA fragment in the resulting transformant was analyzed. From the results of 5' RACE and 3' RACE, the DNA sequence [FIG. 24] coding for the complete coding region of the bioactive polypeptide defined by SEQ ID NO:1 was established. Thus, in FIGS. 24(*a*) and (*b*), the base$^{134}$ is G, the base$^{184}$ is T or C, and the base$^{245}$ was T or C.

The cDNA shown in FIG. 24 was the cDNA encoding a polypeptide consisting of 98 amino acids. The fact that the amino acids in 1–22-positions comprise a cluster of hydrophobic amino acids taken together with the fact taint the N-terminal region of the active peptide begins with Ser in 23-position as shown in Example 14 suggested that the amino acids 1–22 represent a secretion signal sequence. On the other hand, the Gly Arg Arg Arg sequence in 54–57 positions of the polypeptide was found to be a typical amino acid sequence motif which exists in the event of cleavage of a bioactive peptide. As it is the case with this cleavage motif, it is known that because of the presence of Gly, the C-terminus of the product peptide is frequently amidated.

The P-3 N-terminal sequence data of Example 14 and P-2 N-terminal sequence data in Example 16 coupled with this GlyArgArgArg sequence suggest that at least same of the bioactive peptides cut out from the polypeptide encoded by this cDNA are defined by SEQ ID NO:3, SEQ ID NO:4, SEQ ID NO:5, SEQ ID NO:6, SEQ ID NO:7, SEQ ID NO:8, SEQ ID NO:9 or SEQ ID NO:10.

Example 20

Acquisition of a DNA Fragment Comprising the Full Coding Region of Bovine-derived Bioactive Polypeptide cDNA by PCR Using the cDNA prepared with Marathon cDNA amplification kit in Example 17 as a template, a DNA fragment including the entire coding region of bioactive polypeptide cDNA was constructed. First, based on the sequence of cDNA elucidated in Example 19, two primers having base sequences defined by SEQ ID NO:42 and SEQ ID NO:43, respectively, were synthesized. BOVF

5'-GTGTCGACGAATGAAGGCGGTGGGGGCCTGGC-3' (SEQ ID NO:42),

BOVR (24 mer)

5'-AGGCTCCCGCTGTTATTCCTGGAC-3' (SEQ ID NO:43)

BOVF contains the initiation codon of bioactive polypeptide cDNA and is a sense sequence corresponding to −2−+22 (A of the initiation codon ATG being reckoned as +1) with restriction enzyme SalI site added. On the other hand, BOVR is an antisense sequence corresponding to +285−+309 which includes the termination codon of bioactive polypeptide cDNA.

The PCR was conduced as follows. The cDNA prepared using Marathon cDNA amplification kit in Example 17 was diluted 100-fold in tricine-EDTA buffer and using 2.5 µl of the dilution, a reaction mixture was prepared as in Example 2 and subjected to 94° C.×1 minute, 3 cycles of 98° C.×10 seconds, 72° C.×5 minutes, 3 cycles of 98° C.×10 seconds, 70° C.×5 minutes, and 27 cycles of 98° C.×10 seconds, 68° C.×5 minutes. The amplification product was subjected to 2% agarose electrophoresis and ethidium bromide staining and a band of about 320 bp was cut out. The DNA was recovered and subcloned in plasmid vector pCR™II as in Example 3. The vector was introduced into *Escherichia coli* JM109 to provide the transformant *E. coli* JM109/pBOV3. The sequence of the cDNA fragment inserted in the transformant was then analyzed. As a result, this DNA fragment was confirmed to be a fragment covering the entire coding region of the bioactive polypeptide cDNA.

Example 21

1) Synthesis of Ser-Arg-Ala-His-Gln-His-Ser-Met-Glu-Ile-Arg-Thr-Pro-Asp-Ile-Asn-Pro-Ala-Trp-Tyr-Ala-Gly-Arg-Gly-Ile-Arg-Pro-Val-Gly-Arg-Phe-NH$_2$ (19P2-L31) (SEQ ID NO 97)

1) Synthesis of Ser(Bzl)-Arg(Tos)-Ala-His(Bom)-Gln-His(Bom)-Ser(Bzl)-Met-Glu(OcHex)-Ile-Arg(Tos)-Thr(Bzl)-Pro-Asp(OcHex)-Ile-Asn-Pro-Ala-Trp(CHO)-Tyr(Br-Z)-Ala-Gly-Arg(Tos)-Gly-Ile-Arg(Tos)-Pro-Val-Gly-Arg(Tos)-Phe-pMBHA-resin The reactor of a peptide synthesizer (Applied Biosystems 430A) was charged with 0.71 g (0.5 mmole) of commercial p-methyl-BRA resin (Applied Biosystems, currently Perkin Elmer). After wetting with DCM, the initial amino acid Boc-Phe was activated by the HOBt/DCC method and introduced into the p-methyl-BRA resin. The resin was treated with 50% TFA/DCM to remove Boc and make the amino group free and neutralized with DIEA. To this amino group was condensed the next amino acid Boc-Arg (Tos) by the HOBt/DCC method. After the absence of unreacted amino function was verified by ninhydrin test, a sequential condensation of Boc-Gly, Boc-Val, Boc-Pro, Boc-Arg(Tos), Boc-Ile, Boc-Gly, Boc-Arg(Tos), Boc-Gly, Boc-Ala, Boc-Tyr(Br-Z) was carried out. The Boc-Ala, Boc-Tyr (Br-Z), the condensation of which was found insufficient by ninhydrin test, was recondensed to complete the reaction. The resin was dried and a half of the resin was withdrawn. To the remainder, Boc-Trp(CHO), Boc-Ala, Boc-Pro, Boc-Asn, Boc-Ile, Boc-Asp(OcHex), Boc-Pro, Boc-Thr(Bzl), Boc-Arg(Tos), Boc-Ile, Boc-Glu(OcHex), Boc-Met, Boc-Ser (Bzl), Boc-His(Bom), Boc-Gln, Boc-His(Bom), Boc-Ala, Boc-Arg(Tos), Boc-Ser(Bzl) were serially condensed and recondensed until sufficient condensation was confirmed by ninhydrin test. After introduction of the full sequence of amino acids of 19P2-L31, the resin was treated with 50% TFA/DCM to remove Boc groups on the resin and, then, dried to provide 1.28 g of the peptide resin.

2) Synthesis of Ser-Arg-Ala-His-Gln-His-Ser-Met-Glu-Ile-Arg-Thr-Pro-Asp-Ile-Asn-Pro-Ala-Trp-Tyr-Ala-Gly-Arg-Gly-Ile-Arg-Pro-Val-Gly-Arg-Phe-NH$_2$ (19P2-L31) (SEQ ID NO 97)

In a Teflon hydrogen fluoride reactor, the resin obtained in 1) was reacted with 3.8 g of p-cresol, 1 ml of 1,4-butanedithiol, and 10 ml of hydrogen fluoride at 0° C. for 60 minutes. The hydrogen fluoride and 1,4-butanedithiol (1 ml) were distilled off under reduced pressure and the residue was diluted with 100 ml of diethyl ether, stirred, filtered through a glass filter, and the fraction on the filter was dried. This fraction was suspended in 50 ml of 50% acetic acid/H$_2$O and stirred to extract the peptide. After separation of the resin, the extract was concentrated under reduced pressure to about 5 ml and chromatographed on Sephadex G-25 (2×90 cm). Development was carried out with 50% acetic acid/H$_2$O and the 114 ml–181 ml fraction was pooled and lyophilized to recover 290 mg of white powders containing 19P2-L31. The powders were applied to a reversed-phase column of LiChroprep RP-18 (Merck) and repeatedly purified by gradient elution using 0.1% TFA/H$_2$O and 0.1% TFA-containing 30% acetonitrile/H$_2$O. The fraction eluted at about 25% acetonitrile was pooled and lyophilized to provide 71 mg of white powders.

Mass spectrum (M+H)$^+$ 3574.645;

HPLC elution time 18.2 min.

Column conditions;

Column: Wakosil 5C18 (4.6×100 mm);

Eluent: A (0.1% TFA/H$_2$O);

B (0.1% TFA-containing 50 (% acetonitrile/H$_2$O);

Linear gradient elution from A to B (25 min.);

Flow rate: 1.0 ml/min.

Example 22

Synthesis of Ser-Arg-Ala-His-Gln-His-Ser-Met-Glu-Ile-Arg-Thr-Pro-Asp-Ile-Asn-Pro-Ala-Trp-Tyr-Ala-Gly-Arg-Gly-Ile-Arg-Pro-Val-Gly-Arg-Phe-NH$_2$ (19P2-L31) (SEQ ID NO 97)

In 20 ml of 5% acetic acid/H$_2$O was dissolved 6 mg of synthetic 19P2-L31 and the Met only was selectively oxidized with 40 µl of 30% H$_2$O. After completion of the reaction, the reaction mixture was immediately applied to a reversed-phase column of LiChroprep RP-18 (Merck) for purification to provide 5.8 mg of the objective peptide.

Mass spectrum (M+H)$^+$ 3590.531;

C4 RPLC elution time 17.9 min.

Column conditions;

Column: Wakosil 5C18 (4.6×100 mm);

Eluent: A (0.1% TFA/H$_2$O);

B (0.1 TFA-containing 50% aceto nitrile/H$_2$O);

Linear gradient elution from A to B (25 min.);

Flow rate: 1.0 ml/min.

Example 23

Synthesis of Thr-Pro-Asp-Ile-Aln-Pro-Ala-Trp-Tyr-Ala-Gly-Arg-Gly-Ile-Arg-Pro-Val-Gly-Arg-Phe-NH$_2$ (19P2-L20) (SEQ ID NO 98)

To the resin subjected to condensations up to Boc-Tyr (Br-Z) in Example 21-1) was further condensed Boc-Trp (CRO), Boc-Ala, Boc-Pro, Boc-Asn, Boc-Ile, Boc-Asp (OcHex), Boc-Pro, Boc-Thr(Bzl) serially in the same manner to provide 1.14 g of Boc-Thr(Bzl)-Pro-Asp (OcHex)-Ile-Asn-Pro-Ala-Trp(CHO)-Tyr(Br-Z)-Ala-Gly-Arg(Tos)-Gly-Ile-Arg(Tos)-Pro-Val-Gly-Arg(Tos)-Phe-pMBHA-resin. This resin was treated with hydrogen fluoride and columnwise purified in the same manner as Example 21-2) to provide 60 mg of white powders.

Mass spectrum (M+H)$^+$ 2242.149;
HPLC elution time 10.4 min.
Column conditions;
Column: Wakosil 5C18 (4.6×100 mm);
Eluent: A (0.1% TFA-containing 15% aceto nitrile/H$_2$O); B (0.1 TFA-containing 45% aceto nitrile/H$_2$O);
Linear gradient elution from A to B (15 min.);
Flow rate: 1.0 ml/min.

Example 24

Determination of Arachidonic Acid Metabolites-releasing Activity of Synthetic Peptide (19P2-L31)

Figure 25:
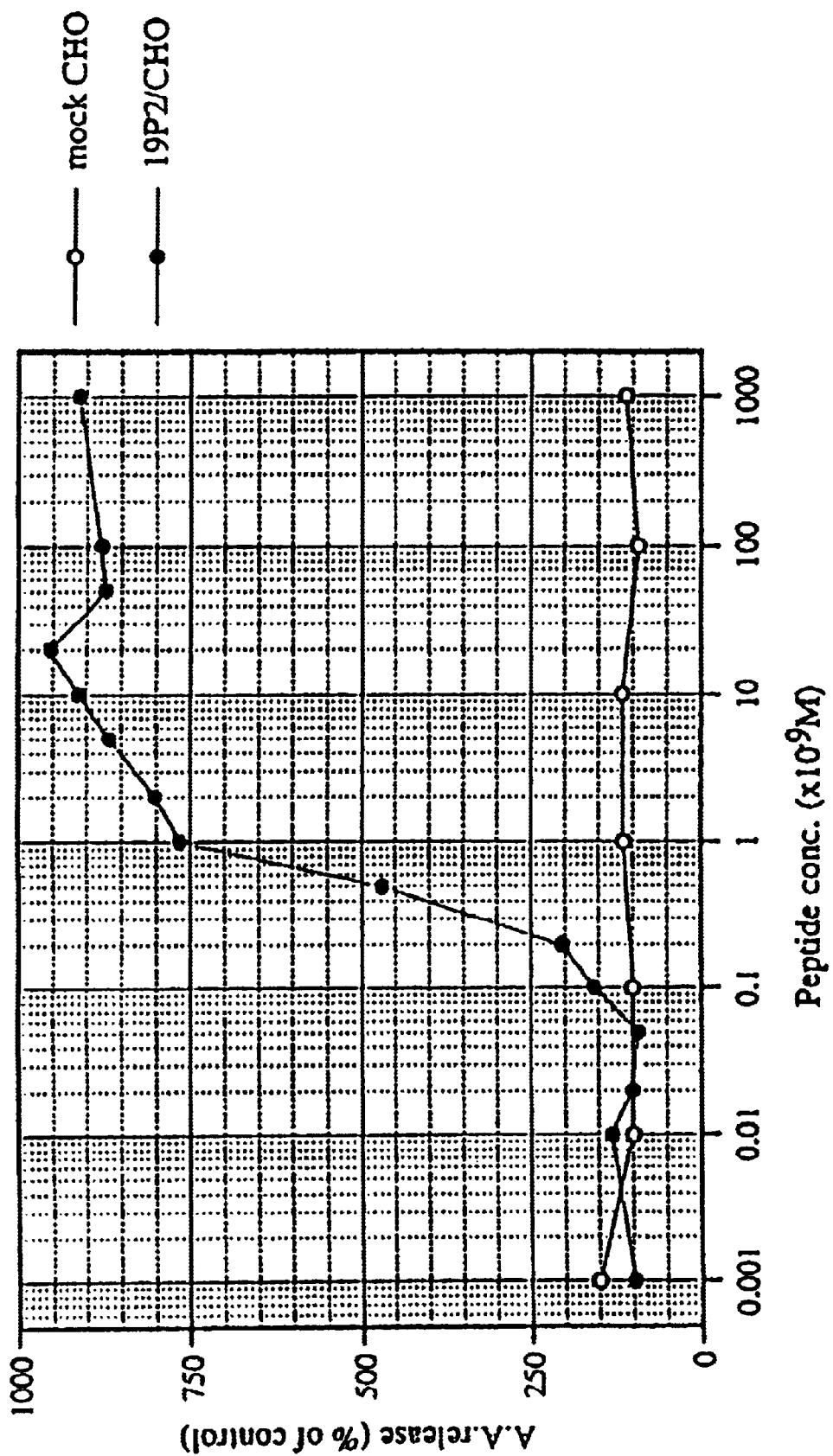
FIG. 25 shows the concentration-dependent activity of synthetic ligand polypeptide (19P2-L31) to specifically promote release of arachidonic acid metabolites from CHO-19P2 cells. The synthetic peptide was dissolved in degassed $dH_2O$ at a final concentration of $10^{-3}$ M and diluted with 0.05% BSA-HBSS to concentrations of $10^{-12}$ M-$10^{-6}$ M. The arachidonic acid metabolite releasing activity was expressed in the measured radioactivity of [$^3$H] arachidonic acid metabolites released in the supernatant when the dilution was added to the cells. As a result, the activity of 19P2-31 to specifically promote release of arachidonic acid metabolites from CHO-19P2 cells was found in a concentration-dependent manner.
Figure 26:
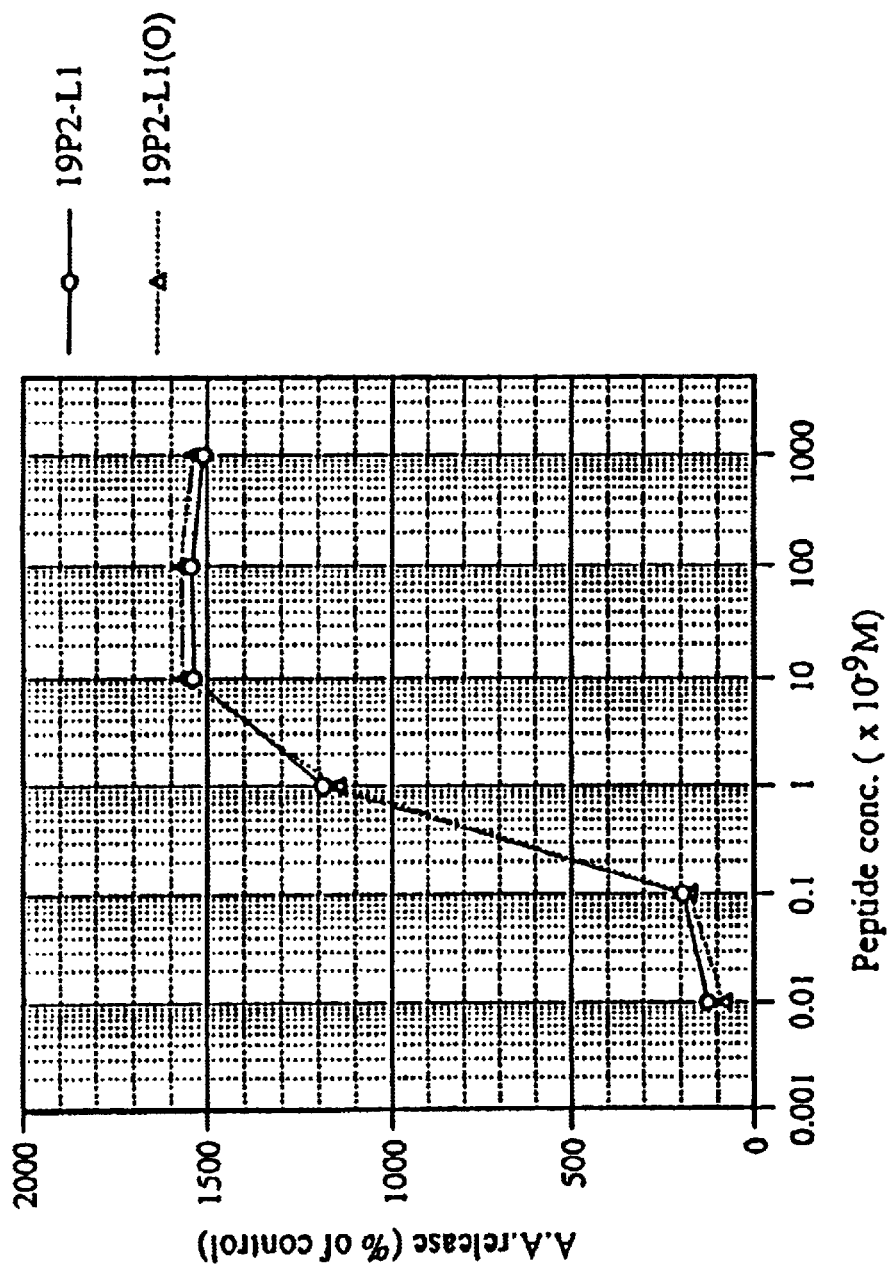
FIG. 26 shows the concentration-dependent activity of synthetic ligand polypeptide (19P2-L31(O)) to specifically promote release of arachidonic acid metabolites from CHO-19P2 cells. The synthetic ligand peptide was dissolved in degassed $dH_2O$ at a final concentration of $10^{-3}$ M and diluted with 0.05% BSA-HBSS to concentrations of $10^{-12}$ M-$10^{-6}$ M. The arachidonic acid metabolite releasing activity was expressed in the measured radioactivity of [$^3$H] arachidonic acid metabolites released in the supernatant when the dilution was added to the cells. As a result, the activity of 19P2-L31(O)) to specifically promote release of arachidonic acid metabolites from CHO-19P2 cells was found in a dose-dependent manner.

The activity of the peptide (19P2-L31) synthesized in Example 21 to specifically release arachidonic acid metabolites from CHO-19P2 cells was assayed in the same manner as Example 11. The synthetic peptide was dissolved in degassed dH20 at a concentration of $10^{-3}$M and diluted with 0.05% BSA-HBSS and the activity to promote release of arachidonic acid metabolites from CHO-19P2 cells at each concentration was assayed using the amount of [$^3$H] arachidonic acid metabolites as the indicator. As a result, concentration-dependent arachidonic acid metabolite-releasing activity was detected over the range of $10^{-12}$M–$10^{-6}$M [FIG. 25]. When the arachidonic acid metabolite-releasing activity of peptide 19P2-L31(O), i.e. the methionine-oxidation product of 19P2-L31 synthesized in Example 22, was compared with that of 19P2-L31, it was found that the activity of 19P2-L31(O)) was equivalent to the activity of 19P2-L31 as can be seen from FIG. 26.

Example 25

Determination of Arachidonic Acid Metabolites-releasing Activity of Synthetic Peptide (19P2-L20)

The activity of the synthetic equivalent (19P2-L20) of natural peptide P-2 as synthesized in Example 23 to specifically promote release of arachidonic acid metabolites from CHO-19P2 cells was determined as in Example 11. Thus, the synthetic peptide was dissolved in degassed dH$_2$O at a final concentration of $10^{-3}$M and this solution was serially diluted with 0.05% BAS-HBSS. The activity to specifically promote release of arachidonic acid metabolites from CHO-19P2 cells at each concentration was assayed using the amount of [$^3$H]arachidonic acid metabolites as the indicator.

Figure 27:
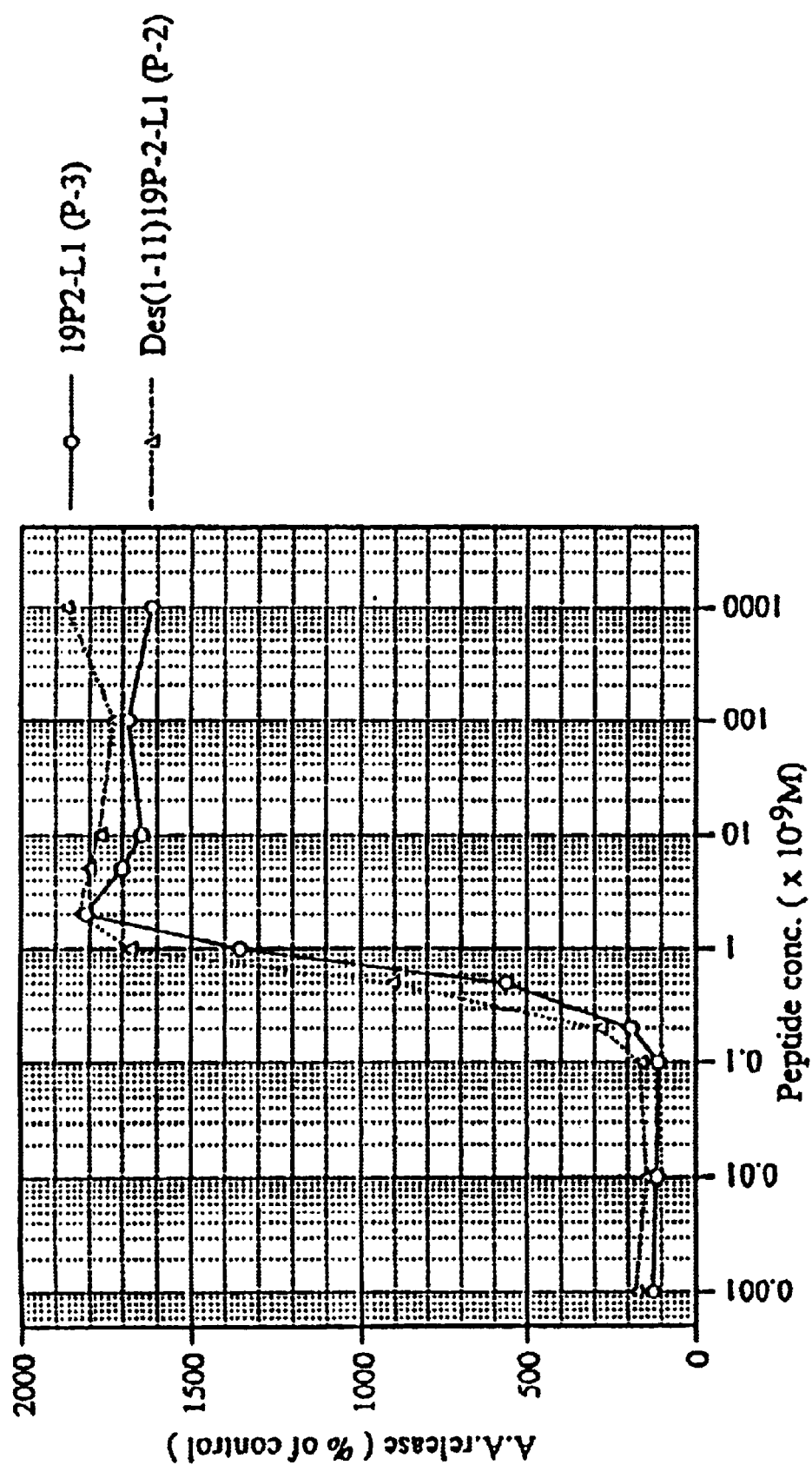
FIG. 27 shows the activity of synthetic ligand polypeptide 19P2-L20 to specifically promote release of arachidonic acid metabolites from CHO-19P2 cells. The synthetic peptide was dissolved in degassed $dH_2O$ at a final concentration of $10^{-3}$ M and diluted with 0.05% BSA-HBSS to concentrations of $10^{-12}$ M-$10^{-6}$ M. The arachidonic acid metabolite releasing activity was expressed in the measured radioactivity of [$^3$H] arachidonic acid metabolites released in the supernatant when the dilution was added to the cells. As a result, the activity of 19P2-L20 to specifically promote release of arachidonic acid metabolites from CHO-19P2 cells was found in a dose-dependent manner.

As a result, concentration-dependent arachidonic acid metabolite-releasing activity was detected over the range of $10^{-12}$–$10^{-6}$M in nearly the same degree as 19P2-L31 [FIG. 27].

Example 26

Analysis of the Coding Region Base Sequence of Bovine Genomic DNA pBOV3 was digested with restriction enzyme EcoRI and after fractionation by agarose gel electrophoresis, the DNA corressponding to the cDNA fragment was recovered to prepare a probe. This DNA was labeled with $^{32}$P using a multiprime DNA labeling kit (Amersham). About 2.0×10$^6$ phages of Bovine Genomic Library (Clontech BL1015j) constructed using cloning vector EMBL3 SP6/T7 and *Escherichia coli* K802 as the host were seeded in an LB agar plate and cultured overnight for plaque formation. The plaques were transferred to a nitrocellulose filter and after alkaline modification and neutralization, heat-treated (80° C., 2 hours) to inactivate the DNA. This filter was incubated with the labeled probe in 50% formamide-Hybri buffer (50% formamide, 5×Denhardt solution, 4×SSPE, 0.1 mg/ml heat-denatured salmon sperm DNA, 0.1% SDS) at 42° C. overnight for hybridization. After this hybridization, the filter was washed with 2×SSC, 0.1% SDS at room temperature for 1.5 hours, and further washed in the same buffer at 55° C. for 30 minutes. Detection of the clone hybridizing with the probe was carried out on Kodak X-ray film (X-OMAT™AR) after 4 days of exposure using a sensitization screen at −80° C. After development of the film, the film was collated with plate positions and the phages which had hybridized were recovered. Then, plating and hybridization were repeated in the same manner for cloning of the pharges.

Figure 28:
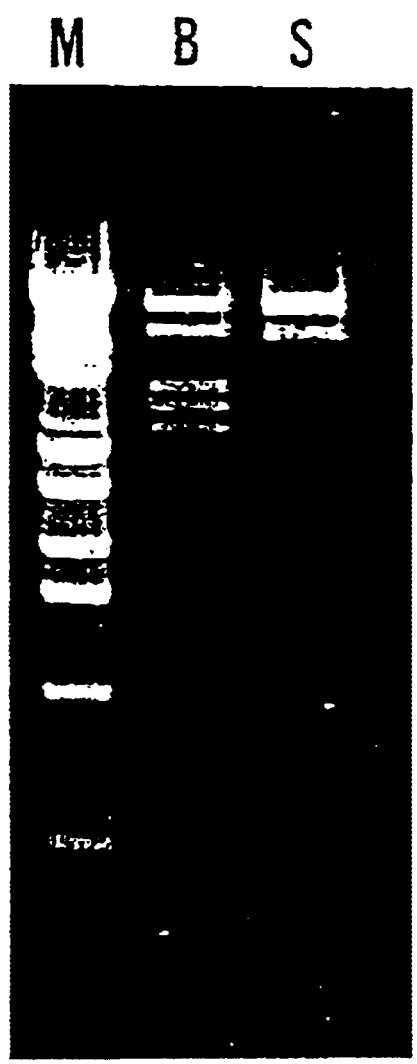
FIG. 28 shows the 1.2% agarose gel electrophoregram of the DNA fragments of the phages cloned from a bovine genomic library as digested with restriction enzymes BamHI (B) and SalI(S). As the DNA size marker (M), StyI digests of .lambda. phage DNA were used. In lane B, two bands derived from the vector were detected in positions between the first (19,329 bp) and second (7.743 bp) marker bands, as well as 3 bands derived from the inserted fragment between the third (6,223 bp) and 5th (3,472 bp) bands. In lane S, two bands derived from the vector were similarly detected but due to the overlap of the band of the inserted fragment, the upper band is thicker than the band in lane B.

The cloned phages were prepared on a large scale by the plate lysate method and the phage DNA was extracted. Then, cleavage at the restriction enzyme SalI and BamHI cleavage sites at both ends of the cloning site of the vector and detection of the inserted fragment d ed-from bovine genomic DNA was carried out by 1.2% agarose gel electrophoresis [FIG. 28]. As a result, in the case of BamHI digestion, 3 fragments were detected in addition to the bands derived from the phages. In the case of SalI digestion, one band overlapping the phage band was detected. The SalI-digested fragment being considered to harbor the full length and in order to subclone this fragment into a plasmid vector, it was ligated to BAP (*E. coli*-derived alkaline phosphatase)-treated plasmid vector pUC18 (Pharmacia) and introduced into *E. coli* JM109. From this microorganism, a genome-derived SalI fragment-inserted plasmid DNA was prepared on a production scale and the base sequence in the neighborhood of its coding region was analyzed using Perkin Elmer Applied Biosystems 370A fluorecent sequencer and the same manufacturer's kit. As a result, the sequence shown in FIG. 29 was obtained. Comparison with the coding region of cDNA reveals that because of its being derived from genomic DNA, the coding region is divided in two by a 472 bp intron [FIG. 30]. FIG. 31 and SEQ ID NO:44 present the amino acid sequence predicted from this bovine genome coding region (excluding the intron region).

Example 27

Preparation of Rat Medulla Oblongata Poly(A$^+$) RNA Fraction and Synthesis of cDNA Using Isogen (Nippon Gene), total RNA was prepared from the dorsal region of rat medulla oblongata and using FastTrack (Invitrogen), poly(A)$^+$ RNA fraction was prepared. To 5 µg of this poly(A)$^+$ RNA was added the primer random DNA hexamer (BRL) and using Moloney mouse leukemia reverse transcriptase (BRL) and the accompanying buffer, complementary DNA was synthesized. The reaction product was precipitated from ethanol and dissolved in 12 µl of DW. In addition, from 1 µg of this poly(A)$^+$ RNA, a cDNA was synthesized using Marathon cDNA amplification kit (Clontech) according to the manual and dissolved in 10 µl of DW.

Example 28

Acquisition of Rat Bioactive Polypeptide cDNA by RACE

To obtain the full coding region of rat bioactive polypeptide cDNA, an experiment was performed in the same manner as the Acquisition of bovine cDNA. First, PCR was carried out using the same primers P5-1 (SEQ ID NO:35) and P3-1 (SEQ ID NO:36) as used in Example 18 as primers and the complementary DNA synthesized in Example 27 using the primer random DNA hexamer (BRL) and Moloney mouse leukemia reverse transcriptase (BRL) as a template. The reaction system was composed of 1.25 µl of the template cDNA, 200 µM of dNTP, 1 µM each of the primers, ExTaq (Takara Shuzo Co., Japan) as DNA polymerase, and 2.5 µl of the accompanying buffer, with a sufficient amount of water to make a total of 25 µl. The reaction was carried out at 94° C. for 1 minute, followed by 40 cycles of 98° C.×10 seconds, 50° C.×30 seconds, and 72° C.×5 seconds, and the reaction mixture was then allowed to stand at 72° C. for 20 seconds. The thermal cycler used was GeneAmp2400 (Perkin Elmer). The amplification product was subjected to 4% agarose electrophoresis and ethidium bromide staining and the band of about 80 bp was cut out. Then, in the manner described in Example 19, the DNA was recovered, subcloned into plasmid vector pCR™II, and introduced into *E. coli* JM109, and the inserted cDNA fragment was sequenced. As a result, a partial sequence of rat bioactive polypeptide could be obtained. Based on this sequence, two primers, namely RA (SEQ ID NO:75) for 3' RACE and RC (SEQ ID NO:76) for 5' RACE were synthesized and 5' and 3' RACEs were carried out.

RA:5'-CARCAYTCCATGGAGACAAGAACCCC-3'
(where R means A or G; Y means T or G) (SEQ ID NO:75)
RC:5'-TACCAGGCAGGATTGATACAGGGG-3' (SEQ ID NO:76)

As a template, the template synthesized using Marathon cDNA amplification kit (Clontech) in Example 27 was diluted 40-fold with the accompanying tricine-EDTA buffer and 2.5 µl of the dilution was used. As primers, RA and the adapter primer AP1 accompanying the kit were used for 3' RACE, and RC and AP1 for 5' RACE. The reaction mixture was prepared in otherwise the same manner as above. The reaction conditions were 94° C.×1 minute, 5 cycles of 98° C.×10 seconds, 72° C.×45 seconds, 3 cycles of 98° C.×10 seconds, 70° C.×45 seconds, and 40 cycles of 98° C.×10 seconds, 68° C.×45 seconds. As a result, a band of about 400 bp was obtained from 3' RACE and bands of about 400 bp and 250 bp from 5' RACE. These bands were recovered in the same manner as above and using them as templates and the primers used in the reaction, sequencing was carried out with Dye Terminator Cycle Sequencing Kit (ABI). As a result, the sequence up to poly A could be obtained from the region considered to be the 5' noncoding region.

Example 29

Acquisition of the Full-length cDNA of Rat Bioactive Polypeptide by PCR

Based on the sequence obtained in Example 28, two primers, viz. rF for the region including the initiation codon (SEQ ID NO:77) and rR for the 3' side from the termination codon (SEQ ID NO:78), were synthesized to amplify the fragment including the full-length cDNA.

| | |
|---|---|
| rF:5'-GGCATCATCCAGGAAGACGGAGCAT-3' | (SEQ ID NO:77) |
| rR:5'-AGCAGAGGAGAGGGAGGGTAGAGGA-3' | (SEQ ID NO:78) |

Using the cDNA prepared using Moloney mouse leukemia reverse transcriptase in Example 27 as a template and ExTaq (Takara Shuzo Co., Japan), PCR was carried out by repeating 40 cycles of 95° C.×30 seconds, 68° C.×60 seconds. The amplification product was subjected to agarose electrophoresis and ethidium bromide staining and a band of about 350 bp was cut out. The DNA was recovered, subcloned into plasmid vector pCR™II, and introduced into *E. coli* JM109 as in Example 19. The plasmid was extracted from the transformant and the base sequence was determined. As a result, *E. coli* JM 109/pRAV3 having the full-length cDNA of rat bioactive polypeptide was obtained [FIG. 32].

Example 30

Synthesis of cDNA from the Human Total Brain Poly(A)+ RNA Fraction

From 1 µg of human total brain poly(A)+ RNA fraction (Clontech), cDNA was synthesized with Marathon cDNA amplification kit (Clontech) according to the manual and dissolved in 10 µl. In addition, the random DNA hexamer (BRL) was added as primer to 5 µg of the same poly(A)+ RNA fraction and using Moloney mouse leukemia reverse transcriptase (BRL) and the accompanying buffer, complementary DNA was synthesized. The reaction product was precipitated from ethanol and dissolved in 30 µl of TE.

Example 31

Acquisition of Human Bioactive Polypeptide cDNA by RACE

From the amino acid sequence of rat bioactive polypeptide established in Example 28 [FIG. 33], the well-preserved regions of rat and bovine polypeptides were selected and the following 3 primers RL1 (SEQ ID NO:79), R3 (SEQ ID NO:80), and R4 (SEQ ID NO:81) were synthesized. Then, amplification of the region flanked by them was attempted by PCR using human cDNA as a template. Referring to FIG. 33, bovine. aa represents the amino acid sequence of bovine polypeptide, bovine. seq represents the base sequence of the DNA coding for bovine polypeptide, and rat. seq represents the base sequence of the DNA coding for rat polypeptide.

R1:5'-ACGTGGCTTCTGTGCTTGCTGC-3' (SEQ ID NO:79)
R3:5'-CCTCATCCCCGGCCCGTGTACCA-3' (SEQ ID NO:80)
R4:5'-TTGCCCTTCTCCTGCCGAAGCGGCCC-3' (SEQ ID NO:81)

The cDNA prepared using Marathon cDNA amplification kit (Clontech) in Example 30 was diluted 30-fold with tricine-EDTA buffer and 0.25 µl of the dilution was used as a template. The reaction mixture was composed of 200 µM of dNTP, 0.2 µM each of the primers R1 and R4, a 50:50 mixture of Taq Start Antibody (Clontech) and DNA polymerase ExTaq (Takara Shuzo Co., Japan), 2.5 µl of the accompanying buffer, and a sufficient amount of water to make a total of 25 µl. The reaction conditions were 94° C.×1 minute, followed by 42 cycles of 98° C.×10 seconds, 68° C.×40 seconds, and 1 minute of standing at 72° C. Then, using 1 µl of a 100-fold dilution of the above reaction mixture in tricine-EDTA buffer as a template, the same reaction mixture as above except that the primer combination was changed to R1 and R3 was prepared and PCR was carried out in the sequence of 94° C.×1 minute and 25 cycles of 98° C.×10 seconds, 68° C.×40 seconds. The amplification product was subjected to 4% agarose electrophoresis and ethidium bromide staining. As a result, a band of about 130 bp was obtained as expected. This band was recovered in the same manner as in Example 28 and using the recovered fragment as a template, sequencing was carried out with Dye Terminator Cycle Sequencing Kit (ABI). As a result, a partial sequence of human bioactive polypeptide could be obtained. Therefore, based on this sequence, primers HA (SEQ ID NO:82) and HB (SEQ ID NO:83) were synthesized for 3' RACE and primers HE (SEQ ID NO:84) and HF (SEQ ID NO:85) for 5' RACE and 5' and 3' RACEs were carried out.

| | |
|---|---|
| HA:5'-GGCGGGGGCTGCAAGTCGTACCCATCG-3' | (SEQ ID NO:82) |
| HB:5'-CGGCACTCCATGGAGATCCGCACCCCT-3' | (SEQ ID NO:83) |
| HE:5'-CAGGCAGGATTGATGTCAGGGGTGCGG-3' | (SEQ ID NO:84) |
| HF:5'-CATGGAGTGCCGATGGGTACGACTTGC-3' | (SEQ ID NO:85) |

As the template, 2.5 µl of a 20-fold dilution of the cDNA prepared in Example 30 in tricine-EDTA buffer was used. For the initial PCR, reaction mixtures were prepared in the same manner as above except that HA and adapter primer AP1 were used for 3' RACE and HE and AP1 for 5' RACE. The reaction sequence was 94° C.×1 minute, 5 cycles of 98° C.×10 seconds, 72° C. for 35 seconds, 5 cycles of 98° C.×10 seconds, 70° C.×35 seconds, and 40 cycles of 98° C.×10 seconds, 68° C.×35 seconds. Then, using 1 µl of a 100-fold dilution of this reaction mixture in tricine-EDTA buffer as a template, a second PCR was carried out in the same cycles as the first PCR. However, the reaction mixture was prepared using primers HB and AP1 for 3' RACE or HF and AP2 for 5' RACE and Klen Taq (Clontech) as DNA polymerase and the accompanying buffer. As a result, a band of about 250 bp was obtained from 3' RACE and a band of about 150 bp from 5'-RACE. These bands were sequenced by the same procedure as above and using them in combination with the partial sequence obtained previously, the sequence from the region presumed to be 5'-noncoding region to polyA of human bioactive polypeptide was obtained.

Example 32

Acquisition of Human Bioactive Polypeptide Full-length cDNA by PCR

Based on the sequence obtained in Example 31, two primers 5H (SEQ ID NO:86) and 3HN (SEQ ID NO:87) were synthesized for amplification of a fragment including full-length cDNA.

| | |
|---|---|
| 5H:5'-GGCCTCCTCGGAGGAGCCAAGGGATGA-3' | (SEQ ID NO:86) |
| 3HN:5'-GGGAAAGGAGCCCGAAGGAGAGGAGAG-3' | (SEQ ID NO:87) |

Using 2.5 µl of the cDNA prepared using Moloney mouse leukemia reverse transcriptase (BRL) in Example 30 as a template and the reaction mixture prepared using Klen Taq DNA polymerase (Clontech), the PCR reaction was conducted in the sequence of 94° C.×1 minute and 40 cycles of 98° C.×10 seconds, 68° C.×30 seconds. The fragment of about 360 bp obtained was recovered and subcloned (pCR™ 2.1 was used as the vector) in otherwise the same manner as Example 29. The plasmid was recovered and its base sequence was determined. As a result, E. coli JM109/ pHOV7 harboring the human bioactive polypeptide full-length cDNA was obtained [FIG. 34]. In regard to the amino acid sequence of the translation region, a comparison was made between this human bioactive polypeptide and the bovine polypeptide shown in Example 20 or the rat polypeptide in Example 29 [FIG. 35].

Example 33

An orphan G-protein coupled receptor, UHR-1, has been cloned from rat hypothalamic suprachiasmic nuclei, and its nucleotide sequences have been reported (Biochemical and Biophysical Research Communications, vol. 209, No.2, pp606–613, 1995., Genbank Accession Number: S77867). A protein coded by UHR-1 showed 91.6% identity over 359 amino acids with that of phGR3, suggesting UHR-1 is a counterpart of hGR3. To confirm this we cloned a cDNA for UHR-1 coding regions and established a CHO cells stably expressing UHR-1 as described below. Poly(A)⁺ RNA was prepared from rat anterior pituitary using a FastTrack Kit (Invitrogen Co.), and cDNA was synthesized from 0.2 I µg of this with Takara RNA PCR Kit (Takara). The cDNA was dissolved in 10 µl of distilled water, and used as a template for the following PCR. To isolate UHR-1 cDNA, two primers, namely 3'-GTTCACAG(GTCGAC)ATGACCTCAC-3' [SEQ ID NO:95] (UHF), and 5'-CTCAGA(GCTAGC)AGAGTGTCATCAG-3' [SEQ ID NO:96] (UHR), were synthesized on the basis of the sequence of UHR-1 submitted to Genbank (Accesion Number: 577867). In these primers, GTCGAC and GCTAGC indicate the SalI and NheI site respectively. Ex Taq (Takara) was admixed with an equal amount of Taq Start Antibody (Clontech Laboratories, Inc.) to prevent amplification of nonspecific products and primer dimers. Reaction mixture was prepared by adding 5 µl of the buffer attached to Ex Taq, 4 µl of dNTPs, 1 µl of the mixed solution of Ex Taq and Taq Start Antibody, and 1 µl of 50 µM each primers. The cDNA was diluted to one fifth with distilled water, and an aliquot (5 µl) was added to the reaction mixture. PCR conditions were as follows: denatured at 95° C. for 2 minutes, followed by 27 cycles at 95° C. for 30 seconds, 65° C. for 30 seconds and 72° C. for 1 minutes, and after these cycles at 72° C. for 7 minutes.

The PCR products were separated with 1.2% agarose gel and stained with ethidium bromide. Slices of agarose gel containing the band about 1.1 kbp were cut out with razor blade, and then filtered using an Ultra Free filter unit (Millipore). The eluent was extracted with phenol: chloroform and precipitated in ethanol. The amplified DNA was subcloned into pCR™II with a TA cloning Kit (Invitrogen Co.), and then introduced into E. coli JM109 competent cells. Transformants were selected in LB (Luria-Bertani) agar culture medium containing ampicillin, IPTG (isopropylthio-beta-D-galactoside), and X-gal (5-bromo-4-chloro-3-indolyl-beta-D-galactoside). The individual clones were cultured in an LB culture medium containing ampicillin and treated with an automatic plasmid extracting machine (Kurabo) to prepare plasmid DNAs respectively. Sequencing was carried out with a ABI PRISM Dye Terminator Cycle Sequencing Kit FS (Perkin-Elmer), and an ABI automatic sequencer. In the FIG. 52, underlines indicate the sequences corresponding to the parts of primer sequences. Double-lined bases indicate the base substitution compared with the sequence data reported, and one of these substitutions was accompanied by an amino acid substitution from $^{289}$Leu(CTC) to $^{289}$Val(GTC). A plasmid, pCRII-UHR-1, containing the UHR-1 cDNA fragment was thus constructed.

UHR-1 cDNA expression plasmid was prepared as follows. First, pCRII-UHR-1 was digested with NheI and SalI.

The resultant fragment of about 1.1 kbp was separated through electrophoresis using a 1.2% agarose gel and precipitated as above. The DNA fragment was then ligated into the NheI-SalI site of pAKKO-111H, with a Ligation System (Takara). A resultant expression plasmid, pAKKO-UHR-1 was introduced into E. coli JM109.

CHO dhfr⁻ cells were grown in 10 cm diameter Petri dishes at the cell number of $1 \times 10^6$, and cultured at 37° C. for 24 hours in α-MEM containing 10% of fetal bovine serum. The expression plasmid (20 μg) was introduced into the cells by a liposome method using a Gene Transfer (Nippon Gene). After 24 hours from the introduction, the medium was substituted with fresh one. After additional 24 hour incubation, the culture medium was changed to a Selection medium, α-MEM without nucleosides containing 10% of dialyzed fetal bovine serum. Culture was carried out until cells growing in the Selection medium were obtained. CHO-UHR-1 which highly expressed UHR-1 was thus established.

Example 34

Radioiodination of 19P2-L31 and Receptor Binding Experiments

19P2-L31 was radioiodinated with [$^{125}$I]-Bolton-Hunter Reagent (NEN.Dupont; NEX-120) as follows. Two hundred microliter of [$^{125}$I]-Bolton-Hunter Reagent was dried in a 500 μl Eppendorf tube with $N_2$ gas. The dried reagent was dissolved in 2 μl of acetonitrile, and then mixed with 4 ml of 50 mM phosphate buffer (pH 8.0) and 4 μl of 19P2-L31 $3 \times 10^4$M. The mixture was incubated at room temperature for 40 min and the reaction was stopped by adding 5 μl of 1.0 M glycine. The all reaction mixture was diluted with 300 μl of 18% acetonitrile and injected onto reverse-phase HPLC column TSK gel ODS-80TM (4.6×100 mm; TOSO). The radioiodinated 19P2-L31 was eluted with a linear gradient of acetonitrile concentration from 18 to 32.4% in 0.1% teifluoroacetic acid for 24 min at a flow rate of 1 ml/min. The peak fraction of radioiodinated 19P2-L31 was collected and diluted with twice volume of 50 mM Tris-HCl(pH7.5) containing 0.1% BSA and 0.05% CRAPS, and then stored at −20° C.

Receptor binding experiments were performed with [$^{125}$I]-19P2-L31 as follows. As receptor-expressing CHO cells, CHO-19P2-9; mono-clone of CHO-19P2, CHO-UHR-1, and mock CHO were used in this experiment. CHO-19P2-9 cells are ones selected from CHO-19P2 cells by ultradilution technique using 96-well microplate as clone which indicated stronger arachidonic acid metabolic-release promoting reaction by 19P2-L31. The mock CHO cells are ones for control which were transformed with expression vector pAKKO alone. These cells cultured in flasks for culturing tissues were harvested with 5 mM EDTA/PBS, and then resuspended in HBSS containing 0.05% BSA and 0.05% CHAPS at $0.5 \times 10^7$ cells/ml. The cell suspensions were incubated with 200 pM [$^{125}$I]-19P2-L31 for 2.5 hr at room temperature in a 100 μl total volume. The reaction mixture were diluted with 2 ml of an ice-cold buffer (50 mM Tris-HCl pH7.5 containing 5 mM EDTA, 0.05% BSA, and 0.05% CHAPS) and immediately filtered though glass filters GF/F (Whattman) which were pre-wetted with the buffer containing 0.3% polyethylenimine. The glass filters were subjected to γ-counting. Non-specific binding was determined in the presence of 200 nM unlabeled 19P2-L31.

Figure 36:
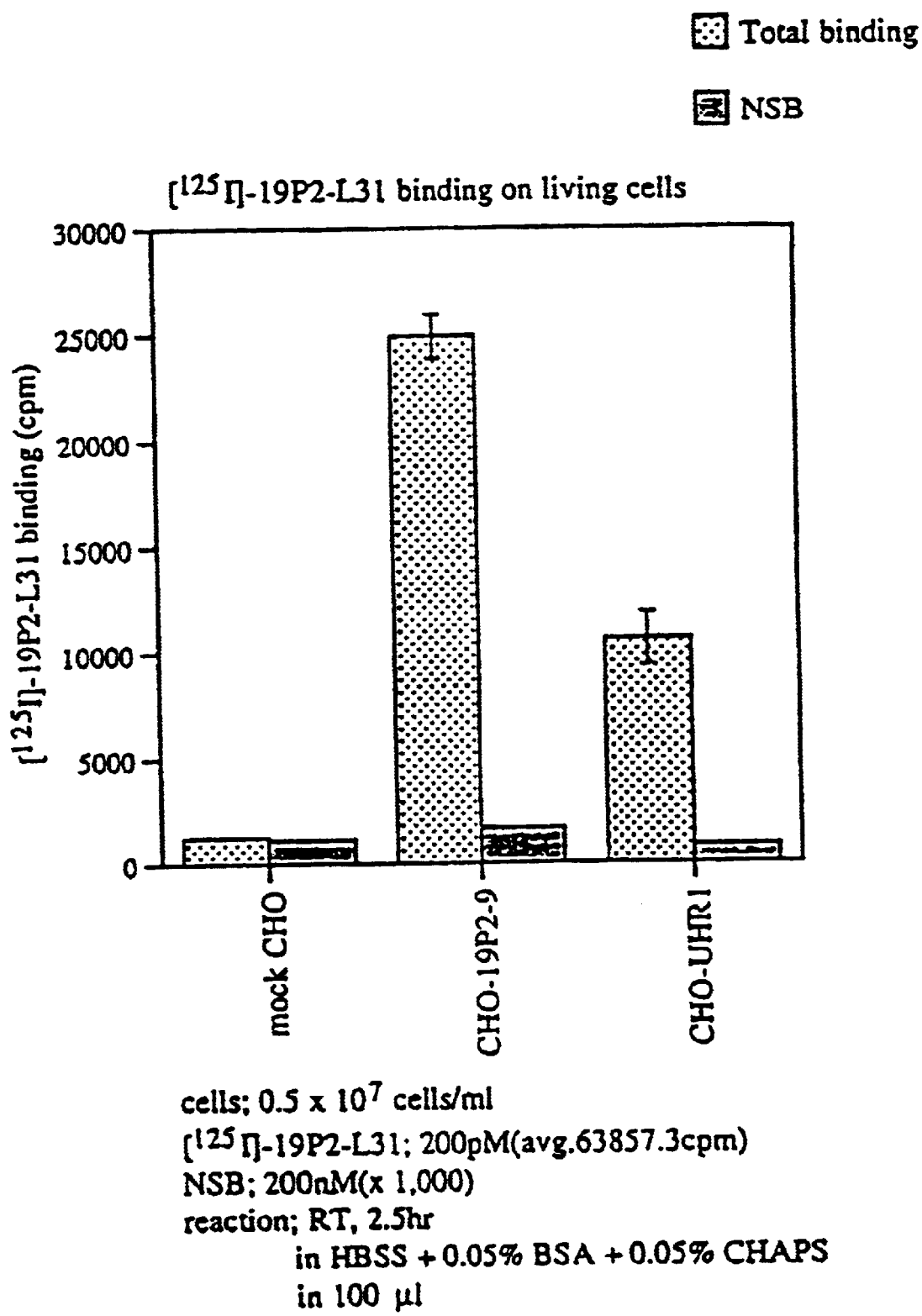
FIG. 36 shows the results of receptor binding experiments on living cells wherein radioiodinated ligand polypeptide is used in the experiments.

[FIG. 36] shows receptor binding experiments with [$^{125}$I]-19P2-L31 on live cells.

Specific binding of [$^{125}$I]-19P2-L31 was detected on CHO cells which were expressed with hGR3 and rat homolog UHR-1 respectively. The experiments were performed in triplicate. These results show that the proteins encoded by hGR3 and UHR-1 is functioning as the specific receptor of 19P2-L31.

Example 35

Release of Arachidonic Acid Metabolites From CHO-19P2-9 and CHO-UHR1 by 19P2-L31

Same as described in Example 11, the release activity of arachidonic acid metabolite was measured on CHO-19P2-9 and CHO-UHR1 and mock CHO.

Figure 37:
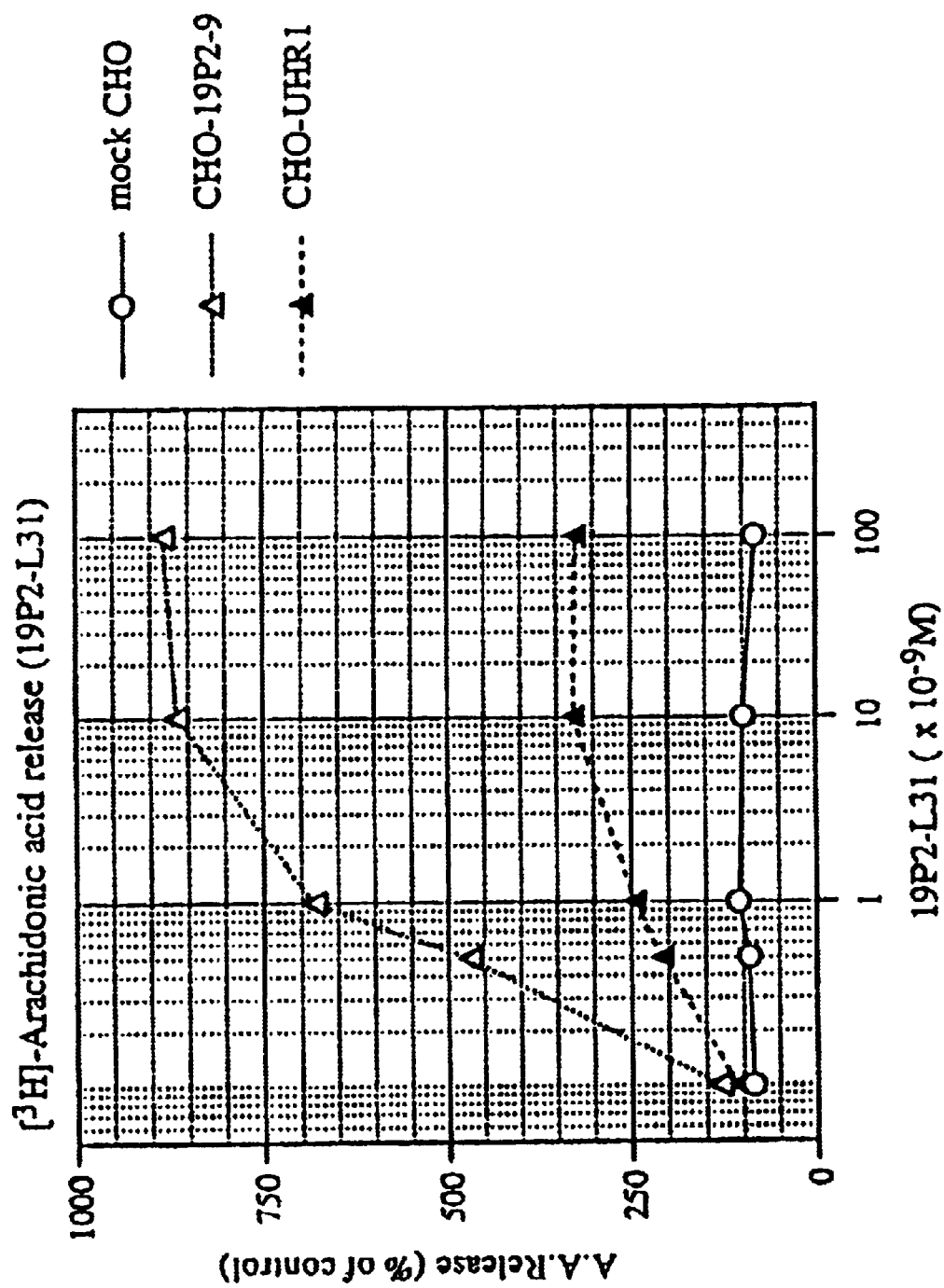
FIG. 37 shows the results of measurements of release of arachidonic acid metabolites from CHO-19P2-9 and CHO-UHR1 by ligand polypeptide.

[FIG. 37] shows the release activity of arachidonic acid metabolite on CHO-19P2-9 and CHO-UHR1 by 19P2-L31.

On CHO cells which were expressed with rat homolog UHR1, the release activity of arachidonic acid metabolite was detected same as CHO-19P2-9. The experiments were performed in duplicate. These results show that the protein encoded by UHR-1 is functioning as the specific receptor as well as hGR3.

Example 36

Quantification of Rat 19P2 Ligand and Rat UHR-1 mRNA, BBRC, 209,606–613, 1995) by RT-PCR (1) Preparation of Poly(A)+ RNA and cDNA Synthesis From Rat Tissues.

Poly(A)+ RNA was isolated from a variety of tissues in rats (Wister strain, male, 8 weeks old) by homogenization with Isogen (Nippon Gene) followed by an oligo (dT)-cellulose chromatogranny (Pharmacia). One μg of poly(A)+ RNA was treated with DNase I (Amplification grade, GibcoBRL) to eliminate the contamination of genomic DNA. DNase I was inactivated by the addition of 25 mM EDTA solution at 65° C. Then RNA (160 ng) was reverse-transcribed in 40 μl of a reaction mixture containing 10 mM of Tris-HCl (pH 8.3), 2.5 μM of random hexamers (Takara), 0.4 mM of each dNTP, and 10 U of AMV reverse transcriptase XL (Takara). The samples were incubated at 30° C. for 10 min followed by 42° C. for 1 h, then 99° C. for 5 min to stop the reaction. The reaction mixture was purified by ethanol precipitation, and then the cDNA was diluted to 40 μl with tricine-EDTA buffer (correspond to 4 ng poly(A)+ RNA/μl).

(2) Construction of Positive Control Plasmid Vectors

Rat glycerolardehyde-3-phasphate-dehydrogenase (G3PDH) and rat UHR-1 cDNAs were isolated from rat pituitary tumor cell line $GH_3$ by means of RT-PCR Poly(A)+ RNA of $GH_3$ was prepared by FastTrack (Invitrogen), and cDNA was synthesized as Example 36(1). Oligonucleotide primers used for the amplification are as follows: rat G3PDH amplification primer set (Clontech), rRECF(5'-CCTGCTGGCCATTCTCCTGTCTTAC-3') (SEQ ID NO:88) and rRECR(5'-GGGTCCAGGTCCCGCAGAAGGTTGA-3') (SEQ ID NO:89) for UHR-1. The fragments amplified from $GH_3$ cDNA were subcloned with a TA cloning Kit (Invitrogen). The recombinant vectors were introduced into E. coli JM109. The transformant clones were cultured in a LB culture medium containing ampicillin, and the plasmid DNAs were prepared with a Quiagen Plasmid Midi Kit (Quiagen). The plasmid of rat ligand polypeptide was prepared from E. coli JM109/pRAV3 which was deposited.

(3) Quantification RT-PCR cDNA and plasmid DNA prepared in (1) and (2) above were diluted with distilled water to adequate concentrations and used as templates of quantitative RT-PCR. G3PDH, UHR-1, and ligand polypeptide cDNA fragments were amplified using human G3PDH amplimer (Clontech), rRECF and rRECR, and r19F(5'-GAAGACGGAGCATGGCCCTGAAGAC-31) (SEQ ID NO:91) and r19R(5'-GGCAGCTGAGTTGGCCAAGTCCAGT-3') (SEQ ID NO:91), respectively. Each reaction sample contained 100 $\mu$M of dNTP mixture, 200 nM of each primer, 4 $\mu$l of template DNA, 0.25 $\mu$l of 50×KlenTaq DNA polymerase mix (Clontech), and 2.5 $\mu$l of the buffer attached to KenTaq DNA polymerase mix in a final volume of 25 $\mu$l. PCR conditions for G3PDH were as follows: denatured at 94° C. for 1 min, followed by 26 cycles at 98° C. for 10 sec, at 65° C. for 20 sec, and at 72° C. for 40 sec. PCR conditions for UHR-1 and ligand polypeptide were as follows: denatured at 94° C. for 1 min, followed by 34 cycles at 98° C. for 10 sec, and at 68° C. for 25 sec. An aliquot 5 $\mu$l of each RT-PCR product was separated with 4% Nusieve 3:1 agarose gel (F.M.C.) electrophoresis and stained with ethidium bromide. The bands were quantified using a densitometry program (Advanced American Biotechnology).

Figure 38:
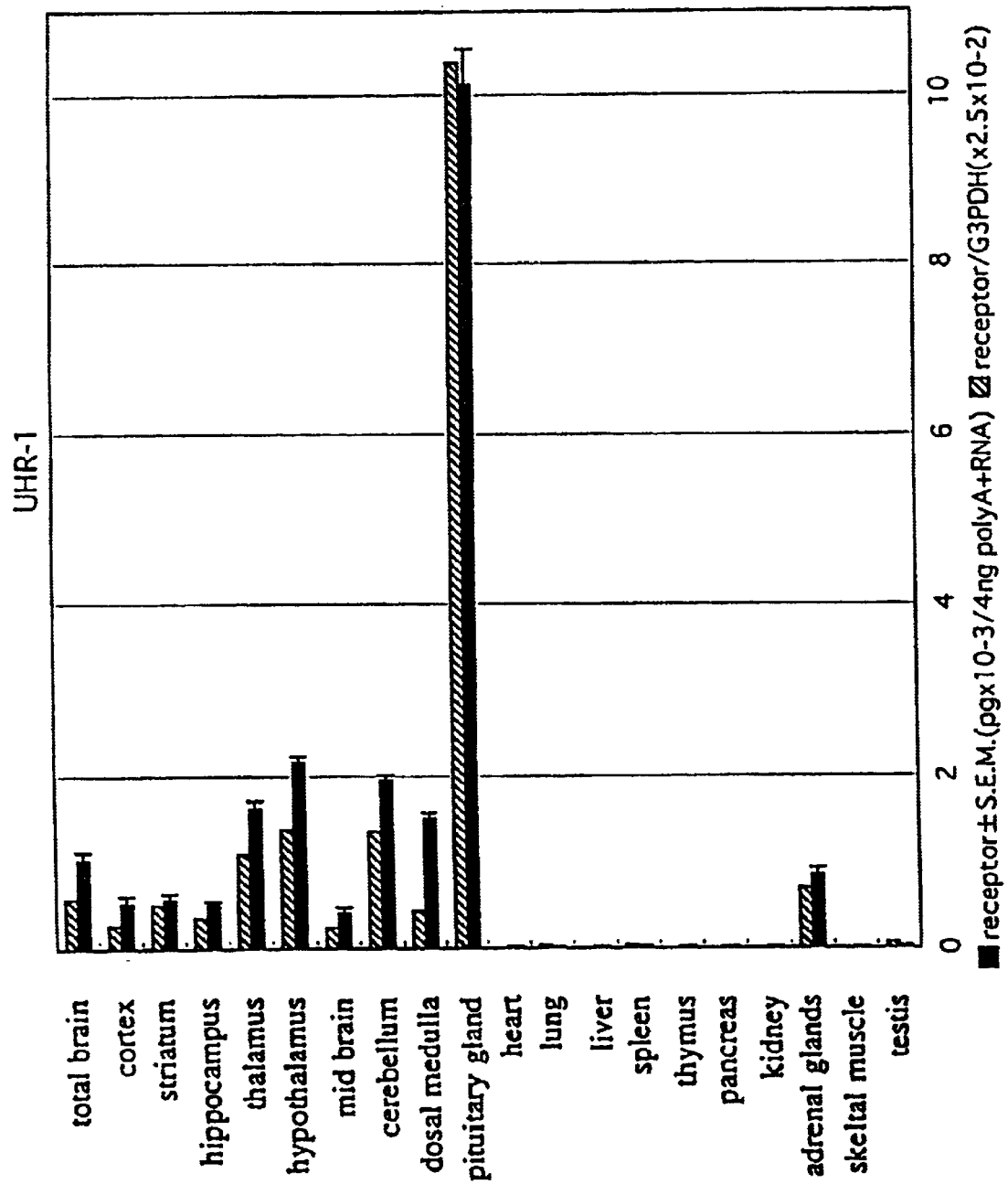
FIG. 38 shows the results of quantification of UHR-1 mRNA by RT-PCR in discrete regions of the brain and tissues in rats.
Figure 39:
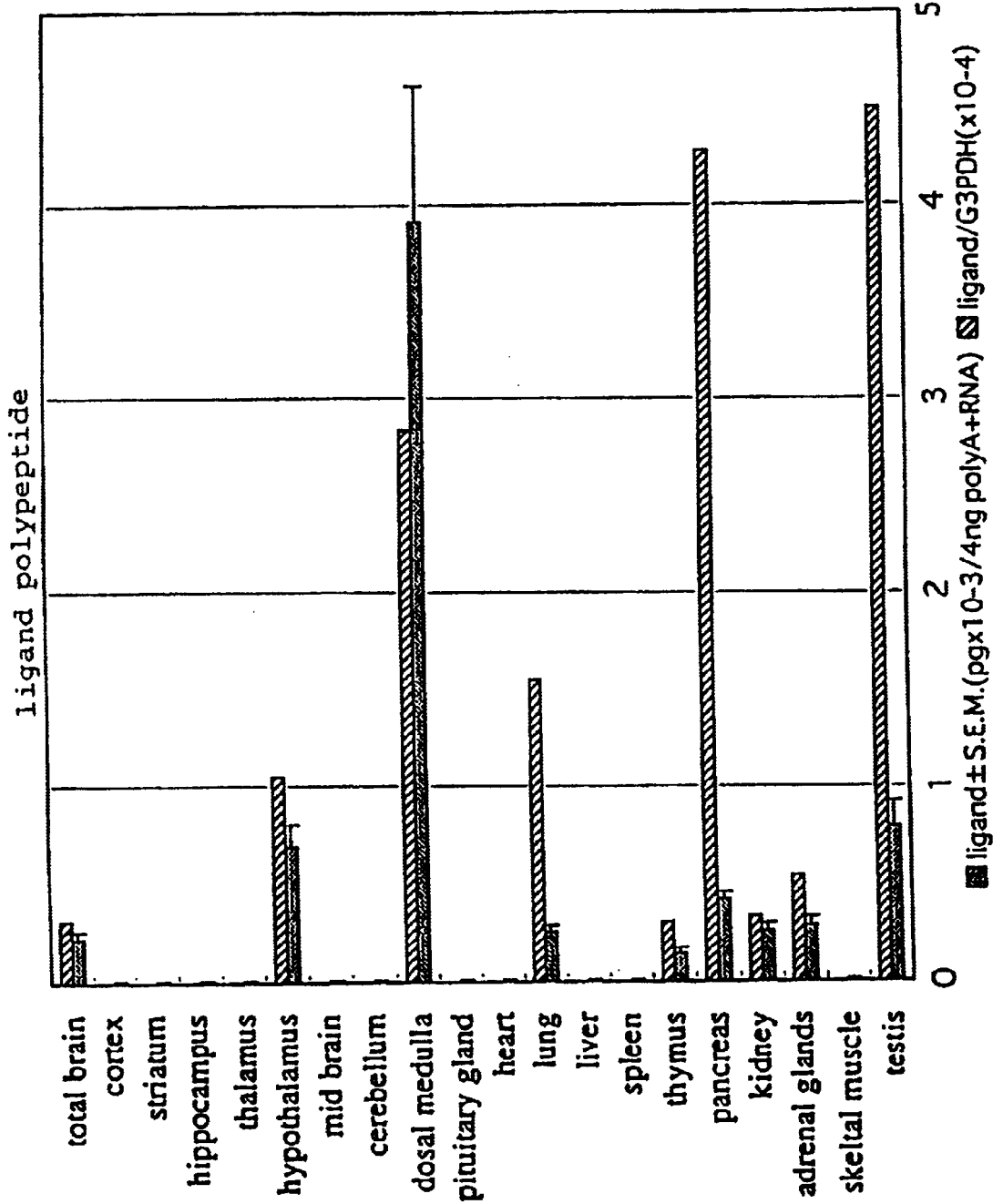
FIG. 39 shows the results of quantification of ligand polypeptide mRNA by RT-PCR in discrete regions of the brain and tissues in rats.

The results measured the expression levels of UHR-1 and ligand polypeptide mRNA in the tissues were shown in FIGS. 38 and 39 respectively. UHR-1 and ligand polypeptide mRNA were detected in all the tissues tested. The highest level of UHR-1 mRNA expression was detected in the pituitary, and moderate expression levels in the brain, whereas poorly expressed in peripheral tissues except for the adrenal glands. Ligand polypeptide mRNA expressed mainly in the hypothalamus and dosal medulla among brain regions, and expressed comparatively high levels in the lung, thymus, pancreas, kidney, adrenal glands, and testis. These results show that the UHR-1 and ligand polypeptide play a significant role for the regulation of function in various tissues.

Example 37

Effect of 19P2-L31 on Glucose-induced Increase in Plasma Insulin Concentration

Male Wistar rats (8–10w) were anesthetized by i.p. injection of pentobarbital (65 mg/kg). Glucose alone (86 mg/rat) or glucose and 19P2-L31 (675 pmol, 2.25 nmol, 6.75 nmol and 67.5 nmol/rat) were administered by bolus injection in the jugular vein. Blood samples were withdrawn from the contralateral vein. Plasma insulin concentration was determined with a radioimnunoassay kit (Amersham).

Figure 40:
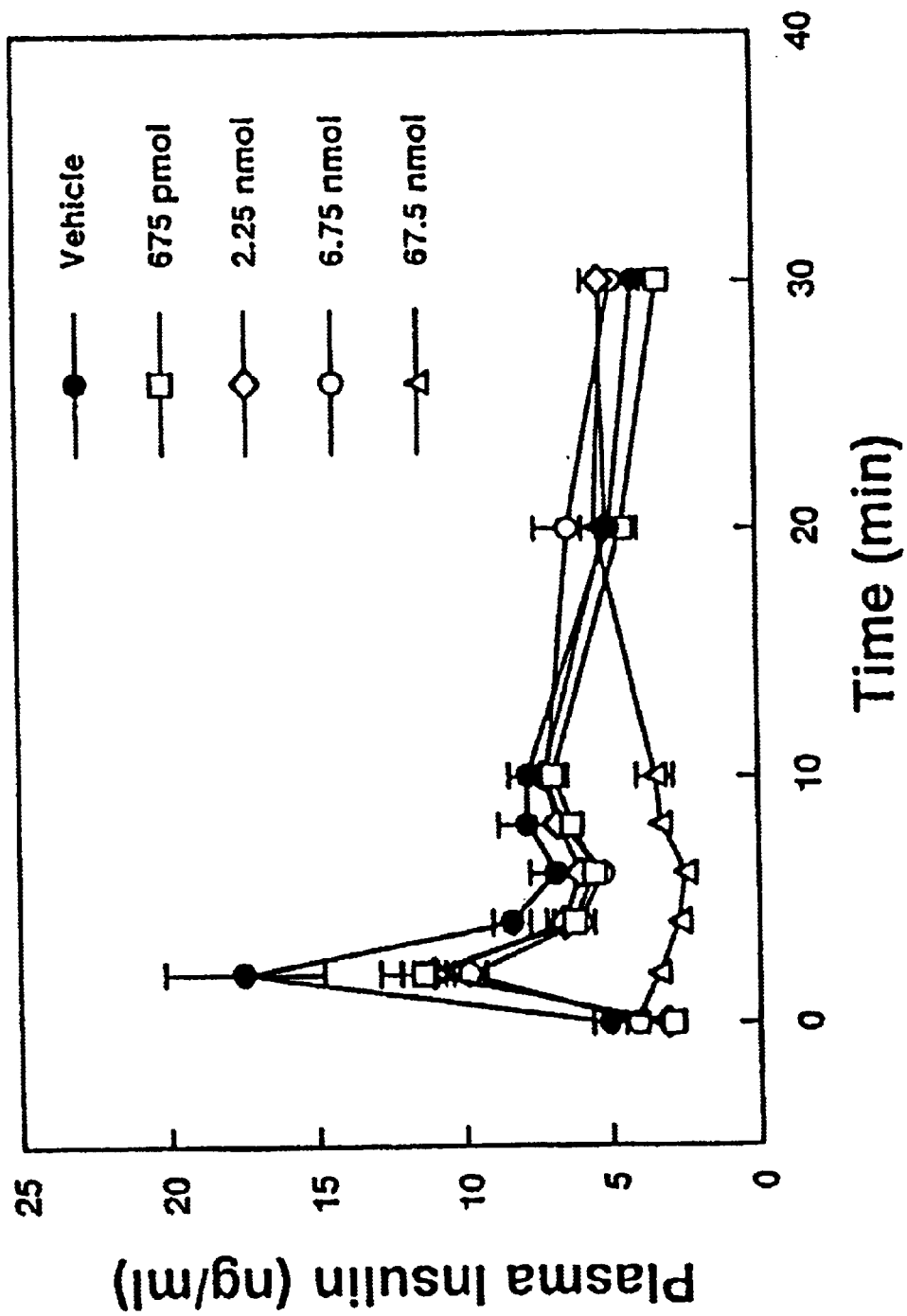
FIG. 40 shows effects of ligand polypeptide on glucose-induced increase in plasma insulin concentration, which is measured by radioimmunoassay.

Administration of 19P2-L31.at the doses of 675 pmol, 2.25 nmol, and 6.75 nmol partially inhibited glucose-induced sharp increase (the first phase) in plasma insulin concentration at 2 min postinjection and the blunt increase (the second phase) after 6 min postinjection. It completely inhibited the first and second phase of increase in insulin concentration at the dose of 67.5 nmol [FIG. 40].

Example 38

Effects of Ligand Polypeptide on Motor Activity of Mouse

The effects of administration of 19P1-L31 to mouse lateral ventricle on motor activity were studied. The mature ICR male mice (weight at operation: about 35 g) were anesthetized by intraperitoneal administration of 50 mg/kg of pentobarbital, and then fixed on a stereotaxic apparatus. The skull of a said mouse was exposed, then a hole was made by dental drill for guide-cannulization into the left lateral ventricle. The tip of a stainless-steel guide-cannula (24 G, length: 5 mm) for drug injection to lateral ventricle, was inserted to the position of AP: +0.6 mm (from bregma), L: left 1 mm and H: −1 mm (from dura matter). The guide-cannula was fixed onto the skull with adhesive. The cannula-implanted mice were housed as described above and were used for behavioral analysis at least 3 days after the operation.

Motor activity such as spontaneous motor activity and rearing was measured while each mouse was in a transparent acrylic cage (24×37×30 cm) within a soundproofed, illuminated (light up: at 6–18 o'clock) box. Tap water and laboratory chow were available ad libitum. Motor activity was measured by means of a Supermex (Muromachi Kikai). Drugs and PBS were administered at 2:30±30 p.m. At the administration, a stainless-steel micro-injection cannula (30 G, length: 6 mm) was inserted into the guide-cannula. The micro-injection cannula was connected to a microsyringe pump with Teflon tube, and injection of PBS or a peptide dissolved in PBS lasted for 2 minutes at a speed of 2 $\mu$l/min. The micro-injection cannula was withdrawn after over a period of 2 minutes from end of injection, then motor activity was meaursed.

The results are expressed as a mean±S.E.M. Student's t test was used to determine the significance of differences between values from the mice treated with a peptide and the PBS-injected controls. For the purpose of this analysis, $p<0.05$ was assumed to be the minimal level of significance.

Figure 41A:
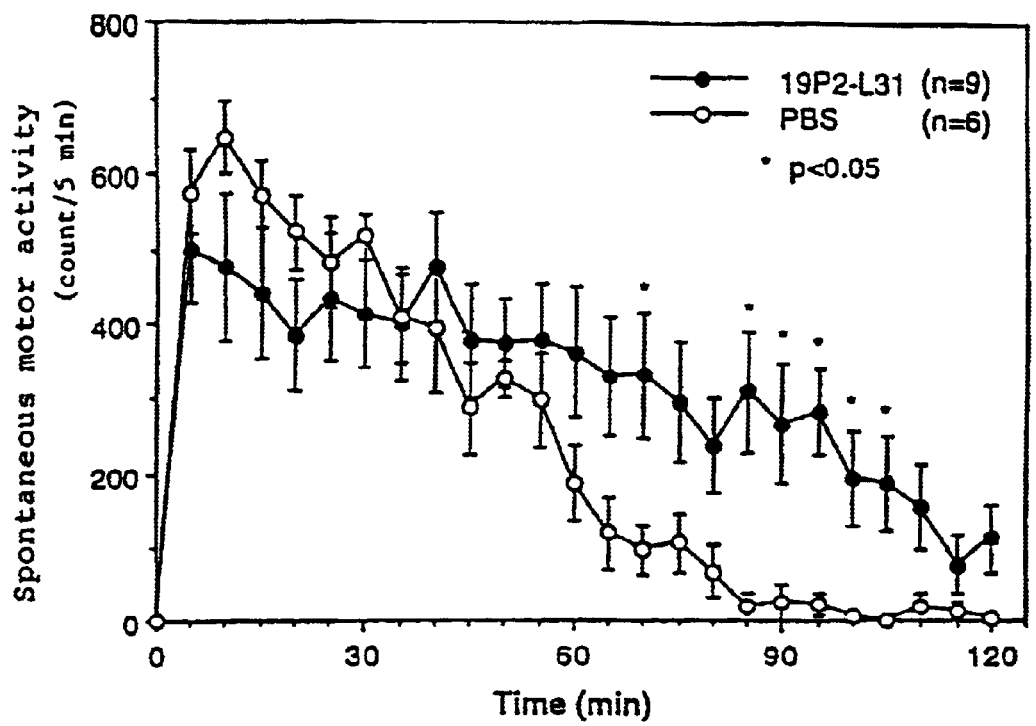
FIG. 41 shows the results of measurements of motor activity by administration of 10 nmol of ligand polypeptide to mouse.
(a) relates to spontaneous motor activity and (b) relates to rearing.
Figure 41B:
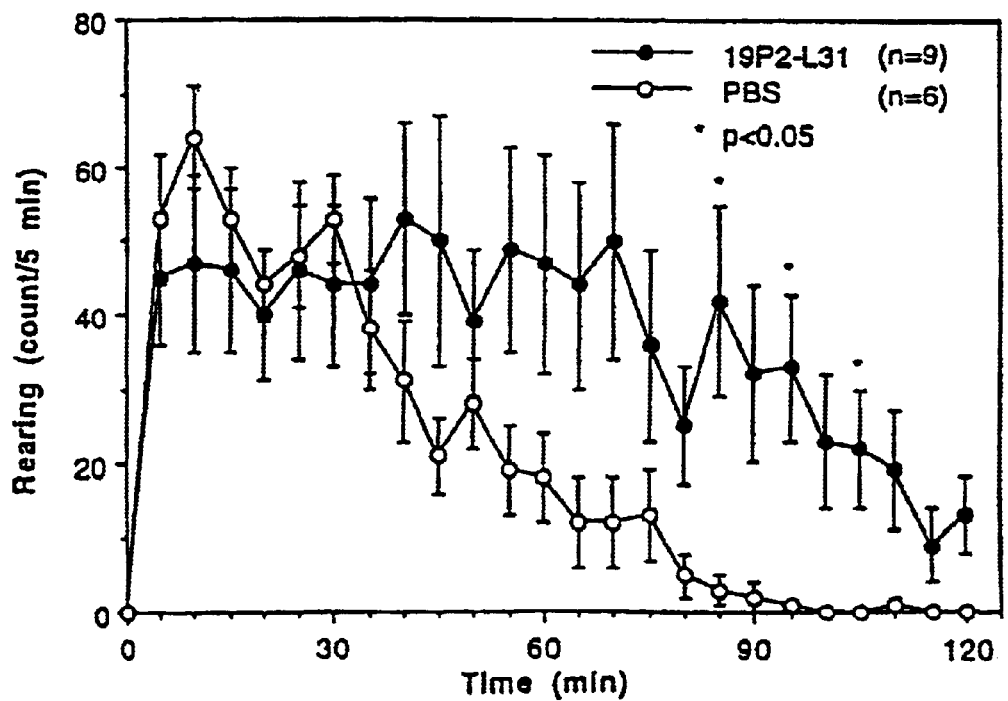
Figure 42A:
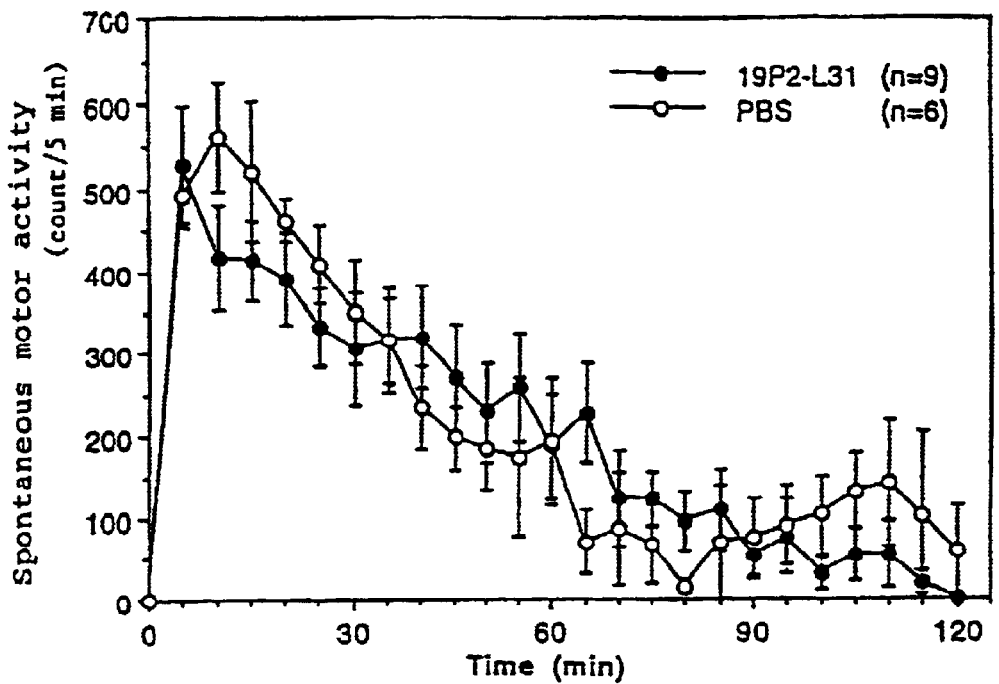
FIG. 42 shows the results of measurements of motor activity by administration of 1 nmol of ligand polypeptide to mouse.
(a) relates to spontaneous motor activity and (b) relates to rearing.
Figure 42B:
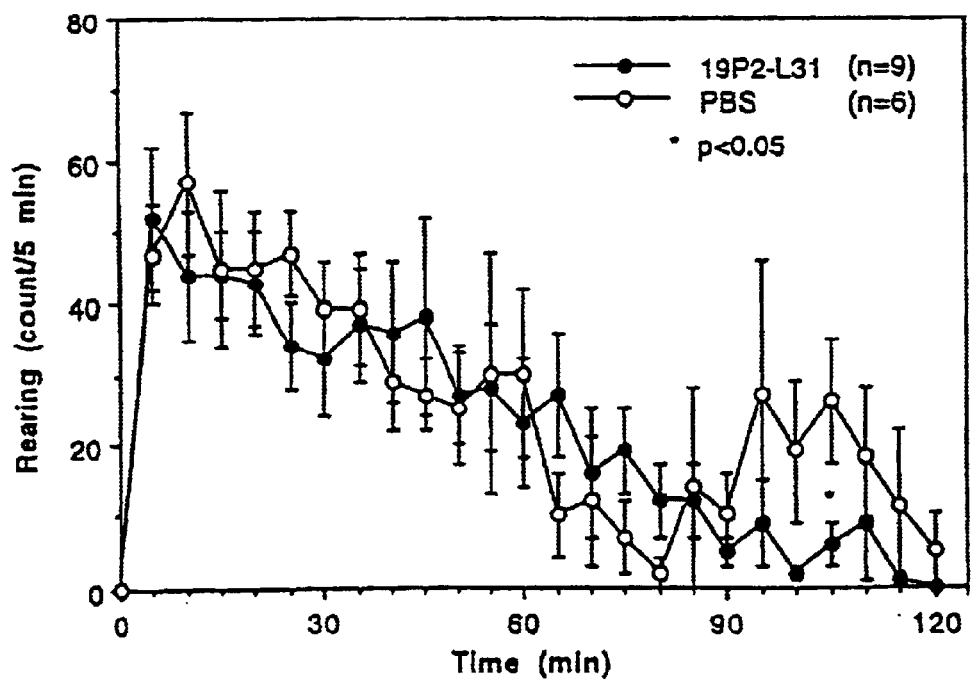
Figure 43A:
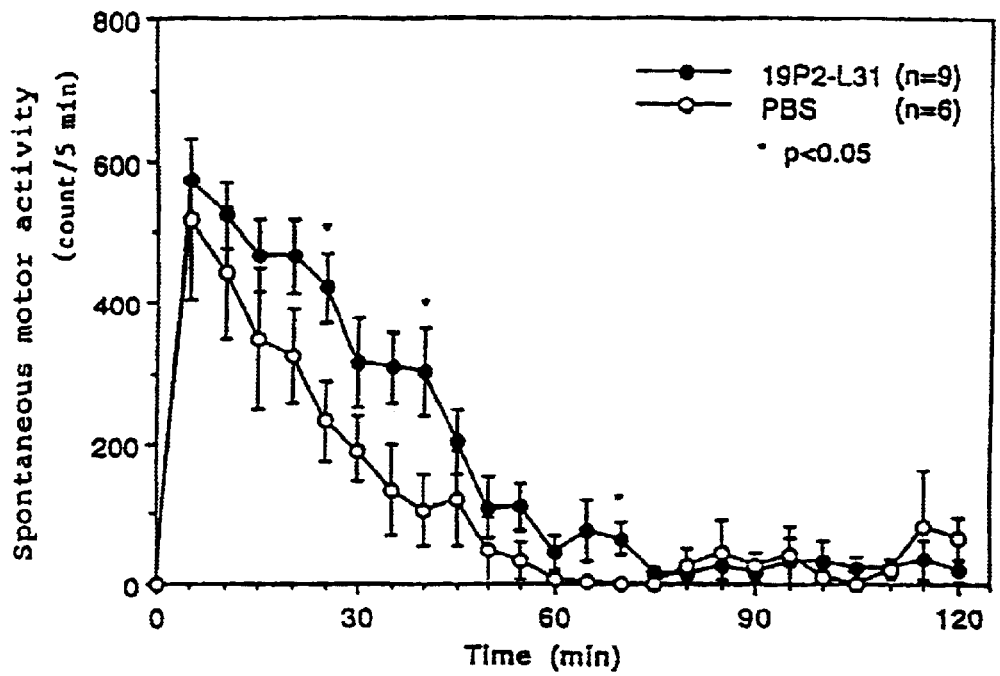
FIG. 43 shows the results of measurements of motor activity by administration of 0.1 nmol of ligand polypeptide to mouse.
(a) relates to spontaneous motor activity and (b) relates to rearing.
Figure 43B:
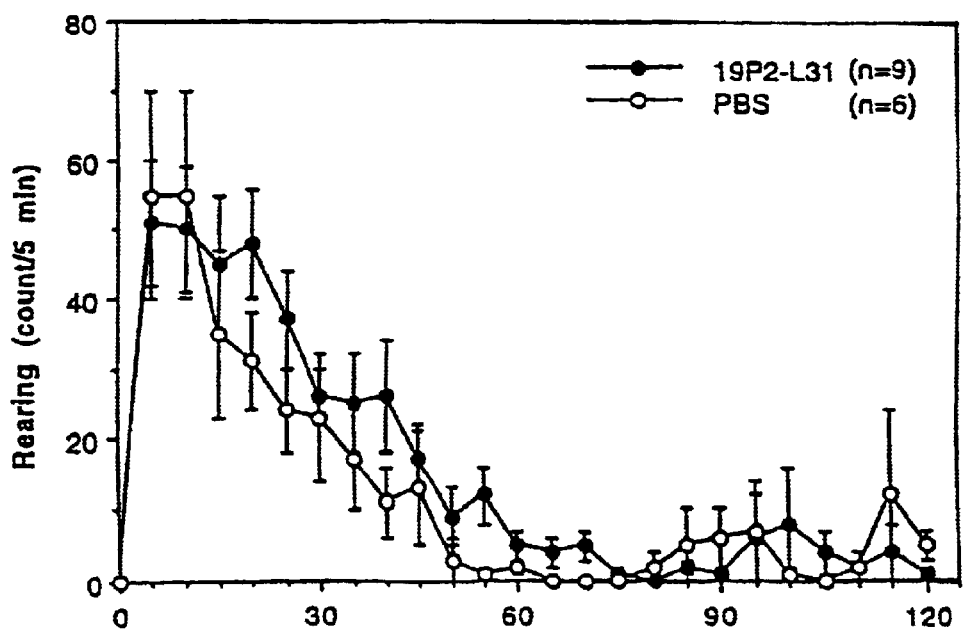
Figure 44A:
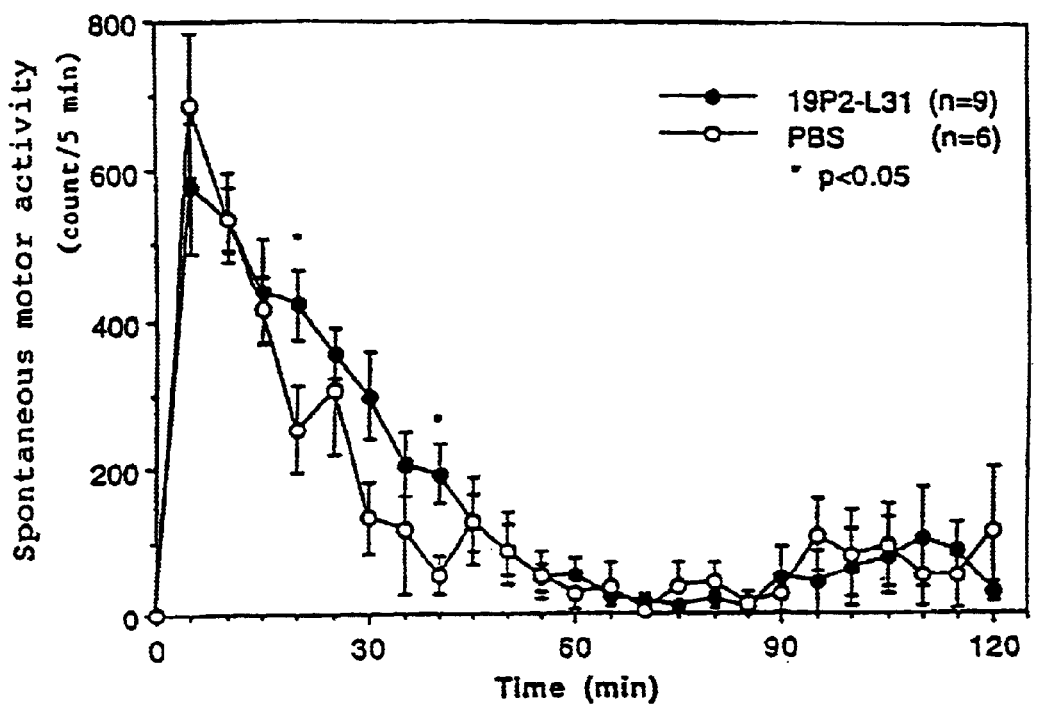
FIG. 44 shows the results of measurements of motor activity by administration of 0.01 nmol of ligand polypeptide to mouse.
(a) relates to spontaneous motor activity and (b) relates to rearing.
Figure 44B:
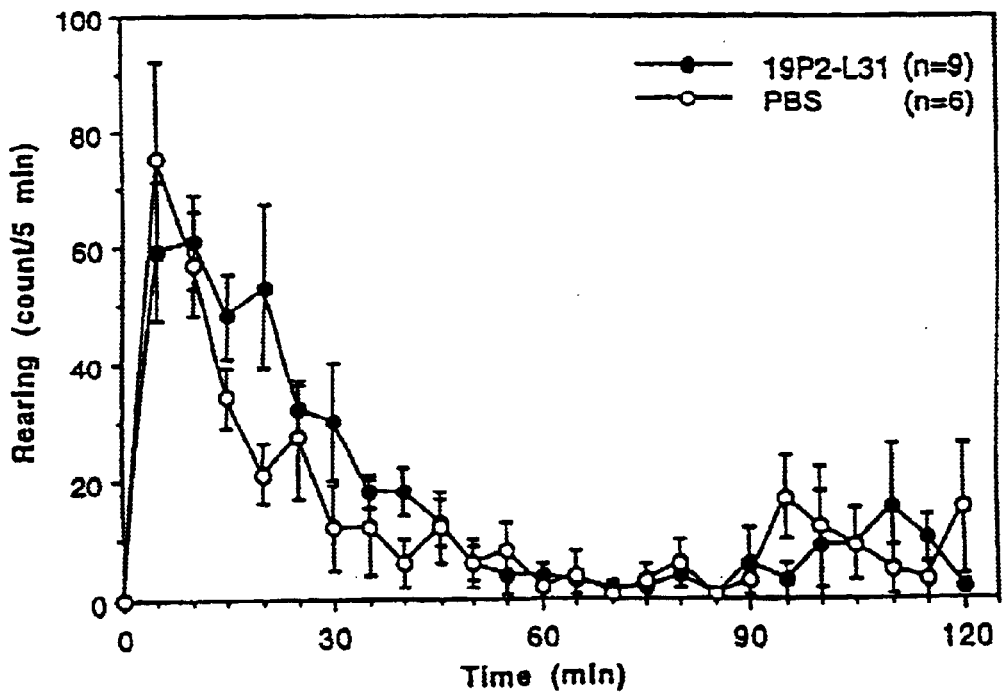

As shown in [FIG. 41], administration of 10 nmol of 19P2-L31 caused a significant increase in spontaneous motor activity at 70–$10^5$ min after injection. Rearing behavior also showed significant variation. While the administration of 1 nmol of 19P2-L31 did not cause statistically significant change of spontaneous motor activity, rearing behavior showed a significant decrease at only 105 min after injection [FIG. 42]. The administration of 0.1 nmol of 19P2-L31 caused a significant increase at 25 min, 40 min and 70 min after injection. In that case, reaching behavior showed an increasing tendency similarly to spontaneous motor activity, however that was not statistically significant [FIG. 43]. The administration of 0.01 nmol of 19P2-L31 caused a significant increase at 20 min and 40 min after injection. In that case, rearing behavior showed an increasing tendency similarly to spontaneous motor activity, however that was not statistically significant [FIG. 44].

Example 39

Effects of Ligand Polypeptide on Reserpine-induced Hypothermia in Mice

The mature ICR male mice (weight at operation: about 35 g) were anesthetized by administration of pentobarbital (50 mg/kg, i.p.), and then fixed on stereotaxic apparatus. The skull of a said mouse was exposed, then a hole was made by dental drill for guide-cannulization into the left lateral ventricle. The tip of a stainless-steel guide-cannula (24 G, length: 5 mm) for drug injection to lateral ventricle, was inserted to the position of AP: +0.6 mm (from bregma), L: left 1 mm and H: −1 mm (from dura matter). The guide-cannula was fixed onto the skull with adhesive. The cannula-implanted mice were housed as described above and were used for measurements of body temperature at least 3 days after the operation. Reserpine (Apoplon; Daiichi Pharmaceutical) was administered to mice at a dose of 3 mg/kg, s.c., and after 15 hours, each mouse was placed in a cage for the measurement. Then a stainless-steel micro-injection cannula (30 G, length: 6 mm) was inserted into the guide-cannula. The micro-injection cannula was connected to a microsyringe pump with Teflon tube, and injection of PBS or a peptide dissolved in PBS lasted for 2 minutes at a speed of 1 µl/min. The micro-injection cannula was withdrawn after over a period of 2 minutes from end of injection, than the temperature in rectum was measured.

The results are expressed as a mean±S.E.M. Student's t test was used to determine the significance of differences between values from the mice treated with a peptide and the PBS-injected controls. For the purpose of this analysis, $p<0.05$ was assumed to be the minimal level of significance.

Figure 45:
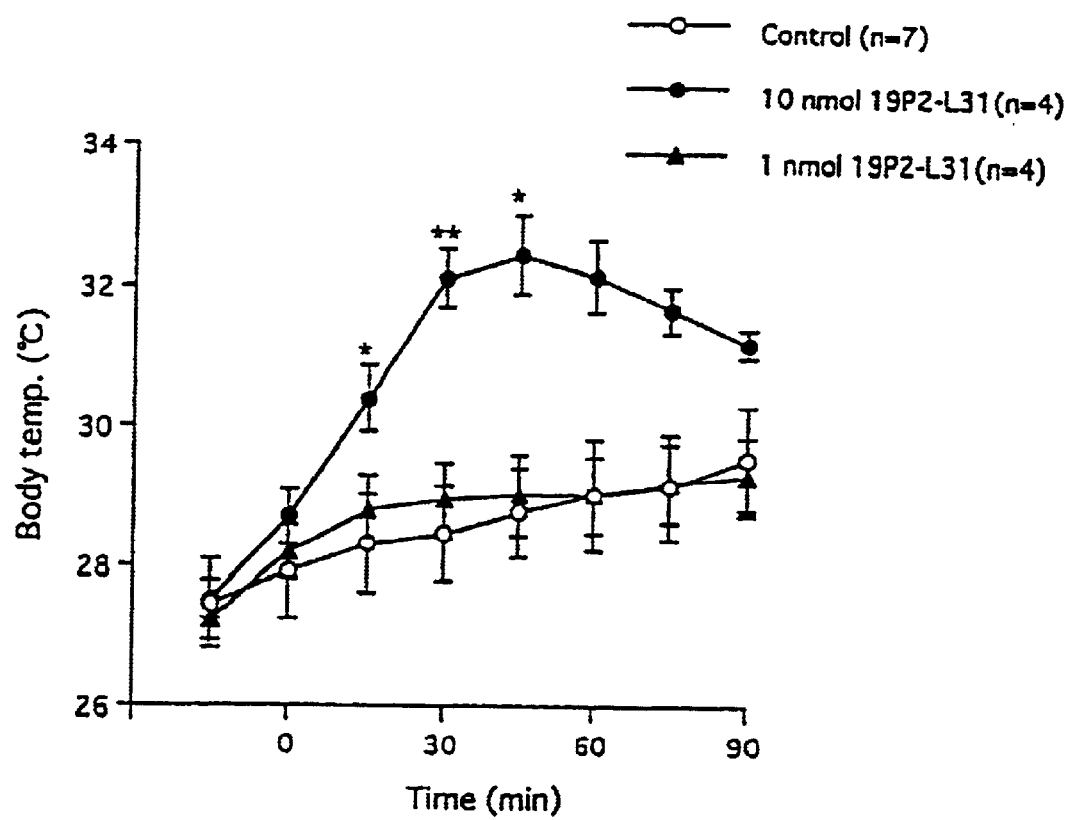
FIG. 45 shows the results of measurements of body temperature which is measured at the time when the ligand polypeptide is administered to the lateral ventricle of mice. The administration of ligand polypeptide is carried out after 15 hours from administration of reserpine at a dose of 3 mg/kg, S.C.

As shown in [FIG. 45], body temperature which was lowered by reserpine increased significantly after a 10 nmol injection of 19P2-L31 in contrast to the control which PBS were administered. This increase of body temperature reached a maximum level at 45 min after administration of the peptide. On the other hand, there was no statistically significant difference in temperature variation between 1 nmol of 19P2-L31 and the PBS-injected control throughout the experimental period.

Example 40

Effects of Ligand Polypeptide on Blood Pressure in Rats

The inventors explored the influence of injection of 19P2-L31 into the area postrema of medula oblongata on blood pressure. Mature male Wistar rats (body weights at operation: ca 300 g) were anesthetized with pentobarbital 50 mg/kg i.p. and each animal was immobilized in a rat brain stereotaxic apparatus. The incisor bar was lowered by 3.3 mm from the interaural line. The skull was exposed, and using a dental drill a hole was made on the skull for implantation of a guide cannula. In addition, anchor screws were buried in two positions around the drilled hole. A stainless-steel guide cannula, AG-12 (0.4 mm inside dia., 0.5 mm out. dia., EICOM), was inserted in such a manner that its leading end would be situated in the upper part of the area postrema. For this purpose, the guide cannula was instered from a forward direction at an angle of 20° with the perpendicular (FIG. 46; Note, however, that the drawing shows a microinjection cannula 1.0 mm longer than the guide cannula). With reference to the atlas of Paxinos and Watson (1986), the stereotaxic coordinates were AP: −6.0 mm (from interaural line), L: 0.0 mm, and H: +1.5 mm (from interaural line). The guide cannula was secured to the skull using an instant adhesive, a dental cement, and anchor pieces. A stainless-steel dummy cannula, AD-12 (0.35 mm out. dia., EICOM), was inserted into the guide cannula and locked in position with a cap nut (EICOM). Thereafter, the rats were kept in individual cages.

About a week of feeding after implantation of the guide cannula for postoperative recuperation, an operation was performed for measurements of blood pressure in conscious state. The rat described above was anesthetized with pentobarbital 50 mg/kg i.p. and immobilized in spine position on a necropsy pad and the left femoral artery was exposed. Polyethylene tubing, SP35 (0.5 mm in. dia., 0.9 mm out. dia., Natsume Seisakusho), was cut to about 60 cm in length and filled with 200 U/ml heparin-containing saline. This tube was inserted about 2.5 cm deep into the femoral artery and secured in position. The free end of the tube was passed under the dorsal skin and exposed in the cervical region (dorsal side).

Figure 46:
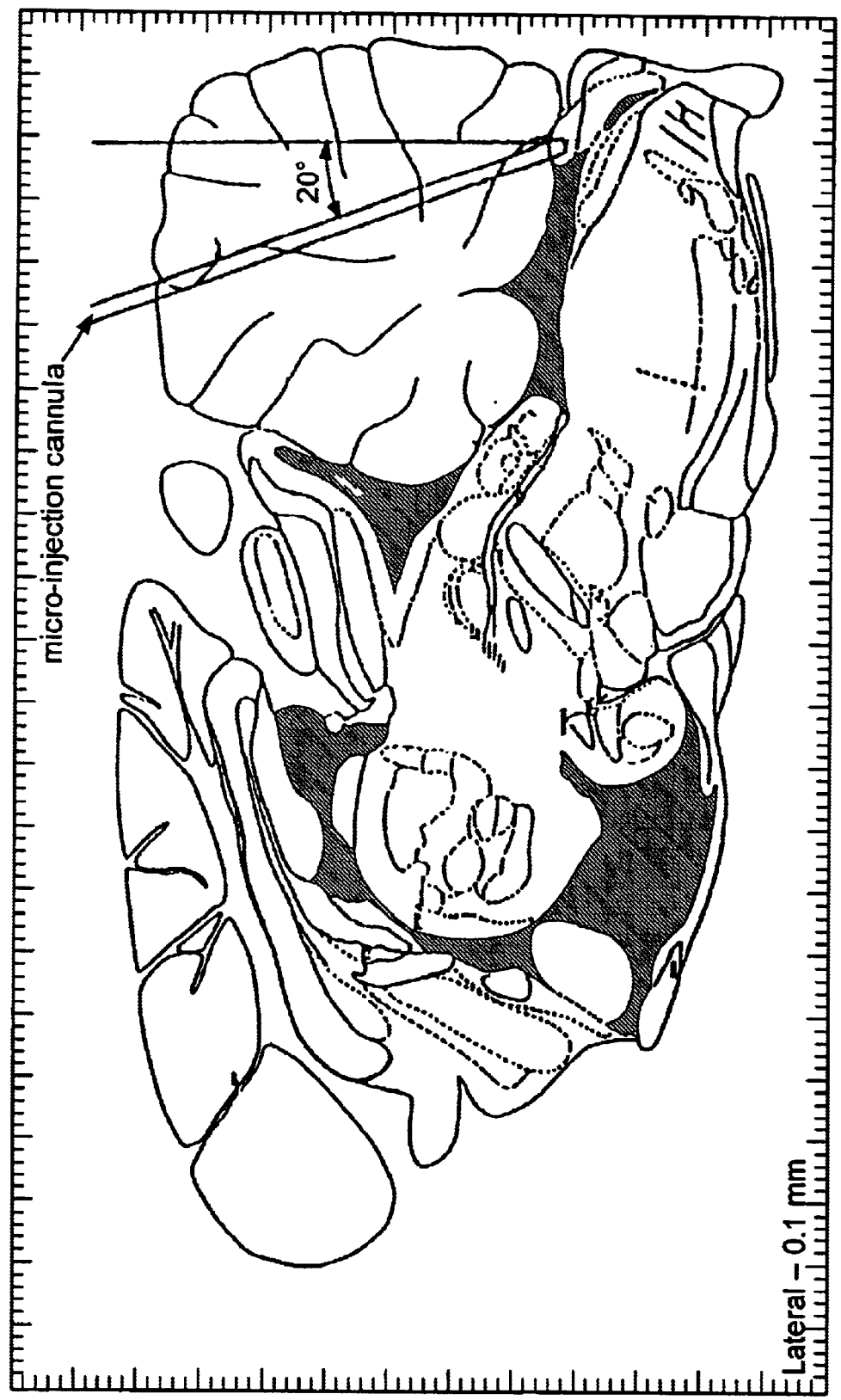
FIG. 46 illustrates the drawing in which the microinjection cannula is inserted into the area postrema at an angle of 20°.

After waiting overnight postoperatively, the polyethylene tube was connected to a transducer (Spectramed) and the blood pressure was measured. After blood pressure readings became steady, the cap nut and dummy cannula were removed from the rat skull and, instead, a stainless steel microinjection cannula (0.17 mm in. dia., 0.35 mm out. dia., EICOM) connected to a Teflon tube (50 cm long, 0.1 mm in. dia., 0.4 mm out. dia., EICOM) was inserted. The length of the microinjection cannula was adjusted beforehand so that its tip would extend 1 mm from the guide cannula (FIG. 46). One end of the Teflon tube was connected to a microsyringe pump and either PBS or 19P2-L31 dissolved in PBS was injected, in a total volume of 2 µl, into the area postrema at a flow rate of 1.0 µl/min.

After measurement of blood pressure, the micro-injection cannula used for injection of 19P2-L31 was disconnected and replaced with a microinjection cannula for injection of a stain (Evans Blue) solution. The stain was infused at the same rate of 1.0 µl/min as the injection of 19P2-L31 for 2 minutes. After a standby time of about 3 minutes, the microinjection cannula was disconnected. The rat was decapitated and the brain was quickly removed and frozen. The brains were cut serial frontal sections on cryostat and the position of dye infusion was confirmed.

Figure 47A:
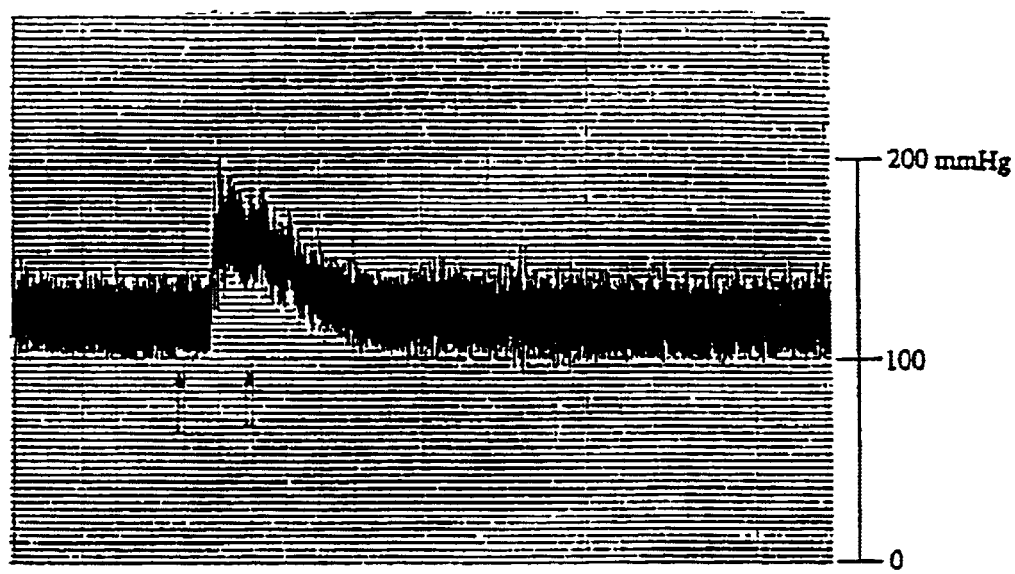
FIG. 47 shows the typical example of direct and average blood pressure which is measured after the injection of ligand polypeptide into the area postrema of rat. It is measured after the injection of 10 nmol of ligand polypeptide at the rate of 1 µl/min, and under the condition of non-anesthesia.
Figure 47B:
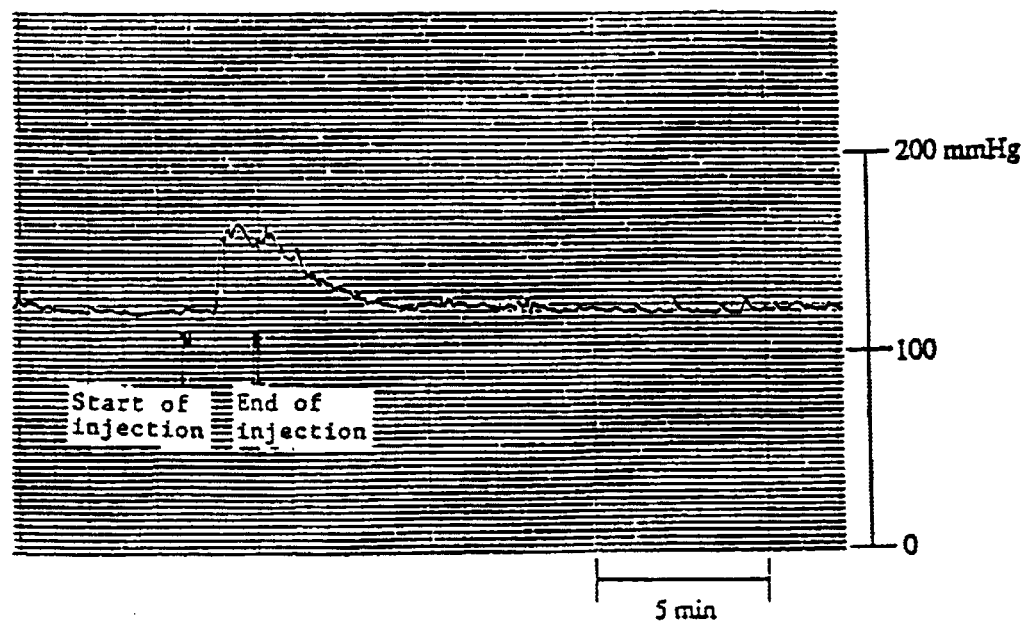

Results of the above experiment showed that injection of 10 nmol of 19P2-L31 into the area postrema of medula oblongata caused an elevation of blood pressure. Typical examples of direct and mean blood pressure are shown in FIG. 47.

Example 41

Effects of Ligand Polypeptide on Plasma Pituitary Hormone Level

The inventors explored the effect of 19P2-L31 administered into the third ventricle on pituitary hormone levels in the plasma. Mature male Wistar rats (body weights at operation: 290–350 g) were anesthetized with pentobarbital, 50 mg/kg i.p., and each immobilized in a rat brain stereotaxic apparatus. The incisor bar was set 3.3 mm lower from the interaural line. The skull was exposed, and using a dental drill a hole was made on the bone for implantation of a guide cannula. In addition, an anchor screw was buried in one position around the hole. A stainless-steel guide cannula, AG-12 (0.4 mm in. dia., 0.5 mm out. dia., EICOM), was inserted in such a manner that its tip would be situated in the upper part of the third ventricle. With reference to the atlas of Paxinos and Watson (1986), the stereotaxic coordinates were AP: +7.2 mm (from interaural line), L: 0.0 mm, and H: +2.0 mm (from interaural line). The guide cannula was secured to the skull using an instant adhesive, a dental cement, and an anchor piece. A stainless-steel dummy cannula, AD-12 (0.35 mm out. dia., EICOM), was then passed through the guide cannula and locked in position with a cap nut (EICOM). After the operation the rats were housed in individual cages and kept for at least 3 days for recuperation before starting the experiment.

The operated rat was anesthetized with pentobarbital 50 mg/kg i.p. and immobilized in dorsal position. After the bilateral jugular veins were exposed, 400 µl of blood was drawn using a 1 ml tuberculin syringe and a 24-G needle (both by Termo). To prevent clotting, the syringe was filled with 20 µl of saline containing 200 U/ml of heparin beforehand. The cap nut and dummy cannula were removed from the rat skull and, instead, a stainless steel microinjection cannula (0.17 mm in. dia., 0.35 mm out. dia., EICOM)

connected to Teflon tube (50 cm long, 0.1 mm in. dia., 0.4 mm out. dia., EICOM) was inserted. The length of the microinjection cannula was adjusted beforehand so that its tip would be emergent from the guide cannula by 1 mm. One end of the Teflon tube was connected to a microsyringe pump and either PBS or 19P2-L31 dissolved in PBS was injected, in a total volume of 10 µl, into the third ventricle at a flow rate of 2.5 µl/min. After a standby time of 1 minute following infusion, the microinjection cannula was disconnected and the dummy cannula was reinstated and locked in position with a cap nut. Immediately before initiation of intraventricular administration and 10, 20, 30, 40, and 60 minutes after initiation of administration, 400 µl portions of blood were drawn from the jugular vein. Each blood sample was centrifuged (5,000 rpm, 10 min.) with a high-speed refrigerated microcentrifuge (MR-150, Tommy Seiko) and the supernatant (plasma) was recovered. The amounts of pituitary hormones [prolactin, luteinizing hormone (LH), adrenocorticotropic hormone (ACTH), thyroid-stimulating hormone (TSH), and growth hormone (GH)] in the plasma were respectively determined by radioimmunoassays.

Figure 48:
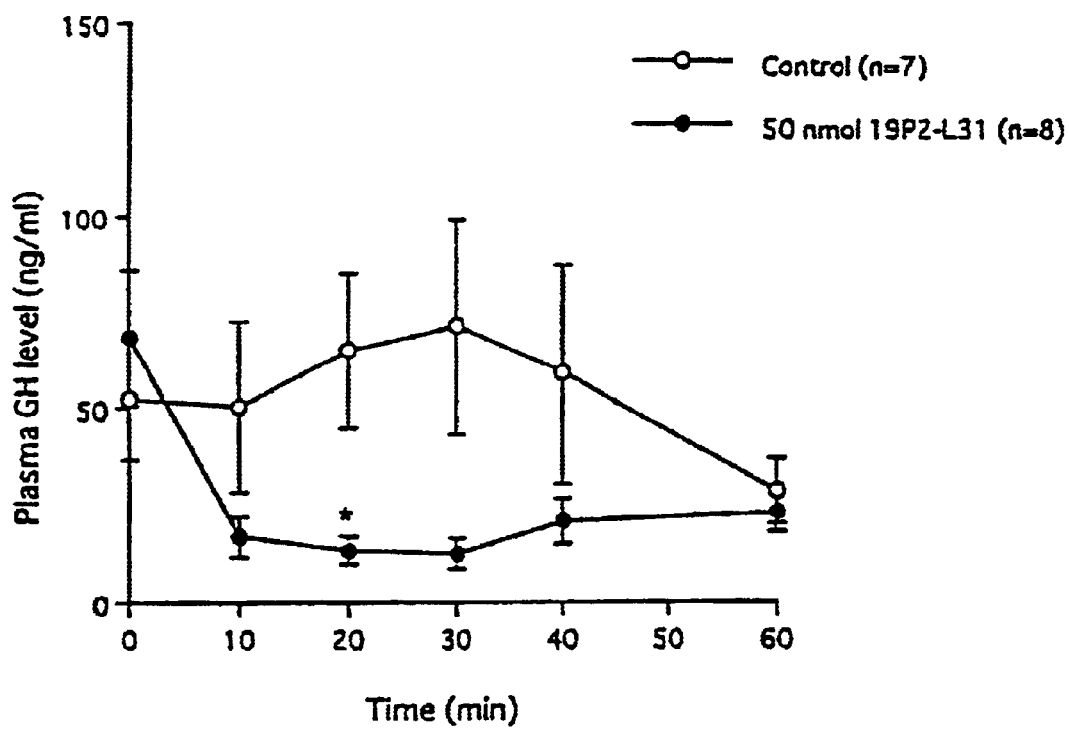
FIG. 48 shows the results of measurements of growth hormone (GH) in plasma when 50 nmol of ligand polypeptide is administered into the third ventricle of rat after anesthesia by pentobarbital.

The results were expressed as a mean±S.E.M. To test for significant difference between the group treated with 19P2-L31 dissolved in PBS and the control group treated with PBS alone, Student's t-test was used. According to the two-tailed test, $p<0.05$ was assumed to be the minimal level of significance. As shown in FIG. 48, the plasma GH level was significantly decreased at 20 minutes after administration of 50 nmol of 19P2-L31 into the third ventricle, as compared with the control group. Tendencies toward decrease were found at 10, 30, and 40 minutes after administration as well but the changes were not statistically significant. At 60 minutes after administration, there was no difference from the control group. As to plasma prolactin, LH, ACTH, and TSH, none showed significant changes.

Example 42

Effects of Ligand Polypeptide on Plasma Growth Hormone (GH) Level in Freely Moving Rats Mature male Wistar rats were anesthetized with pentobarbital 50 mg/kg i.p. and, as in Example 41, a stainless-steel guide cannula AG-12 (0.4 mm in. dia., 0.5 mm out. dia., EICOM) was implanted in position with its tip situated in the upper part of the third ventricle. After the operation the rats were housed in individual cages and kept for at least 3 days for recuperation and, then, a cannula (30 cm long, 0.5 mm in. dia., 0.9 mm out. dia., Natsume Seisakusho) filled with heparin (200 U/ml)-containing saline was inserted into the right atrium from the right jugular vein under pentobarbital anesthesia. The rats were maintained overnight for complete arousal from anesthesia and then transferred to transparent acrylic cages (30 cm×30 cm×35 cm). A 1 ml tuberculin syringe with a 24-G needle (both by Termo) was connected to the cannula inserted in the atrium and 300 µl of blood was drawn. To prevent clotting, the syringe was filled with 20 µl of saline containing 200 U/ml of heparin beforehand. A stainless-steel microinjection cannula (0.17 mm in. dia., 0.35 mm out. dia., EICOM) connected to Teflon tube (50 cm long, 0.1 mm in. dia., 0.4 mm out. dia., EICOM) was inserted into the guide cannula positioned in the third ventricle. The length of the microinjection cannula was adjusted beforehand so that its tip would be extend 1 mm from the guide cannula. One end of the Teflon tube was connected to a microsyringe pump and either PBS or 19P2-L31 dissolved in PBS was injected, in a total volume of 10 µl, into the third ventricle at a flow rate of 2.5 µl/min. Ten minutes after initiation of administration into the third ventricle, 5 µg/kg GHRH-saline was administered via the cannula inserted into the atrium. Immediately before initiation of intraventricular administration and 10, 20, 30, 40, and 60 minutes after administration of GHRH, 300 µl portions of blood were drawn from the jugular vein. Each blood sample was centrifuged (5,000 rpm, 10 min.) and the supernatant (plasma) was recovered. The concentrations of GH in the plasma were determined by radioimmunoassay.

The results were expressed as a mean±S.E.M. To test for significant difference between the group treated with 19P2-L31 dissolved in PBS and the control group treated with PBS alone, Student's t-test was used. According to the two tailed test, $p<0.05$ was assumed to be the minimal level of significance. As. shown in FIG. 49, administration of 5 µg/kg of GHRH elevated the plasma GH level. However, when 50 nmol of 19P2-L31 was administered into the third ventricle, the GHRH-induced elevation of plasma GH was significantly inhibited.

Example 43

Preparation of Rabbit Anti-bovine 19P2-L31 Antibodies

Synthetic peptides containing partial 19P2-L31 sequence [peptide-I: SRAHQHSMEIRTPDC (SEQ ID NO:92), peptide-II: CAWYAGRGIRPVGRFNH$_2$ (SEQ ID NO:93), and peptide-III: CEIRTPDINPAWYAG (SEQ ID NO:94) were conjugated with KLH according to the standard method. Each peptide conjugate (600 µg as a peptide) dissolved in saline was mixed with Freund's complete adjuvant, and the resultant emulsion was subcutaneously injected into three rabbits (NZW, male, 2.5 kg) respectively. Hyperimmunization was carried out three times in total at the same dose of the conjugate as the first injection with Freund's imcomplete adjuvant every three weeks. Antibody titers were determined as follows. Two weeks after the last immunization, blood samples were obtained from the vein of the immunized rabbits respectively. After being incubated at 37° C. for 1 hour, the blood samples were kept at 4° C. over night. Sera were then prepared by means of centrifugation. An aliquot (100 µl) of each serum sample diluted properly was introduced into 96-well polystyrene microplates which were pre-coated with goat anti-rabbit IgG (Fc) antibodies, and then the microplates were incubated at 4° C. for 16 hours. After removing the sera, horse radish peroxidase (HRP)-conjugated peptide-I, II, and III were added to the wells respectively, and then the microplates were incubated at room temperature for 4 hours. After removing the peptides, coloring reaction was done by adding a substrate. The reaction was stopped by adding 100 µl of a stopping solution, and then the absorbance at 450 nm in each well was measured. As shown in FIG. 50, serum samples obtained from the rabbits after the immunization showed binding activities to HRP-conjugated peptides respectively. However, none of binding activities was detected in sera prepared before the immunization. These results indicated that the rabbits received the immunization produced antibodies against peptide-I, II, and III, respectively. To prepare purified IgG antibody fractions, sera obtained from the immunized rabbits was percipitated with anmonium sulfate. The resultant precipitates were dissolved in borate buffer, and then dialyzed with the same buffer. The IgG fractions thus obtained were then subjected onto affinity columns conjugated with peptide-I or 19P2-L31 respectively. After washing the columns with borate buffer and following, with acetate buffer (100 mM, pH 4.5), antibodies bound to the column were eluted with glycine buffer (200 mM, pH 2.0). After being neutralized with 1M Tris, the eluents were used as purified antibodies respectively.

Example 44

Inhibitory Activity of Antibodies Against the Release of Arachldonic Acid Metabolites Induced by 19P2-L31

The purified antibodies prepared as described in Example 43 were tested their inhibitory activity against the release of arachidonic acid metabolites induced by 19P2-L31. The antibodies diluted as indicated in FIG. 51 were mixed with 19P2-L31 ($5 \times 10^{-10}$M) at room temperature for 1 hour, and then the release of arachidonic acid metabolites was examined as described in Example 11. As shown in FIG. 51, the highest inhibitory activity was observed in anti-peptide-II antibodies.

Preparation Example

Fifty milligrams of the compound as obtained in Example 21 is dissolved in 50 ml of Japanese pharmacopoeial, distilled water for injection, and Japanese pharmacopoeial, distilled water for injection is added thereto to make 100 ml. The resulting solution is filtered under a germ-free condition, and the filtrate of 1 ml each is filled in vials for injection, freeze-dried and sealed therein also under a germ-free condition.

Preparation Example

One hundred milligrams of the compound as obtained in Example 21 is dissolved in 50 ml of Japanese pharmacopoeial, distilled water for injection, and Japanese pharmacopoeial, distilled water for injection is added thereto to make 100 ml. The resulting solution is filtered under a germ-free condition, and the filtrate of 1 ml each is filled in vials for injection, freeze-dried and sealed therein also under a germ-free condition.

[Evaluation of the Physiological Activities of Ligand Polypeptide of the Present Invention]

The above examples 37–41 demonstrate that topical administration of ligand polypeptide induces enhancement of spontaneous motor activity and rearing behavior, elevation of body temperature and blood pressure, and decrease in plasma growth hormone concentration. These findings relating to physiological activities are the first proof of various prominent physiologic changes which occur when ligand polypeptide acts on the central nervous system.

Since ligand polypeptide of the present invention, inclusive of its salt, acts on the central nervous systems of warm-blooded animals (e.g. rat, mouse, guinea pig, chicken, rabbit, dog, swine, bovine, sheep, monkey, and man) to induce a variety of pharmacological changes, it is showed that the ligand and salt have the property to alter the intracranial nervous system and endocrine system.

When 19P2-L31 was administered into the lateral ventricle of mice, an increase in the amount of activity was found at the level of 0.01–10 nmol. This fact shows that ligand polypeptide triggers changes in the motor system via the G protein-coupled receptors of the central nervous system. It was also found that administration of the peptide into the lateral ventricle of mice results in elevation of body temperature and that administration into the area postrema of medula oblongata of rats results in elevation of blood pressure. These actions resemble the pharmacologic actions of known central stimulants (e.g. amphetamine, cocaine, methylphenidate, etc.). Therefore, it is showed that ligand polypeptide or a salt thereof releases biologic amines (dopamine, noradrenaline, serotonin) from the nerve ending reservoirs, in the main (Michio Yuzuru and Takeo Yoshikawa, Medical Science, 42, 535–536, 1991).

Furthermore, when 19P2-L31 was injected into the third ventricle of rats, the plasma growth hormone level was depressed. This finding shows that this peptide acts on the hypothalamus and is associated with secretion of pituitary hormones via the hypothalamo-pituitary system. It is also possible that this peptide directly act on the pituitary so as to suppress the release of growth hormone. Growth hormone releasing hormone (GHRH) which regulates secretion of growth hormone from the hypophysis as well as somatostatin exists in the neighborhood of the third ventricle (Masahiro Tohyama et al., Kagakuteki Shinkeikino Kaibogaku (Chemical Neuroanatomy), 167–216, 1987). Therefore, it is showed that 19P2-L31 is modulating release of these substances.

The above facts show that ligand polypeptide is a peptide acting on the central nervous system to control the autonomous nervous system. The fact that the mRNA of this peptide and of its receptor is expressed at high levels in the hypothalamus and medula oblongata also shows the involvement of ligand polypeptide in the modulation of the autonomous nervous system. In fact, the superior center of autonomous nerve peripherals is the medula oblongata and hypothalamus, where as already elucidated the sympathetic nervous system and the para-sympathetic nervous system are integrated to play an important role in both neural regulation and humoral regulation.

The above findings indicate the usefulness of ligand polypeptide or an agonist of ligand polypeptide, or a salt thereof, as a central nervous system stimulant causing enhancement of spontaneous motor activity. Thus, the peptide can be used as a prophylactic and/or therapeutic drug for a variety of diseases such as senile dementia, cerebrovascular dementia (dementia due to cerebrovascular disorder), dementia associated with phylodegenerative retroplastic diseases (e.g. Alzheimer's disease, Parkinson's disease, Pick's disease, Huntington's disease, etc.), dementia due to infectious diseases (e.g. delayed viral infections such as Creutzfelt-Jakob disease), dementia associated with endocrine, metabolic, and toxic diseases (e.g. hypothyroidism, vitamin B12 deficiency, alcoholism, and poisoning due to various drugs, metals, or organic compounds), dementia associated with oncogenous diseases (e.g. brain tumor), dementia due to traumatic diseases (e.g. chronic subdural hematoma), depression (melancholia), hyperkinetic (microencephalopathy) syndrome, or disturbance of consciousness. On the other hand, an antagonist of 19P2 ligand or a salt thereof is of value as a CNS deppressant, for instance, and can be used as an antipsychotic drug, an anti-Huntigton's disease drug, an antianxiety drug, or a hypnotic-sedative.

It was made clear that injection of ligand polypeptide into the area postrema of medula oblongata elevates the blood pressure. Therefore, ligand polypeptide or an agonist of ligand polypeptide, or a salt thereof, is of value as a vasopressor. On the other hand, a ligand polypeptide antagonist or a salt thereof is of value as a depressor.

It was found that when ligand polypeptide acts on the hypothalamus, the plasma growth hormone level is depressed. Hypersecretion of growth hormone triggers somatomegaly and acromegalic gigantism (Katamasu et al., Endocrine Syndrome, 78–80, 1993; Hiroi et al., Endocrine Syndrome, 149–151, 1993). Therefore, ligand polypeptide or a ligand polypeptide antagonist, or a salt thereof, can be used as a prophylactic and/or therapeutic drug for somatomegaly and acromegalic gigantism. Moreover, growth hormone promotes release of glucose from the liver and inhibits the uptake of glucose by muscles and adipose tissues from the blood, causing hyperglycemia and diabetes [Eiji Kobayashi, NaibumpiGensho (Endocrine Phenomena), 1980]. In fact, the secretion of growth hormone is elevated in diabetic patients (Hiroshi Kiyono, Endocrinology and Metabolic Diseases, 385–402, 1994). Therefore, ligand polypeptide or an agonist of ligand polypeptide, or a salt thereof, can be used as a prophylactic and/or therapeutic drug for diabetes, for instance.

On the other hand, an antagonist of ligand polypeptide promotes secretion of growth hormone. Therefore, a ligand polypeptide antagonist or a salt thereof can be used as a prophylactic and/or therapeutic drug for pituitarism leading to a depressed growth hormone level, pituitary dwarfism, and hypoglycemia. Moreover, growth hormone and insulin-like growth factor secreted by growth hormone are effective in amyotrophic lateral sclerosis, osteoporosis, renal failure, and improvement in postoperative nutritional status (Shizume et al., Endocrine Syndrome, 84–87, 1993, Nikkei Bio-Annal 96, 453–454, 1996; Tobiume et al., Clinical Endocrinology, 44, 1205–1214, 1996). Therefore, a ligand polypeptide antagonist or its salt can be used as a prophylactic and/or therapeutic drug for such illnesses.

SEQUENCE LISTING (1) GENERAL INFORMATION:

(iii) NUMBER OF SEQUENCES: 140

(2) INFORMATION FOR SEQ ID NO:1:

(i) SEQUENCE CHARACTERISTICS:
        (A) LENGTH: 98 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:1:

```
Met Lys Ala Val Gly Ala Trp Leu Leu Cys Leu Leu Leu Leu Gly Leu
1               5                   10                  15

Ala Leu Gln Gly Ala Ala Ser Arg Ala His Gln His Ser Met Glu Ile
                20                  25                  30

Arg Thr Pro Asp Ile Asn Pro Ala Trp Tyr Ala Gly Arg Gly Ile Arg
            35                  40                  45

Pro Val Gly Arg Phe Gly Arg Arg Arg Ala Ala Pro Gly Asp Gly Pro
    50                  55                  60

Arg Pro Gly Pro Arg Arg Val Pro Ala Cys Phe Arg Leu Glu Gly Gly
65                  70                  75                  80

Ala Glu Pro Ser Arg Ala Leu Pro Gly Arg Leu Thr Ala Gln Leu Val
                85                  90                  95

Gln Glu
```

(2) INFORMATION FOR SEQ ID NO:2:

(i) SEQUENCE CHARACTERISTICS:
        (A) LENGTH: 294 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:2:

```
ATGAAGGCGG TGGGGGCCTG GCTCCTCTGC CTGCTGCTGC TGGGCCTGGC CCTGCAGGGG     60

GCTGCCAGCA GAGCCCACCA GCACTCCATG GAGATCCGCA CCCCCGACAT CAACCCTGCC    120

TGGTACGCRG GCCGTGGGAT CCGGCCCGTG GGCCGCTTCG GCCGGCGAAG AGCTGCCCYG    180

GGGGACGGAC CCAGGCCTGG CCCCCGGCGT GTGCCGGCCT GCTTCCGCCT GGAAGGCGGY    240
```

GCTGAGCCCT CCCGAGCCCT CCCGGGGCGG CTGACGGCCC AGCTGGTCCA GGAA        294

(2) INFORMATION FOR SEQ ID NO:3:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:3:

```
Ser Arg Ala His Gln His Ser Met Glu Ile Arg Thr Pro Asp Ile Asn
1               5                  10                  15
Pro Ala Trp Tyr Ala Gly Arg Gly Ile Arg Pro Val Gly
            20                  25
```

(2) INFORMATION FOR SEQ ID NO:4:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:4:

```
Thr Pro Asp Ile Asn Pro Ala Trp Tyr Ala Gly Arg Gly Ile Arg Pro
1               5                  10                  15
Val Gly Arg
```

(2) INFORMATION FOR SEQ ID NO:5:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:5:

```
Ser Arg Ala His Gln His Ser Met Glu Ile Arg Thr Pro Asp Ile Asn
1               5                  10                  15
Pro Ala Trp Tyr Ala Gly Arg Gly Ile Arg Pro Val Gly Arg Phe
            20                  25                  30
```

(2) INFORMATION FOR SEQ ID NO:6:

(i) SEQUENCE CHARACTERISTICS:
        (A) LENGTH: 32 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:6:

```
Ser Arg Ala His Gln His Ser Met Glu Ile Arg Thr Pro Asp Ile Asn
1               5                   10                  15

Pro Ala Trp Tyr Ala Gly Arg Gly Ile Arg Pro Val Gly Arg Phe Gly
            20                  25                  30
```

(2) INFORMATION FOR SEQ ID NO:7:

(i) SEQUENCE CHARACTERISTICS:
        (A) LENGTH: 33 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:7:

```
Ser Arg Ala His Gln His Ser Met Glu Ile Arg Thr Pro Asp Ile Asn
1               5                   10                  15

Pro Ala Trp Tyr Ala Gly Arg Gly Ile Arg Pro Val Gly Arg Phe Gly
            20                  25                  30

Arg
```

(2) INFORMATION FOR SEQ ID NO:8:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:8:

```
Thr Pro Asp Ile Asn Pro Ala Trp Tyr Ala Gly Arg Gly Ile Arg Pro
1               5                   10                  15

Val Gly Arg Phe
            20
```

(2) INFORMATION FOR SEQ ID NO:9:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:9:

```
Thr Pro Asp Ile Asn Pro Ala Trp Tyr Ala Gly Arg Gly Ile Arg Pro
1               5                   10                  15

Val Gly Arg Phe Gly
            20
```

(2) INFORMATION FOR SEQ ID NO:10:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:10:

Thr Pro Asp Ile Asn Pro Ala Trp Tyr Ala Gly Arg Gly Ile Arg Pro
1               5                   10                  15

Val Gly Arg Phe Gly Arg
            20

(2) INFORMATION FOR SEQ ID NO:11:

(i) SEQUENCE CHARACTERISTICS:
        (A) LENGTH: 87 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:11:

AGCAGAGCCC ACCAGCACTC CATGGAGATC CGCACCCCCG ACATCAACCC TGCCTGGTAC      60

GCRGGCCGTG GGATCCGGCC CGTGGGC                                         87

(2) INFORMATION FOR SEQ ID NO:12:

(i) SEQUENCE CHARACTERISTICS:
        (A) LENGTH: 57 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:12:

ACCCCCGACA TCAACCCTGC CTGGTACGCR GGCCGTGGGA TCCGGCCCGT GGGCCGC         57

(2) INFORMATION FOR SEQ ID NO:13:

(i) SEQUENCE CHARACTERISTICS:
        (A) LENGTH: 93 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:13:

AGCAGAGCCC ACCAGCACTC CATGGAGATC CGCACCCCCG ACATCAACCC TGCCTGGTAC      60

GCRGGCCGTG GGATCCGGCC CGTGGGCCGC TTC                                  93

(2) INFORMATION FOR SEQ ID NO:14:

(i) SEQUENCE CHARACTERISTICS:
        (A) LENGTH: 96 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:14:

AGCAGAGCCC ACCAGCACTC CATGGAGATC CGCACCCCCG ACATCAACCC TGCCTGGTAC      60

GCRGGCCGTG GGATCCGGCC CGTGGGCCGC TTCGGC                               96

```
(2) INFORMATION FOR SEQ ID NO:15:

(i) SEQUENCE CHARACTERISTICS:
        (A) LENGTH: 99 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:15:

AGCAGAGCCC ACCAGCACTC CATGGAGATC CGCACCCCCG ACATCAACCC TGCCTGGTAC    60

GCRGGCCGTG GGATCCGGCC CGTGGGCCGC TTCGGCCGG                           99

(2) INFORMATION FOR SEQ ID NO:16:

(i) SEQUENCE CHARACTERISTICS:
        (A) LENGTH: 60 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:16:

ACCCCCGACA TCAACCCTGC CTGGTACGCR GGCCGTGGGA TCCGGCCCGT GGGCCGCTTC    60

(2) INFORMATION FOR SEQ ID NO:17:

(i) SEQUENCE CHARACTERISTICS:
        (A) LENGTH: 63 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:17:

ACCCCCGACA TCAACCCTGC CTGGTACGCR GGCCGTGGGA TCCGGCCCGT GGGCCGCTTC    60

GGC                                                                 63

(2) INFORMATION FOR SEQ ID NO:18:

(i) SEQUENCE CHARACTERISTICS:
        (A) LENGTH: 66 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:18:

ACCCCCGACA TCAACCCTGC CTGGTACGCR GGCCGTGGGA TCCGGCCCGT GGGCCGCTTC    60

GGCCGG                                                              66

(2) INFORMATION FOR SEQ ID NO:19:

(i) SEQUENCE CHARACTERISTICS:
        (A) LENGTH: 91 amino acids
        (B) TYPE: amino acid
        (C) STRANDEDNESS: single
        (D) TOPOLOGY: linear (ii) MOLECULE TYPE: protein (v) FRAGMENT TYPE: internal
```

(xi) SEQUENCE DESCRIPTION: SEQ ID NO:19:

Leu Val Leu Val Ile Ala Arg Val Arg Arg Leu His Asn Val Thr Asn
1               5                   10                  15

Phe Leu Ile Gly Asn Leu Ala Leu Ser Asp Val Leu Met Cys Thr Ala
                20                  25                  30

Cys Val Pro Leu Thr Leu Ala Tyr Ala Phe Glu Pro Arg Gly Trp Val
            35                  40                  45

Phe Gly Gly Gly Leu Cys His Leu Val Phe Phe Leu Gln Pro Val Thr
    50                  55                  60

Val Tyr Val Ser Val Phe Thr Leu Thr Ile Ala Val Asp Arg Tyr
65              70                  75                  80

Val Val Leu Val His Pro Leu Arg Arg Arg Ile
                85                  90

(2) INFORMATION FOR SEQ ID NO:20:

(i) SEQUENCE CHARACTERISTICS:
           (A) LENGTH: 59 amino acids
           (B) TYPE: amino acid
           (C) STRANDEDNESS: single
           (D) TOPOLOGY: linear (ii) MOLECULE TYPE: protein (v) FRAGMENT TYPE: internal (xi) SEQUENCE DESCRIPTION: SEQ ID NO:20:

Gly Leu Leu Leu Val Thr Tyr Leu Leu Pro Leu Leu Val Ile Leu Leu
1               5                   10                  15

Ser Tyr Val Arg Val Ser Val Lys Leu Arg Asn Arg Val Val Pro Gly
                20                  25                  30

Cys Val Thr Gln Ser Gln Ala Asp Trp Asp Arg Ala Arg Arg Arg Arg
            35                  40                  45

Thr Phe Cys Leu Leu Val Val Val Val Val
        50                  55

(2) INFORMATION FOR SEQ ID NO:21:

(i) SEQUENCE CHARACTERISTICS:
           (A) LENGTH: 370 amino acids
           (B) TYPE: amino acid
           (C) STRANDEDNESS: single
           (D) TOPOLOGY: linear (ii) MOLECULE TYPE: protein (v) FRAGMENT TYPE: internal (xi) SEQUENCE DESCRIPTION: SEQ ID NO:21:

Met Ala Ser Ser Thr Thr Arg Gly Pro Arg Val Ser Asp Leu Phe Ser
1               5                   10                  15

Gly Leu Pro Pro Ala Val Thr Thr Pro Ala Asn Gln Ser Ala Glu Ala
                20                  25                  30

Ser Ala Gly Asn Gly Ser Val Ala Gly Ala Asp Ala Pro Ala Val Thr
            35                  40                  45

Pro Phe Gln Ser Leu Gln Leu Val His Gln Leu Lys Gly Leu Ile Val
    50                  55                  60

Leu Leu Tyr Ser Val Val Val Val Gly Leu Val Gly Asn Cys Leu
65              70                  75                  80

Leu Val Leu Val Ile Ala Arg Val Arg Arg Leu His Asn Val Thr Asn
                85                  90                  95

-continued

```
Phe Leu Ile Gly Asn Leu Ala Leu Ser Asp Val Leu Met Cys Thr Ala
            100                 105                 110

Cys Val Pro Leu Thr Leu Ala Tyr Ala Phe Glu Pro Arg Gly Trp Val
        115                 120                 125

Phe Gly Gly Leu Cys His Leu Val Phe Leu Gln Pro Val Thr
130                 135                 140

Val Tyr Val Ser Val Phe Thr Leu Thr Thr Ile Ala Val Asp Arg Tyr
145                 150                 155                 160

Val Val Leu Val His Pro Leu Arg Arg Ile Ser Leu Arg Leu Ser
                165                 170                 175

Ala Tyr Ala Val Leu Ala Ile Trp Ala Leu Ser Ala Val Leu Ala Leu
            180                 185                 190

Pro Ala Ala Val His Thr Tyr His Val Glu Leu Lys Pro His Asp Val
        195                 200                 205

Arg Leu Cys Glu Glu Phe Trp Gly Ser Gln Glu Arg Gln Arg Gln Leu
210                 215                 220

Tyr Ala Trp Gly Leu Leu Leu Val Thr Tyr Leu Leu Pro Leu Leu Val
225                 230                 235                 240

Ile Leu Leu Ser Tyr Val Arg Val Ser Val Lys Leu Arg Asn Arg Val
                245                 250                 255

Val Pro Gly Cys Val Thr Gln Ser Gln Ala Asp Trp Asp Arg Ala Arg
            260                 265                 270

Arg Arg Arg Thr Phe Cys Leu Leu Val Val Val Val Phe Ala
        275                 280                 285

Val Cys Trp Leu Pro Leu His Val Phe Asn Leu Leu Arg Asp Leu Asp
    290                 295                 300

Pro His Ala Ile Asp Pro Tyr Ala Phe Gly Leu Val Gln Leu Leu Cys
305                 310                 315                 320

His Trp Leu Ala Met Ser Ser Ala Cys Tyr Asn Pro Phe Ile Tyr Ala
            325                 330                 335

Trp Leu His Asp Ser Phe Arg Glu Glu Leu Arg Lys Leu Leu Val Ala
        340                 345                 350

Trp Pro Arg Lys Ile Ala Pro His Gly Gln Asn Met Thr Val Ser Val
    355                 360                 365

Val Ile
370
```

(2) INFORMATION FOR SEQ ID NO:22:

(i) SEQUENCE CHARACTERISTICS:
        (A) LENGTH: 206 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:22:

```
Leu Val Leu Val Ile Ala Arg Val Arg Leu Tyr Asn Val Thr Asn
1               5                   10                  15

Phe Leu Ile Gly Asn Leu Ala Leu Ser Asp Val Leu Met Cys Thr Ala
            20                  25                  30

Cys Val Pro Leu Thr Leu Ala Tyr Ala Phe Glu Pro Arg Gly Trp Val
        35                  40                  45
```

-continued

```
Phe Gly Gly Gly Leu Cys His Leu Val Phe Phe Leu Gln Ala Val Thr
    50                  55                  60

Val Tyr Val Ser Val Phe Thr Leu Thr Thr Ile Ala Val Asp Arg Tyr
65                      70                  75                  80

Val Val Leu Val His Pro Leu Arg Arg Arg Ile Ser Leu Arg Leu Ser
                85                  90                  95

Ala Tyr Ala Val Leu Ala Ile Trp Val Leu Ser Ala Val Leu Ala Leu
                100                 105                 110

Pro Ala Ala Val His Thr Tyr His Val Glu Leu Lys Pro His Asp Val
                115                 120                 125

Arg Leu Cys Glu Glu Phe Trp Gly Ser Gln Glu Arg Gln Arg Gln Leu
                130                 135                 140

Tyr Ala Trp Gly Leu Leu Val Thr Tyr Leu Leu Pro Leu Leu Val
145                     150                 155                 160

Ile Leu Leu Ser Tyr Ala Arg Val Ser Val Lys Leu Arg Asn Arg Val
                165                 170                 175

Val Pro Gly Arg Val Thr Gln Ser Gln Ala Asp Trp Asp Arg Ala Arg
                180                 185                 190

Arg Arg Arg Thr Phe Cys Leu Leu Val Val Val Val Val
                195                 200                 205
```

(2) INFORMATION FOR SEQ ID NO:23:

(i) SEQUENCE CHARACTERISTICS:
        (A) LENGTH: 126 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:23:

```
Val Val Leu Val His Pro Leu Arg Arg Arg Ile Ser Leu Arg Leu Ser
1               5                   10                  15

Ala Tyr Ala Val Leu Gly Ile Trp Ala Leu Ser Ala Val Leu Ala Leu
                20                  25                  30

Pro Ala Ala Val His Thr Tyr His Val Glu Leu Lys Pro His Asp Val
                35                  40                  45

Ser Leu Cys Glu Glu Phe Trp Gly Ser Gln Glu Arg Gln Arg Gln Ile
    50                  55                  60

Tyr Ala Trp Gly Leu Leu Leu Gly Thr Tyr Leu Leu Pro Leu Leu Ala
65                      70                  75                  80

Ile Leu Leu Ser Tyr Val Arg Val Ser Val Lys Leu Arg Asn Arg Val
                85                  90                  95

Val Pro Gly Ser Val Thr Gln Ser Gln Ala Asp Trp Asp Arg Ala Arg
                100                 105                 110

Arg Arg Arg Thr Phe Cys Leu Leu Val Val Val Val Val Val
                115                 120                 125
```

(2) INFORMATION FOR SEQ ID NO:24:

(i) SEQUENCE CHARACTERISTICS:
        (A) LENGTH: 273 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:24:

| | | | | | |
|---|---|---|---|---|---|
| CTGGTGCTGG | TGATCGCGCG | GGTGCGCCGG | CTGCACAACG | TGACGAACTT | CCTCATCGGC | 60 |
| AACCTGGCCT | TGTCCGACGT | GCTCATGTGC | ACCGCCTGCG | TGCCGCTCAC | GCTGGCCTAT | 120 |
| GCCTTCGAGC | CACGCGGCTG | GGTGTTCGGC | GGCGGCCTGT | GCCACCTGGT | CTTCTTCCTG | 180 |
| CAGCCGGTCA | CCGTCTATGT | GTCGGTGTTC | ACGCTCACCA | CCATCGCAGT | GGACCGGTAC | 240 |
| GTCGTGCTGG | TGCACCCGCT | GAGGCGGCGC | ATC | | | 273 |

(2) INFORMATION FOR SEQ ID NO:25:

(i) SEQUENCE CHARACTERISTICS:
        (A) LENGTH: 177 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:25:

| | | | | | |
|---|---|---|---|---|---|
| GGCCTGCTGC | TGGTCACCTA | CCTGCTCCCT | CTGCTGGTCA | TCCTCCTGTC | TTACGTCCGG | 60 |
| GTGTCAGTGA | AGCTCCGCAA | CCGCGTGGTG | CCGGGCTGCG | TGACCCAGAG | CCAGGCCGAC | 120 |
| TGGGACCGCG | CTCGGCGCCG | GCGCACCTTC | TGCTTGCTGG | TGGTGGTCGT | GGTGGTG | 177 |

(2) INFORMATION FOR SEQ ID NO:26:

(i) SEQUENCE CHARACTERISTICS:
        (A) LENGTH: 1110 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:26:

| | | | | | |
|---|---|---|---|---|---|
| ATGGCCTCAT | CGACCACTCG | GGGCCCCAGG | GTTTCTGACT | TATTTTCTGG | GCTGCCGCCG | 60 |
| GCGGTCACAA | CTCCCGCCAA | CCAGAGCGCA | GAGGCCTCGG | CGGGCAACGG | GTCGGTGGCT | 120 |
| GGCGCGGACG | CTCCAGCCGT | CACGCCCTTC | CAGAGCCTGC | AGCTGGTGCA | TCAGCTGAAG | 180 |
| GGGCTGATCG | TGCTGCTCTA | CAGCGTCGTG | GTGGTCGTGG | GGCTGGTGGG | CAACTGCCTG | 240 |
| CTGGTGCTGG | TGATCGCGCG | GGTGCGCCGG | CTGCACAACG | TGACGAACTT | CCTCATCGGC | 300 |
| AACCTGGCCT | TGTCCGACGT | GCTCATGTGC | ACCGCCTGCG | TGCCGCTCAC | GCTGGCCTAT | 360 |
| GCCTTCGAGC | CACGCGGCTG | GGTGTTCGGC | GGCGGCCTGT | GCCACCTGGT | CTTCTTCCTG | 420 |
| CAGCCGGTCA | CCGTCTATGT | GTCGGTGTTC | ACGCTCACCA | CCATCGCAGT | GGACCGCTAC | 480 |
| GTCGTGCTGG | TGCACCCGCT | GAGGCGGCGC | ATCTCGCTGC | GCCTCAGCGC | CTACGCTGTG | 540 |
| CTGGCCATCT | GGGCGCTGTC | CGCGGTGCTG | GCGCTGCCCG | CCGCCGTGCA | CACCTATCAC | 600 |
| GTGGAGCTCA | AGCCGCACGA | CGTGCGCCTC | TGCGAGGAGT | CTGGGGCTC | CCAGGAGCGC | 660 |
| CAGCGCCAGC | TCTACGCCTG | GGGGCTGCTG | CTGGTCACCT | ACCTGCTCCC | TCTGCTGGTC | 720 |
| ATCCTCCTGT | CTTACGTCCG | GGTGTCAGTG | AAGCTCCGCA | ACCGCGTGGT | GCCGGGCTGC | 780 |
| GTGACCCAGA | GCCAGGCCGA | CTGGGACCGC | GCTCGGCGCC | GGCGCACCTT | CTGCTTGCTG | 840 |
| GTGGTGGTCG | TGGTGGTGTT | CGCCGTCTGC | TGGCTGCCGC | TGCACGTCTT | CAACCTGCTG | 900 |
| CGGGACCTCG | ACCCCCACGC | CATCGACCCT | TACGCCTTTG | GGCTGGTGCA | GCTGCTCTGC | 960 |
| CACTGGCTCG | CCATGAGTTC | GGCCTGCTAC | AACCCCTTCA | TCTACGCCTG | GCTGCACGAC | 1020 |
| AGCTTCCGCG | AGGAGCTGCG | CAAACTGTTG | GTCGCTTGGC | CCCGCAAGAT | AGCCCCCCAT | 1080 |

-continued

```
GGCCAGAATA TGACCGTCAG CGTGGTCATC                                       1110

(2) INFORMATION FOR SEQ ID NO:27:

(i) SEQUENCE CHARACTERISTICS:
        (A) LENGTH: 618 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:27:

CTGGTGCTGG TGATCGCGCG GGTGCGCCGG CTGTACAACG TGACGAATTT CCTCATCGGC        60

AACCTGGCCT TGTCCGACGT GCTCATGTGC ACCGCCTGCG TGCCGCTCAC GCTGGCCTAT       120

GCCTTCGAGC CACGCGGCTG GGTGTTCGGC GGCGGCCTGT GCCACCTGGT CTTCTTCCTG       180

CAGGCGGTCA CCGTCTATGT GTCGGTGTTC ACGCTCACCA CCATCGCAGT GGACCGCTAC       240

GTCGTGCTGG TGCACCCGCT GAGGCGGCGC ATCTCGCTGC GCCTCAGCGC CTACGCTGTG       300

CTGGCCATCT GGGTGCTGTC CGCGGTGCTG GCGCTGCCCG CCGCCGTGCA CACCTATCAC       360

GTGGAGCTCA AGCCGCACGA CGTGCGCCTC TGCGAGGAGT TCTGGGGCTC CCAGGAGCGC       420

CAGCGCCAGC TCTACGCCTG GGGGCTGCTG CTGGTCACCT ACCTGCTCCC TCTGCTGGTC       480

ATCCTCCTGT CTTACGCCCG GGTGTCAGTG AAGCTCCGCA ACCGCGTGGT GCCGGGCCGC       540

GTGACCCAGA GCCAGGCCGA CTGGGACCGC GCTCGGCGCC GGCGCACCTT CTGCTTGCTG       600

GTGGTGGTCG TGGTGGTG                                                   618

(2) INFORMATION FOR SEQ ID NO:28:

(i) SEQUENCE CHARACTERISTICS:
        (A) LENGTH: 378 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:28:

GTGGTTCTGG TGCACCCGCT ACGTCGGCGC ATTTCACTGA GGCTCAGCGC CTACGCGGTG        60

CTGGGCATCT GGGCTCTATC TGCAGTGCTG GCGCTGCCGG CCGCGGTGCA CACCTACCAT       120

GTGGAGCTCA AGCCCCACGA CGTGAGCCTC TGCGAGGAGT TCTGGGGCTC GCAGGAGCGC       180

CAACGCCAGA TCTACGCCTG GGGGCTGCTT CTGGGCACCT ATTTGCTCCC CCTGCTGGCC       240

ATCCTCCTGT CTTACGTACG GGTGTCAGTG AAGCTGAGGA ACCGCGTGGT GCCTGGCAGC       300

GTGACCCAGA GTCAAGCTGA CTGGGACCGA GCGCGTCGCC GCCGCACTTT CTGTCTGCTG       360

GTGGTGGTGG TGGTAGTG                                                   378

(2) INFORMATION FOR SEQ ID NO:29:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:29:

CGTGGSCMTS STGGGCAACN YCCTG                                             25
```

```
(2) INFORMATION FOR SEQ ID NO:30:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:30:

GTNGWRRGGC ANCCAGCAGA KGGCAAA                                   27

(2) INFORMATION FOR SEQ ID NO:31:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:31:

CTGTGYGYSA TYGCNNTKGA YMGSTAC                                   27

(2) INFORMATION FOR SEQ ID NO:32:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:32:

AKGWAGWAGG GCAGCCAGCA GANSRYGAA                                 29

(2) INFORMATION FOR SEQ ID NO:33:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:33:

CTGACTTATT TTCTGGGCTG CCGC                                      24

(2) INFORMATION FOR SEQ ID NO:34:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:34:

AACACCGACA CATAGACGGT GACC                                      24
```

-continued (2) INFORMATION FOR SEQ ID NO:35:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(ix) FEATURE:
        (A) NAME/KEY: modified_base
        (B) LOCATION: 3
        (D) OTHER INFORMATION: /mod_base= i (xi) SEQUENCE DESCRIPTION: SEQ ID NO:35:

GCNCAYCARC AYTGYATGGA                                                  20

(2) INFORMATION FOR SEQ ID NO:36:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(ix) FEATURE:
        (A) NAME/KEY: modified_base
        (B) LOCATION: 3
        (D) OTHER INFORMATION: /mod_base= i (ix) FEATURE:
        (A) NAME/KEY: modified_base
        (B) LOCATION: 9
        (D) OTHER INFORMATION: /mod_base= i (ix) FEATURE:
        (A) NAME/KEY: modified_base
        (B) LOCATION: 18
        (D) OTHER INFORMATION: /mod_base= i (ix) FEATURE:
        (A) NAME/KEY: modified_base
        (B) LOCATION: 24
        (D) OTHER INFORMATION: /mod_base= i (xi) SEQUENCE DESCRIPTION: SEQ ID NO:36:

CCNACGGGNC KDATGCCNCK GCCNGC                                      26

(2) INFORMATION FOR SEQ ID NO:37:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(ix) FEATURE:
        (A) NAME/KEY: modified_base
        (B) LOCATION: 15
        (D) OTHER INFORMATION: /mod_base= i (ix) FEATURE:
        (A) NAME/KEY: modified_base
        (B) LOCATION: 21
        (D) OTHER INFORMATION: /mod_base= i (xi) SEQUENCE DESCRIPTION: SEQ ID NO:37:

ACGGGCCKDA TGCCNCKGCC NGCRTA                                          26

(2) INFORMATION FOR SEQ ID NO:38:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:38:

CCGGCGTACC AGGCAGGGTT                                                 20

(2) INFORMATION FOR SEQ ID NO:39:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:39:

AGGCAGGGTT GATGTCGGGG GTGCGGAT                                        28

(2) INFORMATION FOR SEQ ID NO:40:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:40:

CTGCCAGCAG AGCCCACCAG CACTCCA                                         27

(2) INFORMATION FOR SEQ ID NO:41:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:41:

GTGGGGGCCT GGCTCCTCTG CCTGCTG                                         27

(2) INFORMATION FOR SEQ ID NO:42:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:42:

GTGTCGACGA ATGAAGGCGG TGGGGGCCTG GC                              32

(2) INFORMATION FOR SEQ ID NO:43:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:43:

AGGCTCCCGC TGTTATTCCT GGAC                                       24

(2) INFORMATION FOR SEQ ID NO:44:

(i) SEQUENCE CHARACTERISTICS:
        (A) LENGTH: 98 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:44:

```
Met Lys Ala Val Gly Ala Trp Leu Leu Cys Leu Leu Leu Leu Gly Leu
1               5                  10                  15

Ala Leu Gln Gly Ala Ala Ser Arg Ala His Gln His Ser Met Glu Ile
            20                  25                  30

Arg Thr Pro Asp Ile Asn Pro Ala Trp Tyr Ala Gly Arg Gly Ile Arg
        35                  40                  45

Pro Val Gly Arg Phe Gly Arg Arg Ala Ala Leu Gly Asp Gly Pro
50                  55                  60

Arg Pro Gly Pro Arg Arg Val Pro Ala Cys Phe Arg Leu Glu Gly Gly
65                  70                  75                  80

Ala Glu Pro Ser Arg Ala Leu Pro Gly Arg Leu Thr Ala Gln Leu Val
                85                  90                  95

Gln Glu
```

(2) INFORMATION FOR SEQ ID NO:45:

(i) SEQUENCE CHARACTERISTICS:
        (A) LENGTH: 83 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:45:

```
Met Ala Leu Lys Thr Trp Leu Leu Cys Leu Leu Leu Ser Leu Val
1               5                  10                  15

Leu Pro Gly Ala Ser Ser Arg Ala His Gln His Ser Met Glu Thr Arg
            20                  25                  30

Thr Pro Asp Ile Asn Pro Ala Trp Tyr Thr Gly Arg Gly Ile Arg Pro
        35                  40                  45
```

```
Val Gly Arg Phe Gly Arg Arg Arg Ala Thr Pro Arg Asp Val Thr Gly
 50                  55                  60

Leu Gly Gln Leu Ser Cys Leu Pro Leu Asp Gly Arg Thr Lys Phe Ser
 65                  70                  75                  80

Gln Arg Gly
```

(2) INFORMATION FOR SEQ ID NO:46:

(i) SEQUENCE CHARACTERISTICS:
        (A) LENGTH: 249 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:46:

```
ATGGCCCTGA AGACGTGGCT TCTGTGCTTG CTGCTGCTAA GCTTGGTCCT CCCAGGGGCT    60

TCCAGCCGAG CCCACCAGCA CTCCATGGAG ACAAGAACCC CTGATATCAA TCCTGCCTGG   120

TACACGGGCC GCGGGATCAG GCCTGTGGGC CGCTTCGGCA GGAGAAGGGC AACCCCGAGG   180

GATGTCACTG GACTTGGCCA ACTCAGCTGC CTCCCACTGG ATGGACGCAC CAAGTTCTCT   240

CAGCGTGGA                                                          249
```

(2) INFORMATION FOR SEQ ID NO:47:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:47:

```
Ser Arg Ala His Gln His Ser Met Glu Thr Arg Thr Pro Asp Ile Asn
 1               5                  10                  15

Pro Ala Trp Tyr Thr Gly Arg Gly Ile Arg Pro Val Gly Arg Phe
             20                  25                  30
```

(2) INFORMATION FOR SEQ ID NO:48:

(i) SEQUENCE CHARACTERISTICS:
        (A) LENGTH: 32 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:48:

```
Ser Arg Ala His Gln His Ser Met Glu Thr Arg Thr Pro Asp Ile Asn
 1               5                  10                  15

Pro Ala Trp Tyr Thr Gly Arg Gly Ile Arg Pro Val Gly Arg Phe Gly
             20                  25                  30
```

(2) INFORMATION FOR SEQ ID NO:49:

(i) SEQUENCE CHARACTERISTICS:
        (A) LENGTH: 33 amino acids
        (B) TYPE: amino acid

```
            (C) STRANDEDNESS: single
            (D) TOPOLOGY: linear (ii) MOLECULE TYPE: protein (v) FRAGMENT TYPE: internal (xi) SEQUENCE DESCRIPTION: SEQ ID NO:49:

Ser Arg Ala His Gln His Ser Met Glu Thr Arg Thr Pro Asp Ile Asn
 1               5                  10                  15

Pro Ala Trp Tyr Thr Gly Arg Gly Ile Arg Pro Val Gly Arg Phe Gly
            20                  25                  30

Arg (2) INFORMATION FOR SEQ ID NO:50:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: protein (v) FRAGMENT TYPE: internal (xi) SEQUENCE DESCRIPTION: SEQ ID NO:50:

Thr Pro Asp Ile Asn Pro Ala Trp Tyr Thr Gly Arg Gly Ile Arg Pro
 1               5                  10                  15

Val Gly Arg Phe
            20

(2) INFORMATION FOR SEQ ID NO:51:

(i) SEQUENCE CHARACTERISTICS:
            (A) LENGTH: 21 amino acids
            (B) TYPE: amino acid
            (C) STRANDEDNESS: single
            (D) TOPOLOGY: linear (ii) MOLECULE TYPE: protein (v) FRAGMENT TYPE: internal (xi) SEQUENCE DESCRIPTION: SEQ ID NO:51:

Thr Pro Asp Ile Asn Pro Ala Trp Tyr Thr Gly Arg Gly Ile Arg Pro
 1               5                  10                  15

Val Gly Arg Phe Gly
            20

(2) INFORMATION FOR SEQ ID NO:52:

(i) SEQUENCE CHARACTERISTICS:
            (A) LENGTH: 22 amino acids
            (B) TYPE: amino acid
            (C) STRANDEDNESS: single
            (D) TOPOLOGY: linear (ii) MOLECULE TYPE: protein (v) FRAGMENT TYPE: internal (xi) SEQUENCE DESCRIPTION: SEQ ID NO:52:

Thr Pro Asp Ile Asn Pro Ala Trp Tyr Thr Gly Arg Gly Ile Arg Pro
 1               5                  10                  15

Val Gly Arg Phe Gly Arg
            20
```

(2) INFORMATION FOR SEQ ID NO:53:

(i) SEQUENCE CHARACTERISTICS:
        (A) LENGTH: 93 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:53:

```
AGCCGAGCCC ACCAGCACTC CATGGAGACA AGAACCCCTG ATATCAATCC TGCCTGGTAC    60

ACGGGCCGCG GGATCAGGCC TGTGGGCCGC TTC                                 93
```

(2) INFORMATION FOR SEQ ID NO:54:

(i) SEQUENCE CHARACTERISTICS:
        (A) LENGTH: 96 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:54:

```
AGCCGAGCCC ACCAGCACTC CATGGAGACA AGAACCCCTG ATATCAATCC TGCCTGGTAC    60

ACGGGCCGCG GGATCAGGCC TGTGGGCCGC TTCGGC                              96
```

(2) INFORMATION FOR SEQ ID NO:55:

(i) SEQUENCE CHARACTERISTICS:
        (A) LENGTH: 99 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:55:

```
AGCCGAGCCC ACCAGCACTC CATGGAGACA AGAACCCCTG ATATCAATCC TGCCTGGTAC    60

ACGGGCCGCG GGATCAGGCC TGTGGGCCGC TTCGGCAGG                           99
```

(2) INFORMATION FOR SEQ ID NO:56:

(i) SEQUENCE CHARACTERISTICS:
        (A) LENGTH: 60 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:56:

```
ACCCCTGATA TCAATCCTGC CTGGTACACG GGCCGCGGGA TCAGGCCTGT GGGCCGCTTC    60
```

(2) INFORMATION FOR SEQ ID NO:57:

(i) SEQUENCE CHARACTERISTICS:
        (A) LENGTH: 63 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:57:

ACCCCTGATA TCAATCCTGC CTGGTACACG GGCCGCGGGA TCAGGCCTGT GGGCCGCTTC    60

GGC                                                                 63

(2) INFORMATION FOR SEQ ID NO:58:

(i) SEQUENCE CHARACTERISTICS:
        (A) LENGTH: 66 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:58:

ACCCCTGATA TCAATCCTGC CTGGTACACG GGCCGCGGGA TCAGGCCTGT GGGCCGCTTC    60

GGCAGG                                                              66

(2) INFORMATION FOR SEQ ID NO:59:

(i) SEQUENCE CHARACTERISTICS:
        (A) LENGTH: 87 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:59:

Met Lys Val Leu Arg Ala Trp Leu Leu Cys Leu Leu Met Leu Gly Leu
1               5                   10                  15

Ala Leu Arg Gly Ala Ala Ser Arg Thr His Arg His Ser Met Glu Ile
            20                  25                  30

Arg Thr Pro Asp Ile Asn Pro Ala Trp Tyr Ala Ser Arg Gly Ile Arg
        35                  40                  45

Pro Val Gly Arg Phe Gly Arg Arg Arg Ala Thr Leu Gly Asp Val Pro
    50                  55                  60

Lys Pro Gly Leu Arg Pro Arg Leu Thr Cys Phe Pro Leu Glu Gly Gly
65                  70                  75                  80

Ala Met Ser Ser Gln Asp Gly
                85

(2) INFORMATION FOR SEQ ID NO:60:

(i) SEQUENCE CHARACTERISTICS:
        (A) LENGTH: 261 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:60:

ATGAAGGTGC TGAGGGCCTG GCTCCTGTGC CTGCTGATGC TGGGCCTGGC CCTGCGGGGA    60

GCTGCAAGTC GTACCCATCG GCACTCCATG GAGATCCGCA CCCCTGACAT CAATCCTGCC   120

TGGTACGCCA GTCGCGGGAT CAGGCCTGTG GGCCGCTTCG GTCGGAGGAG GGCAACCCTG   180

GGGGACGTCC CCAAGCCTGG CCTGCGACCC CGGCTGACCT GCTTCCCCCT GGAAGGCGGT   240

GCTATGTCGT CCCAGGATGG C                                            261

(2) INFORMATION FOR SEQ ID NO:61:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:61:

Ser Arg Thr His Arg His Ser Met Glu Ile Arg Thr Pro Asp Ile Asn
1               5                   10                  15

Pro Ala Trp Tyr Ala Ser Arg Gly Ile Arg Pro Val Gly Arg Phe
            20                  25                  30

(2) INFORMATION FOR SEQ ID NO:62:

(i) SEQUENCE CHARACTERISTICS:
        (A) LENGTH: 32 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:62:

Ser Arg Thr His Arg His Ser Met Glu Ile Arg Thr Pro Asp Ile Asn
1               5                   10                  15

Pro Ala Trp Tyr Ala Ser Arg Gly Ile Arg Pro Val Gly Arg Phe Gly
            20                  25                  30

(2) INFORMATION FOR SEQ ID NO:63:

(i) SEQUENCE CHARACTERISTICS:
        (A) LENGTH: 33 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:63:

Ser Arg Thr His Arg His Ser Met Glu Ile Arg Thr Pro Asp Ile Asn
1               5                   10                  15

Pro Ala Trp Tyr Ala Ser Arg Gly Ile Arg Pro Val Gly Arg Phe Gly
            20                  25                  30

Arg (2) INFORMATION FOR SEQ ID NO:64:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:64:

Thr Pro Asp Ile Asn Pro Ala Trp Tyr Ala Ser Arg Gly Ile Arg Pro
1               5                   10                  15

Val Gly Arg Phe
            20

(2) INFORMATION FOR SEQ ID NO:65:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:65:

Thr Pro Asp Ile Asn Pro Ala Trp Tyr Ala Ser Arg Gly Ile Arg Pro
1               5                   10                  15

Val Gly Arg Phe Gly
            20

(2) INFORMATION FOR SEQ ID NO:66:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:66:

Thr Pro Asp Ile Asn Pro Ala Trp Tyr Ala Ser Arg Gly Ile Arg Pro
1               5                   10                  15

Val Gly Arg Phe Gly Arg
            20

(2) INFORMATION FOR SEQ ID NO:67:

(i) SEQUENCE CHARACTERISTICS:
        (A) LENGTH: 93 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:67:

AGTCGTACCC ATCGGCACTC CATGGAGATC CGCACCCCTG ACATCAATCC TGCCTGGTAC    60

GCCAGTCGCG GGATCAGGCC TGTGGGCCGC TTC                                 93

(2) INFORMATION FOR SEQ ID NO:68:

(i) SEQUENCE CHARACTERISTICS:
        (A) LENGTH: 96 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:68:

AGTCGTACCC ATCGGCACTC CATGGAGATC CGCACCCCTG ACATCAATCC TGCCTGGTAC        60

GCCAGTCGCG GGATCAGGCC TGTGGGCCGC TTCGGT        96

(2) INFORMATION FOR SEQ ID NO:69:

(i) SEQUENCE CHARACTERISTICS:
        (A) LENGTH: 99 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:69:

AGTCGTACCC ATCGGCACTC CATGGAGATC CGCACCCCTG ACATCAATCC TGCCTGGTAC        60

GCCAGTCGCG GGATCAGGCC TGTGGGCCGC TTCGGTCGG        99

(2) INFORMATION FOR SEQ ID NO:70:

(i) SEQUENCE CHARACTERISTICS:
        (A) LENGTH: 60 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:70:

ACCCCTGACA TCAATCCTGC CTGGTACGCC AGTCGCGGGA TCAGGCCTGT GGGCCGCTTC        60

(2) INFORMATION FOR SEQ ID NO:71:

(i) SEQUENCE CHARACTERISTICS:
        (A) LENGTH: 63 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:71:

ACCCCTGACA TCAATCCTGC CTGGTACGCC AGTCGCGGGA TCAGGCCTGT GGGCCGCTTC        60

GGT        63

(2) INFORMATION FOR SEQ ID NO:72:

(i) SEQUENCE CHARACTERISTICS:
        (A) LENGTH: 66 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:72:

ACCCCTGACA TCAATCCTGC CTGGTACGCC AGTCGCGGGA TCAGGCCTGT GGGCCGCTTC        60

GGTCGG        66

(2) INFORMATION FOR SEQ ID NO:73:

(i) SEQUENCE CHARACTERISTICS:
        (A) LENGTH: 22 amino acids
        (B) TYPE: amino acid

```
        (C) STRANDEDNESS: single
        (D) TOPOLOGY: linear (ii) MOLECULE TYPE: protein (v) FRAGMENT TYPE: internal (ix) FEATURE:
        (A) NAME/KEY: Modified-site
        (B) LOCATION: 10
        (D) OTHER INFORMATION: /product= "Ala or Thr"

(ix) FEATURE:
        (A) NAME/KEY: Modified-site
        (B) LOCATION: 11
        (D) OTHER INFORMATION: /product= "Gly or Ser"

(ix) FEATURE:
        (A) NAME/KEY: Modified-site
        (B) LOCATION: 21..22
        (D) OTHER INFORMATION: /product= "may be a Gly-Arg or Gly"

(xi) SEQUENCE DESCRIPTION: SEQ ID NO:73:

Thr Pro Asp Ile Asn Pro Ala Trp Tyr Xaa Xaa Arg Gly Ile Arg Pro
1               5                  10                  15

Val Gly Arg Phe Xaa Xaa
            20

(2) INFORMATION FOR SEQ ID NO:74:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: protein (v) FRAGMENT TYPE: internal (ix) FEATURE:
        (A) NAME/KEY: Modified-site
        (B) LOCATION: 3
        (D) OTHER INFORMATION: /product= "Ala or Thr"

(ix) FEATURE:
        (A) NAME/KEY: Modified-site
        (B) LOCATION: 5
        (D) OTHER INFORMATION: /product= "Gln or Arg"

(ix) FEATURE:
        (A) NAME/KEY: Modified-site
        (B) LOCATION: 10
        (D) OTHER INFORMATION: /product= "Ile or Thr"

(xi) SEQUENCE DESCRIPTION: SEQ ID NO:74:

Ser Arg Xaa His Xaa His Ser Met Glu Xaa Arg
1               5                  10

(2) INFORMATION FOR SEQ ID NO:75:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:75:

CARCAYTCCA TGGAGACAAG AACCCC                                       26
```

-continued (2) INFORMATION FOR SEQ ID NO:76:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:76:

TACCAGGCAG GATTGATACA GGGG                                                    24

(2) INFORMATION FOR SEQ ID NO:77:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:77:

GGCATCATCC AGGAAGACGG AGCAT                                                25

(2) INFORMATION FOR SEQ ID NO:78:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:78:

AGCAGAGGAG AGGGAGGGTA GAGGA                                                25

(2) INFORMATION FOR SEQ ID NO:79:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:79:

ACGTGGCTTC TGTGCTTGCT GC                                                      22

(2) INFORMATION FOR SEQ ID NO:80:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:80:

GCCTGATCCC GCGGCCCGTG TACCA                                                25

```
(2) INFORMATION FOR SEQ ID NO:81:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:81:

TTGCCCTTCT CCTGCCGAAG CGGCCC                                          26

(2) INFORMATION FOR SEQ ID NO:82:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:82:

GGCGGGGGCT GCAAGTCGTA CCCATCG                                         27

(2) INFORMATION FOR SEQ ID NO:83:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:83:

CGGCACTCCA TGGAGATCCG CACCCCT                                         27

(2) INFORMATION FOR SEQ ID NO:84:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:84:

CAGGCAGGAT TGATGTCAGG GGTGCGG                                         27

(2) INFORMATION FOR SEQ ID NO:85:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:85:

CATGGAGTGC CGATGGGTAC GACTTGC                                         27
```

-continued (2) INFORMATION FOR SEQ ID NO:86:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:86:

GGCCTCCTCG GAGGAGCCAA GGGATGA                                      27

(2) INFORMATION FOR SEQ ID NO:87:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:87:

GGGAAAGGAG CCCGAAGGAG AGGAGAG                                      27

(2) INFORMATION FOR SEQ ID NO:88:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:88:

CCTGCTGGCC ATTCTCCTGT CTTAC                                          25

(2) INFORMATION FOR SEQ ID NO:89:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:89:

GGGTCCAGGT CCCGCAGAAG GTTGA                                          25

(2) INFORMATION FOR SEQ ID NO:90:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:90:

GAAGACGGAG CATGGCCCTG AAGAC                                          25

(2) INFORMATION FOR SEQ ID NO:91:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:91:

GGCAGCTGAG TTGGCCAAGT CCAGT                                      25

(2) INFORMATION FOR SEQ ID NO:92:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:92:

Ser Arg Ala His Gln His Ser Met Glu Ile Arg Thr Pro Asp Cys
1             5                   10              15

(2) INFORMATION FOR SEQ ID NO:93:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:93:

Cys Ala Trp Tyr Ala Gly Arg Gly Ile Arg Pro Val Gly Arg Phe
1             5                   10              15

(2) INFORMATION FOR SEQ ID NO:94:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:94:

Cys Glu Ile Arg Thr Pro Asp Ile Asn Pro Ala Trp Tyr Ala Gly
1             5                   10              15

(2) INFORMATION FOR SEQ ID NO:95:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:95:

GTTCACAGGT CGACATGACC TCAC                                              24

(2) INFORMATION FOR SEQ ID NO:96:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:96:

CTCAGAGCTA GCAGAGTGTC ATCAG                                             25

(2) INFORMATION FOR SEQ ID NO:97:

(i) SEQUENCE CHARACTERISTICS:
        (A) LENGTH: 31 amino acids
        (B) TYPE: amino acid
        (C) STRANDEDNESS: single
        (D) TOPOLOGY: linear (xi) SEQUENCE DESCRIPTION: SEQ ID NO:97:

Ser Arg Ala His Gln His Ser Met Glu Ile Arg Thr Pro Asp Ile Asn
 1               5                  10                  15

Pro Ala Trp Tyr Ala Gly Arg Gly Ile Arg Pro Val Gly Arg Phe
            20                  25                  30

(2) INFORMATION FOR SEQ ID NO:98:

(i) SEQUENCE CHARACTERISTICS:
        (A) LENGTH: 20 amino acids
        (B) TYPE: amino acid
        (C) STRANDEDNESS: single
        (D) TOPOLOGY: linear (xi) SEQUENCE DESCRIPTION: SEQ ID NO:98:

Thr Pro Asp Ile Asn Pro Ala Trp Tyr Ala Gly Arg Gly Ile Arg Pro
 1               5                  10                  15

Val Gly Arg Phe
            20

(2) INFORMATION FOR SEQ ID NO:99:

(i) SEQUENCE CHARACTERISTICS:
        (A) LENGTH: 669 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 1...669
        (D) OTHER INFORMATION:

(xi) SEQUENCE DESCRIPTION: SEQ ID NO:99:

GTG GGC ATG GTG GGC AAC ATC CTG CTG GTG CTG GTG ATC GCG CGG GTG   48
Val Gly Met Val Gly Asn Ile Leu Leu Val Leu Val Ile Ala Arg Val
 1               5                  10                  15

| | |
|---|---|
| CGC CGG CTG TAC AAC GTG ACG AAT TTC CTC ATC GGC AAC CTG GCC TTG<br>Arg Arg Leu Tyr Asn Val Thr Asn Phe Leu Ile Gly Asn Leu Ala Leu<br>20          25          30 | 96 |
| TCC GAC GTG CTC ATG TGC ACC GCC TGC GTG CCG CTC ACG CTG GCC TAT<br>Ser Asp Val Leu Met Cys Thr Ala Cys Val Pro Leu Thr Leu Ala Tyr<br>35          40          45 | 144 |
| GCC TTC GAG CCA CGC GGC TGG GTG TTC GGC GGC GGC CTG TGC CAC CTG<br>Ala Phe Glu Pro Arg Gly Trp Val Phe Gly Gly Gly Leu Cys His Leu<br>50          55          60 | 192 |
| GTC TTC TTC CTG CAG GCG GTC ACC GTC TAT GTG TCG GTG TTC ACG CTC<br>Val Phe Phe Leu Gln Ala Val Thr Val Tyr Val Ser Val Phe Thr Leu<br>65          70          75          80 | 240 |
| ACC ACC ATC GCA GTG GAC CGC TAC GTC GTG CTG GTG CAC CCG CTG AGG<br>Thr Thr Ile Ala Val Asp Arg Tyr Val Val Leu Val His Pro Leu Arg<br>85          90          95 | 288 |
| CGG CGC ATC TCG CTG CGC CTC AGC GCC TAC GCT GTG CTG GCC ATC TGG<br>Arg Arg Ile Ser Leu Arg Leu Ser Ala Tyr Ala Val Leu Ala Ile Trp<br>100          105          110 | 336 |
| GTG CTG TCC GCG GTG CTG GCG CTG CCC GCC GCC GTG CAC ACC TAT CAC<br>Val Leu Ser Ala Val Leu Ala Leu Pro Ala Ala Val His Thr Tyr His<br>115          120          125 | 384 |
| GTG GAG CTC AAG CCG CAC GAC GTG CGC CTC TGC GAG GAG TTC TGG GGC<br>Val Glu Leu Lys Pro His Asp Val Arg Leu Cys Glu Glu Phe Trp Gly<br>130          135          140 | 432 |
| TCC CAG GAG CGC CAG CGC CAG CTC TAC GCC TGG GGG CTG CTG CTG GTC<br>Ser Gln Glu Arg Gln Arg Gln Leu Tyr Ala Trp Gly Leu Leu Leu Val<br>145          150          155          160 | 480 |
| ACC TAC CTG CTC CCT CTG CTG GTC ATC CTC CTG TCT TAC GCC CGG GTG<br>Thr Tyr Leu Leu Pro Leu Leu Val Ile Leu Leu Ser Tyr Ala Arg Val<br>165          170          175 | 528 |
| TCA GTG AAG CTC CGC AAC CGC GTG GTG CCG GGC CGC GTG ACC CAG AGC<br>Ser Val Lys Leu Arg Asn Arg Val Val Pro Gly Arg Val Thr Gln Ser<br>180          185          190 | 576 |
| CAG GCC GAC TGG GAC CGC GCT CGG CGC CGG CGC ACC TTC TGC TTG CTG<br>Gln Ala Asp Trp Asp Arg Ala Arg Arg Arg Arg Thr Phe Cys Leu Leu<br>195          200          205 | 624 |
| GTG GTG GTC GTG GTG GTG TTC ACC CTC TGC TGG CTG CCC TTC TTC<br>Val Val Val Val Val Val Phe Thr Leu Cys Trp Leu Pro Phe Phe<br>210          215          220 | 669 |

(2) INFORMATION FOR SEQ ID NO:100:

(i) SEQUENCE CHARACTERISTICS:
        (A) LENGTH: 223 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:100:

Val Gly Met Val Gly Asn Ile Leu Leu Val Leu Ile Ala Arg Val
1          5          10          15

Arg Arg Leu Tyr Asn Val Thr Asn Phe Leu Ile Gly Asn Leu Ala Leu
20          25          30

Ser Asp Val Leu Met Cys Thr Ala Cys Val Pro Leu Thr Leu Ala Tyr
35          40          45

Ala Phe Glu Pro Arg Gly Trp Val Phe Gly Gly Gly Leu Cys His Leu
50          55          60

-continued

Val Phe Phe Leu Gln Ala Val Thr Val Tyr Val Ser Val Phe Thr Leu
65                  70                  75                  80

Thr Thr Ile Ala Val Asp Arg Tyr Val Val Leu Val His Pro Leu Arg
                85                  90                  95

Arg Arg Ile Ser Leu Arg Leu Ser Ala Tyr Ala Val Leu Ala Ile Trp
            100                 105                 110

Val Leu Ser Ala Val Leu Ala Leu Pro Ala Ala Val His Thr Tyr His
            115                 120                 125

Val Glu Leu Lys Pro His Asp Val Arg Leu Cys Glu Glu Phe Trp Gly
130                 135                 140

Ser Gln Glu Arg Gln Arg Gln Leu Tyr Ala Trp Gly Leu Leu Val
145                 150                 155                 160

Thr Tyr Leu Leu Pro Leu Leu Val Ile Leu Leu Ser Tyr Ala Arg Val
                165                 170                 175

Ser Val Lys Leu Arg Asn Arg Val Val Pro Gly Arg Val Thr Gln Ser
                180                 185                 190

Gln Ala Asp Trp Asp Arg Ala Arg Arg Arg Thr Phe Cys Leu Leu
        195                 200                 205

Val Val Val Val Val Phe Thr Leu Cys Trp Leu Pro Phe Phe
210                 215                 220

(2) INFORMATION FOR SEQ ID NO:101:

(i) SEQUENCE CHARACTERISTICS:
        (A) LENGTH: 167 amino acids
        (B) TYPE: amino acid
        (C) STRANDEDNESS: single
        (D) TOPOLOGY: linear (xi) SEQUENCE DESCRIPTION: SEQ ID NO:101:

Val Gly Met Val Gly Asn Val Leu Leu Val Leu Ile Ala Arg Val
1               5                   10                  15

Arg Arg Leu His Asn Val Thr Asn Phe Leu Ile Gly Asn Leu Ala Leu
                20                  25                  30

Ser Asp Val Leu Met Cys Thr Ala Cys Val Pro Leu Thr Leu Ala Tyr
            35                  40                  45

Ala Phe Glu Pro Arg Gly Trp Val Phe Gly Gly Gly Leu Cys His Leu
        50                  55                  60

Val Phe Phe Leu Gln Pro Val Thr Val Tyr Val Ser Val Phe Thr Leu
65                  70                  75                  80

Thr Thr Ile Ala Val Asp Arg Tyr Val Val Leu Val His Pro Leu Arg
                85                  90                  95

Arg Arg Ile Gly Leu Leu Leu Val Thr Tyr Leu Leu Pro Leu Leu Val
            100                 105                 110

Ile Leu Leu Ser Tyr Val Arg Val Ser Val Lys Leu Arg Asn Arg Val
        115                 120                 125

Val Pro Gly Cys Val Thr Gln Ser Gln Ala Asp Trp Asp Arg Ala Arg
130                 135                 140

Arg Arg Arg Thr Phe Cys Leu Leu Val Val Val Val Val Phe Ala
145                 150                 155                 160

Ile Cys Trp Leu Pro Tyr Tyr
                165

(2) INFORMATION FOR SEQ ID NO:102:

(i) SEQUENCE CHARACTERISTICS:
        (A) LENGTH: 223 amino acids
        (B) TYPE: amino acid
        (C) STRANDEDNESS: single
        (D) TOPOLOGY: linear (xi) SEQUENCE DESCRIPTION: SEQ ID NO:102:

```
Val Gly Met Val Gly Asn Ile Leu Leu Val Leu Val Ile Ala Arg Val
 1               5                  10                  15

Arg Arg Leu Tyr Asn Val Thr Asn Phe Leu Ile Gly Asn Leu Ala Leu
                20                  25                  30

Ser Asp Val Leu Met Cys Thr Ala Cys Val Pro Leu Thr Leu Ala Tyr
                35                  40                  45

Ala Phe Glu Pro Arg Gly Trp Val Phe Gly Gly Leu Cys His Leu
 50                  55                  60

Val Phe Phe Leu Gln Ala Val Thr Val Tyr Val Ser Val Phe Thr Leu
 65                  70                  75                  80

Thr Thr Ile Ala Val Asp Arg Tyr Val Val Leu Val His Pro Leu Arg
                85                  90                  95

Arg Arg Ile Ser Leu Arg Leu Ser Ala Tyr Ala Val Leu Ala Ile Trp
                100                 105                 110

Val Leu Ser Ala Val Leu Ala Leu Pro Ala Ala Val His Thr Tyr His
                115                 120                 125

Val Glu Leu Lys Pro His Asp Val Arg Leu Cys Glu Glu Phe Trp Gly
                130                 135                 140

Ser Gln Glu Arg Gln Arg Gln Leu Tyr Ala Trp Gly Leu Leu Leu Val
145                 150                 155                 160

Thr Tyr Leu Leu Pro Leu Leu Val Ile Leu Leu Ser Tyr Ala Arg Val
                165                 170                 175

Ser Val Lys Leu Arg Asn Arg Val Val Pro Gly Arg Val Thr Gln Ser
                180                 185                 190

Gln Ala Asp Trp Asp Arg Ala Arg Arg Arg Thr Phe Cys Leu Leu
                195                 200                 205

Val Val Val Val Val Val Phe Thr Leu Cys Trp Leu Pro Phe Phe
210                 215                 220
```

(2) INFORMATION FOR SEQ ID NO:103:

(i) SEQUENCE CHARACTERISTICS:
        (A) LENGTH: 1331 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 118...1227
        (D) OTHER INFORMATION:

(xi) SEQUENCE DESCRIPTION: SEQ ID NO:103:

```
CATCGTCAAG CAGATGAAGA TCATCCACGA GGATGGCTAC TCCGAGGGCC AGCAGAAATT     60

CTGCCCCTTC TTCCCGCGAG TGCTTTCCCG CTCTCCAAAC CCCACTCCCA GGTGGCC ATG   120
                                                                Met
                                                                 1

GCC TCA TCG ACC ACT CGG GGC CCC AGG GTT TCT GAC TTA TTT TCT GGG     168
Ala Ser Ser Thr Thr Arg Gly Pro Arg Val Ser Asp Leu Phe Ser Gly
         5                  10                  15
```

```
CTG CCG CCG GCG GTC ACA ACT CCC GCC AAC CAG AGC GCA GAG GCC TCG        216
Leu Pro Pro Ala Val Thr Thr Pro Ala Asn Gln Ser Ala Glu Ala Ser
     20              25                  30

GCG GGC AAC GGG TCG GTG GCT GGC GCG GAC GCT CCA GCC GTC ACG CCC        264
Ala Gly Asn Gly Ser Val Ala Gly Ala Asp Ala Pro Ala Val Thr Pro
 35              40                  45

TTC CAG AGC CTG CAG CTG GTG CAT CAG CTG AAG GGG CTG ATC GTG CTG        312
Phe Gln Ser Leu Gln Leu Val His Gln Leu Lys Gly Leu Ile Val Leu
50              55                  60                  65

CTC TAC AGC GTC GTG GTG GTC GTG GGG CTG GTG GGC AAC TGC CTG CTG        360
Leu Tyr Ser Val Val Val Val Val Gly Leu Val Gly Asn Cys Leu Leu
             70                  75                  80

GTG CTG GTG ATC GCG CGG GTG CGC CGG CTG CAC AAC GTG ACG AAC TTC        408
Val Leu Val Ile Ala Arg Val Arg Arg Leu His Asn Val Thr Asn Phe
                 85                  90                  95

CTC ATC GGC AAC CTG GCC TTG TCC GAC GTG CTC ATG TGC ACC GCC TGC        456
Leu Ile Gly Asn Leu Ala Leu Ser Asp Val Leu Met Cys Thr Ala Cys
             100                 105                 110

GTG CCG CTC ACG CTG GCC TAT GCC TTC GAG CCA CGC GGC TGG GTG TTC        504
Val Pro Leu Thr Leu Ala Tyr Ala Phe Glu Pro Arg Gly Trp Val Phe
         115                 120                 125

GGC GGC GGC CTG TGC CAC CTG GTC TTC TTC CTG CAG CCG GTC ACC GTC        552
Gly Gly Gly Leu Cys His Leu Val Phe Phe Leu Gln Pro Val Thr Val
130                 135                 140                 145

TAT GTG TCG GTG TTC ACG CTC ACC ACC ATC GCA GTG GAC CGC TAC GTC        600
Tyr Val Ser Val Phe Thr Leu Thr Thr Ile Ala Val Asp Arg Tyr Val
                 150                 155                 160

GTG CTG GTG CAC CCG CTG AGG CGG CGC ATC TCG CTG CGC CTC AGC GCC        648
Val Leu Val His Pro Leu Arg Arg Arg Ile Ser Leu Arg Leu Ser Ala
             165                 170                 175

TAC GCT GTG CTG GCC ATC TGG GCG CTG TCC GCG GTG CTG GCG CTG CCC        696
Tyr Ala Val Leu Ala Ile Trp Ala Leu Ser Ala Val Leu Ala Leu Pro
         180                 185                 190

GCC GCC GTG CAC ACC TAT CAC GTG GAG CTC AAG CCG CAC GAC GTG CGC        744
Ala Ala Val His Thr Tyr His Val Glu Leu Lys Pro His Asp Val Arg
195                 200                 205

CTC TGC GAG GAG TTC TGG GGC TCC CAG GAG CGC CAG CGC CAG CTC TAC        792
Leu Cys Glu Glu Phe Trp Gly Ser Gln Glu Arg Gln Arg Gln Leu Tyr
210                 215                 220                 225

GCC TGG GGG CTG CTG CTG GTC ACC TAC CTG CTC CCT CTG CTG GTC ATC        840
Ala Trp Gly Leu Leu Leu Val Thr Tyr Leu Leu Pro Leu Leu Val Ile
                 230                 235                 240

CTC CTG TCT TAC GTC CGG GTG TCA GTG AAG CTC CGC AAC CGC GTG GTG        888
Leu Leu Ser Tyr Val Arg Val Ser Val Lys Leu Arg Asn Arg Val Val
             245                 250                 255

CCG GGC TGC GTG ACC CAG AGC CAG GCC GAC TGG GAC CGC GCT CGG CGC        936
Pro Gly Cys Val Thr Gln Ser Gln Ala Asp Trp Asp Arg Ala Arg Arg
         260                 265                 270

CGG CGC ACC TTC TGC TTG CTG GTG GTG GTC GTG GTG TTC GCC GTC        984
Arg Arg Thr Phe Cys Leu Leu Val Val Val Val Val Phe Ala Val
275                 280                 285

TGC TGG CTG CCG CTG CAC GTC TTC AAC CTG CTG CGG GAC CTC GAC CCC       1032
Cys Trp Leu Pro Leu His Val Phe Asn Leu Leu Arg Asp Leu Asp Pro
290                 295                 300                 305

CAC GCC ATC GAC CCT TAC GCC TTT GGG CTG GTG CAG CTG CTC TGC CAC       1080
His Ala Ile Asp Pro Tyr Ala Phe Gly Leu Val Gln Leu Leu Cys His
                 310                 315                 320

TGG CTC GCC ATG AGT TCG GCC TGC TAC AAC CCC TTC ATC TAC GCC TGG       1128
Trp Leu Ala Met Ser Ser Ala Cys Tyr Asn Pro Phe Ile Tyr Ala Trp
             325                 330                 335
```

```
CTG CAC GAC AGC TTC CGC GAG GAG CTG CGC AAA CTG TTG GTC GCT TGG    1176
Leu His Asp Ser Phe Arg Glu Glu Leu Arg Lys Leu Leu Val Ala Trp
    340                 345                 350

CCC CGC AAG ATA GCC CCC CAT GGC CAG AAT ATG ACC GTC AGC GTG GTC    1224
Pro Arg Lys Ile Ala Pro His Gly Gln Asn Met Thr Val Ser Val Val
    355                 360                 365

ATC TGATGCCACT TAGCCAGGCC TTGGTCAAGG AGCTCCACTT CAACTGGCCT CCTAGG  1283
Ile
370

GCACCACTCG AGGTCAATCT GGTGCTTATT CTCAGCACCA GAGCTAGC              1331

(2) INFORMATION FOR SEQ ID NO:104:

(i) SEQUENCE CHARACTERISTICS:
        (A) LENGTH: 370 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:104:

Met Ala Ser Ser Thr Thr Arg Gly Pro Arg Val Ser Asp Leu Phe Ser
1               5                   10                  15

Gly Leu Pro Pro Ala Val Thr Thr Pro Ala Asn Gln Ser Ala Glu Ala
            20                  25                  30

Ser Ala Gly Asn Gly Ser Val Ala Gly Ala Asp Ala Pro Ala Val Thr
        35                  40                  45

Pro Phe Gln Ser Leu Gln Leu Val His Gln Leu Lys Gly Leu Ile Val
    50                  55                  60

Leu Leu Tyr Ser Val Val Val Val Gly Leu Val Gly Asn Cys Leu
65                  70                  75                  80

Leu Val Leu Val Ile Ala Arg Val Arg Leu His Asn Val Thr Asn
                85                  90                  95

Phe Leu Ile Gly Asn Leu Ala Leu Ser Asp Val Leu Met Cys Thr Ala
            100                 105                 110

Cys Val Pro Leu Thr Leu Ala Tyr Ala Phe Glu Pro Arg Gly Trp Val
            115                 120                 125

Phe Gly Gly Gly Leu Cys His Leu Val Phe Phe Leu Gln Pro Val Thr
    130                 135                 140

Val Tyr Val Ser Val Phe Thr Leu Thr Thr Ile Ala Val Asp Arg Tyr
145                 150                 155                 160

Val Val Leu Val His Pro Leu Arg Arg Arg Ile Ser Leu Arg Leu Ser
                165                 170                 175

Ala Tyr Ala Val Leu Ala Ile Trp Ala Leu Ser Ala Val Leu Ala Leu
            180                 185                 190

Pro Ala Ala Val His Thr Tyr His Val Glu Leu Lys Pro His Asp Val
        195                 200                 205

Arg Leu Cys Glu Glu Phe Trp Gly Ser Gln Glu Arg Gln Arg Gln Leu
    210                 215                 220

Tyr Ala Trp Gly Leu Leu Leu Val Thr Tyr Leu Leu Pro Leu Leu Val
225                 230                 235                 240

Ile Leu Leu Ser Tyr Val Arg Val Ser Val Lys Leu Arg Asn Arg Val
                245                 250                 255

Val Pro Gly Cys Val Thr Gln Ser Gln Ala Asp Trp Asp Arg Ala Arg
            260                 265                 270
```

```
        Arg Arg Arg Thr Phe Cys Leu Leu Val Val Val Val Val Phe Ala
                275                 280                 285

Val Cys Trp Leu Pro Leu His Val Phe Asn Leu Leu Arg Asp Leu Asp
            290                 295                 300

Pro His Ala Ile Asp Pro Tyr Ala Phe Gly Leu Val Gln Leu Leu Cys
        305                 310                 315                 320

His Trp Leu Ala Met Ser Ser Ala Cys Tyr Asn Pro Phe Ile Tyr Ala
                        325                 330                 335

Trp Leu His Asp Ser Phe Arg Glu Glu Leu Arg Lys Leu Leu Val Ala
                    340                 345                 350

Trp Pro Arg Lys Ile Ala Pro His Gly Gln Asn Met Thr Val Ser Val
                    355                 360                 365

Val Ile
            370

(2) INFORMATION FOR SEQ ID NO:105:

(i) SEQUENCE CHARACTERISTICS:
           (A) LENGTH: 434 base pairs
           (B) TYPE: nucleic acid
           (C) STRANDEDNESS: single
           (D) TOPOLOGY: linear (ix) FEATURE:
           (A) NAME/KEY: Coding Sequence
           (B) LOCATION: 1...432
           (D) OTHER INFORMATION:

(xi) SEQUENCE DESCRIPTION: SEQ ID NO:105:

CTG TGT GTC ATC GCG GTG GAT AGG TAC GTG GTT CTG GTG CAC CCG CTA        48
    Leu Cys Val Ile Ala Val Asp Arg Tyr Val Val Leu Val His Pro Leu
    1               5                   10                  15

CGT CGG CGC ATT TCA CTG AGG CTC AGC GCC TAC GCG GTG CTG GGC ATC        96
    Arg Arg Arg Ile Ser Leu Arg Leu Ser Ala Tyr Ala Val Leu Gly Ile
                    20                  25                  30

TGG GCT CTA TCT GCA GTG CTG GCG CTG CCG GCC GCG GTG CAC ACC TAC       144
    Trp Ala Leu Ser Ala Val Leu Ala Leu Pro Ala Ala Val His Thr Tyr
                35                  40                  45

CAT GTG GAG CTC AAG CCC CAC GAC GTG AGC CTC TGC GAG GAG TTC TGG       192
    His Val Glu Leu Lys Pro His Asp Val Ser Leu Cys Glu Glu Phe Trp
        50                  55                  60

GGC TCG CAG GAG CGC CAA CGC CAG ATC TAC GCC TGG GGG CTG CTT CTG       240
    Gly Ser Gln Glu Arg Gln Arg Gln Ile Tyr Ala Trp Gly Leu Leu Leu
    65                  70                  75                  80

GGC ACC TAT TTG CTC CCC CTG CTG GCC ATC CTC CTG TCT TAC GTA CGG       288
    Gly Thr Tyr Leu Leu Pro Leu Leu Ala Ile Leu Leu Ser Tyr Val Arg
                    85                  90                  95

GTG TCA GTG AAG CTG AGG AAC CGC GTG GTG CCT GGC AGC GTG ACC CAG       336
    Val Ser Val Lys Leu Arg Asn Arg Val Val Pro Gly Ser Val Thr Gln
                    100                 105                 110

AGT CAA GCT GAC TGG GAC CGA GCG CGT CGC CGC CGC ACT TTC TGT CTG       384
    Ser Gln Ala Asp Trp Asp Arg Ala Arg Arg Arg Arg Thr Phe Cys Leu
                115                 120                 125

CTG GTG GTG GTG GTG GTA GTG TTC ACG CTC TGC TGG CTG CCC TTC TAC C     433
    Leu Val Val Val Val Val Val Phe Thr Leu Cys Trp Leu Pro Phe Tyr
            130                 135                 140

T                                                                    434
```

-continued (2) INFORMATION FOR SEQ ID NO:106:

(i) SEQUENCE CHARACTERISTICS:
        (A) LENGTH: 144 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:106:

```
Leu Cys Val Ile Ala Val Asp Arg Tyr Val Val Leu Val His Pro Leu
  1               5                  10                  15

Arg Arg Arg Ile Ser Leu Arg Leu Ser Ala Tyr Ala Val Leu Gly Ile
             20                  25                  30

Trp Ala Leu Ser Ala Val Leu Ala Leu Pro Ala Ala Val His Thr Tyr
         35                  40                  45

His Val Glu Leu Lys Pro His Asp Val Ser Leu Cys Glu Glu Phe Trp
 50                  55                  60

Gly Ser Gln Glu Arg Gln Arg Gln Ile Tyr Ala Trp Gly Leu Leu Leu
 65                  70                  75                  80

Gly Thr Tyr Leu Leu Pro Leu Leu Ala Ile Leu Leu Ser Tyr Val Arg
                 85                  90                  95

Val Ser Val Lys Leu Arg Asn Arg Val Val Pro Gly Ser Val Thr Gln
                100                 105                 110

Ser Gln Ala Asp Trp Asp Arg Ala Arg Arg Arg Thr Phe Cys Leu
            115                 120                 125

Leu Val Val Val Val Val Phe Thr Leu Cys Trp Leu Pro Phe Tyr
        130                 135                 140
```

(2) INFORMATION FOR SEQ ID NO:107:

(i) SEQUENCE CHARACTERISTICS:
        (A) LENGTH: 167 amino acids
        (B) TYPE: amino acid
        (C) STRANDEDNESS: single
        (D) TOPOLOGY: linear (xi) SEQUENCE DESCRIPTION: SEQ ID NO:107:

```
Val Gly Met Val Gly Asn Val Leu Leu Val Leu Ile Ala Arg Val
  1               5                  10                  15

Arg Arg Leu His Asn Val Thr Asn Phe Leu Ile Gly Asn Leu Ala Leu
             20                  25                  30

Ser Asp Val Leu Met Cys Thr Ala Cys Val Pro Leu Thr Leu Ala Tyr
         35                  40                  45

Ala Phe Glu Pro Arg Gly Trp Val Phe Gly Gly Leu Cys His Leu
 50                  55                  60

Val Phe Phe Leu Gln Pro Val Thr Val Tyr Val Ser Val Phe Thr Leu
 65                  70                  75                  80

Thr Thr Ile Ala Val Asp Arg Tyr Val Val Leu Val His Pro Leu Arg
                 85                  90                  95

Arg Arg Ile Gly Leu Leu Leu Val Thr Tyr Leu Leu Pro Leu Leu Val
                100                 105                 110

Ile Leu Leu Ser Tyr Val Arg Val Ser Val Lys Leu Arg Asn Arg Val
            115                 120                 125

Val Pro Gly Cys Val Thr Gln Ser Gln Ala Asp Trp Asp Arg Ala Arg
        130                 135                 140
```

```
Arg Arg Arg Thr Phe Cys Leu Leu Val Val Val Val Val Phe Ala
145                 150                 155                 160

Ile Cys Trp Leu Pro Tyr Tyr
                165
```

(2) INFORMATION FOR SEQ ID NO:108:

(i) SEQUENCE CHARACTERISTICS:
        (A) LENGTH: 223 amino acids
        (B) TYPE: amino acid
        (C) STRANDEDNESS: single
        (D) TOPOLOGY: linear (xi) SEQUENCE DESCRIPTION: SEQ ID NO:108:

```
Val Gly Met Val Gly Asn Ile Leu Leu Val Leu Val Ile Ala Arg Val
1               5                   10                  15

Arg Arg Leu Tyr Asn Val Thr Asn Phe Leu Ile Gly Asn Leu Ala Leu
                20                  25                  30

Ser Asp Val Leu Met Cys Thr Ala Cys Val Pro Leu Thr Leu Ala Tyr
            35                  40                  45

Ala Phe Glu Pro Arg Gly Trp Val Phe Gly Gly Leu Cys His Leu
50                  55                  60

Val Phe Phe Leu Gln Ala Val Thr Val Tyr Val Ser Val Phe Thr Leu
65                  70                  75                  80

Thr Thr Ile Ala Val Asp Arg Tyr Val Val Leu Val His Pro Leu Arg
                85                  90                  95

Arg Arg Ile Ser Leu Arg Leu Ser Ala Tyr Ala Val Leu Ala Ile Trp
                100                 105                 110

Val Leu Ser Ala Val Leu Ala Leu Pro Ala Ala Val His Thr Tyr His
            115                 120                 125

Val Glu Leu Lys Pro His Asp Val Arg Leu Cys Glu Glu Phe Trp Gly
130                 135                 140

Ser Gln Glu Arg Gln Arg Gln Leu Tyr Ala Trp Gly Leu Leu Leu Val
145                 150                 155                 160

Thr Tyr Leu Leu Pro Leu Leu Val Ile Leu Leu Ser Tyr Ala Arg Val
                165                 170                 175

Ser Val Lys Leu Arg Asn Arg Val Val Pro Gly Arg Val Thr Gln Ser
                180                 185                 190

Gln Ala Asp Trp Asp Arg Ala Arg Arg Arg Arg Thr Phe Cys Leu Leu
                195                 200                 205

Val Val Val Val Val Val Phe Thr Leu Cys Trp Leu Pro Phe Phe
210                 215                 220
```

(2) INFORMATION FOR SEQ ID NO:109:

(i) SEQUENCE CHARACTERISTICS:
        (A) LENGTH: 144 amino acids
        (B) TYPE: amino acid
        (C) STRANDEDNESS: single
        (D) TOPOLOGY: linear (xi) SEQUENCE DESCRIPTION: SEQ ID NO:109:

```
Leu Cys Val Ile Ala Val Asp Arg Tyr Val Val Leu Val His Pro Leu
1               5                   10                  15

Arg Arg Arg Ile Ser Leu Arg Leu Ser Ala Tyr Ala Val Leu Gly Ile
                20                  25                  30

Trp Ala Leu Ser Ala Val Leu Ala Leu Pro Ala Ala Val His Thr Tyr
            35                  40                  45
```

```
His Val Glu Leu Lys Pro His Asp Val Ser Leu Cys Glu Glu Phe Trp
 50                  55                  60

Gly Ser Gln Glu Arg Gln Arg Gln Ile Tyr Ala Trp Gly Leu Leu Leu
 65                  70                  75                  80

Gly Thr Tyr Leu Leu Pro Leu Leu Ala Ile Leu Leu Ser Tyr Val Arg
                 85                  90                  95

Val Ser Val Lys Leu Arg Asn Arg Val Pro Gly Ser Val Thr Gln
                100                 105                 110

Ser Gln Ala Asp Trp Asp Arg Ala Arg Arg Arg Thr Phe Cys Leu
            115                 120                 125

Leu Val Val Val Val Val Phe Thr Leu Cys Trp Leu Pro Phe Tyr
    130                 135                 140
```

(2) INFORMATION FOR SEQ ID NO:110:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 1...75
        (D) OTHER INFORMATION:

(xi) SEQUENCE DESCRIPTION: SEQ ID NO:110:

```
GCC CAC CAG CAC TCC ATG GAG ATC CGC ACC CCC GAC ATC AAC CCT GCC      48
Ala His Gln His Ser Met Glu Ile Arg Thr Pro Asp Ile Asn Pro Ala
 1               5                  10                  15

TGG TAC GCG GGC CGT GGG ATC CGG CCC G                                76
Trp Tyr Ala Gly Arg Gly Ile Arg Pro
                20                  25
```

(2) INFORMATION FOR SEQ ID NO:111:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:111:

```
Ala His Gln His Ser Met Glu Ile Arg Thr Pro Asp Ile Asn Pro Ala
 1               5                  10                  15

Trp Tyr Ala Gly Arg Gly Ile Arg Pro
                20                  25
```

(2) INFORMATION FOR SEQ ID NO:112:

(i) SEQUENCE CHARACTERISTICS:
        (A) LENGTH: 126 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 6...125
        (D) OTHER INFORMATION:

(xi) SEQUENCE DESCRIPTION: SEQ ID NO:112:

```
GTGGA ATG AAG GCG GTG GGG GCC TGG CTC CTC TGC CTG CTG CTG CTG GGC        50
      Met Lys Ala Val Gly Ala Trp Leu Leu Cys Leu Leu Leu Leu Gly
      1               5                   10                  15

CTG GCC CTG CAG GGG GCT GCC AGC AGA GCC CAC CAG CAC TCC ATG GAG          98
Leu Ala Leu Gln Gly Ala Ala Ser Arg Ala His Gln His Ser Met Glu
                20                  25                  30

ATC CGC ACC CCC GAC ATC AAC CCT GCC T                                   126
Ile Arg Thr Pro Asp Ile Asn Pro Ala
            35                  40
```

(2) INFORMATION FOR SEQ ID NO:113:

(i) SEQUENCE CHARACTERISTICS:
        (A) LENGTH: 40 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:113:

```
Met Lys Ala Val Gly Ala Trp Leu Leu Cys Leu Leu Leu Gly Leu
1               5                   10                  15

Ala Leu Gln Gly Ala Ala Ser Arg Ala His Gln His Ser Met Glu Ile
            20                  25                  30

Arg Thr Pro Asp Ile Asn Pro Ala
        35                  40
```

(2) INFORMATION FOR SEQ ID NO:114:

(i) SEQUENCE CHARACTERISTICS:
        (A) LENGTH: 380 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 6...299
        (D) OTHER INFORMATION:
        (A) NAME/KEY: Modified Base
        (B) LOCATION: 43...43
        (D) OTHER INFORMATION: Xaa is Ala
        (A) NAME/KEY: Modified Base
        (B) LOCATION: 80...80
        (D) OTHER INFORMATION: Xaa is Gly (xi) SEQUENCE DESCRIPTION: SEQ ID NO:114:

```
GTGGA ATG AAG GCG GTG GGG GCC TGG CTC CTC TGC CTG CTG CTG CTG GGC        50
      Met Lys Ala Val Gly Ala Trp Leu Leu Cys Leu Leu Leu Leu Gly
      1               5                   10                  15

CTG GCC CTG CAG GGG GCT GCC AGC AGA GCC CAC CAG CAC TCC ATG GAG          98
Leu Ala Leu Gln Gly Ala Ala Ser Arg Ala His Gln His Ser Met Glu
                20                  25                  30

ATC CGC ACC CCC GAC ATC AAC CCT GCC TGG TAC GCR GGC CGT GGG ATC         146
Ile Arg Thr Pro Asp Ile Asn Pro Ala Trp Tyr Xaa Gly Arg Gly Ile
            35                  40                  45

CGG CCC GTG GGC CGC TTC GGC CGG CGA AGA GCT GCC CCG GGG GAC GGA         194
Arg Pro Val Gly Arg Phe Gly Arg Arg Arg Ala Ala Pro Gly Asp Gly
        50                  55                  60

CCC AGG CCT GGC CCC CGG CGT GTG CCG GCC TGC TTC CGC CTG GAA GGC         242
Pro Arg Pro Gly Pro Arg Arg Val Pro Ala Cys Phe Arg Leu Glu Gly
    65                  70                  75
```

```
GGY GCT GAG CCC TCC CGA GCC CTC CCG GGG CGG CTG ACG GCC CAG CTG      290
Xaa Ala Glu Pro Ser Arg Ala Leu Pro Gly Arg Leu Thr Ala Gln Leu
 80              85                  90                  95

GTC CAG GAA TAACAGCGGG AGCCTGCCCC CCACCCCTCC TCCTCCACCA GCCACCTTC    348
Val Gln Glu

CCTCCAGTCC TAATAAAAGC AGCTGGCTTG TT                                   380
```

(2) INFORMATION FOR SEQ ID NO:115:

(i) SEQUENCE CHARACTERISTICS:
        (A) LENGTH: 98 amino acids
        (B) TYPE: amino acid
        (C) STRANDEDNESS: single
        (D) TOPOLOGY: linear (ii) MOLECULE TYPE: protein (v) FRAGMENT TYPE: internal (ix) FEATURE:
        (A) NAME/KEY: Modified Base
        (B) LOCATION: 43...43
        (D) OTHER INFORMATION: Xaa is Ala
        (A) NAME/KEY: Modified Base
        (B) LOCATION: 80...80
        (D) OTHER INFORMATION: Xaa is Gly (xi) SEQUENCE DESCRIPTION: SEQ ID NO:115:

```
Met Lys Ala Val Gly Ala Trp Leu Leu Cys Leu Leu Leu Leu Gly Leu
 1               5                  10                  15

Ala Leu Gln Gly Ala Ala Ser Arg Ala His Gln His Ser Met Glu Ile
                20                  25                  30

Arg Thr Pro Asp Ile Asn Pro Ala Trp Tyr Xaa Gly Arg Gly Ile Arg
            35                  40                  45

Pro Val Gly Arg Phe Gly Arg Arg Ala Ala Pro Gly Asp Gly Pro
        50                  55                  60

Arg Pro Gly Pro Arg Arg Val Pro Ala Cys Phe Arg Leu Glu Gly Xaa
 65                  70                  75                  80

Ala Glu Pro Ser Arg Ala Leu Pro Gly Arg Leu Thr Ala Gln Leu Val
                85                  90                  95

Gln Glu
```

(2) INFORMATION FOR SEQ ID NO:116:

(i) SEQUENCE CHARACTERISTICS:
        (A) LENGTH: 380 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 6...299
        (D) OTHER INFORMATION:
        (A) NAME/KEY: Modified Base
        (B) LOCATION: 43...43
        (D) OTHER INFORMATION: Xaa is Ala
        (A) NAME/KEY: Modified Base
        (B) LOCATION: 80...80
        (D) OTHER INFORMATION: Xaa is Gly (xi) SEQUENCE DESCRIPTION: SEQ ID NO:116:

```
GTGGA ATG AAG GCG GTG GGG GCC TGG CTC CTC TGC CTG CTG CTG GGC        50
      Met Lys Ala Val Gly Ala Trp Leu Leu Cys Leu Leu Leu Gly
       1               5                  10                  15
```

```
CTG GCC CTG CAG GGG GCT GCC AGC AGA GCC CAC CAG CAC TCC ATG GAG        98
Leu Ala Leu Gln Gly Ala Ala Ser Arg Ala His Gln His Ser Met Glu
             20                  25                  30

ATC CGC ACC CCC GAC ATC AAC CCT GCC TGG TAC GCR GGC CGT GGG ATC       146
Ile Arg Thr Pro Asp Ile Asn Pro Ala Trp Tyr Xaa Gly Arg Gly Ile
         35                  40                  45

CGG CCC GTG GGC CGC TTC GGC CGG CGA AGA GCT GCC CTG GGG GAC GGA       194
Arg Pro Val Gly Arg Phe Gly Arg Arg Arg Ala Ala Leu Gly Asp Gly
     50                  55                  60

CCC AGG CCT GGC CCC CGG CGT GTG CCG GCC TGC TTC CGC CTG GAA GGC       242
Pro Arg Pro Gly Pro Arg Arg Val Pro Ala Cys Phe Arg Leu Glu Gly
 65                  70                  75

GGY GCT GAG CCC TCC CGA GCC CTC CCG GGG CGG CTG ACG GCC CAG CTG       290
Xaa Ala Glu Pro Ser Arg Ala Leu Pro Gly Arg Leu Thr Ala Gln Leu
 80                  85                  90                  95

GTC CAG GAA TAACAGCGGG AGCCTGCCCC CCACCCCTCC TCCTCCACCA GCCACCTTC     348
Val Gln Glu

CCTCCAGTCC TAATAAAAGC AGCTGGCTTG TT                                   380

(2) INFORMATION FOR SEQ ID NO:117:

(i) SEQUENCE CHARACTERISTICS:
        (A) LENGTH: 98 amino acids
        (B) TYPE: amino acid
        (C) STRANDEDNESS: single
        (D) TOPOLOGY: linear (ii) MOLECULE TYPE: protein (v) FRAGMENT TYPE: internal (ix) FEATURE:
        (A) NAME/KEY: Modified Base
        (B) LOCATION: 43...43
        (D) OTHER INFORMATION: Xaa is Ala
        (A) NAME/KEY: Modified Base
        (B) LOCATION: 80...80
        (D) OTHER INFORMATION: Xaa is Gly (xi) SEQUENCE DESCRIPTION: SEQ ID NO:117:

Met Lys Ala Val Gly Ala Trp Leu Leu Cys Leu Leu Leu Gly Leu
 1               5                  10                  15

Ala Leu Gln Gly Ala Ala Ser Arg Ala His Gln His Ser Met Glu Ile
             20                  25                  30

Arg Thr Pro Asp Ile Asn Pro Ala Trp Tyr Xaa Gly Arg Gly Ile Arg
         35                  40                  45

Pro Val Gly Arg Phe Gly Arg Arg Arg Ala Ala Leu Gly Asp Gly Pro
     50                  55                  60

Arg Pro Gly Pro Arg Arg Val Pro Ala Cys Phe Arg Leu Glu Gly Xaa
 65                  70                  75                  80

Ala Glu Pro Ser Arg Ala Leu Pro Gly Arg Leu Thr Ala Gln Leu Val
                 85                  90                  95

Gln Glu (2) INFORMATION FOR SEQ ID NO:118:

(i) SEQUENCE CHARACTERISTICS:
        (A) LENGTH: 769 base pairs
        (B) TYPE: nucleic acid
        (C) STRANDEDNESS: single
        (D) TOPOLOGY: linear
```

(xi) SEQUENCE DESCRIPTION: SEQ ID NO:118:

```
ATGAAGGCGG TGGGGGCCTG GCTCCTCTGC CTGCTGCTGC TGGGCCTGGC CCTGCAGGGG      60
GCTGCCAGCA GAGCCCACCA GCACTCCATG GAGATCCGCA GTGAGTGTCT AGCCCCGCCC     120
CTGCCCCCAG GGGTCACAGG GGGGGCCTGG CCACTTCCTG GGCTGGGACA TCCTTGCTAA     180
GCATCCTGGG GTTGGGGTTT GGCCTCCTGT TCCCCAGACC CTTCCCCCAG GTGGCCCGGA     240
CAGGTGCTCC CAAGGGTCCC GGCCCAGCAC ACGGGGGAGG GTCACTCCTC ACCACACGGG     300
TGGCCTGGGG CTGAGTGCAC GTCACCCATG AGAACGGGGC TGTGAGGACA GGAAAGGAAG     360
GGGAGTGTGT CCTGGTGTGA GTCTGAAATC CTACTTCCCA AAGCCACCCC AGCACCAGAA     420
ATGGGCGCTC CGGGTGAACC TCCTGTGCGG GTGGGTGGTC CTGGCATGGC CTGGGCGACA     480
GGCAGCCATG AGCTGAGCAC ACACCCGGCC CGGCCACCAG GGCTGTATGC TCCAGGGCAC     540
AGGCCTCCAT GCGCTCTTCT CTCTCTTTCC AGCCCCCGAC ATCAACCCTG CCTGGTACGC     600
AGGCCGTGGG ATCCGGCCCG TGGGCCGCTT CGGCCGGCGA AGAGCTGCCC TGGGGGACGG     660
ACCCAGGCCT GGCCCCCGGC GTGTGCCGGC CTGCTTCCGC CTGGAAGGCG GTGCTGAGCC     720
CTCCCGAGCC CTCCCGGGGC GGCTGACGGC CCAGCTGGTC CAGGAATAA                 769
```

(2) INFORMATION FOR SEQ ID NO:119:

(i) SEQUENCE CHARACTERISTICS:
        (A) LENGTH: 769 base pairs
        (B) TYPE: nucleic acid
        (C) STRANDEDNESS: single
        (D) TOPOLOGY: linear (xi) SEQUENCE DESCRIPTION: SEQ ID NO:119:

```
ATGAAGGCGG TGGGGGCCTG GCTCCTCTGC CTGCTGCTGC TGGGCCTGGC CCTGCAGGGG      60
GCTGCCAGCA GAGCCCACCA GCACTCCATG GAGATCCGCA GTGAGTGTCT AGCCCCGCCC     120
CTGCCCCCAG GGGTCACAGG GGGGGCCTGG CCACTTCCTG GGCTGGGACA TCCTTGCTAA     180
GCATCCTGGG GTTGGGGTTT GGCCTCCTGT TCCCCAGACC CTTCCCCCAG GTGGCCCGGA     240
CAGGTGCTCC CAAGGGTCCC GGCCCAGCAC ACGGGGGAGG GTCACTCCTC ACCACACGGG     300
TGGCCTGGGG CTGAGTGCAC GTCACCCATG AGAACGGGGC TGTGAGGACA GGAAAGGAAG     360
GGGAGTGTGT CCTGGTGTGA GTCTGAAATC CTACTTCCCA AAGCCACCCC AGCACCAGAA     420
ATGGGCGCTC CGGGTGAACC TCCTGTGCGG GTGGGTGGTC CTGGCATGGC CTGGGCGACA     480
GGCAGCCATG AGCTGAGCAC ACACCCGGCC CGGCCACCAG GGCTGTATGC TCCAGGGCAC     540
AGGCCTCCAT GCGCTCTTCT CTCTCTTTCC AGCCCCCGAC ATCAACCCTG CCTGGTACGC     600
AGGCCGTGGG ATCCGGCCCG TGGGCCGCTT CGGCCGGCGA AGAGCTGCCC TGGGGGACGG     660
ACCCAGGCCT GGCCCCCGGC GTGTGCCGGC CTGCTTCCGC CTGGAAGGCG GTGCTGAGCC     720
CTCCCGAGCC CTCCCGGGGC GGCTGACGGC CCAGCTGGTC CAGGAATAA                 769
```

(2) INFORMATION FOR SEQ ID NO:120:

(i) SEQUENCE CHARACTERISTICS:
        (A) LENGTH: 297 base pairs
        (B) TYPE: nucleic acid
        (C) STRANDEDNESS: single
        (D) TOPOLOGY: linear (xi) SEQUENCE DESCRIPTION: SEQ ID NO:120:

```
ATGAAGGCGG TGGGGGCCTG GCTCCTCTGC CTGCTGCTGC TGGGCCTGGC CCTGCAGGGG      60
GCTGCCAGCA GAGCCCACCA GCACTCCATG GAGATCCGCA CCCCCGACAT CAACCCTGCC     120
```

```
TGGTACGCGG GCCGTGGGAT CCGGCCCGTG GGCCGCTTCG GCCGGCGAAG AGCTGCCCCG    180

GGGGACGGAC CCAGGCCTGG CCCCCGGCGT GTGCCGGCCT GCTTCCGCCT GGAAGGCGGC    240

GCTGAGCCCT CCCGAGCCCT CCCGGGGCGG CTGACGGCCC AGCTGGTCCA GGAATAA      297
```

(2) INFORMATION FOR SEQ ID NO:121:

(i) SEQUENCE CHARACTERISTICS:
        (A) LENGTH: 297 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 1...294
        (D) OTHER INFORMATION:

(xi) SEQUENCE DESCRIPTION: SEQ ID NO:121:

```
ATG AAG GCG GTG GGG GCC TGG CTC CTC TGC CTG CTG CTG GGC CTG         48
Met Lys Ala Val Gly Ala Trp Leu Leu Cys Leu Leu Leu Gly Leu
 1               5                  10                  15

GCC CTG CAG GGG GCT GCC AGC AGA GCC CAC CAG CAC TCC ATG GAG ATC     96
Ala Leu Gln Gly Ala Ala Ser Arg Ala His Gln His Ser Met Glu Ile
                20                  25                  30

CGC ACC CCC GAC ATC AAC CCT GCC TGG TAC GCA GGC CGT GGG ATC CGG    144
Arg Thr Pro Asp Ile Asn Pro Ala Trp Tyr Ala Gly Arg Gly Ile Arg
         35                  40                  45

CCC GTG GGC CGC TTC GGC CGG CGA AGA GCT GCC CTG GGG GAC GGA CCC    192
Pro Val Gly Arg Phe Gly Arg Arg Arg Ala Ala Leu Gly Asp Gly Pro
 50                  55                  60

AGG CCT GGC CCC CGG CGT GTG CCG GCC TGC TTC CGC CTG GAA GGC GGT    240
Arg Pro Gly Pro Arg Arg Val Pro Ala Cys Phe Arg Leu Glu Gly Gly
65                  70                  75                  80

GCT GAG CCC TCC CGA GCC CTC CCG GGG CGG CTG ACG GCC CAG CTG GTC    288
Ala Glu Pro Ser Arg Ala Leu Pro Gly Arg Leu Thr Ala Gln Leu Val
                 85                  90                  95

CAG GAA TAA                                                         297
Gln Glu
```

(2) INFORMATION FOR SEQ ID NO:122:

(i) SEQUENCE CHARACTERISTICS:
        (A) LENGTH: 98 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:122:

```
Met Lys Ala Val Gly Ala Trp Leu Leu Cys Leu Leu Leu Gly Leu
 1               5                  10                  15

Ala Leu Gln Gly Ala Ala Ser Arg Ala His Gln His Ser Met Glu Ile
                20                  25                  30

Arg Thr Pro Asp Ile Asn Pro Ala Trp Tyr Ala Gly Arg Gly Ile Arg
         35                  40                  45

Pro Val Gly Arg Phe Gly Arg Arg Arg Ala Ala Leu Gly Asp Gly Pro
 50                  55                  60

Arg Pro Gly Pro Arg Arg Val Pro Ala Cys Phe Arg Leu Glu Gly Gly
65                  70                  75                  80
```

```
Ala Glu Pro Ser Arg Ala Leu Pro Gly Arg Leu Thr Ala Gln Leu Val
            85                  90                  95

Gln Glu (2) INFORMATION FOR SEQ ID NO:123:

(i) SEQUENCE CHARACTERISTICS:
        (A) LENGTH: 364 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 24...272
        (D) OTHER INFORMATION:

(xi) SEQUENCE DESCRIPTION: SEQ ID NO:123:

GGCATCATCC AGGAAGACGG AGC ATG GCC CTG AAG ACG TGG CTT CTG TGC TTG     53
                         Met Ala Leu Lys Thr Trp Leu Leu Cys Leu
                          1               5                  10

CTG CTG CTA AGC TTG GTC CTC CCA GGG GCT TCC AGC CGA GCC CAC CAG      101
Leu Leu Leu Ser Leu Val Leu Pro Gly Ala Ser Ser Arg Ala His Gln
            15                  20                  25

CAC TCC ATG GAG ACA AGA ACC CCT GAT ATC AAT CCT GCC TGG TAC ACG      149
His Ser Met Glu Thr Arg Thr Pro Asp Ile Asn Pro Ala Trp Tyr Thr
        30                  35                  40

GGC CGC GGG ATC AGG CCT GTG GGC CGC TTC GGC AGG AGA AGG GCA ACC      197
Gly Arg Gly Ile Arg Pro Val Gly Arg Phe Gly Arg Arg Arg Ala Thr
    45                  50                  55

CCG AGG GAT GTC ACT GGA CTT GGC CAA CTC AGC TGC CTC CCA CTG GAT      245
Pro Arg Asp Val Thr Gly Leu Gly Gln Leu Ser Cys Leu Pro Leu Asp
60                  65                  70

GGA CGC ACC AAG TTC TCT CAG CGT GGA TAACACCCCA GCTCGAGAAG ACAGTGC    299
Gly Arg Thr Lys Phe Ser Gln Arg Gly
75                  80

TGCTGAGCCC AAGCCCACAC TCCCTGTCCC CTGCAGACCC TCCTCTACCC TCCCTCTCCT   359

CTGCT                                                                364

(2) INFORMATION FOR SEQ ID NO:124:

(i) SEQUENCE CHARACTERISTICS:
        (A) LENGTH: 83 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:124:

Met Ala Leu Lys Thr Trp Leu Leu Cys Leu Leu Leu Ser Leu Val
 1               5                  10                  15

Leu Pro Gly Ala Ser Ser Arg Ala His Gln His Ser Met Glu Thr Arg
            20                  25                  30

Thr Pro Asp Ile Asn Pro Ala Trp Tyr Thr Gly Arg Gly Ile Arg Pro
        35                  40                  45

Val Gly Arg Phe Gly Arg Arg Arg Ala Thr Pro Arg Asp Val Thr Gly
    50                  55                  60
```

```
Leu Gly Gln Leu Ser Cys Leu Pro Leu Asp Gly Arg Thr Lys Phe Ser
65                  70                  75                  80

Gln Arg Gly
```

(2) INFORMATION FOR SEQ ID NO:125:

(i) SEQUENCE CHARACTERISTICS:
        (A) LENGTH: 297 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 1...297
        (D) OTHER INFORMATION:

(xi) SEQUENCE DESCRIPTION: SEQ ID NO:125:

```
gtg ggc atg gtg ggc aac gtc ctg ctg gtg ctg gtg atc gcg cgg gtg    48
Val Gly Met Val Gly Asn Val Leu Leu Val Leu Val Ile Ala Arg Val
1               5                   10                  15 cgc cgg ctg cac aac gtg acg aac ttc ctc atc ggc aac ctg gcc ttg    96
Arg Arg Leu His Asn Val Thr Asn Phe Leu Ile Gly Asn Leu Ala Leu
            20                  25                  30 tcc gac gtg ctc atg tgc acc gcc tgc gtg ccg ctc acg ctg gcc tat   144
Ser Asp Val Leu Met Cys Thr Ala Cys Val Pro Leu Thr Leu Ala Tyr
        35                  40                  45 gcc ttc gag cca cgc ggc tgg gtg ttc ggc ggc ggc ctg tgc cac ctg   192
Ala Phe Glu Pro Arg Gly Trp Val Phe Gly Gly Gly Leu Cys His Leu
    50                  55                  60 gtc ttc ttc ctg cag ccg gtc acc gtc tat gtg tcg gtg ttc acg ctc   240
Val Phe Phe Leu Gln Pro Val Thr Val Tyr Val Ser Val Phe Thr Leu
65                  70                  75                  80 acc acc atc gca gtg gac cgg tac gtc gtg ctg gtg cac ccg ctg agg   288
Thr Thr Ile Ala Val Asp Arg Tyr Val Val Leu Val His Pro Leu Arg
            85                  90                  95 cgg cgc atc                                                        297
Arg Arg Ile
```

(2) INFORMATION FOR SEQ ID NO:126:

(i) SEQUENCE CHARACTERISTICS:
        (A) LENGTH: 99 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:126:

```
Val Gly Met Val Gly Asn Val Leu Leu Val Leu Val Ile Ala Arg Val
1               5                   10                  15

Arg Arg Leu His Asn Val Thr Asn Phe Leu Ile Gly Asn Leu Ala Leu
            20                  25                  30

Ser Asp Val Leu Met Cys Thr Ala Cys Val Pro Leu Thr Leu Ala Tyr
        35                  40                  45

Ala Phe Glu Pro Arg Gly Trp Val Phe Gly Gly Gly Leu Cys His Leu
    50                  55                  60

Val Phe Phe Leu Gln Pro Val Thr Val Tyr Val Ser Val Phe Thr Leu
65                  70                  75                  80
```

```
         Thr Thr Ile Ala Val Asp Arg Tyr Val Val Leu Val His Pro Leu Arg
                         85                  90                  95

Arg Arg Ile (2) INFORMATION FOR SEQ ID NO:127:

(i) SEQUENCE CHARACTERISTICS:
          (A) LENGTH: 204 base pairs
          (B) TYPE: nucleic acid
          (C) STRANDEDNESS: single
          (D) TOPOLOGY: linear (ix) FEATURE:
          (A) NAME/KEY: Coding Sequence
          (B) LOCATION: 1...204
          (D) OTHER INFORMATION:

(xi) SEQUENCE DESCRIPTION: SEQ ID NO:127:

ggc ctg ctg ctg gtc acc tac ctg ctc cct ctg ctg gtc atc ctc ctg     48
         Gly Leu Leu Leu Val Thr Tyr Leu Leu Pro Leu Leu Val Ile Leu Leu
          1               5                  10                  15 tct tac gtc cgg gtg tca gtg aag ctc cgc aac cgc gtg gtg ccg ggc     96
         Ser Tyr Val Arg Val Ser Val Lys Leu Arg Asn Arg Val Val Pro Gly
                         20                  25                  30 tgc gtg acc cag agc cag gcc gac tgg gac cgc gct cgg cgc cgg cgc    144
         Cys Val Thr Gln Ser Gln Ala Asp Trp Asp Arg Ala Arg Arg Arg Arg
                     35                  40                  45 acc ttc tgc ttg ctg gtg gtg gtc gtg gtg gtg ttt gcc atc tgc tgg    192
         Thr Phe Cys Leu Leu Val Val Val Val Val Val Phe Ala Ile Cys Trp
                 50                  55                  60 ttg cct tac tac                                                    204
         Leu Pro Tyr Tyr
          65

(2) INFORMATION FOR SEQ ID NO:128:

(i) SEQUENCE CHARACTERISTICS:
          (A) LENGTH: 68 amino acids
          (B) TYPE: amino acid
          (C) STRANDEDNESS: single
          (D) TOPOLOGY: linear (ii) MOLECULE TYPE: protein (v) FRAGMENT TYPE: internal (xi) SEQUENCE DESCRIPTION: SEQ ID NO:128:

Gly Leu Leu Leu Val Thr Tyr Leu Leu Pro Leu Leu Val Ile Leu Leu
          1               5                  10                  15

Ser Tyr Val Arg Val Ser Val Lys Leu Arg Asn Arg Val Val Pro Gly
                         20                  25                  30

Cys Val Thr Gln Ser Gln Ala Asp Trp Asp Arg Ala Arg Arg Arg Arg
                     35                  40                  45

Thr Phe Cys Leu Leu Val Val Val Val Val Val Phe Ala Ile Cys Trp
                 50                  55                  60

Leu Pro Tyr Tyr
          65

(2) INFORMATION FOR SEQ ID NO:129:

(i) SEQUENCE CHARACTERISTICS:
          (A) LENGTH: 168 amino acids
          (B) TYPE: amino acid
          (C) STRANDEDNESS: single
          (D) TOPOLOGY: linear
```

```
        (ii) MOLECULE TYPE: protein (v) FRAGMENT TYPE: internal (xi) SEQUENCE DESCRIPTION: SEQ ID NO:129:

Val Gly Met Val Gly Asn Val Leu Leu Val Leu Val Ile Ala Arg Val
 1               5                  10                  15

Arg Arg Leu His Asn Val Thr Asn Phe Leu Ile Gly Asn Leu Ala Leu
                20                  25                  30

Ser Asp Val Leu Met Cys Thr Ala Cys Val Pro Leu Thr Leu Ala Tyr
            35                  40                  45

Ala Phe Glu Pro Arg Gly Trp Val Phe Gly Gly Leu Cys His Leu
50                  55                  60

Val Phe Phe Leu Gln Pro Val Thr Val Tyr Val Ser Val Phe Thr Leu
65                  70                  75                  80

Thr Thr Ile Ala Val Asp Arg Tyr Val Val Leu Val His Pro Leu Arg
                85                  90                  95

Arg Arg Ile Gly Leu Leu Leu Val Thr Tyr Tyr Leu Leu Pro Leu Leu
                100                 105                 110

Val Ile Leu Leu Ser Tyr Val Arg Val Ser Val Lys Leu Arg Asn Arg
            115                 120                 125

Val Val Pro Gly Cys Val Thr Gln Ser Gln Ala Asp Trp Asp Arg Ala
130                 135                 140

Arg Arg Arg Arg Thr Phe Cys Leu Leu Val Val Val Val Val Val Phe
145                 150                 155                 160

Ala Ile Cys Trp Leu Pro Tyr Tyr
                165

(2) INFORMATION FOR SEQ ID NO:130:

(i) SEQUENCE CHARACTERISTICS:
            (A) LENGTH: 228 amino acids
            (B) TYPE: amino acid
            (C) STRANDEDNESS: single
            (D) TOPOLOGY: linear (ii) MOLECULE TYPE: protein (v) FRAGMENT TYPE: internal (xi) SEQUENCE DESCRIPTION: SEQ ID NO:130:

Leu Gly Val Ser Gly Asn Leu Ala Leu Ile Ile Ile Leu Lys Gln
 1               5                  10                  15

Lys Glu Met Arg Asn Val Thr Asn Ile Leu Ile Val Asn Leu Ser Phe
                20                  25                  30

Ser Asp Leu Leu Val Ala Val Met Cys Leu Pro Phe Thr Phe Val Tyr
            35                  40                  45

Thr Leu Met Asp His Trp Val Phe Gly Glu Thr Met Cys Lys Leu Asn
50                  55                  60

Pro Phe Val Gln Cys Val Ser Ile Thr Val Ser Ile Phe Ser Leu Val
65                  70                  75                  80

Leu Ile Ala Val Glu Arg His Gln Leu Ile Ile Asn Pro Arg Gly Trp
                85                  90                  95

Arg Pro Asn Asn Arg His Ala Tyr Ile Gly Ile Thr Val Ile Trp Val
                100                 105                 110

Leu Ala Val Ala Ser Ser Leu Pro Phe Val Ile Tyr Gln Ile Leu Thr
            115                 120                 125
```

```
Asp Glu Pro Phe Gln Asn Val Ser Leu Ala Ala Phe Lys Asp Lys Tyr
    130                 135                 140

Val Cys Phe Asp Lys Phe Pro Ser Asp Ser His Arg Leu Ser Tyr Thr
145                 150                 155                 160

Thr Leu Leu Leu Val Leu Gln Tyr Phe Gly Pro Leu Cys Phe Ile Phe
                165                 170                 175

Ile Cys Tyr Phe Lys Ile Tyr Ile Arg Leu Lys Arg Arg Asn Asn Met
            180                 185                 190

Met Asp Lys Ile Arg Asp Ser Lys Tyr Arg Ser Ser Glu Thr Lys Arg
        195                 200                 205

Ile Asn Val Met Leu Leu Ser Ile Val Val Ala Phe Ala Val Cys Trp
210                 215                 220

Leu Pro Leu Thr
225
```

(2) INFORMATION FOR SEQ ID NO:131:

(i) SEQUENCE CHARACTERISTICS:
        (A) LENGTH: 98 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:131:

```
Met Lys Ala Val Gly Ala Trp Leu Leu Cys Leu Leu Leu Gly Leu
1               5                   10                  15

Ala Leu Gln Gly Ala Ala Ser Arg Ala His Gln His Ser Met Glu Ile
                20                  25                  30

Arg Thr Pro Asp Ile Asn Pro Ala Trp Tyr Ala Gly Arg Gly Ile Arg
            35                  40                  45

Pro Val Gly Arg Phe Gly Arg Arg Ala Ala Pro Gly Asp Gly Pro
50                  55                  60

Arg Pro Gly Pro Arg Arg Val Pro Ala Cys Phe Arg Leu Glu Gly Gly
65                  70                  75                  80

Ala Glu Pro Ser Arg Ala Leu Pro Gly Arg Leu Thr Ala Gln Leu Val
                85                  90                  95

Gln Glu
```

(2) INFORMATION FOR SEQ ID NO:132:

(i) SEQUENCE CHARACTERISTICS:
        (A) LENGTH: 380 base pairs
        (B) TYPE: nucleic acid
        (C) STRANDEDNESS: single
        (D) TOPOLOGY: linear (xi) SEQUENCE DESCRIPTION: SEQ ID NO:132:

```
gtggaatgaa ggcggtgggg gcctggctcc tctgcctgct gctgctgggc ctggccctgc    60 aggggctgc cagcagagcc caccagcact ccatggagat ccgcaccccc gacatcaacc    120
ctgcctggta cgcgggccgt gggatccggc ccgtgggccg cttcggccgg cgaagagctg    180
ccccggggga cggacccagg cctggccccc ggcgtgtgcc ggcctgcttc cgcctggaag    240
gcggcgctga gccctcccga gccctcccgg ggcggctgac ggcccagctg gtccaggaat    300
aacagcggga gcctgccccc caccctcct cctccaccag ccacttccc tccagtccta    360
```
ataaaagcag ctggcttgtt                                                    380

(2) INFORMATION FOR SEQ ID NO:133:

(i) SEQUENCE CHARACTERISTICS:
        (A) LENGTH: 364 base pairs
        (B) TYPE: nucleic acid
        (C) STRANDEDNESS: single
        (D) TOPOLOGY: linear (xi) SEQUENCE DESCRIPTION: SEQ ID NO:133:

ggcatcatcc aggaagacgg agcatggccc tgaagacgtg gcttctgtgc ttgctgctgc          60
taagcttggt cctcccaggg gcttcaagcc gagcccacca gcactccatg gagacaagaa         120
cccctgatat caatcctgcc tggtacacgg gccgcgggat caggcctgtg ggccgcttcg         180
gcaggagaag ggcaaccccg agggatgtca ctggacttgg ccaactcagc tgcctcccac         240
tggatggacg caccaagttc tctcagcgtg gataacaccc cagctcgaga agacagtgct         300
gctgagccca agcccacact ccctgtcccc tgcagaccct cctctaccct ccctctcctc         360
tgct                                                                     364

(2) INFORMATION FOR SEQ ID NO:134:

(i) SEQUENCE CHARACTERISTICS:
        (A) LENGTH: 361 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 24..284
        (D) OTHER INFORMATION:

(xi) SEQUENCE DESCRIPTION: SEQ ID NO:134:

ggcctcctcg gaggagccaa ggg atg aag gtg ctg agg gcc tgg ctc ctg tgc         53
                         Met Lys Val Leu Arg Ala Trp Leu Leu Cys
                          1               5                  10 ctg ctg atg ctg ggc ctg gcc ctg cgg gga gct gca agt cgt acc cat          101
Leu Leu Met Leu Gly Leu Ala Leu Arg Gly Ala Ala Ser Arg Thr His
             15                  20                  25 cgg cac tcc atg gag atc cgc acc cct gac atc aat cct gcc tgg tac          149
Arg His Ser Met Glu Ile Arg Thr Pro Asp Ile Asn Pro Ala Trp Tyr
         30                  35                  40 gcc agt cgc ggg atc agg cct gtg ggc cgc ttc ggt cgg agg agg gca          197
Ala Ser Arg Gly Ile Arg Pro Val Gly Arg Phe Gly Arg Arg Arg Ala
     45                  50                  55 acc ctg ggg gac gtc ccc aag cct ggc ctg cga ccc cgg ctg acc tgc          245
Thr Leu Gly Asp Val Pro Lys Pro Gly Leu Arg Pro Arg Leu Thr Cys
 60                  65                  70 ttc ccc ctg gaa ggc ggt gct atg tcg tcc cag gat ggc tgacagccag           294
Phe Pro Leu Glu Gly Gly Ala Met Ser Ser Gln Asp Gly
 75                  80                  85 cttgtcaaga aactcactct ggagcctccc ccaccccacc ctctcctctc cttcgggctc        354
ctttccc                                                                  361

(2) INFORMATION FOR SEQ ID NO:135:

(i) SEQUENCE CHARACTERISTICS:
        (A) LENGTH: 87 amino acids
        (B) TYPE: amino acid
        (C) STRANDEDNESS: single
        (D) TOPOLOGY: linear

```
    (ii) MOLECULE TYPE: protein (v) FRAGMENT TYPE: internal (xi) SEQUENCE DESCRIPTION: SEQ ID NO:135:

Met Lys Val Leu Arg Ala Trp Leu Leu Cys Leu Leu Met Leu Gly Leu
1               5                   10                  15

Ala Leu Arg Gly Ala Ala Ser Arg Thr His Arg His Ser Met Glu Ile
            20                  25                  30

Arg Thr Pro Asp Ile Asn Pro Ala Trp Tyr Ala Ser Arg Gly Ile Arg
        35                  40                  45

Pro Val Gly Arg Phe Gly Arg Arg Ala Thr Leu Gly Asp Val Pro
50                  55                  60

Lys Pro Gly Leu Arg Pro Arg Leu Thr Cys Phe Pro Leu Glu Gly Gly
65                  70                  75                  80

Ala Met Ser Ser Gln Asp Gly
                85

(2) INFORMATION FOR SEQ ID NO:136:

(i) SEQUENCE CHARACTERISTICS:
        (A) LENGTH: 98 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:136:

Met Lys Ala Val Gly Ala Trp Leu Leu Cys Leu Leu Leu Gly Leu
1               5                   10                  15

Ala Leu Gln Gly Ala Ala Ser Arg Ala His Gln His Ser Met Glu Ile
            20                  25                  30

Arg Thr Pro Asp Ile Asn Pro Ala Trp Tyr Ala Gly Arg Gly Ile Arg
        35                  40                  45

Pro Val Gly Arg Phe Gly Arg Arg Ala Ala Pro Gly Asp Gly Pro
50                  55                  60

Arg Pro Gly Pro Arg Val Pro Ala Cys Arg Phe Leu Glu Gly Gly
65                  70                  75                  80

Ala Glu Pro Ser Arg Ala Leu Pro Gly Arg Leu Thr Ala Gln Leu Val
                85                  90                  95

Gln Glu (2) INFORMATION FOR SEQ ID NO:137:

(i) SEQUENCE CHARACTERISTICS:
        (A) LENGTH: 83 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:137:

Met Ala Leu Lys Thr Trp Leu Leu Cys Leu Leu Leu Ser Leu Val
1               5                   10                  15

Leu Pro Gly Ala Ser Ser Arg Ala His Gln His Ser Met Glu Thr Arg
            20                  25                  30
```

```
Thr Pro Asp Ile Asn Pro Ala Trp Tyr Thr Gly Arg Gly Ile Arg Pro
    35              40                  45

Val Gly Arg Phe Gly Arg Arg Arg Ala Thr Pro Arg Asp Val Thr Gly
 50              55                  60

Leu Gly Gln Leu Ser Cys Leu Pro Leu Asp Gly Arg Thr Lys Phe Ser
65              70                  75                      80

Gln Arg Gly (2) INFORMATION FOR SEQ ID NO:138:

(i) SEQUENCE CHARACTERISTICS:
        (A) LENGTH: 87 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:138:

Met Lys Val Leu Arg Ala Trp Leu Leu Cys Leu Leu Met Leu Gly Leu
 1               5                  10                  15

Ala Leu Arg Gly Ala Ala Ser Arg Thr His Arg His Ser Met Glu Ile
             20                  25                  30

Arg Thr Pro Asp Ile Asn Pro Ala Trp Tyr Ala Ser Arg Gly Ile Arg
         35                  40                  45

Pro Val Gly Arg Phe Gly Arg Arg Arg Ala Thr Leu Gly Asp Val Pro
     50                  55                  60

Lys Pro Gly Leu Arg Pro Arg Leu Thr Cys Phe Pro Leu Glu Gly Gly
65              70                  75                      80

Ala Met Ser Ser Gln Asp Gly
                85

(2) INFORMATION FOR SEQ ID NO:139:

(i) SEQUENCE CHARACTERISTICS:
        (A) LENGTH: 1116 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 1...1110
        (D) OTHER INFORMATION:

(xi) SEQUENCE DESCRIPTION: SEQ ID NO:139:

atg acc tca ctg ccc cct gga acc act ggg gac ccc gat ttg ttt tct      48
Met Thr Ser Leu Pro Pro Gly Thr Thr Gly Asp Pro Asp Leu Phe Ser
 1               5                  10                  15 ggg ccg tcg cca gcc ggc tcc act cca gcc aac cag agt gca gag gct      96
Gly Pro Ser Pro Ala Gly Ser Thr Pro Ala Asn Gln Ser Ala Glu Ala
             20                  25                  30 tca gag agc aat gtg tct gcg acg gtt ccc aga gct gca gca gtc acg     144
Ser Glu Ser Asn Val Ser Ala Thr Val Pro Arg Ala Ala Ala Val Thr
         35                  40                  45 ccg ttc cag agc ctg caa cta gtg cac cag ctg aag gca ctg atc gtg     192
Pro Phe Gln Ser Leu Gln Leu Val His Gln Leu Lys Ala Leu Ile Val
     50                  55                  60 atg ctg tac agc atc gtg gtg gtc gtg ggt ctg gtg ggc aac tgc ctt     240
Met Leu Tyr Ser Ile Val Val Val Val Gly Leu Val Gly Asn Cys Leu
65              70                  75                      80
```

-continued

| | | |
|---|---|---|
| ctt gtg ctg gtg atc gcg cgc gtg cgc cgg ctg cac aac gtg acc aac<br>Leu Val Leu Val Ile Ala Arg Val Arg Arg Leu His Asn Val Thr Asn<br>                     85                         90                      95 | 288 |
| ttc ctc atc ggc aac ctg gcc ttg tcc gat gtg ctc atg tgt gcc gcc<br>Phe Leu Ile Gly Asn Leu Ala Leu Ser Asp Val Leu Met Cys Ala Ala<br>                 100                        105                  110 | 336 |
| tgt gtg cct ctc acg ctg gcc tac gcc ttt gaa cct cgt ggc tgg gtg<br>Cys Val Pro Leu Thr Leu Ala Tyr Ala Phe Glu Pro Arg Gly Trp Val<br>        115                         120                  125 | 384 |
| ttc ggt gga ggc ctg tgc cac ctt gtt ttc ctg cag ccg gtc acc<br>Phe Gly Gly Gly Leu Cys His Leu Val Phe Leu Gln Pro Val Thr<br>130                      135                      140 | 432 |
| gtc tac gta tcg gtg ttc aca ctc acc aca atc gct gtg gac cgc tat<br>Val Tyr Val Ser Val Phe Thr Leu Thr Thr Ile Ala Val Asp Arg Tyr<br>145                    150                      155                  160 | 480 |
| gtg gtt ctg gtg cac ccg cta cgt cgg cgc att tca ctg aag ctc agc<br>Val Val Leu Val His Pro Leu Arg Arg Arg Ile Ser Leu Lys Leu Ser<br>                 165                      170                  175 | 528 |
| gcc tac gct gtg ctg ggc atc tgg gct cta tct gca gtg ctg gcg ctg<br>Ala Tyr Ala Val Leu Gly Ile Trp Ala Leu Ser Ala Val Leu Ala Leu<br>        180                         185                  190 | 576 |
| ccg gcc gcg gtg cac acc tac cat gta gag ctc aag ccc cac gac gtg<br>Pro Ala Ala Val His Thr Tyr His Val Glu Leu Lys Pro His Asp Val<br>                 195                      200                  205 | 624 |
| cgc ctc tgc gag gag ttc tgg ggt tcg cag gag cgc cag cga cag atc<br>Arg Leu Cys Glu Glu Phe Trp Gly Ser Gln Glu Arg Gln Arg Gln Ile<br>        210                         215                  220 | 672 |
| tat gcc tgg ggg ctg ctg ctg ggc acc tat ttg ctc ccc ctg ctg gcc<br>Tyr Ala Trp Gly Leu Leu Leu Gly Thr Tyr Leu Leu Pro Leu Leu Ala<br>225                    230                      235                  240 | 720 |
| att ctc ctg tct tac gtc cgg gtg tcg gtg aag ttg cgg aac cgc gtg<br>Ile Leu Leu Ser Tyr Val Arg Val Ser Val Lys Leu Arg Asn Arg Val<br>                 245                      250                  255 | 768 |
| gtg cct ggc agc gtg acc cag agc cag gct gac tgg gac cga gcg cgt<br>Val Pro Gly Ser Val Thr Gln Ser Gln Ala Asp Trp Asp Arg Ala Arg<br>        260                         265                  270 | 816 |
| cgc cgt cgc act ttc tgc ctg ctg gtg gtg gtg gtg gtc gtg ttc gcg<br>Arg Arg Arg Thr Phe Cys Leu Leu Val Val Val Val Val Val Phe Ala<br>                 275                      280                  285 | 864 |
| gtc tgc tgg ctg cct ctg cac att ttc aac ctg ctg cgg gac ctg gac<br>Val Cys Trp Leu Pro Leu His Ile Phe Asn Leu Leu Arg Asp Leu Asp<br>        290                         295                  300 | 912 |
| ccg cgt gcc atc gac ccc tac gcc ttc ggg ctg gtg cag ctc ctc tgc<br>Pro Arg Ala Ile Asp Pro Tyr Ala Phe Gly Leu Val Gln Leu Leu Cys<br>305                    310                      315                  320 | 960 |
| cac tgg ctt gcc atg agc tcc gcc tgc tac aac ccc ttc atc tat gcg<br>His Trp Leu Ala Met Ser Ser Ala Cys Tyr Asn Pro Phe Ile Tyr Ala<br>                 325                      330                  335 | 1008 |
| tcg ctg cac gac agc ttc cga gag gag cta cgc aag atg ctt ctg tct<br>Ser Leu His Asp Ser Phe Arg Glu Glu Leu Arg Lys Met Leu Leu Ser<br>        340                         345                  350 | 1056 |
| tgg ccc cgc aag atc gtg cct cat ggc cag aat atg acc gtc agt gtg<br>Trp Pro Arg Lys Ile Val Pro His Gly Gln Asn Met Thr Val Ser Val<br>                 355                      360                  365 | 1104 |
| gtc atc tgatga<br>Val Ile<br>        370 | 1116 |

-continued (2) INFORMATION FOR SEQ ID NO:140:

(i) SEQUENCE CHARACTERISTICS:
        (A) LENGTH: 370 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:140:

```
Met Thr Ser Leu Pro Pro Gly Thr Thr Gly Asp Pro Asp Leu Phe Ser
1               5                   10                  15

Gly Pro Ser Pro Ala Gly Ser Thr Pro Ala Asn Gln Ser Ala Glu Ala
            20                  25                  30

Ser Glu Ser Asn Val Ser Ala Thr Val Pro Arg Ala Ala Ala Val Thr
        35                  40                  45

Pro Phe Gln Ser Leu Gln Leu Val His Gln Leu Lys Ala Leu Ile Val
    50                  55                  60

Met Leu Tyr Ser Ile Val Val Val Gly Leu Val Gly Asn Cys Leu
65                  70                  75                  80

Leu Val Leu Val Ile Ala Arg Val Arg Arg Leu His Asn Val Thr Asn
                85                  90                  95

Phe Leu Ile Gly Asn Leu Ala Leu Ser Asp Val Leu Met Cys Ala Ala
            100                 105                 110

Cys Val Pro Leu Thr Leu Ala Tyr Ala Phe Glu Pro Arg Gly Trp Val
        115                 120                 125

Phe Gly Gly Gly Leu Cys His Leu Val Phe Phe Leu Gln Pro Val Thr
    130                 135                 140

Val Tyr Val Ser Val Phe Thr Leu Thr Thr Ile Ala Val Asp Arg Tyr
145                 150                 155                 160

Val Val Leu Val His Pro Leu Arg Arg Arg Ile Ser Leu Lys Leu Ser
                165                 170                 175

Ala Tyr Ala Val Leu Gly Ile Trp Ala Leu Ser Ala Val Leu Ala Leu
            180                 185                 190

Pro Ala Ala Val His Thr Tyr His Val Glu Leu Lys Pro His Asp Val
        195                 200                 205

Arg Leu Cys Glu Glu Phe Trp Gly Ser Gln Glu Arg Gln Arg Gln Ile
    210                 215                 220

Tyr Ala Trp Gly Leu Leu Leu Gly Thr Tyr Leu Leu Pro Leu Leu Ala
225                 230                 235                 240

Ile Leu Leu Ser Tyr Val Arg Val Ser Val Lys Leu Arg Asn Arg Val
                245                 250                 255

Val Pro Gly Ser Val Thr Gln Ser Gln Ala Asp Trp Asp Arg Ala Arg
            260                 265                 270

Arg Arg Arg Thr Phe Cys Leu Leu Val Val Val Val Val Phe Ala
    275                 280                 285

Val Cys Trp Leu Pro Leu His Ile Phe Asn Leu Leu Arg Asp Leu Asp
    290                 295                 300

Pro Arg Ala Ile Asp Pro Tyr Ala Phe Gly Leu Val Gln Leu Leu Cys
305                 310                 315                 320

His Trp Leu Ala Met Ser Ser Ala Cys Tyr Asn Pro Phe Ile Tyr Ala
                325                 330                 335

Ser Leu His Asp Ser Phe Arg Glu Glu Leu Arg Lys Met Leu Leu Ser
            340                 345                 350
```

```
                                    -continued
Trp Pro Arg Lys Ile Val Pro His Gly Gln Asn Met Thr Val Ser Val
        355                 360                 365
Val Ile
    370
```

What is claimed is:

1. An isolated labeled polypeptide which comprises an amino acid sequence represented by SEQ ID NO:73 or its amide or ester, or a salt therof.

2. The isolated labeled polypeptide or its amide or ester, or a salt thereof, as claimed in claim 1, which is labeled with [$^{3}$H], [$^{125}$I], [$^{14}$C] or [$^{35}$S].

3. The isolated labeled polypeptide or its amide or ester, or a salt thereof, as claimed in claim 1, which is labeled with [$^{125}$I].

4. The isolated labeled polypeptide as claimed in claim 1, which comprises the amino acid sequence represented by SEQ ID NO:3, SEQ ID NO:4, SEQ D NO:5, SEQ ID NO:6, SEQ ID NO:7, SEQ ID NO:8, SEQ ID NO:9, SEQ ID NO:10, SEQ ID NO:47, SEQ ID NO:48, SEQ ID NO:49, SEQ ID NO:50, SEQ ID NO:51, SEQ ID NO:52, SEQ ID NO:61, SEQ ID NO:62, SEQ ID NO:63, SEQ ID NO:64, SEQ ID NO:65 or SEQ ID NO:66.

5. The isolated labeled polypeptide as claimed in claim 4, which comprises the amino acid sequence represented by SEQ ID NO:61 or SEQ ID NO:64, and C-terminus of the polypeptide is amidated.

6. The isolated labeled polypeptide which comprises the amino acid sequence represented by SEQ ID NO:61 or SEQ ID NO:64, and the C-terminus of the polypeptide is amidated and labeled with [$^{125}$I].

7. The isolated polypeptide which comprises an amino acid sequence represented by SEQ ID NO:61 or SEQ ID NO:64, wherein the C-terminus of the polypeptide is amidated.

* * * * *

UNITED STATES PATENT AND TRADEMARK OFFICE
CERTIFICATE OF CORRECTION

PATENT NO. : 6,794,491 B1
DATED : September 21, 2004
INVENTOR(S) : S. Hinuma et al.

It is certified that error appears in the above-identified patent and that said Letters Patent is hereby corrected as shown below:

<u>Title page,</u>
Item [62], Related U.S. Application Data, should read as follows:
-- PCT/JP96/03821 on Dec. 26, 1996, now Pat. No. 6,228,984. --

Signed and Sealed this

Tenth Day of May, 2005

JON W. DUDAS
*Director of the United States Patent and Trademark Office*